United States Patent
Antoniades et al.

(10) Patent No.: US 12,102,463 B2
(45) Date of Patent: *Oct. 1, 2024

(54) RADIOMIC SIGNATURE OF AN EPICARDIAL REGION

(71) Applicant: Oxford University Innovation Limited, Oxford (GB)

(72) Inventors: Charalambos Antoniades, Oxford (GB); Alexios Antonopoulos, Oxford (GB); Henry West, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 675 days.

This patent is subject to a terminal disclaimer.

(21) Appl. No.: 17/289,041

(22) PCT Filed: Oct. 29, 2019

(86) PCT No.: PCT/GB2019/053058
§ 371 (c)(1),
(2) Date: Apr. 27, 2021

(87) PCT Pub. No.: WO2020/089609
PCT Pub. Date: May 7, 2020

(65) Prior Publication Data
US 2022/0061790 A1 Mar. 3, 2022

(30) Foreign Application Priority Data

Oct. 29, 2018 (GR) .............................. 20180100490
Dec. 10, 2018 (GB) ..................................... 1820044

(51) Int. Cl.
*A61B 6/50* (2024.01)
*G06T 7/00* (2017.01)
(Continued)

(52) U.S. Cl.
CPC ............ *A61B 6/503* (2013.01); *G06T 7/0012* (2013.01); *G06T 7/11* (2017.01); *G06T 7/40* (2013.01);
(Continued)

(58) Field of Classification Search
CPC ....... A61B 6/032; A61B 6/037; A61B 6/5217; A61B 6/5235; A61B 6/503; A61B 6/504;
(Continued)

(56) References Cited

U.S. PATENT DOCUMENTS

2013/0004040 A1 1/2013 Chen et al.
2013/0190592 A1* 7/2013 Coppini ................ G06T 11/003
600/407

(Continued)

FOREIGN PATENT DOCUMENTS

GB 2557263 A * 6/2018 ............... A61B 6/03
JP 2014-534889 A 12/2014
(Continued)

OTHER PUBLICATIONS

Michael T. Lu, "Epicardial and paracardial adipose tissue volume and attenuation Association with high-risk coronary plaque on computed tomographic angiography in the ROMICAT II trial," May 20, 2016, Atherosclerosis 251 (2016), pp. 47-50.*

(Continued)

*Primary Examiner* — Omar S Ismail
(74) *Attorney, Agent, or Firm* — Thomas |Horstemeyer, LLP

(57) ABSTRACT

A method for characterising an epicardial region using medical imaging data of a subject. The method comprises calculating the value of an epicardial radiomic signature of the epicardial region using the medical imaging data. Also disclosed is a method for deriving an epicardial radiomic signature indicative of cardiac health. The method com- (Continued)

prises using a radiomic dataset to construct an epicardial radiomic signature. Also disclosed are systems for performing the aforementioned methods.

30 Claims, 14 Drawing Sheets

(51) Int. Cl.
  G06T 7/11 (2017.01)
  G06T 7/40 (2017.01)
  G16H 30/40 (2018.01)
  G16H 50/20 (2018.01)
(52) U.S. Cl.
  CPC ............ *G16H 30/40* (2018.01); *G16H 50/20* (2018.01); *G06T 2207/10081* (2013.01); *G06T 2207/20081* (2013.01); *G06T 2207/30048* (2013.01)
(58) Field of Classification Search
  CPC . G06T 2207/10081; G06T 2207/20064; G06T 2207/20081; G06T 2207/20084; G06T 7/0012; G06T 7/11; G06T 7/40; G06T 7/42; G06T 7/45; G06T 2207/30048; G06T 7/41; G16H 10/60; G16H 30/20; G16H 30/40; G16H 50/20; G16H 50/30; G16H 50/70
  See application file for complete search history.

(56) References Cited

U.S. PATENT DOCUMENTS

| | | | |
|---|---|---|---|
| 2016/0063175 A1* | 3/2016 | Choi ................. | A61B 5/02028 703/11 |
| 2017/0337681 A1 | 11/2017 | Lure et al. | |
| 2018/0144472 A1* | 5/2018 | Kullberg ............ | G01R 33/4828 |
| 2019/0114767 A1* | 4/2019 | Muehlberg ............ | G06T 11/008 |
| 2021/0077009 A1* | 3/2021 | Viswanath ........... | A61B 5/4255 |
| 2021/0113146 A1* | 4/2021 | Pogue .................... | H04N 19/96 |
| 2021/0166389 A1* | 6/2021 | Denzinger ........... | A61B 6/5217 |

FOREIGN PATENT DOCUMENTS

| | | |
|---|---|---|
| JP | 2017-529146 A | 10/2017 |
| WO | 2016/024128 A1 | 2/2016 |

OTHER PUBLICATIONS

Chun-Qiang Lu,"Diabetes risk assessment with imaging: a radiomics study of abdominal CT," Dec. 6, 2018, European Radiology (2019) 29,pp. 2233-2239.*
Lina Yu,"iVAR: Interactive Visual Analytics of Radiomics Features from Large-Scale Medical Images," 2017 IEEE International Conference on Big Data,pp. 3916-3922.*
Klara J. Rosenquist,"Visceral and Subcutaneous Fat Quality and Cardiometabolic Risk," Nov. 9, 2012, JACC: Cardiovascular Imaging vol. 6,No. 7,2013,pp. 762-769.*
Joseph M. Company,"Epicardial fat gene expression after aerobic exercise training in pigs with coronary atherosclerosis: relationship to visceral and subcutaneous fat," Oct. 7, 2010,J Appl Physiol 109: 1904-1912, 2010,doi:10.1152/japplphysiol.00621.2010, pp. 1904-1910.*
Evangelos K. Oikonomou,"Artificial intelligence inmedical imaging: A radiomic guide to precision phenotyping of cardiovascular disease," Feb. 24, 2020, European Society of Cardiology, Cardiovascular Research (2020) 116,pp. 2040-2051.*
Mohammad Edalat-Javid,"Cardiac SPECT radiomic features repeatability and reproducibility: A multi-scanner phantom study," Apr. 24, 2020,Journal of Nuclear Cardiology,vol. 28, No. 6,pp. 2730-2740.*
Rong Yuan,"Radiomics in RayPlus: a Web-Based Tool for Texture Analysis in Medical Images," Oct. 22, 2018,Journal of Digital Imaging (2019) 32,pp. 269-273.*
Frederic Commandeur,"Deep Learning for Quantification of Epicardial and Thoracic Adipose Tissue From Non-Contrast CT," Jul. 31, 2018,IEEE Transactions on Medical Imaging, vol. 37, No. 8, Aug. 2018,pp. 1836-1844.*
Michael T. Lu, "Epicardial and paracardial adipose tissue volyme and attenuation Association with high-risk coronary plaque on computed tomographic angiography in the ROMICAT II trial," May 20, 2016,Atherosclerosis 251 (2016),pp. 47-50.*
E.O. Rodrigues,A. Conci et al. , "Towards the automated segmentation of epicardial and mediastinal fats: A multi-manufacturer approach using intersubject registration and random forest," Jun. 18, 2015, 2015 IEEE International Conference on Industrial Technology (ICIT), IEEE, Mar. 17, 2015, pp. 1779-1783.*
Japanese Office Action for Application No. 2021-514975, dated Jun. 19, 2023, pp. 1-18 (Translation Included).
International Search Report and Written Opinion for WO 2020/089609 (PCT/GB2019/053058), dated Dec. 9, 2019, pp. 1-17.
UK Search Report for GB 1820044.4, dated Jun. 17, 2019, pp. 1-5.
Yuan Rong et al: "Radiomics in RayPlus: a Web-Based Tool for Texture Analysis in Medical Images", Journal of Digital Imaging, Springer-Verlag, Cham, vol. 32, No. 2, Oct. 22, 2018 (Oct. 22, 2018), pp. 269-275.
Yu Lina et al: "iVAR: Interactive visual analytics of radiomics features from large-scale medical images", 2017 IEEE International Conference on Big Data (Big Data), IEEE, Dec. 11, 2017 (Dec. 11, 2017), pp. 3916-3923.
Nikolaos Alexopoulos et al: "Effect of Intensive Versus Moderate Lipid-Lowering Therapy on Epicardial Adipose Tissue in Hyperlipidemic Post-Menopausal Women", Journal of the American College of Cardiology, vol. 61, No. 19, May 1, 2013 (May 1, 2013), pp. 1956-1961.
Lu Michael T et al: "Epicardial and paracardial adipose tissue volume and attenuation—Association with high-risk coronary plaque on computed tomographic angiography in the ROMICAT II trial", Atherosclerosis, Elsevier, Amsterdam, NL, vol. 251, May 20, 2016 (May 20, 2016), pp. 47-54.
Mohammad Edalat-Javid et al: "Cardiac SPECT Radiomics Features Repeatability and Reproducibility: A Multi Scanner Phantom Study", arxiv.org, Cornell University Library, 201 Olin Library Cornell University Ithaca, NY 14853, Sep. 11, 2019 (Sep. 11, 2019).
Rodrigues E 0 et al: "Towards the automated segmentation of epicardial and mediastinal fats: A multi-manufacturer approach using intersubject registration and random forest", 2015 IEEE International Conference on Industrial Technology (ICIT), IEEE, Mar. 17, 2015 (Mar. 17, 2015), pp. 1779-1785.
Chinese Office Action for Application No. 2019800737112, dated Oct. 27, 2023, pp. 1-29 (Translation Included).
Towards the automated segmentation of epicardial and mediastinal fats: A multi-manufacturer approach using intersubject registration and random forest, 2015 IEEE International Conference on Industrial Technology (ICIT), IEEE, Mar. 17, 2015, É. O. Rodrigues et al., pp. 1779-1785.

* cited by examiner

Confidence Level: 0.95

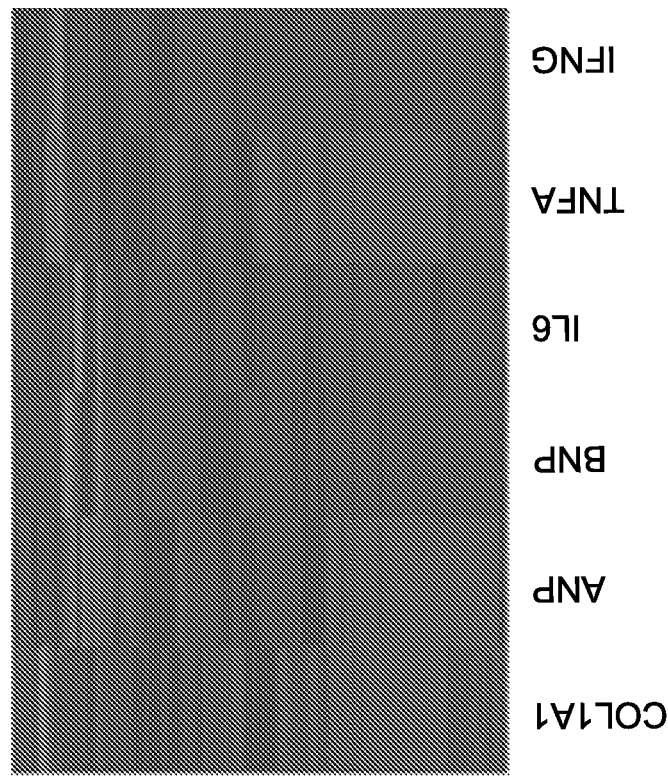
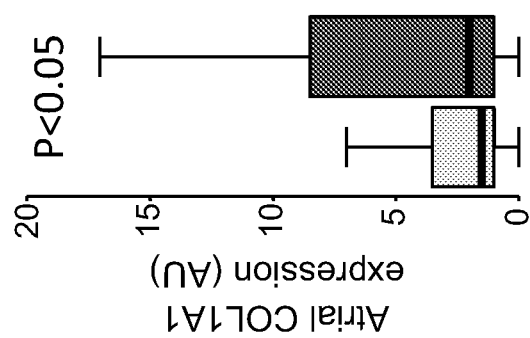
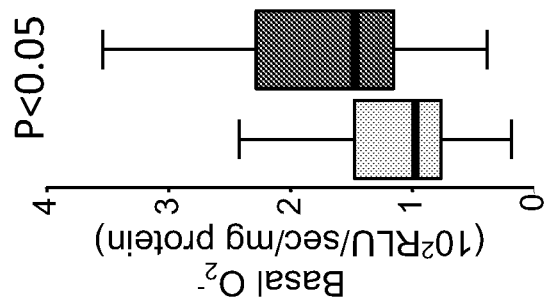
Figure 5(b)
Figure 5(c)
Figure 5(d)

CTA scan  
Ground Truth  
*Manual segmentation*  
Predicted  
*Machine segmentation*

RADIOMIC SIGNATURE OF AN EPICARDIAL REGION

CROSS-REFERENCE TO RELATED APPLICATIONS

This application is the National Stage of International Application No. PCT/GB2019/053058, filed Oct. 29, 2019, which claims priority to GR 20180100490, filed Oct. 29, 2018 and GB 1820044.4, filed Dec. 10, 2018, which are entirely incorporated herein by reference.

FIELD OF THE INVENTION

The invention relates to methods of characterising an epicardial region, in particular using a radiomic signature, and systems for the same. The invention also relates to methods of deriving such signatures, and systems for the same.

BACKGROUND

Heart (i.e. cardiac) conditions, including ischaemic heart disease, heart failure, cardiomyopathy, and arrhythmias such as atrial fibrillation (AF), poses a global burden on healthcare systems and patients' quality of life, as does ischaemic stroke. Although the study of heart function is feasible by imaging (e.g. by echocardiography or cardiac magnetic resonance), currently there are no means to study myocardial tissue phenotype and disease (e.g. atrial redox state, fibrosis or pro-fibrotic signalling), which is often the underlying cause of such conditions.

Epicardial adiposity is an independent risk factor for development of heart conditions and stroke. For example, in clinical studies employing imaging, expansion of epicardial adipose tissue volume has been found to be independently associated with atrial fibrillation risk (Antonopoulos, A. S. & Antoniades, C. The role of epicardial adipose tissue in cardiac biology: classic concepts and emerging roles. *J Physiol*, doi:10.1113/JP273049 (2017)). Vice versa, atrial disease results in the fatty infiltration of atrial myocardium via enhanced natriuretic peptide signaling-induced adipogenesis (Suffee, N. et al. Atrial natriuretic peptide regulates adipose tissue accumulation in adult atria. *Proc Natl Acad Sci USA* 114, E771-E780, doi:10.1073/pnas.1610968114 (2017)).

Computerised tomography is now increasingly used for the imaging of human adipose tissue (e.g. to quantify fat volumes), and volumetric assessment of epicardial adiposity has been successfully used for cardiac risk assessment in clinical studies (Antonopoulos, A. S. et al. Mutual Regulation of Epicardial Adipose Tissue and Myocardial Redox State by PPAR-gamma/Adiponectin Signalling. *Circ Res* 118, 842-855, doi:10.1161/CIRCRESAHA.115.307856 (2016)). In particular, CT imaging has been employed as a non-invasive means to study body adiposity by identifying voxels of fat based on their CT attenuation or radiodensity (e.g. −190 to −30 Hounsfield Units), and fat volume measurements are established prognostic biomarkers of cardiovascular disease risk (Rosito, G. A. et al. Pericardial fat, visceral abdominal fat, cardiovascular disease risk factors, and vascular calcification in a community-based sample: the Framingham Heart Study. *Circulation* 117, 605-613, doi:10.1161/CIRCULATIONAHA.107.743062 (2008)).

Although, this volumetric approach can be used to reliably describe and quantify epicardial adiposity, it is only indirectly and poorly linked to features of adipose tissue biology and underlying myocardial biology and disease. Other methods that rely on direct assessment of heart (e.g. atrial) function or volumes e.g. by echocardiography or cardiac magnetic resonance cannot provide reliable information on heart tissue phenotype and disease. Therefore, there is an unmet need for non-invasive methods for assessing cardiac health, in particular myocardial health, and for detecting or diagnosing myocardial disease, such as myocardial oxidative stress, inflammation and/or fibrosis. There is also a need for non-invasive methods for assessing the risk of developing cardiac conditions, in particular the risk of developing heart arrhythmia, such as AF. There is also a need for non-invasive methods for assessing the risk of ischaemic stroke.

SUMMARY OF THE INVENTION

According to a first aspect of the invention, there is provided a method for characterising an epicardial region (for example its phenotype, e.g. composition and/or texture) using medical imaging data of a subject. The method may be used for indirectly characterising cardiac tissue, for example the myocardium. In particular, the method may be used for characterising or assessing myocardial health, in particular of the myocardium adjacent to the epicardial region. For example, the method may be used for detecting or identifying myocardial disease such as fibrosis, inflammation, and/or oxidative stress, in particular fibrosis. The method may comprise calculating the value of an epicardial radiomic signature of the epicardial region using the medical imaging data. The epicardial radiomic signature may be calculated using or on the basis of measured values of a plurality of epicardial radiomic features of the epicardial region. The measured values of the epicardial radiomic features may be calculated from or using the medical imaging data.

The epicardial radiomic signature may provide a measure of the texture of the epicardial region. At least one of the epicardial radiomic features may provide a measure of the texture of the epicardial region, for example at least one of the epicardial radiomic features may be a texture statistic.

The epicardial radiomic signature (i.e. its value) may be indicative of cardiac health, in particular myocardial health. For example, the epicardial radiomic signature may be indicative of, or associated with (e.g. statistically significantly associated with), myocardial disease. The epicardial radiomic signature may be indicative of myocardial inflammation. The epicardial radiomic signature may be indicative of myocardial redox state or oxidative stress. The epicardial radiomic signature may be indicative of myocardial fibrosis.

The epicardial radiomic signature (i.e. its value) may be predictive of the likelihood of the subject developing a cardiac or heart condition. The heart condition may be associated with myocardial disease, in particular with myocardial fibrosis. The heart condition may be heart arrhythmia (for example atrial fibrillation), ischaemic heart disease, heart failure, and/or cardiomyopathy.

The epicardial radiomic signature may be predictive of the likelihood of the subject experiencing or suffering stroke, specifically ischemic stroke. The epicardial radiomic signature may be associated with or indicative of risk of stroke, for example increased or high risk of stroke compared to the general population.

The epicardial region may comprise or consist of a peri-atrial region, for example a peri-left atrial region. The peri-left atrial region may comprise or consist of epicardial regions adjacent to the intra-atrial septum and/or the anterior left atrium wall (i.e. the region immediately anterior to the left atrium. These regions comprise or consist of epicardial adipose tissue and epicardial connective tissues.

At least one of the epicardial radiomic features may be calculated from a wavelet transformation of the attenuation values.

The plurality of epicardial radiomic features may comprise at least two epicardial radiomic features selected from the epicardial radiomic features of groups 1 to 15, as identified in Table 3. The at least two epicardial radiomic features may each be selected from different groups. Groups 1 to 15 may be limited to those epicardial radiomic features that are correlated with the significant epicardial radiomic feature to a degree of |rho|≥0.800. Groups 1 to 15 may be limited to those epicardial radiomic features that are correlated with the significant epicardial radiomic feature to a degree of |rho|≥0.850. Groups 1 to 15 may be limited to those epicardial radiomic features that are correlated with the significant epicardial radiomic feature to a degree of |rho|≥0.900. Groups 1 to 15 may be limited to those epicardial radiomic features that are correlated with the significant epicardial radiomic feature to a degree of |rho|≥0.950.

The plurality of epicardial radiomic features may comprise at least two epicardial radiomic features selected from the epicardial radiomic features of groups 1 to 16, as identified in Table 3b. The at least two epicardial radiomic features may each be selected from different groups. Groups 1 to 16 may be limited to those epicardial radiomic features that are correlated with the significant epicardial radiomic feature to a degree of |rho|≥0.800. Groups 1 to 16 may be limited to those epicardial radiomic features that are correlated with the significant epicardial radiomic feature to a degree of |rho|≥0.850. Groups 1 to 16 may be limited to those epicardial radiomic features that are correlated with the significant epicardial radiomic feature to a degree of |rho|≥0.900. Groups 1 to 16 may be limited to those epicardial radiomic features that are correlated with the significant epicardial radiomic feature to a degree of |rho|≥0.950.

The at least two epicardial radiomic features may comprise at least two of Inverse Difference Moment HHH, Minimum LHH, Low Gray Level Zone Emphasis LLL, Maximum Probability LLL, Busyness LHH, Zone Entropy LLL, Run Entropy LLL Maximum 3D Diameter, Long Run High Gray Level Emphasis LLL, Joint Average LLL, Difference Entropy LLL, Sum Entropy HHH, Difference Entropy LHH, Sum Squares LHH, and Gray Level Variance LHH (GLDM).

The at least two epicardial radiomic features may consist of 15 epicardial radiomic features and may consist of Inverse Difference Moment HHH, Minimum LHH, Low Gray Level Zone Emphasis LLL, Maximum Probability LLL, Busyness LHH, Zone Entropy LLL, Run Entropy LLL Maximum 3D Diameter, Long Run High Gray Level Emphasis LLL, Joint Average LLL, Difference Entropy LLL, Sum Entropy HHH, Difference Entropy LHH, Sum Squares LHH, and Gray Level Variance LHH (GLDM).

The at least two epicardial radiomic features may comprise at least two of $10^{th}$ Percentile, ID HHL, Variance, Gray Level Non Uniformity Normalized (GLRLM), Dependence Variance HLL, Size Zone Non-Uniformity LHL, Skewness, Root Mean Squared, Gray Level Non Uniformity LLH, Large Area Emphasis LLH, IDMN HHH, Zone Percentage HHL, Kurtosis, Size Zone Non Uniformity Normalized HHH, Difference Entropy LLL, and Autocorrelation HHL.

The at least two epicardial radiomic features may consist of 16 epicardial radiomic features and may consist of $10^{th}$ Percentile, ID HHL, Variance, Gray Level Non Uniformity Normalized (GLRLM), Dependence Variance HLL, Size Zone Non-Uniformity LHL, Skewness, Root Mean Squared, Gray Level Non Uniformity LLH, Large Area Emphasis LLH, IDMN HHH, Zone Percentage HHL, Kurtosis, Size Zone Non Uniformity Normalized HHH, Difference Entropy LLL, and Autocorrelation HHL.

The plurality of epicardial radiomic features may comprise at least two epicardial radiomic features selected from the epicardial radiomic features of clusters A to D, as identified in Table 1, Table 2 or Table 3. The at least two epicardial radiomic features may each be selected from different clusters.

The plurality of epicardial radiomic features may comprise at least two epicardial radiomic features selected from the epicardial radiomic features of clusters A to D, as identified in Table 1b, Table 2b or Table 3b. The at least two epicardial radiomic features may each be selected from different clusters.

The plurality of epicardial radiomic features may comprise at least two epicardial radiomic features selected from the epicardial radiomic features of clusters A to D, wherein: cluster A consists of Inverse Difference Moment HHH, Minimum LHH, Zone Variance LLL, Low Gray Level Zone Emphasis LLL, Maximum Probability LLL, Elongation, Cluster Shade LLL, Busyness LHH, Gray Level Non Uniformity LLL, and Skewness HHH; cluster B consists of Zone Entropy LLL, Cluster Prominence LLL, Gray Level Variance LLL (GLDM), and Run Entropy LLL; cluster C consists of Least Axis, Maximum 2D Diameter Row, Major Axis, Maximum 2D Diameter Column, Maximum 2D Diameter Slice, and Maximum 3D Diameter; and cluster D consists of Autocorrelation LLH, Long Run High Gray Level Emphasis LLL, Joint Average LLL, Autocorrelation LLL, Difference Entropy LLL, Difference Entropy LLH, Sum of Squares HLH, Sum of Squares HHH, Sum Entropy HHH, Gray Level Variance LLH (GLDM), Difference Entropy LHH, Sum Squares LHH, and Gray Level Variance LHH (GLDM). The at least two epicardial radiomic features may each be selected from different clusters.

The plurality of epicardial radiomic features may comprise at least two epicardial radiomic features selected from the epicardial radiomic features of clusters A to D, wherein: cluster A consists of Inverse Difference Moment HHH, Minimum LHH, Low Gray Level Zone Emphasis LLL, Maximum Probability LLL, and Busyness LHH; cluster B consists of Zone Entropy LLL, and Run Entropy LLL; cluster C consists of Maximum 3D Diameter; and cluster D consists of Long Run High Gray Level Emphasis LLL, Joint Average LLL, Difference Entropy LLL, Sum Entropy HHH, Difference Entropy LHH, Sum Squares LHH, and Gray Level Variance LHH (GLDM). The at least two epicardial radiomic features may each be selected from different clusters.

The at least two epicardial radiomic features may comprise at least three epicardial radiomic features. The at least two epicardial radiomic features may comprise at least four epicardial radiomic features. The at least two epicardial radiomic features may comprise at least 15 radiomic epicardial features. The at least two epicardial radiomic features may comprise at least 16 epicardial radiomic features The medical imaging data may comprise attenuation values for each of a plurality of voxels corresponding to at least the epicardial region.

The method may further comprise identifying the epicardial region using the medical imaging data. The epicardial region is identified using manual contouring. The epicardial region may include only voxels of the medical imaging data having an attenuation value falling within a given range of attenuation values. The given range may be from about −190 to about −30 Hounsfield Units.

The method may further comprise identifying the epicardial region using an automated segmentation algorithm. The segmentation algorithm may have been trained using machine learning, in particular deep learning, to segment the medical imaging data.

The epicardial region may comprise or consists of voxels of the medical imaging data having an attenuation value falling within a given range of attenuation values. The given range of attenuation values may correspond to adipose and/or connective tissue.

The given range may comprise or encompass attenuation values above and below −30 Hounsfield Units. The given range may be from about −190 to about −30 Hounsfield Units or from about −190 to about +150 Hounsfield Units. Alternatively, the given range may comprise or include these ranges.

The method may further comprise segmenting the epicardial region. The values of the plurality of epicardial radiomic features may be calculated from the segmented epicardial region.

The value of each of the plurality of epicardial radiomic features may be calculated from raw attenuation values, binned attenuation values, or a wavelet transformation of the attenuation values.

The method may further comprise predicting the risk of the subject developing a cardiac condition based on at least the calculated value of the epicardial radiomic signature. The cardiac condition may be heart arrhythmia, for example atrial fibrillation. For example, the method may further comprise predicting the risk of the subject developing postoperative heart arrhythmia.

The method may further comprise predicting or categorising the risk of the subject experiencing or suffering ischaemic stroke based on at least the calculated value of the epicardial radiomic signature.

The method may further comprise identifying, based on the calculated value of the epicardial radiomic signature, whether an individual is at risk of stroke, for example at a high or increased risk of stroke, for example relative to the general population.

The method may further comprise administering or prescribing a preventative treatment, such as a medication, to the individual to reduce the risk of stroke if the individual is identified as being at risk of stroke.

The method may further comprise evaluating the cardiac health or myocardial health of the subject based on at least the calculated value of the epicardial radiomic signature.

The method may further comprise determining whether the subject has a myocardial disease based on at least the calculated value of the epicardial radiomic signature. The myocardial disease may be fibrosis. The myocardial disease may be inflammation. The myocardial disease may be oxidative stress.

The epicardial radiomic signature may be calculated using, or on the basis of (i.e. may consist or comprise of), a decision tree, in particular a regression tree.

The epicardial radiomic signature may comprise a weighted sum of the plurality of epicardial radiomic features. The epicardial radiomic signature may be linearly related to the weighted sum of the plurality of epicardial radiomic features.

According to a second aspect of the invention, there is provided a method for deriving an epicardial radiomic signature. The radiomic signature may be indicative of cardiac health or disease, in particular myocardial health or disease. The radiomic signature may be indicative of or predictive of risk of stroke. For example, the radiomic signature may be suitable for identifying individuals at risk of stroke. The epicardial radiomic signature may be suitable for indirectly characterising cardiac tissue, for example the myocardium. In particular, the signature may be suitable for characterising or assessing, or may be indicative of, myocardial health or disease, in particular of the myocardium adjacent to an epicardial region. For example, the signature may be indicative of, or may be suitable for detecting or identifying, myocardial disease such as fibrosis, inflammation, and/or oxidative stress, in particular fibrosis. The method may comprise using a radiomic dataset to construct an epicardial radiomic signature indicative of cardiac health or disease. The epicardial radiomic signature may be calculated on the basis of a second plurality of epicardial radiomic features of an epicardial region. The dataset may comprise the values of a first plurality of epicardial radiomic features of an epicardial region obtained from medical imaging data of the epicardial region for each of a plurality of individuals. The plurality of individuals may comprise a first group of individuals having, or identified as having, (at the time the medical imaging data were collected) or having previously had a heart condition or myocardial disease or a history of stroke and a second group of individuals not having, or identified as not having, (at the time the medical imaging data were collected) the heart condition or myocardial disease or history of stroke, and optionally having no history of the heart condition. The second plurality of epicardial radiomic features is selected from amongst the first plurality of epicardial radiomic features, for example based on an analysis of, or using, the dataset. In particular, the second plurality of epicardial radiomic features may be selected from amongst the first plurality of epicardial radiomic features to provide an epicardial radiomic signature that is indicative of cardiac health and/or disease and/or that is predictive of the risk of developing the heart condition or experiencing stroke, as determined from the dataset, for example using a machine learning algorithm.

The method may further comprise using the dataset to identify significant epicardial radiomic features from amongst the first plurality of epicardial radiomic features that are each identified as being significantly associated with the cardiac condition or myocardial disease or history of stroke, as determined from the dataset. The second plurality of epicardial radiomic features may comprise at least two epicardial radiomic features that may be selected to be, or to be collinear with (in particular identified as being collinear with), different significant epicardial radiomic features. Each of the at least two epicardial radiomic features of the second plurality of epicardial radiomic features may be selected to be significantly associated with the cardiac condition or myocardial disease or history of stroke, as determined from the dataset.

The method may further comprise using a feature selection algorithm (e.g. a machine learning feature selection algorithm) to identify a subset of the epicardial radiomic features (optionally a subset of the significant epicardial radiomic features) that the radiomic signature should be calculated on the basis of (i.e. optimal features). In other words, the subset of radiomic features are predicted to maximise the accuracy (e.g. optimise or maximise the association of the radiomic signature with the cardiac condition or myocardial disease or history of stroke) of the epicardial radiomic signature, e.g. when the epicardial radiomic signature is calculated on the basis of (only) the subset of epicardial radiomic features (and is optimised). The subset of epicardial radiomic features may maximise the association of a preliminary epicardial radiomic signature with the cardiac condition or myocardial disease or history of stroke (when the preliminary epicardial radiomic signature is calculated on the basis of the subset of the significant epicardial radiomic features), as determined from the dataset. The at least two epicardial radiomic features may be selected to be, or may be selected to be collinear with, different epicardial radiomic features belonging to the subset. The at least two epicardial radiomic features may comprise all of the epicardial radiomic features belonging to the subset, or collinear equivalents thereof that are collinear with the epicardial radiomic features, as determined from the dataset. In other words, the at least two epicardial radiomic features may comprise each of, or epicardial radiomic features that are collinear with each of, the epicardial radiomic features belonging to the subset.

The method may further comprise identifying groups of epicardial radiomic features, each of the groups comprising one of the significant epicardial radiomic features and collinear equivalents thereof that are collinear with the significant epicardial radiomic feature, as determined from the dataset. The at least two epicardial radiomic features may be selected from different groups.

The method may further comprise identifying a plurality of clusters of the significant epicardial radiomic features by performing a cluster analysis (e.g. using a clustering algorithm, in particular a machine learning clustering algorithm), for example a correlation cluster analysis. The at least two epicardial radiomic features may each be selected from, or be selected to be collinear with significant epicardial radiomic features from, different clusters. The cluster analysis may identify the clusters based on the strength of the correlations between the significant epicardial radiomic features. The intra-cluster correlations may be stronger than the inter-cluster correlations. For example, the epicardial radiomic features within each cluster may be correlated with each other to a greater degree than they are correlated with epicardial radiomic features in other clusters.

The cluster analysis may be a hierarchical cluster analysis, a k-means cluster analysis, a distribution-based cluster analysis, or a density-based cluster analysis. In particular, the cluster analysis may be a hierarchical cluster analysis. The cluster analysis, for example the cluster algorithm, may identify the clusters based on a distance between the epicardial radiomic features, for example the squared Euclidean distance between the epicardial radiomic features, for example in a correlation plot. The cluster algorithm may identify the clusters based on the distance between the features in correlation space, where the distance between each pair of features corresponds to the degree to which those features are correlated, i.e. the closer the two features are in correlation space the more correlated they are with one another.

Two epicardial radiomic features may be identified as collinear if they are correlated to an extent at least equal to a correlation threshold. The correlations between the epicardial radiomic features may be calculated using Spearman's rho coefficient. Alternatively, collinearity between epicardial radiomic features may be calculated using other measures of pairwise correlation, such as Pearson's correlation coefficient (Pearson's r). The correlation threshold may be at least about |rho|=0.75.

An epicardial radiomic feature may be identified as being significantly associated with the cardiac condition or myocardial disease or history of stroke if it is associated with the cardiac condition or myocardial disease or history of stroke above a significance threshold. The significance threshold may be at least about $\alpha=0.05$, for example about $\alpha=0.05$. A statistical correction to correct for multiple comparisons, such as a Benjamini-Hochberg correction, may be applied to the significance threshold. The association of the epicardial radiomic features with the cardiac condition or myocardial disease or history of stroke may be calculated based on a receiver operating characteristic (ROC) curve analysis, in particular using an area under the curve (AUC) measurement (i.e. the C-statistic), as will be readily understood by those skilled in the art.

The epicardial radiomic signature may be constructed to be correlated with the cardiac condition or myocardial disease or history of stroke using, or as determined from, the dataset. The epicardial radiomic signature may be constructed to be significantly associated with the cardiac condition or myocardial disease or history of stroke using, or as determined from, the dataset. The epicardial radiomic signature may be identified as being significantly associated with the cardiac condition or myocardial disease or history of stroke if it is associated with the cardiac condition or myocardial disease or history of stroke above a significance threshold, as determined from the dataset. The significance threshold may be at least about $\alpha=0.05$, for example about $\alpha=0.05$. The association of the epicardial radiomic signature with the cardiac condition or myocardial disease or history of stroke may be calculated based on a receiver operating characteristic (ROC) curve analysis, in particular using an area under the curve (AUC) measurement (i.e. the C-statistic), as will be readily understood by those skilled in the art.

The dataset may be divided into a training cohort dataset and a test cohort dataset. The step of constructing the epicardial radiomic signature may comprise deriving the signature using the training cohort dataset and validating the signature using the test cohort dataset.

The step of constructing the epicardial radiomic signature may comprise refining the epicardial radiomic signature to increase the association of the epicardial radiomic signature with the cardiac condition or myocardial disease or history of stroke.

The step of constructing the epicardial radiomic signature may be performed using multi-fold cross-validation. The step of constructing the epicardial radiomic signature may be performed using recursive feature elimination, for example with a random forest algorithm.

The step of constructing the epicardial radiomic signature may be performed using a machine learning algorithm. For example, the step of constructing the epicardial radiomic signature may comprise identifying a subset of the significant epicardial radiomic features that are to be included in the signature, for example using a feature selection machine learning algorithm. The feature selection may be performed using recursive feature elimination, for example using a random forest algorithm. The step of constructing the epicardial radiomic signature may then comprise refining or optimising the epicardial radiomic signature based on the subset of epicardial radiomic features identified in the feature selection step, for example using a machine learning algorithm. For example, a second machine learning algorithm (e.g. a radiomic signature optimisation algorithm) may be used to refine or optimise the epicardial radiomic signature calculated using the subset of epicardial radiomic features, for example using multi-fold cross-validation. In other words, the second machine learning algorithm refines or optimises an epicardial radiomic signature calculated on the basis of the subset of significant epicardial radiomic features. The second machine learning algorithm may be a decision tree learning algorithm.

The epicardial radiomic signature may be calculated using a decision tree. The epicardial radiomic signature may be calculated using a regression tree.

The epicardial radiomic signature may be constructed to provide a measure of the texture of the epicardial region.

At least one of the second plurality of epicardial radiomic features, for example at least one of the at least two epicardial radiomic features, may provide a measure of the texture of the epicardial region. For example, each of the second plurality of epicardial radiomic features may provide a measure of the texture of the epicardial region (i.e. each of the at epicardial radiomic features may be texture statistics).

The cardiac condition may be associated with (e.g. at least partly caused by or correlated with) cardiac health or disease, in particular myocardial health or disease.

For example, the cardiac condition may be associated with myocardial redox state or oxidative stress. For example, the cardiac condition may be associated with myocardial inflammation. In particular, the cardiac condition may be associated with myocardial fibrosis. The epicardial radiomic signature may therefore be constructed to be associated with or indicative of cardiac health or disease, for example myocardial fibrosis.

The myocardial disease may be inflammation, oxidative stress, or fibrosis, in particular fibrosis.

The cardiac condition may be heart arrhythmia. The heart arrhythmia may be atrial fibrillation.

The method may further comprise calculating the value of the derived epicardial radiomic signature for an epicardial region of a patient or subject. For example, the method may further comprise characterising an epicardial region of a patient or subject by calculating the value of the derived epicardial radiomic signature. The value of the derived radiomic signature may be calculated based on or using medical imaging data of at least the epicardial region of the patient or subject. The value of the derived radiomic signature may be calculated using or based at least on the values of the second plurality radiomic features of the epicardial region of the patient or subject.

The method may therefore be for deriving an spicardial radiomic signature and characterising an epicardial region using the derived radiomic signature.

The method may further comprise configuring a system for calculating the value of the derived epicardial radiomic signature for a patient or subject. For example, the method may further comprise configuring a system for characterising an epicardial region of the a patient or subject by calculating the value of the derived epicardial radiomic signature for the patient or subject. The system may be configured to calculate the value of the derived epicardial radiomic signature using or based on medical imaging data of at least an epicardial region of the patient or subject. The system may be configured to calculate the value of the derived epicardial radiomic signature using or based at least on the values of the second plurality of epicardial radiomic features of the epicardial region of the patient or subject.

The method may therefore be for deriving an epicardial radiomic signature and configuring a system for character-ising an epicardial region of a patient using the derived epicardial radiomic signature.

The method may further comprise loading computer-readable instructions onto a computer-readable memory. The instructions, when executed by a computer, cause the computer to calculate the value of the derived epicardial radiomic signature for a patient or subject. For example, the instructions may cause the computer to characterise an epicardial region of the a patient or subject by calculating the value of the derived epicardial radiomic signature for the patient or subject. The instructions may cause the computer to calculate the value of the derived epicardial radiomic signature using or based on medical imaging data of at least an epicardial region of the patient or subject. For example, the instructions may cause the computer to calculate the value of the derived epicardial radiomic signature using or based at least on the values of the second plurality of epicardial radiomic features of the epicardial region of the patient or subject. The instructions may be a computer program.

The system may be configured to receive the medical imaging data or values of the second plurality of radiomic features as an input. The system may be configured to output (e.g. display) the calculated value of the radiomic signature or a value based on the calculated value of the radiomic signature. The system may be configured to output an indication of the myocardial health of the patient. The system may be configured to output an indication of whether the patient has a myocardial disease. The system may be configured to output an indication of the risk of the patient developing a cardiac condition. The system may be configured to output an indication of the risk of the patient experiencing stroke. The system may be a computer system.

The method may comprise providing instructions for configuring a system for calculating the value of the derived radiomic signature for a patient or subject.

The medical imaging data may be radiographic data. The medical imaging data may be computed tomography data.

The epicardial region may comprise epicardial adipose tissue.

The epicardial radiomic signature of the invention may also be calculated on the basis of further epicardial radiomic features of the epicardial region in addition to the at least two epicardial radiomic features referred to above. For example, the epicardial radiomic signature may comprise other epicardial radiomic features in addition to the at least two epicardial radiomic features. Thus, it may be said that the epicardial radiomic signature is calculated on the basis of a plurality of epicardial radiomic features, and the plurality of epicardial radiomic features may comprise the at least two epicardial radiomic features.

The methods of the invention may also comprise the step of calculating the epicardial radiomic features from the medical imaging data.

According to a third aspect of the invention, there is provided a system configured to perform any of the methods described above. The system may be a computer system. The system may comprise a processor configured to perform the steps of the method. The system may comprise a memory loaded with executable instructions for performing the steps of the method.

According to a fourth aspect of the invention, there is provided use of an epicardial radiomic signature for any of the above-described purposes, for example to characterise an epicardial region, to assess cardiac health, to detect myocardial disease, to predict the risk of developing a cardiac condition, or to predict or categories the risk of experiencing stroke. The epicardial radiomic signature may be calculated on the basis of measured values of a plurality of epicardial radiomic features of the epicardial region.

The epicardial region may be or may comprise epicardial tissue, for example epicardial adipose tissue, in particular periatrial epicardial adipose tissue. The epicardial region may also comprise water, and/or other soft tissue structures within the epicardial region. For example, the epicardial region may comprise connective tissue.

BRIEF DESCRIPTION OF THE FIGURES

The invention will now be described with reference to the appended figures, in which:

FIG. 2 illustrates various aspects of the principal component analysis of periatrial adipose tissue radiomic features.

FIG. 3 illustrates the unsupervised hierarchical clustering of selected radiomic features and a radiomics correlation heat map.

FIG. 4 illustrates various aspects of the machine learning approach used for identification of the radiomic fingerprint of atrial fibrillation, and therefore myocardial phenotype, on periatrial adipose tissue.

FIG. 5 illustrates the validation of the developed epicardial radiomic signature (score) against atrial biology and risk for atrial fibrillation development. FIG. 5(b) shows that a high periatrial epicardial radiomic score was associated with the gene expression profile of atrial myocardium in Arm B patients. FIG. 5(c) shows that a periatrial epicardial radiomic score of 6 or higher (right, darker shading) was associated with significantly increased atrial expression of collagen (COL1A1) than a score of less than 6 (left, lighter shading) and FIG. 5(d) shows that a periatrial epicardial radiomic score of 6 or higher (right, darker shading) was associated with significantly increased superoxide (O2-) generation than a score of less than 6 (left, lighter shading).

FIG. 6 illustrates the development of the Atriomic Stroke Algorithm.

DETAILED DESCRIPTION

Figure 1:
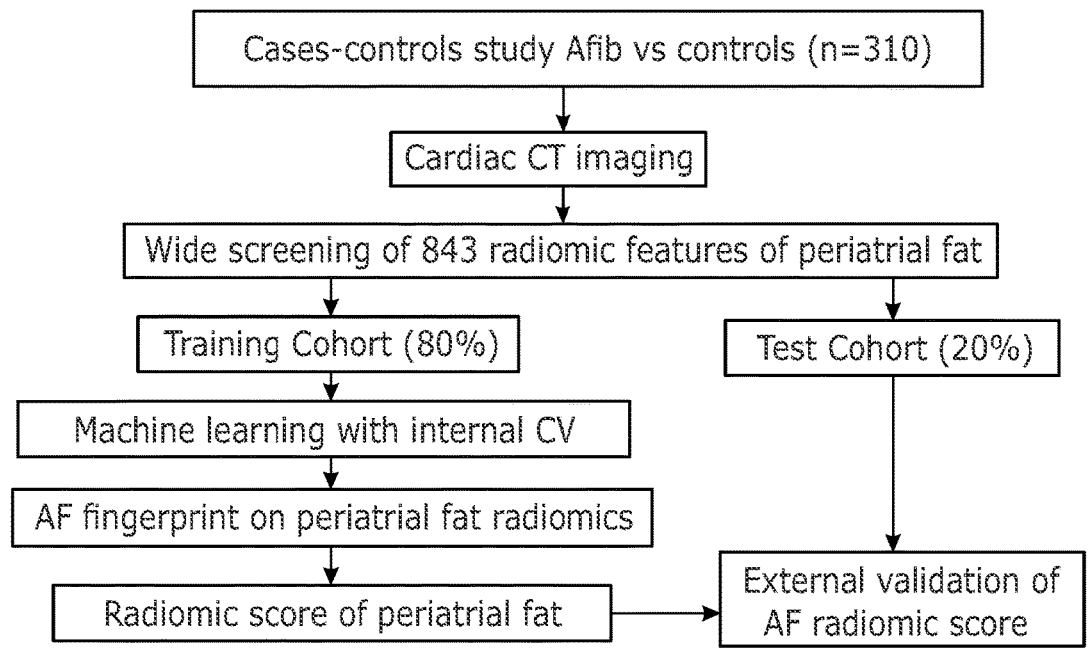
FIG. 1 illustrates, using flow charts, the methods used to derive and validate an epicardial radiomic signature. Afib/AF: atrial fibrillation; CV: cross validation; CABG: coronary artery bypass grafting; POAF: postoperative atrial fibrillation.
Figure 1:
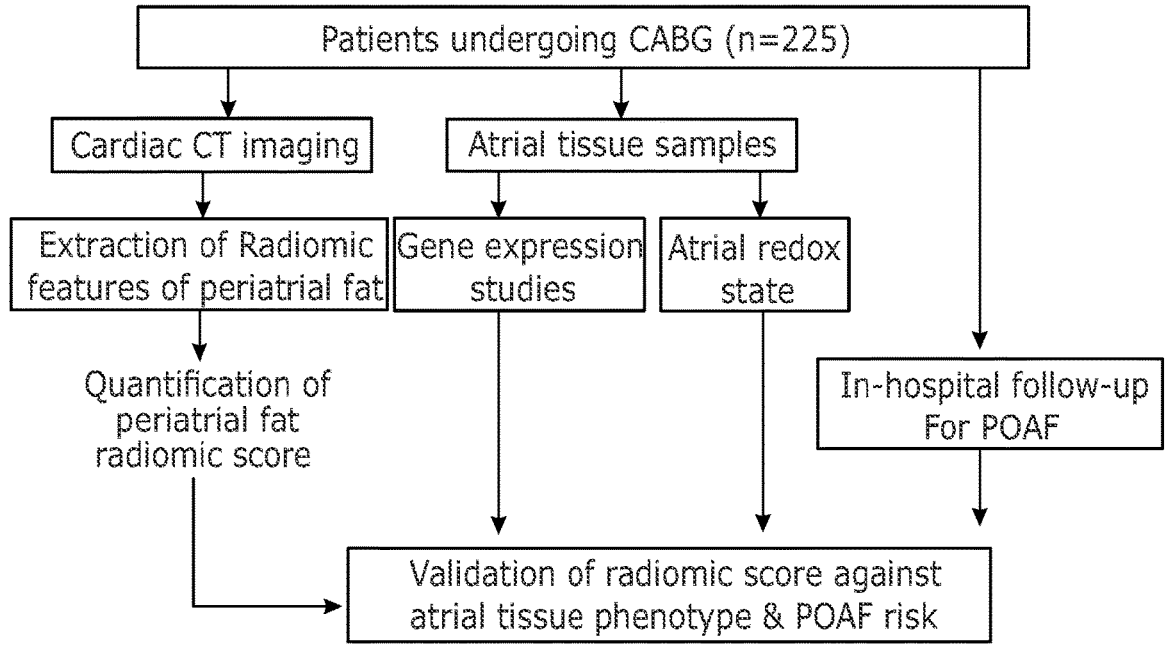

The inventors have discovered that an epicardial radiomic signature (otherwise known as a "score" or "index") calculated on the basis of two or more (i.e. a plurality of) different radiomic features of the ECR (i.e. epicardial radiomic features) can be used to indirectly evaluate or assess cardiac (in particular myocardial) health and to detect myocardial disease or predict or categories the risk of stroke, specifically ischaemic stroke. For example, the radiomic signature of the invention is indicative of or associated with, and may therefore be used to indirectly and non-invasively assess, evaluate, or characterise cardiac (e.g. myocardial) health or disease, for example myocardial fibrosis, myocardial redox state (in particular oxidative stress), myocardial inflammation, and myocardial gene expression patterns. The radiomic signature of the invention may be indicative of or associated with, and may therefore be used to indirectly and non-invasively assess the risk of, future incidence of stroke. In general, as used herein, "associated" may be taken to mean "statistically associated", for example "statistically significantly associated". The signature of the invention may therefore be used to predict the risk of developing, or to determine whether a patient has, a heart condition such as heart arrhythmia (for example atrial fibrillation), ischaemic heart disease, heart failure, and/or cardiomyopathy, which are commonly associated with myocardial disease, in particular myocardial fibrosis. The signature of the invention may be used to predict the risk of a patient experiencing or suffering a stroke, or to identify those at risk of stroke, for example at a high risk of suffering a stroke. In particular, the signature may be used to determine whether a patient has a myocardial disease, or a heart condition associated with myocardial disease. The signature may therefore be used in risk stratification for development of heart disease.

The radiomic signature of the invention is therefore preferably calculated on the basis of two or more radiomic features of an ECR and provides a tool for non-invasively characterising or phenotyping the ECR, and therefore also for indirectly phenotyping or evaluating the health of cardiac tissue such as myocardium, for example atrial myocardium.

If an individual, e.g. a patient, is identified as being at high risk of suffering a stroke based on the calculated value of the radiomic signature, treatment (e.g. medication) may be administered to the patient to reduce their risk of stroke. For example, the treatment may comprise prescribing medication to reduce the risk of stroke, such as anticoagulation or antithrombotic medication.

The invention exploits the fact that the cardiac tissue and the adjacent ECR, in particular tissues within the ECR such as adipose tissue, interact in a bidirectional manner. For example cardiac dysfunction may result in the fatty infiltration of myocardium via enhanced natriuretic peptide signaling-induced adipogenesis. Vice versa, myocardial disease or dysfunction may induce changes in the surrounding epicardial adipose tissue. In particular, the invention exploits the effect that this interaction has on the texture (e.g. the spatial non-uniformity or variability) of the ECR tissues, and the radiomic signature of the invention may therefore be constructed to provide a measure of the texture of the ECR or epicardial tissue.

The epicardial radiomic signature of the invention may be used on its own to characterise the ECR or to provide diagnostic or prognostic information, or it may be combined with existing models, such as those including demographics and conventional risk factors.

The epicardial region (ECR) refers to a region or volume adjacent to (and outside of) the heart, for example adjacent to the myocardium. The ECR may be a region or volume of epicardial tissue (ECT) or may comprise or consist of ECT. Epicardial tissue is tissue located adjacent to the heart (i.e. the myocardium) and is located within (i.e. enclosed by) the pericardium. Tissue is a complex biological structure, and may comprise cells (e.g. adipocytes, neurons, etc.) and extracellular structures and materials (such as water) which may occupy the intercellular spaces. In particular, the ECR may be a region of epicardial adipose tissue (EAT) or may comprise or consist of EAT. The ECR may therefore alternatively be referred to as a region or volume of EAT. The epicardial region may be a periatrial region (i.e. adjacent to an atrium of the heart). In particular, the epicardial region may be a region of periatrial adipose tissue, or may comprise or consist of periatrial adipose tissue, such as periatrial epicardial adipose tissue. In the case of embodiments relating to stroke, the ECR preferably comprises or consists of one or more peri-atrial regions, preferably one or more peri-left atrial regions. In particular, the ECR preferably comprises or consists of the epicardial regions adjacent to the intra-atrial septum (i.e. the intra-atrial septum epicardial region) and/or the region immediately anterior to the left or right atrium (i.e. the anterior left atrium epicardial region). Where epicardial regions are referred to herein with reference to an anatomical region of the heart itself (e.g. intra-atrial septum), it should be understood that this refers to the epicardial region adjacent to said anatomical region of the heart, for example the epicardial region in which epicardial adipose is found. Also, where the left atrium is referred to, it should be understood that this could equally refer to the right atrium. This is because radiomic features characterising these regions have been found to maximise the association of the signature with stroke risk. Moreover, the ECR may comprise, in addition to adipose tissue, connective tissue, particularly in the embodiments relating to stroke. Where used herein, the term epicardial region may be used interchangeably with region of interest, wherein the region of interest comprises or consists of an epicardial region.

The invention exploits a radiomic approach. Radiomics is a field of imaging in which a large amount of quantitative information is extracted from imaging data using data-characterization algorithms. The resulting features, referred to as radiomic features, range from simple volumetric, shape-related or first order statistics (such as mean or median attenuation), to second and higher order statistics that describe the texture of a segmented volume or region and the spatial relationship of voxels with similar or different attenuation values. Such features can identify imaging patterns of significant clinical value that cannot be recognized by the naked eye and have the potential to maximize the diagnostic yield of non-invasive ECR phenotyping.

The signature of the invention is derived and calculated on the basis of radiomic features, for example those extracted from medical imaging data. In particular, the medical imaging data from which the radiomic features are extracted may correspond to at least an epicardial region (ECR), for example periatrial epicardial adipose tissue, and optionally also to the heart and/or other tissue adjacent or surrounding the ECR. As used herein, the terms "epicardial radiomic signature" or "ECR radiomic signature" refer to a radiomic signature calculated on the basis of at least two epicardial radiomic features, where epicardial radiomic features are radiomic features that are calculated from medical imaging data of at least an epicardial region. The medical imaging data typically comprise radiodensity (or attenuation) values, usually expressed in Hounsfield Units (HU), for a plurality of voxels of the relevant region, in this case the ECR, and optionally also the adjacent tissues.

The medical imaging data are preferably computed tomography (CT) data, but other forms of medical imaging data (e.g. radiography data) that provide attenuation (or radiodensity) data for voxels of the imaged region may be used instead, such as three-dimensional computed laminography data. Typically, the medical imaging data used in the invention are three-dimensional imaging data. Throughout the following, where CT or another medical imaging technique is referred to, it should be understood that other suitable medical imaging techniques could alternatively be used.

The ECR may include only voxels having a radiodensity (or attenuation) falling within a given or predetermined range and/or located within a delineated region. For example, the ECR may be identified by a person such as an operator, for example by manual contouring or delineation. The operator may identify the ECR through an inspection of the imaging data, for example the CT image. The ECR may therefore include only voxels located within the delineated region. Alternatively, the ECR may be include only voxels located within a given or predetermined distance from the outer surface of the heart, for example the outer surface of the heart muscle (myocardium).

The given distance may be a set or fixed value, such as about 5 mm. The ECR may be located between the left and right pulmonary veins. Alternatively or in addition to identifying the spatial extent of the ECR, the ECR may be identified by applying a radiodensity (or attenuation) mask to the data and identifying the PCT as including only those voxels having a radiodensity falling within a given or predetermined range. For example, the ECR may include only those voxels having a radiodensity in the Hounsfield Unit range of about −190 HU to about +30 HU. In particular, the ECR may be defined as including only voxels having a radiodensity in the Hounsfield Unit range of about −190 HU to about −30 HU. This range of attenuation values generally corresponds to the radiodensity of adipose tissue. However, other ranges could be used or included, for example about −30 to about +30 Hounsfield Units, which generally corresponds to the radiodensity of water. In particular, where the signature is predictive of stroke, the range may be broader and may encompass other epicardial tissues in addition to adipose, such as epicardial connective tissue. Thus, the range may include voxels having a radiodensity above −30 HU. In other words, the ECR may comprise voxels having a radiodensity above (and below) −30 HU. For example, the range may be from about −190 HU to about +150 HU. For example, the range may encompass at least the range of about −190 HU to about +150 HU.

Preferably, the ECR is identified using an automated algorithm. The algorithm may have been trained using machine learning, in particular deep learning, to identify the ECR. For example, the algorithm may have been trained using medical imaging data in which the ECR has been manually identified and segmented. Using an automated segmentation algorithm has the advantage that the entire process may be automated and performed by a computer. The automated ECR region identification or segmentation algorithm may identify sub-regions of the ECR and may combine said sub-regions to identify the ECR of interest. For example, the ECR may identify the inra-atrial septum (epicardial) region and the anterior left (or right) atrial (epicardial) region and may merge these two regions to identify the ECR, or region of interest.

The ECR may be segmented prior to calculating the radiomic features and the radiomic features calculated from the segmented data. The segmented volume or region corresponds to the ECR, and segmentation may remove data corresponding to voxels that are outside of the ECR. Segmentation may therefore be achieved by identifying the ECR, as described above, and then removing any voxels from the data that are identified as not being part of the ECR, for example those voxels corresponding to surrounding or adjacent tissue voxels. The segmented ECR may then be extracted and used to calculate the radiomic features. For example, the segmentation may be performed by an automated algorithm, as described above.

Calculation of the radiomic features from the medical imaging data may be performed using a computer program, or software. Various commercially available software packages exist for this purpose, such as 3D Slicer (available at http://www.slicer.org; see Fedorov, A. et al. 3D Slicer as an image computing platform for the Quantitative Imaging Network. *Magn Reson Imaging* 30, 1323-1341, doi:10.1016/j.mri.2012.05.001 (2012)). The radiomic features may be shape-related statistics, first-order statistics, or texture statistics (e.g. second and higher order statistics). Shape-related and first-order radiomic features may be calculated using the raw radiodensity (HU) values of the ECR voxels. For calculation of texture features (e.g. Gray Level Co-occurrence Matrix [GLCM], Gray Level Dependence Matrix [GLDM], Gray Level Run-Length Matrix [GLRLM], Gray Level Size Zone Matrix [GLSZM], and Neighbouring Gray Tone Difference Matrix [NGTDM], see Tables R1-R7), ECR voxel radiodensity or attenuation values are preferably discretized into a plurality of bins, preferably into 16 bins, preferably of equal width (e.g. width of ten HU), to reduce noise while allowing a sufficient resolution to detect biologically significant spatial changes in ECR attenuation. Discretization into 16 bins is recommended as the optimal approach to increase the signal-to-noise ratio of images for radiomic analysis. However, discretization into more or fewer than 16 bins is also possible. To enforce symmetrical, rotationally-invariant results, some or all of the radiomic features, in particular the texture statistics (GLCM etc), may be calculated in all (orthogonal) directions and then averaged (e.g. using the mean or other average of the individually calculated values of the feature in each of the directions).

Some or all of the radiomic features, in particular those relating to first order and texture-based statistics, may also be calculated for three-dimensional wavelet transformations of the original image data resulting in a number of additional sets of radiomic features, for example as described by Guo et al. (Guo X, Liu X, Wang H, et al. Enhanced CT images by the wavelet transform improving diagnostic accuracy of chest nodules. *J Digit Imaging* 2011; 24(1): 44-9). Wavelet transformation decomposes the data into high and low frequency components. At high frequency (shorter time intervals), the resulting wavelets can capture discontinuities, ruptures and singularities in the original data. At low frequency (longer time intervals), the wavelets characterize the coarse structure of the data to identify the long-term trends. Thus, the wavelet analysis allows extraction of hidden and significant temporal features of the original data, while improving the signal-to-noise ratio of imaging studies. The data may be decomposed by a discrete wavelet transform into a plurality (e.g. eight) wavelet decompositions by passing the data through a multi-level (e.g. three level) filter bank. At each level, the data are decomposed into high- and low-frequency components by high- and low-pass filters, respectively. Thus, if a three level filter bank is used, eight wavelet decompositions result, corresponding to HHH, HHL, HLH, HLL, LHH, LHL, LLH and LLL, where H refers to "high-pass", and L refers to "low-pass". Of course, more or fewer than eight levels could alternatively be used to decompose the data. Such decompositions may be performed using widely available software, such as the such as the Slicer Radiomics software package which incorporates the Pyradiomics library. Optionally, the radiomic features may all be calculated on the basis of the original (raw) data, i.e. with no wavelet transformation applied. Thus, where lists, groups or clusters of radiomic features are disclosed herein, it should be understood that these could be reduced to exclude those radiomic features that are calculated on the basis of wavelet transformations. Where a radiomic feature is calculated on the basis of a wavelet decomposition or transformation of the data this is denoted by a suffix indicating which wavelet decomposition the radiomic feature has been calculated on the basis of (e.g. HHH for high-pass, high-pass, high-pass). So, for example, "Skewness LLL" denotes the radiomic feature "Skewness" as calculated on the basis of the LLL wavelet decomposition. Where no suffix is present, the radiomic feature is calculated on the basis of the original (or raw) data.

Deriving a Radiomic Signature

The invention provides a method for deriving a radiomic signature for characterising an ECR (for example a region of periatrial epicardial adipose tissue), for example for predicting the risk or identifying those at risk of stroke, for predicting the risk of developing a heart condition such as heart arrhythmia or for diagnosing or detecting myocardial disease. The radiomic signature is indicative of the underlying myocardial health of the myocardium adjacent to the ECR, and in particular of myocardial disease such as fibrosis or oxidative stress, which are known to cause a variety of heart conditions, such as arrhythmia. The presence of a cardiac condition known to be associated with myocardial disease, such as fibrosis and/or oxidative stress, may therefore be used as a surrogate marker of myocardial health or disease and used to derive the radiomic signature of the invention. The radiomic signature may therefore be derived using medical imaging data for a plurality of individuals or patients (a cohort of individuals), the plurality of individuals comprising a first group of individuals having, or with a history of, a cardiac (i.e. heart) condition known to be associated with myocardial disease, for example atrial fibrillation, and a second group of individuals without the heart condition, for example in sinus rhythm, and preferably with no history of the cardiac condition. Similarly, a known history of stroke may be used instead of the presence of a cardiac condition, particularly where the aim is to derive a signature that is associated with or predictive of the risk of stroke. Alternatively, the presence of a myocardial disease such as fibrosis may be used directly to construct the signature of the invention. Therefore, the patients may instead be divided into two groups either having or not having myocardial disease. However, it is generally not possible to detect myocardial disease non-invasively, whereas cardiac conditions such as arrhythmias can be detected or diagnosed by non-invasive means (e.g. ECG). It is therefore preferred to use a cardiac condition associated with myocardial disease rather than the myocardial disease itself to construct the signature.

As used herein, the term cardiac (or heart) condition is used to mean an abnormal functioning of the heart, for example an arrhythmia or heart failure. A heart condition is therefore generally observable using non-invasive means because it is observable through the dysfunction of the heart. Myocardial disease or health, on the other hand, refers to the underlying biology or phenotype of the myocardium itself, for example the composition or structure of the myocardium, and invasive means such as biopsies are usually required to determine whether they are present.

Fibrosis may be defined as the excess deposition of extracellular matrix in the myocardium (cardiac muscle) resulting from the activation and/or proliferation of cardiac fibroblasts. Myocardial redox state refers to the balance of pro-oxidant and anti-oxidant molecules in a tissue, and depends on the generation of reactive oxygen species and their elimination from antioxidant defence systems. Myocardial inflammation is the inflammation of the myocardium and may be defined as the expression of pro-inflammatory mediators.

The method typically involves performing a case-control study of (human) patients with versus without the cardiac condition or myocardial disease. The individuals having (or with a history of) the cardiac condition or myocardial disease are the cases (first group) and the individuals without the cardiac condition or myocardial disease are the controls (second group). Alternatively, the first group (cases) may consist of individuals with a history of stroke and the second group (controls) may consist of individuals having no history of stroke. Therefore, wherever a cardiac condition or myocardial disease is mentioned below, it should be understood that this could instead be a history of stroke. Similarly, where where prediction of developing a cardiac condition, myocardial disease (or similar) is mentioned, it should be understood that this could instead be the prediction of suffering or experiencing a stroke, specifically subsequent to the recording of the imaging data. Thus, instead of the signature being indicative of or predictive of developing a cardiac condition, it could instead be indicative of or predictive of suffering a stroke. Case-control matching, for example 1:1 matching, is preferably performed to match cases with controls, for example using an automated algorithm. The case-control matching may be performed so that each case in the first group is matched with a corresponding control in the second group. The cases and controls may be matched for clinical demographics (such as age, sex, obesity status, cardiovascular risk factors), cohort and/or technical parameters related to imaging data acquisition (e.g. tube voltage and CT scanner used).

A stepwise approach may then be followed to develop a radiomic signature. First, a plurality of radiomic features are calculated from the medical imaging data for each of the plurality of individuals, for example as described above. The radiomic features may comprise a selection or all of the radiomic features as defined in Tables R1-R7, and each of the radiomic features may be calculated based on the raw image data and/or on one or more wavelet transformations of the image data (or wavelet decompositions), as described above. Preferably, each of the radiomic features is calculated for the raw image data and for the aforementioned eight three-dimensional wavelet decompositions of the image data. Thus, a radiomic dataset comprising the measured or calculated values of a plurality of radiomic features for each of the individuals is obtained.

In the case of developing signatures associated with or predictive of stroke, the method may comprise identifying and optionally segmenting a plurality of epicardial regions. In other words, the ECR may comprise or consist of a plurality of sub-regions, and the method may comprise segmenting the ECR itself and one or more sub-regions of the ECR and extracting radiomic features for the ECR and the one or more sub-regions. The plurality of radiomic features may therefore comprise of radiomic features of the ECR and of the one or more sub-regions of the ECR.

For example, the method may comprise segmenting an ECR comprising one or more (e.g. all) of the following sub-regions: 1) the intra-atrial septum (epicardial) region, 2) the anterior left (or right) atrial (epicardial) region (the region adjacent the anterior surface of the left atrium), and 3) the left (or right) atrial appendage (epicardial) region. The sub-regions may also comprise regions that result from merging the original sub-regions. For example, the sub-regions may also comprise merged sub-regions comprising or consisting of adjacent sub-regions, specifically sub-regions 1+2 and/or 2+3. The method may then comprise calculating the features of the ECR and each of the ECR sub-regions. Preferably, the ECR comprises or consists of sub-regions 1+2+3, and the sub-regions are sub-regions 1, 2, 3, 1+2 and 2+3.

The radiomic features may also be calculated for both a narrower HU range corresponding to adipose tissue (e.g. about −190 HU to about −30 HU) and a broader HU range corresponding to other epicardial tissues in addition to adipose (e.g. about −190 HU to about +150 HU). This is useful because it increases the physiological information encapsulated in the radiomic features and therefore improves the pool of information from which the signature may be constructed. For example, different tissue types may provide different markers of cardiac health. This is particularly the case for the prediction of stroke.

Radiomic features that are found to be not significantly associated (e.g. correlated) with the cardiac condition or myocardial disease above a significance threshold based on an analysis of the data may then be removed from the plurality of radiomic features. The association of each radiomic feature with the cardiac condition or myocardial disease may be calculated on the basis of a receiver operating characteristic curve (ROC) analysis, in particular an area under the curve (AUC) calculation, based on the data for the plurality of individuals. The significance threshold is preferably about $\alpha=0.05$ or lower, for example a may be in the range of from 0.001 to 0.05. The significance threshold is preferably about $\alpha=0.05$. However, the significance threshold may be about $\alpha=0.04$. Alternatively, the significance threshold may be about $\alpha=0.03$. Alternatively, the significance threshold may be about $\alpha=0.02$. Alternatively, the significance threshold may be about $\alpha=0.01$. Alternatively, the significance threshold may be about $\alpha=0.005$. Alternatively, the significance threshold may be about $\alpha=0.002$. The end result should be that any radiomic features that are not significantly associated with the presence of the cardiac condition or myocardial disease (as determined or calculated from the data, for example based on an analysis of the data) are removed from the plurality of radiomic features. In other words, the method comprises selecting those features that are significantly associated or correlated with the cardiac condition or myocardial disease. This has the advantage that the number of radiomic features to be further processed to construct the signature is much reduced, thus reducing the complexity of the subsequent signature construction and reducing the computational burden of doing so. The reason for selecting the significant radiomic features is that these are, to a first approximation, most likely to combine to provide a radiomic signature that is associated with cardiac health because they have already been shown to be independently associated with cardial health.

When determining whether a feature is statistically significantly associated with the cardiac condition or myocardial disease, a statistical adjustment may be applied to correct for multiple comparisons and to decrease the false discovery rate (FDR). For example, the Benjamini-Hochberg correction may be applied, for example using a false discovery rate of about 0.10. Alternatively, a Bonferroni correction may be applied to the significance threshold. The Bonferroni correction may be applied based on the number of principal components which account for a given amount of variability in the study sample based on a principal component analysis. For example, the given amount may be about 99.5%. In other words the m value used to correct the a value (by dividing a by m, i.e. a/m) is the number of principal components that account for the given amount of variability. For this reason, a principal component analysis of the radiomic features may be performed on the data for the plurality of individuals.

The remaining, or "significant", radiomic features (i.e. those that are found to be statistically significantly associated with the cardiac condition or myocardial disease) may then grouped or "clustered" into a plurality of clusters of similar, or correlated, features. The degree of correlation between features is a measure of the extent to which two radiomic features tend to vary with one another between different individuals. The pairwise correlations may be calculated using Spearman's rho coefficient or other measures of correlation, such as Pearson's correlation coefficient. The clustering may be performed, for example, using a hierarchical clustering method (such as a hierarchical clustering algorithm) to sort the significant radiomic features into the plurality of clusters. The hierarchical clustering may be performed unsupervised, i.e. independently of the strength of the correlations of the radiomic features with the cardiac condition or myocardial disease. In other words, the clustering may be performed on the strength of the correlations of the features with one another so that radiomic features are clustered together with those that they are most correlated with. Specifically, the intra-cluster correlations may be stronger than the inter-cluster correlations, i.e. the correlations between features within a cluster are stronger than those between features in different clusters. The final identification of the clusters may be performed by inspection of the correlation data by a person, e.g. an operator. For example, the operator may inspect a dendrogram representative of the hierarchical clustering of the radiomic features and/or a two-dimensional correlation plot (or heatmap) which plots the correlations of each of the radiomic features with each other radiomic features (and itself) and may identify the clusters based on this inspection of the radiomic feature inter-correlation data. In the correlation heatmap the radiomic features may be arranged along the x- and y-axes of the correlation plot in the order determined from the hierarchical clustering (i.e. with the features being located adjacent to the features with which they are most closely associated or correlated). This visual inspection may be used together with the hierarchical clustering to identify the appropriate clusters of radiomic features. Alternatively, the clusters may be identified through the hierarchical clustering or visual inspection alone.

The radiomic signature may be constructed based on at least two (or all) of the significant plurality of features (i.e. the features found to be significantly associated with the cardiac condition or myocardial disease), the at least two radiomic features being different to one another. Preferably, the radiomic signature is constructed based on at least two of the significant plurality of features, wherein the at least two radiomic features are selected from different clusters. For example, the radiomic signature may be constructed based on at least one radiomic feature selected from each cluster. Other radiomic features may also be included in the initial signature to be optimised, for example two or more radiomic features from any or all of the clusters may be included in the initial signature. However, in order to provide a signature more strongly associated with the cardiac condition or myocardial disease, and therefore of enhanced diagnostic and prognostic usefulness, it is preferable to include at least two radiomic features, each from a different cluster. This is because features from different clusters provide complementary phenotypic information relating to the ECR. In particular, radiomic features from different clusters are likely to be sensitive to different phenotypic characteristics of the ECR because they have been found not to vary in a similar manner to one another, which demonstrates that they are sensitive to different phenotypic characteristics of the ECR. The radiomic signature should therefore preferably be calculated on the basis of (the measured values of) at least two radiomic features, each selected from a different cluster. For example, the radiomic signature may comprise at least three radiomic features, each selected from a different cluster. Alternatively, the initial radiomic signature may comprise at least four radiomic features, each selected from a different cluster. Alternatively, the initial radiomic signature may comprise at least five radiomic features, each selected from a different cluster. Alternatively, the initial radiomic signature may comprise at least six radiomic features, each selected from a different cluster. Preferably, the initial radiomic signature may comprise one radiomic feature from each cluster.

The construction of the radiomic signature may involve refining or optimising the radiomic signature, in particular using data for a subset of the cohort known as the "training" cohort. This involves refining or optimising the signature to improve the correlation or association of the signature with the heart condition based on the data.

The signature may comprise (i.e. the value of the signature may be calculated using) a decision tree, with the input variables being or comprising the radiomic features of the signature. The target variable or outcome may be calculated by the decision tree based on the input variables. In particular, because the radiomic features are continuous variables, the decision tree may be a regression tree. The decision tree algorithm uses branched options at each tree node, and this process repeated at multiple levels results in the final branch or tree leaves. Each observation (i.e. set of radiomic feature values input into the decision tree) is thus assigned to a final leaf and this gives a relevant classification probability for the presence of the disease or condition (similar logistic regression probability). Formulating the radiomic signature as a decision tree was found to give the best sensitivity for the assessment of cardiac health. In particular, a decision tree was found to provide the best accuracy for discriminating patients with, versus those without the cardiac condition or myocardial disease.

Alternatively, the signature may comprise a weighted sum of the values of each of the radiomic features included in the signature, and the weighing of each of the radiomic features may be progressively optimised or refined. The coefficients by which each of the radiomic features is multiplied are generally referred to as beta ($\beta$) coefficients, and it is these beta coefficients that may be optimised or refined.

The signature may be constructed or derived using one or more machine learning algorithms. For example, the contributions of the radiomic features to the signature may be refined using a machine learning algorithm to increase or maximise the association of the signature with the cardiac condition or myocardial disease. For example, a plurality (preferably all) of the significant radiomic features (i.e. those that are significantly associated with the cardiac condition or myocardial disease) may be input into a first machine learning algorithm. The first machine learning algorithm may be used to identify the optimum number of and identity of the significant radiomic features that are to be included in the signature, in particular to maximize its accuracy for discriminating for the cardiac condition or myocardial disease. In other words, the construction of the radiomic signature may comprise a feature selection step in which the radiomic features to be included in the signature are selected. In the feature selection step a feature selection algorithm (e.g. a machine learning algorithm) may select a subset of the radiomic features to be included in the final signature, in particular that are predicted to maximise the association of the final signature with the cardiac condition or myocardial disease. This has the advantage of reducing the complexity optimising the final signature because it reduces the number of radiomic features that need to be considered. The first machine learning algorithm that performs this feature selection step may use recursive feature elimination, for example with a random forest algorithm. However, other algorithms could alternatively be used. The first machine learning algorithm may be constrained to require the resulting signature to comprise at least two radiomic features selected from different clusters. For example, the machine learning algorithm may be constrained to require the resulting signature to comprise at least one radiomic feature selected from each of the clusters.

Once the number and identity of the radiomic features to be included in the signature are identified, a second machine learning algorithm may be used to optimise the contributions of each of the features identified by the first machine learning algorithm to the signature. In other words, the construction of the radiomic signature may comprise the step of refining or optimising the radiomic signature to increase of maximise its association with the cardiac condition or myocardial disease using a second machine learning algorithm. The second machine learning algorithm may be a decision tree learning algorithm (for example if the radiomic signature comprises or is a decision tree), and is preferably a gradient boosting algorithm, in particular an extreme gradient boosting algorithm. Gradient boosting algorithms are well-known decision tree learning algorithms for classification/regression. The initial cohort (or plurality of individuals) may be split, for example using a random seed, into a training and a test cohort. The training cohort may consist of about 80% of the individuals from the initial cohort and the test cohort may consist of about 20% of the individuals from the initial cohort. The signature may be derived or refined using the data for the training cohort and validated using data for the test cohort. For example, the signature may be constructed using internal cross-validation. The internal cross validation may be multi-fold, for example 5-fold.

Alternatively, the signature may be constructed from the significant radiomic features using a single machine learning algorithm, rather than in the two-step process described above. For example, a single machine learning algorithm, such as a decision tree learning algorithm with inherent feature selection, could be used to identify the features to be included in the final signature and to refine or optimise the signature. For example, the number of radiomic features to be included in the final signature may be preselected or predetermined and input as a parameter into the machine learning algorithm, or may be left open and selected by the machine learning algorithm itself, which also refines and optimises the radiomic signature. In other words, the machine learning algorithm may include a feature selection function.

Although the method described above results in the radiomic signature being constructed from only radiomic features that are found to be significantly associated with the cardiac condition or myocardial disease (i.e. the "significant" features), it is not necessary for the radiomic signature to include only significant radiomic features. Therefore, the construction of the radiomic signature discussed above need not be performed using only significant radiomic features and may be performed without first selecting only the significant radiomic features so that non-significant features are also included in the construction of the signature. Alternatively, any or all of the significant radiomic features from which the signature is constructed may be substituted with a radiomic feature that is highly correlated, or collinear, with that significant feature, i.e. a collinear equivalent. A signature in which one or more of the significant features is replaced a feature that is collinear with that feature will generally perform similarly to a signature calculated on the basis of only the significant features because, by definition, collinear features behave very similarly to one another. In fact, it is possible that replacing one or more (or even all) of the significant features with alternative features that are collinear with the replaced significant features could result in a signature having an enhanced prognostic value, and this has in fact been found to be the case in some instances. This is because although the original features are generally the most independently associated with the clinical endpoint, they are not necessarily the best-performing features when combined into a signature.

Thus, the method of deriving the signature may comprise replacing one or all of the significant radiomic features with radiomic features that are found to be collinear with the replaced significant features. In particular, once the significant features that maximise the signature's association with the cardiac condition or myocardial disease have been identified, any or all of those significant features may be replaced by a feature that is collinear with the replaced significant feature. The radiomic signature may therefore include (i.e. be calculated on the basis of) at least two of the significant radiomic features or their collinear equivalents. For example, the radiomic signature may comprise one or more significant radiomic feature and one or more collinear equivalents of other significant radiomic features. Preferably, the at least two significant radiomic features are selected from different clusters (or the substitute features correspond to significant radiomic features belonging to different clusters). Preferably, the radiomic signature comprises at least two of the significant radiomic features (or their collinear equivalents) that are found to maximise the signature's accuracy for predicting the cardiac condition or myocardial disease.

The method of deriving the signature may therefore comprise evaluating pairwise correlations between the radiomic features and identifying groups of radiomic features that are correlated or collinear with the significant radiomic features. The correlations between the radiomic features are calculated using the measured values of the radiomic features for the plurality of individuals. Collinear radiomic features may be identified as those that are correlated with each other across the individuals to a degree at least equal to a given correlation threshold. The correlation threshold preferably applies to both positive and negative correlations, for example the correlation threshold may be expressed as a modulus. The pairwise correlations may be calculated using Spearman's rho coefficient and the correlation threshold may be at least about |rho|=0.75, for example about |rho|=0.75, so that all pairs of radiomic features that are correlated with each other at the level of |rho|≥0.75 are considered to be collinear with each other. Alternatively, the correlation threshold may be at least about |rho|=0.9, for example about |rho|=0.9 Alternatively, the correlation threshold may be at least about |rho|=0.9, for example about |rho|=0.9. As will be readily understood in the field, the correlation or collinearity is a measure of how closely two radiomic features vary together from one individual to the next and may be calculated on the basis of the measured radiomic feature values for the plurality of individuals.

The radiomic signature may then be constructed from at least two radiomic features selected from different groups of collinear features. In other words, the signature may be constructed from at least two different significant radiomic features or substitute radiomic features that are collinear with the two different significant radiomic features.

As mentioned above, the signature may include a weighted sum of the calculated values of a plurality of radiomic features. The signature may also include other terms, such as the addition or subtraction of a constant, or multiplication by a factor. However, typically, if the signature includes a weighted sum it will be linearly related to the weighted sum of radiomic feature values in some way.

The radiomic signature may take the form of, or include the term (for example, the signature may be calculated on the basis of a function including the term):

$$A \pm \Sigma b_i \mathrm{rf}_i$$

where A is a constant (which can be zero or non-zero), $b_i$ is the weighting coefficient (or beta patameter) for the radiomic feature i, and $rf_i$ is the measured value of the radiomic feature i.

However, preferably the value of the radiomic signature is calculated using a decision tree. In this case, the decision tree may output a predicted probability (P) of the presence of the cardiac condition or myocardial disease based on the measured values of the radiomic features that are input into the decision tree. The final value of the signature may therefore be related to P in some way. In other words, the radiomic signature may simply be P, or it may be calculated using the value P. For example, the signature may also include other terms, such as the addition or subtraction of a constant, or multiplication by a factor or constant. However, typically the signature will be linearly related to the output of the decision tree. For example, the radiomic signature may be calculated as A×P, where A is a constant. A may, for example, be 10.

In general, in the above-described methods, bivariate associations between radiomic features may be assessed by the non-parametric Spearman's rho ($\rho$) coefficient.

The Radiomic Signature

The ECR radiomic signature of the invention is calculated on the basis of measured values of radiomic features obtained from medical imaging data. In particular, the ECR radiomic signature is preferably calculated on the basis of at least two radiomic features.

To improve the prognostic and diagnostic value of the signature, the signature is preferably calculated on the basis of at least two different radiomic features selected from different clusters of similar or correlated radiomic features, as described above. This reduces redundancy and improves the diversity of information included in the calculation of the signature because the features from different clusters relate to different textural aspects of the ECR.

Figure 3A:
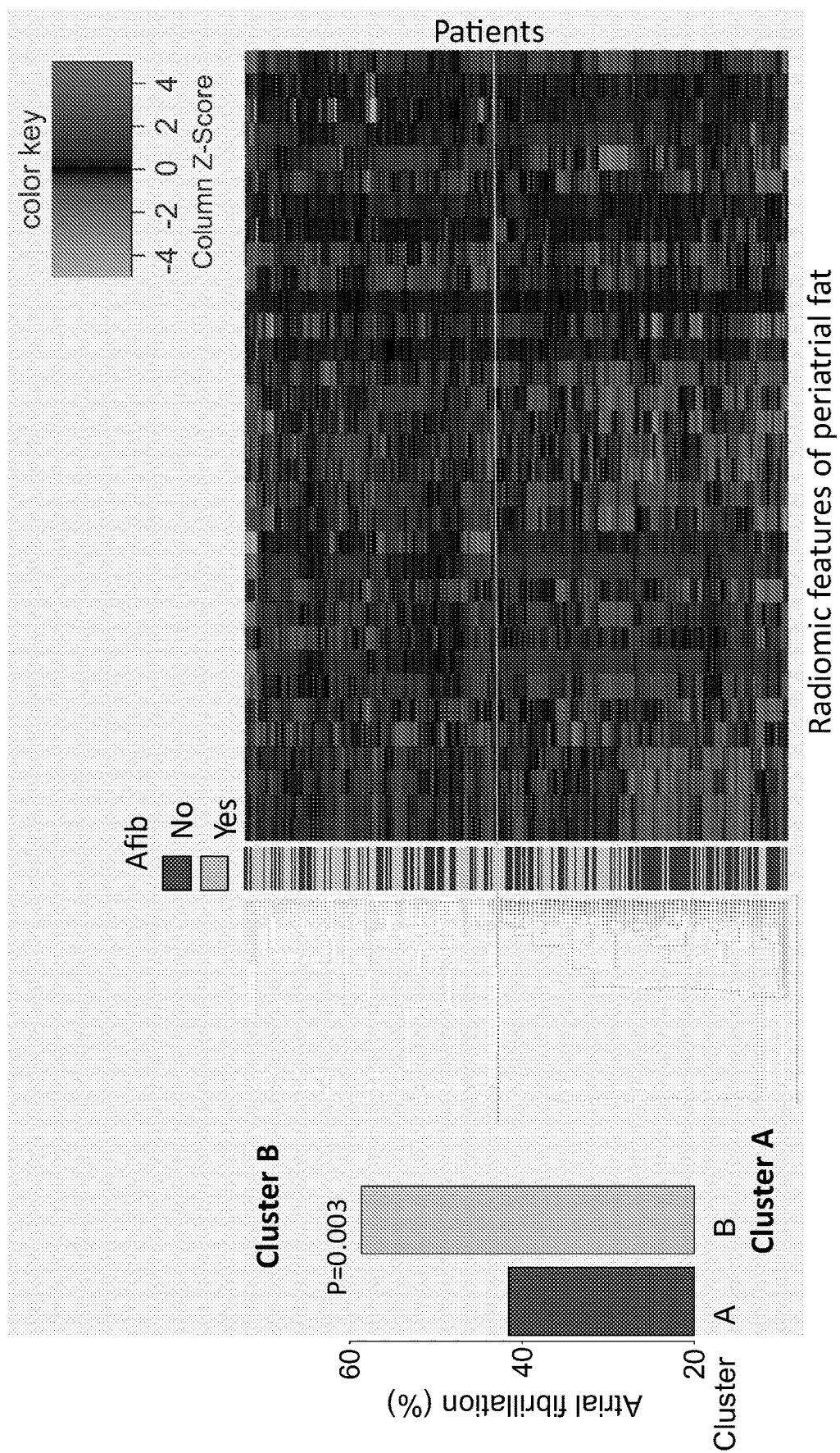
FIG. 3(a) illustrates the unsupervised hierarchical clustering of the patients (individuals) of Arm A using the 33 filtered radiomic features that are significantly associated with atrial fibrillation. Distinct radiomic features are represented on x-axis, and the individual patients (observations) on y-axis. A row dendrogram identifies the two distinct clusters of patients.
Figure 3B:
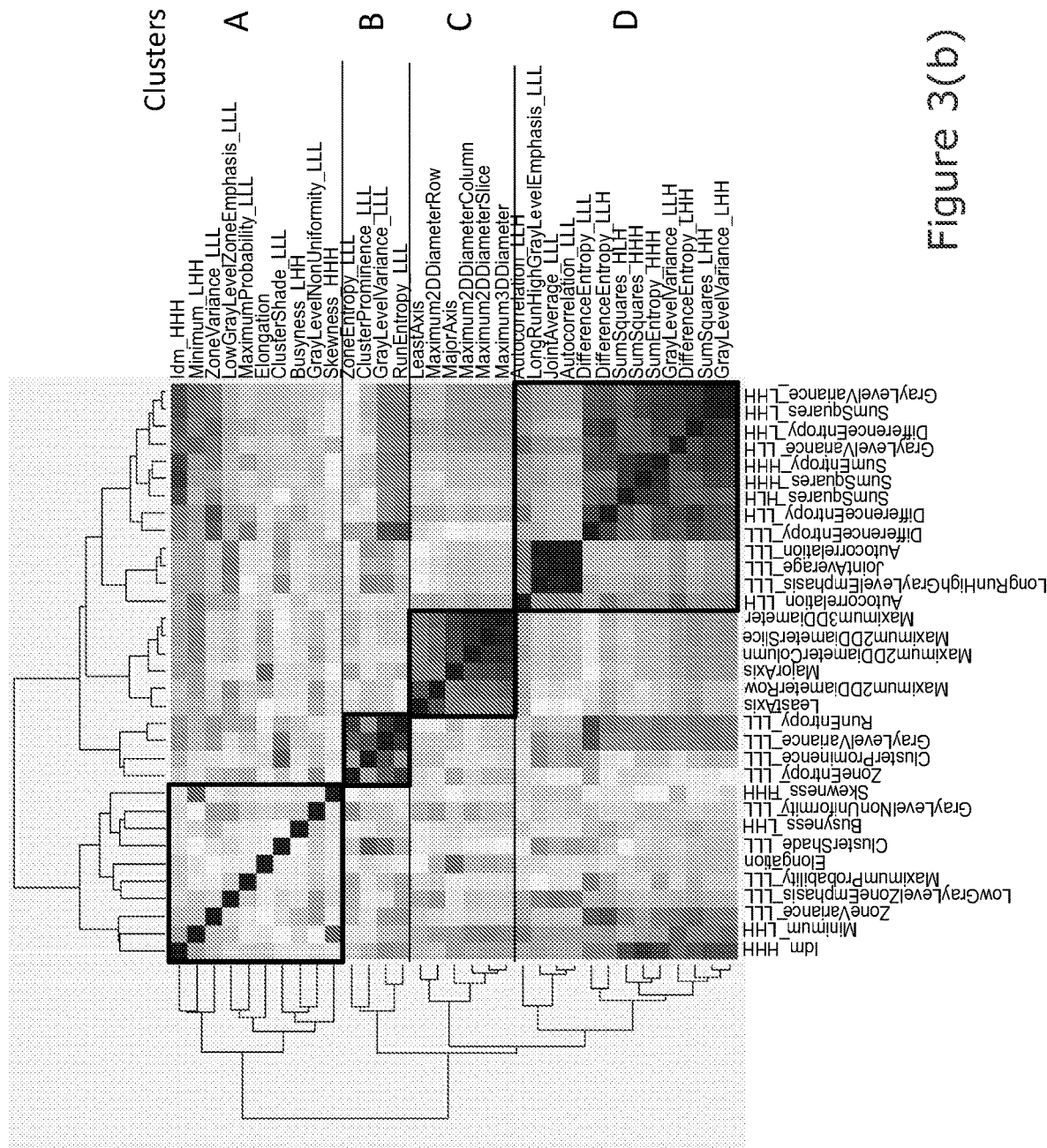
FIG. 3(b) shows a correlation heat map plotting the strength of inter-correlation between the 33 selected radiomic features and illustrates the clustering of the selected radiomic features by use of the squared euclidean distance between the selected radiomic features. The P-values are calculated from chi-square.

Four clusters (A-D) have been identified using a hierarchical clustering algorithm (see the Examples). The members of the four clusters are identified in Table 1 (and FIG. 3b). The radiomic signature may comprise at least two of the radiomic features from Table 1. Advantageously, the radiomic signature may be calculated on the basis of radiomic features selected from at least two of the clusters A-D identified in Table 1, the at least two radiomic features being selected from different clusters. Preferably, the radiomic signature may be calculated on the basis of at least one radiomic feature selected from each of the clusters A-D identified in Table 1.

TABLE 1

Radiomic feature clusters

| Radiomic feature | Cluster |
|---|---|
| Inverse Difference Moment HHH | A |
| Minimum LHH | A |
| Zone Variance LLL | A |
| Low Gray Level Zone Emphasis LLL | A |
| Maximum Probability LLL | A |
| Elongation | A |
| Cluster Shade LLL | A |
| Busyness LHH | A |
| Gray Level Non Uniformity LLL | A |
| Skewness HHH | A |
| Zone Entropy LLL | B |
| Cluster Prominence LLL | B |
| Gray Level Variance LLL (GLDM) | B |
| Run Entropy LLL | B |
| Least Axis | C |

TABLE 1-continued

Radiomic feature clusters

| Radiomic feature | Cluster |
|---|---|
| Maximum 2D Diameter Row | C |
| Major Axis | C |
| Maximum 2D Diameter Column | C |
| Maximum 2D Diameter Slice | C |
| Maximum 3D Diameter | C |
| Autocorrelation LLH | D |
| Long Run High Gray Level Emphasis LLL | D |
| Joint Average LLL | D |
| Autocorrelation LLL | D |
| Difference Entropy LLL | D |
| Difference Entropy LLH | D |
| Sum of Squares HLH | D |
| Sum of Squares HHH | D |
| Sum Entropy HHH | D |
| Gray Level Variance LLH (GLDM) | D |
| Difference Entropy LHH | D |
| Sum Squares LHH | D |
| Gray Level Variance LHH (GLDM) | D |

15 radiomic features were found to maximise the radiomic signature's association with a cardiac condition, and these are shown in Table 2. The radiomic signature may advantageously be calculated on the basis of at least two of the radiomic features from Table 2. Preferably, the radiomic signature is calculated on the basis of at least two radiomic features, each of the at least two radiomic features being selected from different clusters A-D. Further preferably, the radiomic signature may be calculated on the basis of at least one radiomic feature selected from each of the clusters A-D identified in Table 2. To maximise the radiomic signature's association with the cardiac condition the radiomic signature may be calculated on the basis of all of the 15 radiomic features listed in Table 2.

TABLE 2

Further optimised radiomic feature clusters

| Radiomic feature | Cluster |
|---|---|
| Inverse Difference Moment HHH | A |
| Minimum LHH | A |
| Low Gray Level Zone Emphasis LLL | A |
| Maximum Probability LLL | A |
| Busyness LHH | A |
| Zone Entropy LLL | B |
| Run Entropy LLL | B |
| Maximum 3D Diameter | C |
| Long Run High Gray Level Emphasis LLL | D |
| Joint Average LLL | D |
| Difference Entropy LLL | D |
| Sum Entropy HHH | D |
| Difference Entropy LHH | D |
| Sum Squares LHH | D |
| Gray Level Variance LHH (GLDM) | D |

As previously mentioned, the significant radiomic features of Tables 1 and 2 may be substituted with other radiomic features that are correlated, or collinear, with the replaced significant radiomic feature (i.e. collinear equivalents) to obtain a signature of similar diagnostic and prognostic usefulness. The radiomic signature may therefore be calculated on the basis of (i.e. comprise) at least two of the radiomic features selected from Table 3. Each of the groups identified in Table 3 includes one of the 15 significant radiomic features that have been found to maximise the association of the signature with the cardiac condition along with those radiomic features that have been calculated to be collinear with that significant feature to a degree of at least |rho|=0.75, where rho is Spearman's rho. Thus, the radiomic signature may be constructed as set out above, but with one or more of the significant radiomic features of Table 2 being replaced with a radiomic feature that is collinear with that feature, as set out in Table 3. For example, the radiomic signature may be calculated on the basis of at least two radiomic features, each of the at least two radiomic features being selected from different groups of Table 3. In particular, the radiomic signature may be calculated on the basis of at least two radiomic features that are selected from groups corresponding to significant features belonging to different clusters A-D. Further preferably, the radiomic signature may be calculated on the basis of at least one radiomic feature selected from each of the clusters A-D identified in Table 2 or collinear equivalents thereof. In other words, the radiomic signature may be calculated on the basis of at least one radiomic feature selected from each of the clusters A-D identified in Table 3 below.

TABLE 3

Groups of radiomic features collinear with significant features

| Radiomic features | \|rho\| with significant feature |
|---|---|
| Group 1 (cluster A) | |
| Inverse Difference Moment HHH | 1.000 |
| Inverse Difference Normalized HHH | 0.988 |
| Contrast HHH (GLCM) | 0.976 |
| Range HHH | 0.79 |
| Complexity HHH | 0.79 |
| Maximum HHH | 0.756 |
| Large Dependence High Gray Level Emphasis HHH | 0.752 |
| Short Run Low Gray Level Emphasis HHH | 0.744 |
| Group 2 (cluster A) | |
| Minimum LHH | 1.000 |
| Long Run Low Gray Level Emphasis LHH | 0.96 |
| Short Run High Gray Level Emphasis LHH | 0.965 |
| High Gray Level Emphasis LHH | 0.961 |
| High Gray Level Run Emphasis LHH | 0.961 |
| Small Area High Gray Level Emphasis LHH | 0.96 |
| High Gray Level Zone Emphasis LHH | 0.958 |
| Autocorrelation LHH | 0.954 |
| Joint Average LHH | 0.952 |
| Sum Average LHH | 0.952 |
| Short Run Low Gray Level Emphasis LHH | 0.944 |
| Long Run High Gray Level Emphasis LHH | 0.944 |
| Range LHH | 0.944 |
| Low Gray Level Emphasis LHH | 0.943 |
| Low Gray Level Run Emphasis LHH | 0.943 |
| Large Dependence Low Gray Level Emphasis LHH | 0.941 |
| Low Gray Level Zone Emphasis LHH | 0.94 |
| Small Area Low Gray Level Emphasis LHH | 0.932 |
| Small Dependence High Gray Level Emphasis LHH | 0.931 |
| Complexity LHH | 0.905 |
| Large Dependence High Gray Level Emphasis LHH | 0.795 |
| Cluster Prominence LHH | 0.792 |
| Gray Level Variance LHH (GLSZM) | 0.768 |
| Maximum LHH | 0.757 |
| Group 3 (cluster A) | |
| Low Gray Level Zone Emphasis LLL | 1.000 |
| Short Run Low Gray Level Emphasis LLL | 0.992 |
| Low Gray Level Run Emphasis LLL | 0.991 |
| Low Gray Level Emphasis LLL | 0.99 |
| Long Run Low Gray Level Emphasis LLL | 0.989 |
| Small Area Low Gray Level Emphasis LLL | 0.978 |
| Small Dependence Low Gray Level Emphasis LLL | 0.971 |
| Large Area Low Gray Level Emphasis LLL | 0.875 |
| Large Dependence Low Gray Level Emphasis LLL | 0.85 |
| Group 4 (cluster A) | |
| Maximum Probability LLL | 1.000 |
| Joint Energy LLL | 0.938 |
| Joint Entropy LLL | 0.932 |
| Maximum Probability | 0.904 |
| Joint Energy | 0.873 |
| Joint Entropy | 0.857 |
| Gray Level Non Uniformity Normalized | 0.818 |
| Energy LHL | 0.817 |
| Uniformity | 0.816 |
| Size Zone Non Uniformity | 0.816 |
| Sum Entropy | 0.814 |
| Gray Level Non Uniformity Normalized | 0.81 |
| Entropy | 0.81 |
| Gray Level Non Uniformity Normalized LLL | 0.806 |
| Uniformity LLL | 0.805 |
| Mean | 0.803 |
| Gray Level Non Uniformity Normalized LLL | 0.802 |
| Root Mean Squared | 0.802 |
| Interquartile Range | 0.798 |
| Sum Entropy LLL | 0.797 |
| Robust Mean Absolute Deviation | 0.795 |
| Size Zone Non Uniformity HLL | 0.794 |
| Size Zone Non Uniformity LHL | 0.793 |
| 10th Percentile | 0.792 |
| Energy HHL | 0.776 |
| Median | 0.775 |
| Dependence Non Uniformity LHL | 0.774 |
| Entropy LLL | 0.773 |
| Mean Absolute Deviation | 0.773 |
| Energy LLH | 0.765 |
| Run Entropy LLL | 0.763 |
| Interquartile Range LLL | 0.76 |
| Size Zone Non Uniformity LLH | 0.758 |
| Energy HLL | 0.755 |
| Sum of Squares | 0.754 |
| Dependence Non Uniformity HLL | 0.753 |
| Robust Mean Absolute Deviation LLL | 0.752 |
| 10th Percentile LLL | 0.751 |
| Energy LHH | 0.751 |
| Dependence Non Uniformity | 0.75 |
| Run Entropy | 0.75 |
| Group 5 (cluster A) | |
| Busyness LHH | 1.000 |
| Strength LHH | 0.988 |
| Strength HHH | 0.777 |
| Busyness HHH | 0.776 |
| Busyness LHL | 0.767 |
| Large Area Low Gray Level Emphasis LHH | 0.757 |
| Group 6 (cluster B) | |
| Zone Entropy LLL | 1.000 |
| Dependence Entropy LLL | 0.986 |
| Root Mean Squared LLL | 0.876 |
| Mean LLL | 0.869 |
| Run Entropy | 0.864 |
| Dependence Entropy | 0.864 |
| Median LLL | 0.86 |
| Median | 0.838 |
| Mean | 0.826 |
| 10th Percentile LLL | 0.825 |
| Uniformity | 0.824 |
| Gray Level Non Uniformity Normalized (GLDM) | 0.812 |
| Root Mean Squared | 0.811 |
| 90th Percentile | 0.809 |
| Entropy | 0.795 |
| 10th Percentile | 0.766 |
| Interquartile Range LLL | 0.762 |
| Run Entropy LLL | 0.76 |

TABLE 3-continued

Groups of radiomic features collinear with significant features

| Radiomic features | \|rho\| with significant feature |
|---|---|
| Robust Mean Absolute Deviation LLL | 0.753 |
| Gray Level Non Uniformity Normalized LLL (GLDM) | 0.751 |
| Uniformity LLL | 0.75 |
| Group 7 (cluster B) | |
| Run Entropy LLL | 1.000 |
| Entropy LLL | 0.996 |
| Mean Absolute Deviation LLL | 0.98 |
| Mean Absolute Deviation | 0.975 |
| Robust Mean Absolute Deviation | 0.969 |
| Robust Mean Absolute Deviation LLL | 0.969 |
| Variance | 0.966 |
| Gray Level Variance (GLDM) | 0.966 |
| Gray Level Variance LLL (GLDM) | 0.965 |
| Variance LLL | 0.965 |
| Gray Level Variance LLL (GLSZM) | 0.965 |
| Gray Level Variance (GLZM) | 0.964 |
| Interquartile Range | 0.963 |
| Interquartile Range LLL | 0.962 |
| Entropy | 0.961 |
| Gray Level Variance LLL (GLDM) | 0.959 |
| Root Mean Squared | 0.952 |
| Run Entropy | 0.941 |
| Gray Level Variance (GLDM) | 0.939 |
| Sum Entropy | 0.938 |
| Sum of Squares | 0.935 |
| Sum Entropy LLL | 0.933 |
| Sum of Squares LLL | 0.929 |
| Cluster Tendency | 0.918 |
| Cluster Tendency LLL | 0.913 |
| Joint Entropy | 0.892 |
| Root Mean Squared LLL | 0.889 |
| Contrast (GLCM) | 0.873 |
| Joint Entropy LLL | 0.839 |
| Cluster Prominence | 0.823 |
| Cluster Prominence LLL | 0.819 |
| Low Gray Level Emphasis | 0.793 |
| Short Run Low Gray Level Emphasis | 0.791 |
| Low Gray Level Run Emphasis | 0.791 |
| Long Run Low Gray Level Emphasis | 0.777 |
| Zone Entropy LLL | 0.76 |
| Low Gray Level Zone Emphasis | 0.756 |
| Uniformity LLL | 0.989 |
| Gray Level Non Uniformity Normalized LLL (GLDM) | 0.989 |
| Gray Level Non Uniformity Normalized LLL (GLSZM) | 0.988 |
| 10th Percentile | 0.973 |
| 10th Percentile LLL | 0.942 |
| Gray Level Non Uniformity Normalized (GLDM) | 0.937 |
| Gray Level Non Uniformity Normalized (GLSZM) | 0.935 |
| Mean | 0.929 |
| Uniformity | 0.923 |
| Joint Energy | 0.89 |
| Median | 0.844 |
| Joint Energy LLL | 0.843 |
| Maximum Probability | 0.812 |
| Mean LLL | 0.805 |
| Maximum Probability LLL | 0.763 |
| Group 8 (cluster C) | |
| Maximum 3D Diameter | 1.000 |
| Maximum 2D Diameter Slice | 0.946 |
| Maximum 2D Diameter Column | 0.889 |
| Major Axis | 0.801 |
| Group 9 (cluster D) | |
| Long Run High Gray Level Emphasis LLL | 1.000 |
| High Gray Level Emphasis LLL | 0.996 |
| High Gray Level Run Emphasis LLL | 0.996 |
| High Gray Level Zone Emphasis LLL | 0.996 |
| Short Run High Gray Level Emphasis LLL | 0.995 |
| Autocorrelation LLL | 0.993 |
| Joint Average LLL | 0.989 |
| Small Area High Gray Level Emphasis LLL | 0.969 |
| Small Dependence High Gray Level Emphasis LLL | 0.921 |
| Minimum LLL | 0.866 |
| Large Dependence Low Gray Level Emphasis LLL | 0.824 |
| Large Dependence High Gray Level Emphasis LLL | 0.813 |
| Large Area High Gray Level Emphasis LLL | 0.808 |
| Large Area Low Gray Level Emphasis LLL | 0.787 |
| Long Run Low Gray Level Emphasis LLL | 0.775 |
| Low Gray Level Emphasis LLL | 0.765 |
| Low Gray Level Run Emphasis LLL | 0.763 |
| Short Run Low Gray Level Emphasis LLL | 0.76 |
| Group 10 (cluster D) | |
| Joint Average LLL | 1.000 |
| Autocorrelation LLL | 0.998 |
| Long Run High Gray Level Emphasis LLL | 0.989 |
| High Gray Level Emphasis LLL | 0.985 |
| High Gray Level Run Emphasis LLL | 0.985 |
| High Gray Level Zone Emphasis LLL | 0.984 |
| Short Run High Gray Level Emphasis LLL | 0.983 |
| Small Area High Gray Level Emphasis LLL | 0.954 |
| Small Dependence High Gray Level Emphasis LLL | 0.904 |
| Minimum LLL | 0.842 |
| Large Dependence Low Gray Level Emphasis LLL | 0.834 |
| Large Dependence High Gray Level Emphasis LLL | 0.822 |
| Large Area High Gray Level Emphasis LLL | 0.816 |
| Large Area Low Gray Level Emphasis LLL | 0.797 |
| Long Run Low Gray Level Emphasis LLL | 0.796 |
| Low Gray Level Emphasis LLL | 0.787 |
| Low Gray Level Run Emphasis LLL | 0.784 |
| Short Run Low Gray Level Emphasis LLL | 0.782 |
| Low Gray Level Zone Emphasis LLL | 0.75 |
| Group 11 (cluster D) | |
| Difference Entropy LLL | 1.000 |
| Difference Average LLL | 0.995 |
| Contrast LLL (NGTDM) | 0.986 |
| Difference Entropy | 0.977 |
| Inverse Difference LLL | 0.974 |
| Contrast (GLCM) | 0.972 |
| Difference Variance | 0.97 |
| Inverse Difference Moment LLL | 0.965 |
| Difference Average | 0.964 |
| Inverse Variance LLL | 0.962 |
| Inverse Variance | 0.956 |
| Difference Variance LLL | 0.946 |
| Inverse Difference | 0.944 |
| Inverse Difference Moment | 0.943 |
| Inverse Difference Moment Normalized | 0.932 |
| Inverse Difference Normalized | 0.925 |
| Contrast (GNGTDM) | 0.915 |
| Joint Entropy | 0.896 |
| Sum Entropy LHL | 0.884 |
| Joint Energy LHL | 0.87 |
| Run Entropy LHL | 0.869 |
| Size Zone Non Uniformity Normalized LLL | 0.869 |
| Small Area Emphasis LLL | 0.869 |
| Short Run Emphasis | 0.868 |
| Size Zone Non Uniformity Normalized | 0.868 |
| Small Area Emphasis | 0.868 |
| Gray Level Non Uniformity Normalized LHL (GLSZM) | 0.867 |
| Joint Entropy LHL | 0.867 |
| Short Run Emphasis LLL | 0.867 |
| Small Dependence Emphasis LLL | 0.867 |
| Dependence Non Uniformity Normalized LLL | 0.866 |
| Gray Level Non Uniformity Normalized LHL (GLDM) | 0.866 |
| Small Dependence Emphasis | 0.866 |
| Entropy LHL | 0.865 |
| Long Run Emphasis LLL | 0.865 |
| Mean Absolute Deviation LHL | 0.865 |
| Robust Mean Absolute Deviation LHL | 0.865 |
| Uniformity LHL | 0.865 |
| Interquartile Range LHL | 0.864 |
| Joint Energy | 0.864 |
| Run Length Non Uniformity Normalized LLL | 0.864 |
| Run Percentage LLL | 0.864 |

TABLE 3-continued

Groups of radiomic features collinear with significant features

| Radiomic features | \|rho\| with significant feature |
|---|---|
| Zone Percentage LLL | 0.863 |
| Long Run Emphasis | 0.862 |
| Sum of Squares LHL | 0.862 |
| Complexity LLL | 0.86 |
| Run Length Non Uniformity Normalized | 0.86 |
| Run Percentage | 0.86 |
| Zone Percentage | 0.86 |
| Cluster Tendency LHL | 0.858 |
| Run Variance LLL | 0.858 |
| Large Dependence Emphasis LLL | 0.857 |
| Dependence Non Uniformity Normalized | 0.856 |
| Run Variance | 0.854 |
| Gray Level Variance LHL (GLDM) | 0.853 |
| Large Area Emphasis LLL | 0.853 |
| Variance LHL | 0.853 |
| Gray Level Variance LHL (GLSZM) | 0.852 |
| Large Dependence Emphasis | 0.852 |
| Large Area Emphasis | 0.848 |
| Maximum Probability LHL | 0.848 |
| Root Mean Squared LHL | 0.845 |
| Difference Entropy LHL | 0.842 |
| Gray Level Variance LHL (GLRLM) | 0.839 |
| Zone Variance LLL | 0.838 |
| Dependence Variance LLL | 0.837 |
| Inverse Difference LHL | 0.837 |
| Inverse Difference Moment LHL | 0.836 |
| Zone Variance | 0.836 |
| Large Area High Gray Level Emphasis | 0.833 |
| 90th Percentile LHL | 0.832 |
| Sum Entropy LLH | 0.829 |
| Difference Average LHL | 0.828 |
| Sum of Squares | 0.827 |
| Dependence Entropy LHH | 0.825 |
| Contrast LHL (GLCM) | 0.824 |
| Joint Energy HLL | 0.824 |
| Difference Entropy HLL | 0.823 |
| Difference Variance LHL | 0.823 |
| Dependence Variance | 0.819 |
| Maximum Probability HLL | 0.819 |
| Complexity | 0.817 |
| Joint Entropy HLL | 0.815 |
| Joint Energy LLL | 0.811 |
| Sum Entropy LHH | 0.811 |
| Inverse Variance LHL | 0.809 |
| 90th Percentile LLH | 0.808 |
| Inverse Difference HLL | 0.806 |
| Inverse Difference Moment HLL | 0.806 |
| Difference Variance HLL | 0.805 |
| Cluster Tendency LHH | 0.804 |
| Difference Average HLL | 0.8 |
| Cluster Tendency LLH | 0.799 |
| Contrast HLL (GLCM) | 0.798 |
| Run Entropy LHH | 0.797 |
| Inverse Variance HLL | 0.796 |
| Joint Energy LLH | 0.794 |
| Joint Energy HHL | 0.793 |
| Joint Entropy LLL | 0.793 |
| Run Entropy LLH | 0.793 |
| Joint Entropy LLH | 0.791 |
| Large Dependence High Gray Level Emphasis | 0.791 |
| Maximum Probability HHL | 0.791 |
| Joint Entropy HHL | 0.789 |
| Sum Entropy HHL | 0.789 |
| Gray Level Non Uniformity Normalized HLL (GLDM) | 0.788 |
| Robust Mean Absolute Deviation LLH | 0.788 |
| Uniformity HLL | 0.788 |
| Cluster Prominence LHL | 0.787 |
| Complexity LHL | 0.786 |
| Entropy LLH | 0.786 |
| Gray Level Non Uniformity Normalized LLH (GLDM) | 0.786 |
| Mean Absolute Deviation LLH | 0.785 |
| Run Entropy HHL | 0.785 |
| Uniformity LLH | 0.785 |
| Gray Level Non Uniformity Normalized LLH (GLSZM) | 0.784 |
| Interquartile Range HLL | 0.784 |
| Interquartile Range LLH | 0.784 |
| Maximum Probability LLH | 0.784 |
| Robust Mean Absolute Deviation HLL | 0.784 |
| Gray Level Non Uniformity Normalized HHL (GLDM) | 0.783 |
| Long Run Emphasis LHL | 0.783 |
| Robust Mean Absolute Deviation HHL | 0.783 |
| Run Variance LHL | 0.783 |
| Uniformity HHL | 0.783 |
| Interquartile Range HHL | 0.781 |
| Joint Entropy LHH | 0.781 |
| Sum of Squares LLH | 0.781 |
| 10th Percentile HHL | 0.78 |
| 90th Percentile HHL | 0.78 |
| Entropy HHL | 0.78 |
| Cluster Tendency HHL | 0.779 |
| Gray Level Non Uniformity Normalized HLL (GLSZM) | 0.779 |
| Mean Absolute Deviation HHL | 0.779 |
| 10th Percentile LHL | 0.777 |
| Difference Entropy HHL | 0.777 |
| Sum of Squares HHL | 0.777 |
| Contrast LLL (GLCM) | 0.776 |
| Gray Level Variance HHL (GLDM) | 0.776 |
| Variance HHL | 0.776 |
| Entropy HLL | 0.775 |
| Gray Level Non Uniformity Normalized HHL (GLSZM) | 0.775 |
| Gray Level Variance HHL (GLSZM) | 0.775 |
| Inverse Difference HHL | 0.775 |
| Joint Energy LHH | 0.775 |
| Root Mean Squared HHL | 0.775 |
| Short Run Emphasis LHL | 0.775 |
| Sum of Squares LHH | 0.775 |
| 10th Percentile LHH | 0.774 |
| Inverse Difference Moment HHL | 0.774 |
| Mean Absolute Deviation LHH | 0.774 |
| Run Percentage LHL | 0.774 |
| Zone Percentage LHL | 0.774 |
| Dependence Non Uniformity Normalized LHL | 0.773 |
| Entropy LHH | 0.773 |
| Gray Level Non Uniformity Normalized LHH (GLSZM) | 0.773 |
| Large Dependence Emphasis LHL | 0.772 |
| Interquartile Range LHH | 0.771 |
| Maximum Probability LHH | 0.771 |
| Small Dependence Emphasis LHL | 0.771 |
| Uniformity LHH | 0.771 |
| Large Area Emphasis LHL | 0.77 |
| Robust Mean Absolute Deviation LHH | 0.77 |
| Root Mean Squared LLH | 0.77 |
| Difference Average HHL | 0.769 |
| Small Dependence Low Gray Level Emphasis | 0.769 |
| Entropy LLL | 0.767 |
| Gray Level Variance (GLDM) | 0.767 |
| Run Length Non Uniformity Normalized LHL | 0.767 |
| Variance | 0.767 |
| Zone Variance LHL | 0.767 |
| Cluster Prominence HHL | 0.766 |
| Dependence Variance LHL | 0.766 |
| Gray Level Variance LHH (GLDM) | 0.766 |
| Root Mean Squared LHH | 0.766 |
| Gray Level Variance (GLSZM) | 0.765 |
| Variance LHH | 0.765 |
| Contrast HHL (GLCM) | 0.764 |
| Dependence Entropy HHL | 0.764 |
| Size Zone Non Uniformity Normalized LHL | 0.764 |
| Small Area Emphasis LHL | 0.764 |
| Sum Entropy HHH | 0.764 |
| Difference Variance HHL | 0.762 |
| Gray Level Variance HHL (GLRLM) | 0.762 |
| Dependence Entropy LHL | 0.761 |
| Gray Level Variance LLH (GLSZM) | 0.761 |
| Run Entropy HLL | 0.761 |
| Variance LLH | 0.761 |
| 90th Percentile LHH | 0.76 |
| Mean Absolute Deviation HLL | 0.76 |

TABLE 3-continued

Groups of radiomic features collinear with significant features

| Radiomic features | \| rho \| with significant feature |
|---|---|
| Gray Level Variance LLH (GLDM) | 0.759 |
| Cluster Tendency HHH | 0.758 |
| Difference Entropy LLH | 0.757 |
| Inverse Difference Moment LLH | 0.756 |
| Gray Level Non Uniformity Normalized LHH (GLDM) | 0.755 |
| Inverse Difference LLH | 0.755 |
| Mean Absolute Deviation | 0.755 |
| 90th Percentile HLL | 0.754 |
| Group 12 (cluster D) | |
| Sum Entropy HHH | 1.000 |
| Cluster Tendency HHH | 0.984 |
| Cluster Prominence HHH | 0.972 |
| Joint Entropy HHH | 0.971 |
| Joint Energy HHH | 0.967 |
| Difference Entropy HHH | 0.961 |
| Difference Variance HHH | 0.959 |
| Sum of Squares HHH | 0.956 |
| Gray Level Non Uniformity Normalized HHH (GLSZM) | 0.946 |
| Uniformity HHH | 0.946 |
| Entropy HHH | 0.945 |
| Gray Level Variance HHH (GLDM) | 0.943 |
| Gray Level Variance HHH (GLSZM) | 0.943 |
| Root Mean Squared HHH | 0.937 |
| Variance HHH | 0.937 |
| Mean Absolute Deviation HHH | 0.932 |
| 10th Percentile HHH | 0.927 |
| Robust Mean Absolute Deviation HHH | 0.924 |
| 90th Percentile HHH | 0.923 |
| Interquartile Range HHH | 0.923 |
| Gray Level Non Uniformity Normalized HHH (GLDM) | 0.908 |
| Gray Level Variance HHH (GLRLM) | 0.905 |
| Sum Entropy LHH | 0.887 |
| Joint Entropy HHL | 0.886 |
| Difference Entropy HHL | 0.885 |
| Cluster Tendency LHH | 0.883 |
| Joint Energy HHL | 0.883 |
| Long Run Emphasis HHL | 0.882 |
| Maximum Probability HHL | 0.882 |
| Short Run Emphasis HHL | 0.882 |
| Large Area Low Gray Level Emphasis HHL | 0.881 |
| Sum Entropy HHL | 0.88 |
| Size Zone Non Uniformity Normalized HHL | 0.877 |
| Sum of Squares HHL | 0.877 |
| Difference Variance HHL | 0.876 |
| Joint Entropy LHH | 0.876 |
| Run Length Non Uniformity Normalized HHL | 0.876 |
| Cluster Tendency HHL | 0.875 |
| Contrast HHL (GLCM) | 0.875 |
| Difference Average HHL | 0.875 |
| Inverse Difference HHL | 0.875 |
| Large Dependence Emphasis HHL | 0.875 |
| Run Percentage HHL | 0.875 |
| Run Variance HHL | 0.875 |
| Small Area Emphasis HHL | 0.875 |
| Inverse Difference Moment HHL | 0.874 |
| Small Dependence Emphasis HHL | 0.873 |
| Sum of Squares LHH | 0.873 |
| Gray Level Variance LHH (GLDM) | 0.872 |
| Root Mean Squared HHL | 0.872 |
| Variance HHL | 0.872 |
| Difference Variance LHH | 0.871 |
| Entropy HHL | 0.871 |
| Gray Level Variance HHL (GLDM) | 0.871 |
| Gray Level Variance HHL (GLSZM) | 0.871 |
| Gray Level Variance LHH (GLSZM) | 0.871 |
| Mean Absolute Deviation HHL | 0.871 |
| Root Mean Squared LHH | 0.871 |
| Variance LHH | 0.871 |
| Joint Energy HLH | 0.87 |
| 90th Percentile HHL | 0.869 |
| Joint Energy LHH | 0.869 |
| Dependence Non Uniformity Normalized HHL | 0.868 |
| Entropy LHH | 0.868 |
| Gray Level Non Uniformity Normalized HHL (GLSZM) | 0.868 |
| Joint Entropy HLH | 0.868 |
| Uniformity HHL | 0.868 |
| Cluster Prominence HHL | 0.867 |
| Cluster Prominence LHH | 0.867 |
| Mean Absolute Deviation LHH | 0.867 |
| 10th Percentile HHL | 0.866 |
| Maximum Probability HLH | 0.866 |
| Robust Mean Absolute Deviation HHL | 0.866 |
| Difference Entropy LHH | 0.865 |
| Gray Level Non Uniformity Normalized LHH (GLSZM) | 0.865 |
| Maximum Probability LHH | 0.865 |
| Zone Percentage HHL | 0.865 |
| Uniformity LHH | 0.864 |
| Interquartile Range HHL | 0.863 |
| 90th Percentile LHH | 0.862 |
| Dependence Variance HHL | 0.861 |
| Robust Mean Absolute Deviation LHH | 0.861 |
| Interquartile Range LHH | 0.859 |
| Run Entropy LHH | 0.859 |
| Small Dependence High Gray Level Emphasis HHL | 0.859 |
| Sum Entropy HLH | 0.858 |
| Contrast LHH (GLCM) | 0.856 |
| 10th Percentile LHH | 0.855 |
| Gray Level Variance HHL (GLRLM) | 0.855 |
| Cluster Tendency HLH | 0.854 |
| Run Entropy HHL | 0.854 |
| Small Area Emphasis HLH | 0.854 |
| Difference Entropy HLL | 0.853 |
| Gray Level Non Uniformity Normalized HHL (GLDM) | 0.852 |
| Large Dependence Low Gray Level Emphasis HHL | 0.852 |
| Size Zone Non Uniformity Normalized HLH | 0.852 |
| Inverse Difference HLH | 0.851 |
| Long Run Emphasis HLH | 0.851 |
| Sum of Squares HLH | 0.851 |
| Run Entropy HHL | 0.849 |
| Small Area Emphasis HLL | 0.849 |
| Inverse Difference Moment HLH | 0.848 |
| Size Zone Non Uniformity Normalized HLL | 0.848 |
| Short Run Emphasis HLL | 0.847 |
| Small Dependence Emphasis HLL | 0.847 |
| Difference Variance HLL | 0.846 |
| Large Dependence Emphasis HLL | 0.846 |
| Difference Average LHH | 0.845 |
| Difference Variance HLH | 0.845 |
| Gray Level Variance HLH (GLDM) | 0.845 |
| Root Mean Squared HLH | 0.845 |
| Run Percentage HLL | 0.845 |
| Short Run Emphasis HLL | 0.845 |
| Variance HLH | 0.845 |
| Gray Level Variance HLH (GLSZM) | 0.844 |
| Long Run Emphasis HLL | 0.844 |
| Run Length Non Uniformity Normalized HLL | 0.844 |
| Zone Percentage HLL | 0.844 |
| 10th Percentile HLH | 0.843 |
| Cluster Prominence HLH | 0.843 |
| Dependence Non Uniformity Normalized HLL | 0.843 |
| Entropy HLH | 0.843 |
| Gray Level Non Uniformity Normalized LHH (GLDM) | 0.843 |
| Small Dependence Emphasis HLH | 0.843 |
| Difference Average HLH | 0.842 |
| Mean Absolute Deviation HLH | 0.842 |
| Run Variance HLH | 0.842 |
| Run Variance HLL | 0.842 |
| Robust Mean Absolute Deviation HLH | 0.841 |
| Gray Level Non Uniformity Normalized HLH (GLSZM) | 0.84 |
| Uniformity HLH | 0.84 |
| Interquartile Range HLH | 0.839 |
| Joint Entropy HLL | 0.839 |
| Inverse Difference Moment LHH | 0.838 |
| Joint Energy HLL | 0.838 |
| Large Area Emphasis HLL | 0.838 |
| Small Dependence Emphasis | 0.838 |
| Complexity HHL | 0.837 |

TABLE 3-continued

Groups of radiomic features collinear with significant features

| Radiomic features | \| rho \| with significant feature |
|---|---|
| Dependence Variance HLL | 0.837 |
| Large Area Emphasis HHL | 0.837 |
| 90th Percentile HLH | 0.836 |
| Inverse Difference LHH | 0.836 |
| Run Percentage HLH | 0.836 |
| Run Variance | 0.836 |
| Zone Percentage | 0.836 |
| Contrast HLH (GLCM) | 0.835 |
| Long Run Emphasis | 0.835 |
| Large Area Emphasis | 0.833 |
| Run Length Non Uniformity Normalized HLH | 0.833 |
| Size Zone Non Uniformity Normalized | 0.833 |
| Small Area Emphasis | 0.833 |
| Large Dependence Emphasis HLH | 0.832 |
| Dependence Non Uniformity Normalized | 0.831 |
| Large Dependence Emphasis | 0.831 |
| Run Percentage | 0.831 |
| Short Run Emphasis | 0.831 |
| Zone Percentage HLH | 0.831 |
| Zone Variance HLL | 0.831 |
| Contrast HLL (GLCM) | 0.83 |
| Large Area Low Gray Level Emphasis HLH | 0.828 |
| Zone Variance | 0.828 |
| Difference Average HLL | 0.827 |
| Gray Level Variance LHH (GLRLM) | 0.827 |
| Inverse Difference HLL | 0.827 |
| Dependence Entropy HHH | 0.826 |
| Difference Entropy | 0.826 |
| Inverse Difference Moment HLL | 0.826 |
| Joint Energy LHL | 0.826 |
| Joint Energy LLH | 0.826 |
| Run Length Non Uniformity Normalized | 0.826 |
| Zone Variance HHL | 0.826 |
| Difference Entropy LHL | 0.825 |
| Small Area High Gray Level Emphasis HHL | 0.825 |
| Maximum Probability | 0.824 |
| Gray Level Variance HLH (GLRLM) | 0.823 |
| Inverse Variance | 0.823 |
| Dependence Entropy LHH | 0.821 |
| Gray Level Non Uniformity Normalized HLH_GLSDM | 0.821 |
| Inverse Difference LHL | 0.821 |
| Inverse Difference Moment LHL | 0.821 |
| Small Dependence High Gray Level Emphasis HLH | 0.821 |
| Dependence Non Uniformity Normalized HLH | 0.82 |
| Joint Entropy LHL | 0.82 |
| Long Run Emphasis LHL | 0.819 |
| Run Variance LHL | 0.819 |
| Inverse Difference Moment LLH | 0.818 |
| Joint Entropy LLH | 0.818 |
| Large Dependence Emphasis LHL | 0.818 |
| Dependence Variance | 0.817 |
| Dependence Variance LHL | 0.817 |
| Inverse Difference LLH | 0.817 |
| Maximum Probability LHL | 0.817 |
| Difference Average | 0.816 |
| Run Entropy HLH | 0.816 |
| Dependence Non Uniformity Normalized LHL | 0.814 |
| Difference Entropy LLH | 0.814 |
| Large Area Emphasis LHL | 0.814 |
| Maximum Probability LLH | 0.814 |
| Contrast (GLCM) | 0.813 |
| Run Percentage LHL | 0.813 |
| Short Run Emphasis LHL | 0.813 |
| Short Run High Gray Level Emphasis HHL | 0.813 |
| Sum Entropy LLH | 0.813 |
| Long Run Low Gray Level Emphasis HHL | 0.812 |
| Short Run Emphasis LHH | 0.812 |
| Small Dependence Emphasis LHH | 0.812 |
| Zone Percentage LHL | 0.812 |
| Zone Variance LHL | 0.812 |
| Inverse Difference | 0.811 |
| Inverse Difference Moment | 0.811 |
| Small Dependence Emphasis LHL | 0.811 |
| Zone Percentage LHH | 0.811 |
| Inverse Variance HLL | 0.81 |
| Large Dependence Low Gray Level Emphasis HLH | 0.81 |
| Difference Average LHL | 0.809 |
| Small Area High Gray Level Emphasis HHH | 0.809 |
| Run Variance LLH | 0.808 |
| Difference Variance LHL | 0.807 |
| Large Area Low Gray Level Emphasis HLL | 0.807 |
| Run Length Non Uniformity Normalized LHL | 0.807 |
| Contrast LHL (GLCM) | 0.805 |
| Dependence Variance HLH | 0.805 |
| Inverse Difference Normalized | 0.805 |
| Maximum LLL | 0.805 |
| Run Length Non Uniformity Normalized LHH | 0.805 |
| Inverse Difference Moment Normalized | 0.804 |
| Long Run Emphasis LLH | 0.804 |
| Size Zone Non Uniformity HHH | 0.802 |
| Size Zone Non Uniformity Normalized LHL | 0.802 |
| Small Area Emphasis LHL | 0.802 |
| Interquartile Range LHL | 0.801 |
| Gray Level Non Uniformity Normalized LHL (GLSZM) | 0.8 |
| Run Percentage LHH | 0.8 |
| Small Area High Gray Level Emphasis HLH | 0.8 |
| Uniformity LHL | 0.8 |
| Difference Average LLH | 0.799 |
| Difference Variance | 0.799 |
| Large Area High Gray Level Emphasis | 0.799 |
| Long Run Emphasis LHH | 0.799 |
| Small Dependence High Gray Level Emphasis HHH | 0.799 |
| High Gray Level Run Emphasis HHL | 0.798 |
| Range HHL | 0.798 |
| Robust Mean Absolute Deviation LHL | 0.798 |
| High Gray Level Emphasis HHL | 0.797 |
| Inverse Variance LHL | 0.797 |
| Inverse Variance LLH | 0.797 |
| Uniformity HLL | 0.797 |
| Gray Level Non Uniformity Normalized HLL_GLSDM | 0.796 |
| Large Dependence Emphasis LLH | 0.796 |
| Entropy LHL | 0.795 |
| Sum of Squares LLH | 0.795 |
| Interquartile Range HLL | 0.794 |
| Interquartile Range LLH | 0.794 |
| Robust Mean Absolute Deviation HLL | 0.794 |
| Sum Entropy LHL | 0.794 |
| 90th Percentile LLH | 0.793 |
| Complexity | 0.792 |
| Dependence Non Uniformity Normalized LLH | 0.792 |
| Gray Level Non Uniformity Normalized LHL (GLDM) | 0.792 |
| Robust Mean Absolute Deviation LLH | 0.792 |
| Run Percentage LLH | 0.792 |
| Small Dependence Emphasis LLH | 0.792 |
| Entropy HLL | 0.791 |
| High Gray Level Zone Emphasis HHL | 0.791 |
| Short Run Emphasis LLH | 0.791 |
| Uniformity LLH | 0.791 |
| Zone Percentage LLH | 0.791 |
| Dependence Variance LLH | 0.79 |
| Gray Level Non Uniformity Normalized LLH (GLSZM) | 0.79 |
| Mean Absolute Deviation LHL | 0.79 |
| Sum of Squares LHL | 0.79 |
| Contrast LLH (GLCM) | 0.789 |
| Large Area Low Gray Level Emphasis LHH | 0.789 |
| Entropy LLH | 0.788 |
| Cluster Tendency LLH | 0.787 |
| Mean Absolute Deviation LLH | 0.787 |
| Size Zone Non Uniformity Normalized LLH | 0.787 |
| Small Area Emphasis LLH | 0.787 |
| Complexity HLH | 0.786 |
| High Gray Level Run Emphasis HHH | 0.786 |
| Large Area Emphasis LLH | 0.786 |
| Large Dependence Emphasis LHH | 0.786 |
| Difference Variance LLH | 0.785 |
| Informational Measure of Correlation 1 | 0.785 |
| Large Area Low Gray Level Emphasis LHL | 0.784 |
| Run Length Non Uniformity Normalized LLH | 0.784 |

TABLE 3-continued

Groups of radiomic features collinear with significant features

| Radiomic features | \| rho \| with significant feature |
|---|---|
| Run Variance LHH | 0.784 |
| Complexity HLL | 0.783 |
| Large Dependence Emphasis LLL | 0.783 |
| Dependence Non Uniformity Normalized LLL | 0.782 |
| Short Run High Gray Level Emphasis HLH | 0.782 |
| Run Entropy LHL | 0.781 |
| Small Dependence Emphasis LLL | 0.781 |
| Dependence Variance LLL | 0.78 |
| Gray Level Non Uniformity Normalized HLL (GLDM) | 0.78 |
| Gray Level Non Uniformity Normalized LLH (GLDM) | 0.78 |
| Gray Level Variance LHL (GLDM) | 0.78 |
| High Gray Level Zone Emphasis HHH | 0.78 |
| Large Area Emphasis HLH | 0.78 |
| Large Area Emphasis LLL | 0.78 |
| Long Run Emphasis LLL | 0.78 |
| Mean Absolute Deviation HLL | 0.78 |
| Run Percentage LLL | 0.78 |
| Short Run Emphasis LLL | 0.78 |
| Zone Percentage LLL | 0.78 |
| Zone Variance LLH | 0.78 |
| Run Length Non Uniformity Normalized LLL | 0.779 |
| Variance LHL | 0.779 |
| Complexity LHL | 0.778 |
| Gray Level Variance LHL (GLSZM) | 0.778 |
| Long Run Low Gray Level Emphasis HLH | 0.778 |
| Run Variance LLL | 0.778 |
| Zone Variance LLL | 0.777 |
| Range HHH | 0.776 |
| Small Area Emphasis LLL | 0.776 |
| Sum of Squares HLL | 0.776 |
| Variance HLL | 0.776 |
| Gray Level Variance HLL (GLSZM) | 0.775 |
| Gray Level Variance HLL (GLDM) | 0.775 |
| Inverse Difference Moment LLL | 0.775 |
| Size Zone Non Uniformity Normalized HHH | 0.775 |
| Size Zone Non Uniformity Normalized LLL | 0.775 |
| Small Dependence High Gray Level Emphasis LHH | 0.775 |
| Inverse Difference LLL | 0.774 |
| Minimum HHH | 0.773 |
| Minimum HHL | 0.773 |
| Run Entropy LLH | 0.773 |
| Small Area Emphasis HHH | 0.773 |
| 10th Percentile HLL | 0.771 |
| Inverse Variance LLL | 0.771 |
| High Gray Level Emphasis HHH | 0.769 |
| Root Mean Squared LLH | 0.769 |
| Small Dependence High Gray Level Emphasis HLL | 0.769 |
| Gray Level Variance LHL (GLRLM) | 0.768 |
| Gray Level Variance LLH (GLDM) | 0.768 |
| Autocorrelation HHL | 0.767 |
| Variance LLH | 0.767 |
| 10th Percentile LHL | 0.766 |
| Maximum HHL | 0.766 |
| Short Run High Gray Level Emphasis HHH | 0.766 |
| Gray Level Variance LLH (GLSZM) | 0.765 |
| Sum Entropy HLL | 0.765 |
| Difference Entropy LLL | 0.764 |
| Cluster Tendency LHL | 0.763 |
| Zone Variance HLH | 0.763 |
| Difference Average LLL | 0.762 |
| Large Dependence Low Gray Level Emphasis LHL | 0.762 |
| Root Mean Squared HLL | 0.762 |
| Complexity LHH | 0.761 |
| High Gray Level Emphasis HLH | 0.761 |
| Large Dependence Low Gray Level Emphasis HLL | 0.761 |
| High Gray Level Run Emphasis HLH | 0.76 |
| Root Mean Squared LHL | 0.76 |
| Small Dependence High Gray Level Emphasis LHL | 0.76 |
| Dependence Entropy HHL | 0.756 |
| Run Entropy HLL | 0.756 |
| Large Dependence Low Gray Level Emphasis LHH | 0.755 |
| Size Zone Non Uniformity HHL | 0.755 |
| Cluster Tendency HLL | 0.753 |
| Maximum Probability HHH | 0.753 |
| Group 13 (cluster D) | |
| Difference Entropy LHH | 1.000 |
| Contrast LHH (GLCM) | 0.997 |
| Difference Average LHH | 0.996 |
| Joint Entropy LHH | 0.996 |
| Difference Variance LHH | 0.993 |
| Sum of Squares LHH | 0.993 |
| Entropy LHH | 0.988 |
| Mean Absolute Deviation LHH | 0.987 |
| Gray Level Variance LHH (GLDM) | 0.985 |
| Robust Mean Absolute Deviation LHH | 0.985 |
| Root Mean Squared LHH | 0.985 |
| Sum Entropy LHH | 0.985 |
| Variance LHH | 0.985 |
| Gray Level Variance LHH (GLSZM) | 0.984 |
| Interquartile Range LHH | 0.983 |
| Cluster Tendency LHH | 0.982 |
| 90th Percentile LHH | 0.981 |
| Run Entropy LHH | 0.972 |
| Short Run Emphasis LHH | 0.944 |
| Run Length Non Uniformity Normalized LHH | 0.936 |
| Cluster Prominence LHH | 0.934 |
| Small Dependence Emphasis LHH | 0.933 |
| Run Percentage LHH | 0.932 |
| Interquartile Range HHH | 0.93 |
| Robust Mean Absolute Deviation HHH | 0.929 |
| 90th Percentile HHH | 0.928 |
| Mean Absolute Deviation HHH | 0.927 |
| Gray Level Variance LHH (GLRLM) | 0.926 |
| Root Mean Squared HHH | 0.921 |
| Variance HHH | 0.921 |
| Zone Percentage LHH | 0.913 |
| Joint Entropy HHH | 0.91 |
| Dependence Entropy LHH | 0.906 |
| Difference Entropy HHH | 0.906 |
| Sum of Squares HHH | 0.902 |
| Entropy HHH | 0.9 |
| Difference Variance HHH | 0.896 |
| Gray Level Variance HHH (GLSZM) | 0.893 |
| Gray Level Variance HHH (GLDM) | 0.893 |
| Difference Entropy LLH | 0.871 |
| Difference Entropy LHL | 0.868 |
| Sum Entropy HHH | 0.865 |
| Gray Level Variance HHH (GLRLM) | 0.864 |
| Cluster Prominence HHH | 0.861 |
| Difference Average LLH | 0.86 |
| Run Percentage LHL | 0.859 |
| Difference Average LHL | 0.857 |
| Short Run Emphasis LHL | 0.857 |
| Dependence Non Uniformity Normalized LHL | 0.856 |
| Small Dependence Emphasis LHL | 0.856 |
| Zone Percentage LHL | 0.855 |
| Joint Entropy LLH | 0.854 |
| Size Zone Non Uniformity Normalized LHH | 0.854 |
| Size Zone Non Uniformity Normalized LHL | 0.853 |
| Small Area Emphasis LHL | 0.853 |
| Contrast LHL (GLCM) | 0.851 |
| Run Length Non Uniformity Normalized LHL | 0.85 |
| Contrast LLH (GLCM) | 0.849 |
| Difference Variance LHL | 0.848 |
| Run Percentage LLH | 0.845 |
| Short Run Emphasis LLH | 0.843 |
| Small Area Emphasis LHH | 0.843 |
| Joint Entropy LHL | 0.842 |
| Dependence Non Uniformity Normalized LLH | 0.841 |
| Small Area Emphasis LLH | 0.841 |
| Small Dependence Emphasis LLH | 0.841 |
| Size Zone Non Uniformity Normalized LLH | 0.84 |
| Difference Variance LLH | 0.839 |
| Zone Percentage LLH | 0.838 |
| Small Dependence High Gray Level Emphasis LHH | 0.837 |
| Interquartile Range LLH | 0.836 |
| Robust Mean Absolute Deviation LLH | 0.835 |

TABLE 3-continued

Groups of radiomic features collinear with significant features

| Radiomic features | \| rho \| with significant feature |
|---|---|
| Run Length Non Uniformity Normalized LLH | 0.835 |
| Complexity LHH | 0.833 |
| Small Dependence Emphasis | 0.833 |
| Run Percentage | 0.832 |
| Sum of Squares LLH | 0.832 |
| Zone Percentage | 0.832 |
| Entropy LLH | 0.831 |
| Mean Absolute Deviation LLH | 0.831 |
| Short Run Emphasis | 0.83 |
| Dependence Non Uniformity Normalized | 0.828 |
| Sum Entropy LLH | 0.826 |
| Run Length Non Uniformity Normalized | 0.825 |
| Size Zone Non Uniformity Normalized | 0.825 |
| Small Area Emphasis | 0.825 |
| Interquartile Range LHL | 0.822 |
| Robust Mean Absolute Deviation LHL | 0.821 |
| Difference Entropy | 0.82 |
| Short Run Emphasis HHL | 0.819 |
| Small Area Emphasis HHL | 0.818 |
| Size Zone Non Uniformity Normalized HHL | 0.817 |
| Entropy LHL | 0.816 |
| Size Zone Non Uniformity HHH | 0.815 |
| Difference Average | 0.814 |
| Run Entropy LLH | 0.813 |
| Run Length Non Uniformity Normalized HHL | 0.813 |
| Run Percentage HHL | 0.813 |
| Cluster Tendency HHH | 0.811 |
| 90th Percentile LLH | 0.81 |
| Gray Level Variance LLH (GLDM) | 0.81 |
| Small Area Emphasis HHH | 0.81 |
| Variance LLH | 0.81 |
| Mean Absolute Deviation LHL | 0.809 |
| Small Dependence Emphasis HHL | 0.809 |
| Contrast (GLCM) | 0.808 |
| Small Area Emphasis HLH | 0.808 |
| Cluster Tendency LLH | 0.807 |
| Gray Level Variance LLH (GLSZM) | 0.807 |
| Sum of Squares LHL | 0.807 |
| Dependence Non Uniformity Normalized HHL | 0.805 |
| Root Mean Squared LLH | 0.805 |
| Size Zone Non Uniformity Normalized HHH | 0.805 |
| Size Zone Non Uniformity Normalized HLH | 0.805 |
| Complexity LHL | 0.802 |
| Difference Entropy HHL | 0.801 |
| Informational Measure of Correlation 1 | 0.801 |
| Total Energy LHH | 0.801 |
| Run Entropy LHL | 0.8 |
| Zone Percentage HHL | 0.799 |
| Difference Average HHL | 0.798 |
| Sum Entropy LHL | 0.796 |
| Gray Level Variance LHL (GLDM) | 0.795 |
| Variance LHL | 0.795 |
| Gray Level Variance LHL (GLSZM) | 0.794 |
| Contrast HHL (GLCM) | 0.791 |
| Difference Variance | 0.789 |
| Difference Variance HHL | 0.787 |
| Short Run Emphasis HLH | 0.787 |
| Joint Entropy HHL | 0.786 |
| Small Area High Gray Level Emphasis HHH | 0.785 |
| Small Dependence High Gray Level Emphasis LHL | 0.785 |
| Difference Entropy HLH | 0.784 |
| Small Dependence Emphasis HLH | 0.784 |
| Gray Level Variance LLH (GLRLM) | 0.783 |
| Dependence Non Uniformity Normalized LLL | 0.78 |
| Gray Level Variance LHL (GLRLM) | 0.78 |
| Interquartile Range HHL | 0.779 |
| Run Percentage LLL | 0.779 |
| Zone Percentage LLL | 0.779 |
| Robust Mean Absolute Deviation HHL | 0.778 |
| Short Run Emphasis LLL | 0.778 |
| Size Zone Non Uniformity LHH | 0.778 |
| Small Dependence Emphasis LLL | 0.778 |
| Run Length Non Uniformity Normalized LLL | 0.777 |
| Complexity | 0.775 |
| Run Percentage HLH | 0.775 |
| Contrast HHH (GLCM) | 0.774 |
| Maximum LHH | 0.774 |
| Mean Absolute Deviation HHL | 0.774 |
| Entropy HHL | 0.773 |
| Size Zone Non Uniformity Normalized LLL | 0.773 |
| Small Area Emphasis LLL | 0.773 |
| Difference Average HLH | 0.772 |
| Sum of Squares HHL | 0.772 |
| 90th Percentile HHL | 0.771 |
| Root Mean Squared HHL | 0.771 |
| Run Length Non Uniformity Normalized HLH | 0.771 |
| Variance HHL | 0.771 |
| Gray Level Variance HHL (GLSZM) | 0.77 |
| Gray Level Variance HHL (GLDM) | 0.769 |
| Root Mean Squared LHL | 0.767 |
| Joint Entropy HLH | 0.766 |
| Run Entropy HHH | 0.765 |
| Zone Percentage HLH | 0.765 |
| Total Energy HHH | 0.763 |
| Cluster Tendency LHL | 0.762 |
| Sum Entropy HHL | 0.762 |
| Energy LHH | 0.761 |
| Contrast HLH (GLCM) | 0.759 |
| Difference Variance HLH | 0.759 |
| Dependence Non Uniformity Normalized LHH | 0.758 |
| Small Dependence High Gray Level Emphasis HHL | 0.758 |
| Cluster Tendency HHL | 0.757 |
| Short Run High Gray Level Emphasis LHH | 0.757 |
| Dependence Non Uniformity Normalized HLH | 0.756 |
| Robust Mean Absolute Deviation HLH | 0.752 |
| Small Area High Gray Level Emphasis LHL | 0.752 |
| Interquartile Range HLH | 0.751 |
| Range LHH | 0.751 |
| Small Dependence High Gray Level Emphasis HHH | 0.75 |
| Group 14 (cluster D) | |
| Sum of Squares LHH | 1.000 |
| Cluster Tendency LHH | 0.996 |
| Entropy LHH | 0.996 |
| Gray Level Variance LHH (GLDM) | 0.996 |
| Joint Entropy LHH | 0.996 |
| Gray Level Variance LHH (GLSZM) | 0.995 |
| Mean Absolute Deviation LHH | 0.995 |
| Root Mean Squared LHH | 0.995 |
| Variance LHH | 0.995 |
| Contrast LHH (GLCM) | 0.994 |
| Difference Entropy LHH | 0.993 |
| Difference Variance LHH | 0.992 |
| Sum Entropy LHH | 0.992 |
| Difference Average LHH | 0.99 |
| Robust Mean Absolute Deviation LHH | 0.99 |
| Interquartile Range LHH | 0.989 |
| 90th Percentile LHH | 0.988 |
| Run Entropy LHH | 0.982 |
| Cluster Prominence LHH | 0.956 |
| Short Run Emphasis LHH | 0.947 |
| Small Dependence Emphasis LHH | 0.939 |
| Run Length Non Uniformity Normalized LHH | 0.938 |
| Run Percentage LHH | 0.935 |
| Gray Level Variance LHH (GLRLM) | 0.929 |
| Interquartile Range HHH | 0.929 |
| Robust Mean Absolute Deviation HHH | 0.928 |
| 90th Percentile HHH | 0.927 |
| Dependence Entropy LHH | 0.927 |
| Mean Absolute Deviation HHH | 0.927 |
| Zone Percentage LHH | 0.926 |
| Root Mean Squared HHH | 0.923 |
| Variance HHH | 0.923 |
| Joint Entropy HHH | 0.908 |
| Entropy HHH | 0.904 |
| Difference Entropy HHH | 0.903 |
| Sum of Squares HHH | 0.902 |
| Gray Level Variance HHH (GLSZM) | 0.899 |

TABLE 3-continued

Groups of radiomic features collinear with significant features

| Radiomic features | \| rho \| with significant feature |
|---|---|
| Gray Level Variance HHH (GLDM) | 0.899 |
| Difference Variance HHH | 0.895 |
| Run Percentage LHL | 0.885 |
| Difference Entropy LHL | 0.884 |
| Dependence Non Uniformity Normalized LHL | 0.883 |
| Short Run Emphasis LHL | 0.883 |
| Small Dependence Emphasis LHL | 0.883 |
| Zone Percentage LHL | 0.883 |
| Difference Entropy LLH | 0.88 |
| Size Zone Non Uniformity Normalized LHL | 0.88 |
| Small Area Emphasis LHL | 0.88 |
| Difference Average LHL | 0.879 |
| Run Length Non Uniformity Normalized LHL | 0.876 |
| Difference Average LLH | 0.874 |
| Sum Entropy HHH | 0.873 |
| Contrast LHL (GLCM) | 0.872 |
| Cluster Prominence HHH | 0.869 |
| Difference Variance LHL | 0.867 |
| Run Percentage LLH | 0.866 |
| Small Area Emphasis LLH | 0.866 |
| Small Dependence Emphasis | 0.866 |
| Short Run Emphasis LLH | 0.865 |
| Size Zone Non Uniformity Normalized LLH | 0.865 |
| Small Dependence Emphasis LLH | 0.865 |
| Zone Percentage | 0.865 |
| Contrast LLH (GLCM) | 0.864 |
| Dependence Non Uniformity Normalized LLH | 0.864 |
| Joint Entropy LLH | 0.863 |
| Run Percentage | 0.862 |
| Zone Percentage LLH | 0.862 |
| Short Run Emphasis | 0.861 |
| Dependence Non Uniformity Normalized | 0.859 |
| Gray Level Variance HHH (GLRLM) | 0.859 |
| Joint Entropy LHL | 0.859 |
| Mean Absolute Deviation LLH | 0.859 |
| Robust Mean Absolute Deviation LLH | 0.859 |
| Size Zone Non Uniformity Normalized | 0.859 |
| Small Area Emphasis | 0.859 |
| Interquartile Range LLH | 0.858 |
| Entropy LLH | 0.857 |
| Run Length Non Uniformity Normalized LLH | 0.856 |
| Run Length Non Uniformity Normalized | 0.855 |
| Sum of Squares LLH | 0.855 |
| Difference Variance LLH | 0.854 |
| Small Dependence High Gray Level Emphasis LHH | 0.853 |
| Interquartile Range LHL | 0.848 |
| Robust Mean Absolute Deviation LHL | 0.847 |
| Complexity LHH | 0.843 |
| Difference Entropy | 0.843 |
| Entropy LHL | 0.842 |
| Gray Level Variance LLH (GLDM) | 0.842 |
| Sum Entropy LLH | 0.842 |
| Variance LLH | 0.842 |
| Difference Average | 0.841 |
| Short Run Emphasis HHL | 0.841 |
| Run Entropy LLH | 0.84 |
| Small Area Emphasis HHL | 0.84 |
| Gray Level Variance LLH (GLSZM) | 0.839 |
| Size Zone Non Uniformity Normalized HHL | 0.839 |
| Root Mean Squared LLH | 0.838 |
| 90th Percentile LLH | 0.836 |
| Contrast (GLCM) | 0.836 |
| Mean Absolute Deviation LHL | 0.835 |
| Run Percentage HHL | 0.835 |
| Cluster Tendency LLH | 0.834 |
| Run Length Non Uniformity Normalized HHL | 0.833 |
| Small Dependence Emphasis HHL | 0.833 |
| Size Zone Non Uniformity Normalized LHH | 0.832 |
| Sum of Squares LHL | 0.831 |
| Small Area Emphasis HLH | 0.828 |
| Dependence Non Uniformity Normalized HHL | 0.827 |
| Cluster Tendency HHH | 0.826 |
| Run Entropy LHL | 0.825 |
| Size Zone Non Uniformity Normalized HLH | 0.825 |
| Zone Percentage HHL | 0.825 |
| Complexity LHL | 0.823 |
| Gray Level Variance LHL (GLSZM) | 0.822 |
| Variance LHL | 0.822 |
| Gray Level Variance LHL (GLDM) | 0.82 |
| Small Area Emphasis LHH | 0.819 |
| Sum Entropy LHL | 0.817 |
| Difference Entropy HHL | 0.816 |
| Difference Variance | 0.816 |
| Dependence Non Uniformity Normalized LLL | 0.815 |
| Difference Average HHL | 0.815 |
| Gray Level Variance LLH (GLRLM) | 0.815 |
| Zone Percentage LLL | 0.815 |
| Run Percentage LLL | 0.814 |
| Size Zone Non Uniformity HHH | 0.814 |
| Small Dependence Emphasis LLL | 0.814 |
| Short Run Emphasis LLL | 0.813 |
| Run Length Non Uniformity Normalized LLL | 0.811 |
| Informational Measure of Correlation 1 | 0.808 |
| Size Zone Non Uniformity Normalized LLL | 0.808 |
| Small Area Emphasis LLL | 0.808 |
| Complexity | 0.807 |
| Contrast HHL (GLCM) | 0.807 |
| Small Dependence High Gray Level Emphasis LHL | 0.807 |
| Short Run Emphasis HLH | 0.806 |
| Small Dependence Emphasis HLH | 0.806 |
| Gray Level Variance LHL (GLRLM) | 0.805 |
| Joint Entropy HHL | 0.802 |
| Difference Variance HHL | 0.801 |
| Interquartile Range HHL | 0.801 |
| Robust Mean Absolute Deviation HHL | 0.8 |
| Small Area Emphasis HHH | 0.798 |
| Mean Absolute Deviation HHL | 0.795 |
| Root Mean Squared LHL | 0.795 |
| Run Percentage HLH | 0.795 |
| Size Zone Non Uniformity Normalized HHH | 0.795 |
| Entropy HHL | 0.794 |
| 90th Percentile HHL | 0.792 |
| Root Mean Squared HHL | 0.792 |
| Total Energy LHH | 0.792 |
| Variance HHL | 0.792 |
| Difference Entropy HLH | 0.791 |
| Gray Level Variance HHL (GLSZM) | 0.791 |
| Sum of Squares HHL | 0.79 |
| Gray Level Variance HHL (GLDM) | 0.789 |
| Run Length Non Uniformity Normalized HLH | 0.788 |
| Zone Percentage HLH | 0.788 |
| Cluster Tendency LHL | 0.787 |
| Difference Average HLH | 0.787 |
| Small Area High Gray Level Emphasis HHH | 0.787 |
| Maximum LHH | 0.784 |
| Difference Average LLL | 0.781 |
| Sum Entropy HHL | 0.779 |
| Small Dependence High Gray Level Emphasis HHL | 0.777 |
| Cluster Tendency HHL | 0.776 |
| Dependence Non Uniformity Normalized HLH | 0.775 |
| Difference Entropy LLL | 0.775 |
| Joint Entropy HLH | 0.774 |
| Short Run High Gray Level Emphasis LHH | 0.774 |
| Contrast HLH (GLCM) | 0.773 |
| Run Entropy HHH | 0.772 |
| Size Zone Non Uniformity LHH | 0.772 |
| Small Area High Gray Level Emphasis LHL | 0.772 |
| Robust Mean Absolute Deviation HLH | 0.769 |
| Interquartile Range HLH | 0.768 |
| Difference Variance HLH | 0.767 |
| Range LHH | 0.767 |
| Mean Absolute Deviation HLH | 0.765 |
| Run Entropy HHL | 0.765 |
| Cluster Prominence HHL | 0.764 |
| Gray Level Variance HLH (GLDM) | 0.764 |
| Entropy HLH | 0.763 |
| Root Mean Squared HLH | 0.763 |
| Small Dependence High Gray Level Emphasis HHH | 0.763 |

TABLE 3-continued

Groups of radiomic features collinear with significant features

| Radiomic features | \| rho \| with significant feature |
|---|---|
| Variance HLH | 0.763 |
| Gray Level Variance HHL (GLRLM) | 0.762 |
| Gray Level Variance HLH (GLSZM) | 0.761 |
| Energy LHH | 0.76 |
| Small Area High Gray Level Emphasis LHH | 0.759 |
| Complexity HHL | 0.758 |
| Contrast HHH (GLCM) | 0.758 |
| 90th Percentile HLH | 0.757 |
| Sum of Squares HLH | 0.756 |
| Run Percentage HLL | 0.752 |
| Size Zone Non Uniformity HHL | 0.752 |
| Complexity LLH | 0.751 |
| Dependence Non Uniformity Normalized HLL | 0.751 |
| Small Dependence Emphasis HLL | 0.751 |
| 90th Percentile LHL | 0.75 |
| Dependence Non Uniformity Normalized LHH | 0.75 |
| Zone Percentage HLL | 0.75 |
| Group 15 (cluster D) | |
| Gray Level Variance LHH (GLDM) | 1.000 |
| Root Mean Squared LHH | 0.999 |
| Variance LHH | 0.999 |
| Entropy LHH | 0.997 |
| Mean Absolute Deviation LHH | 0.995 |
| Sum of Squares LHH | 0.995 |
| Gray Level Non Uniformity Normalized LHH (GLDM) | 0.993 |
| Cluster Tendency LHH | 0.992 |
| Uniformity LHH | 0.992 |
| Contrast LHH (GLCM) | 0.988 |
| Difference Variance LHH | 0.988 |
| Run Entropy LHH | 0.988 |
| 90th Percentile LHH | 0.987 |
| Joint Entropy LHH | 0.987 |
| Robust Mean Absolute Deviation LHH | 0.986 |
| 10th Percentile LHH | 0.985 |
| Interquartile Range LHH | 0.985 |
| Sum Entropy LHH | 0.984 |
| Difference Average LHH | 0.981 |
| Joint Energy LHH | 0.981 |
| Inverse Difference Moment LHH | 0.977 |
| Inverse Difference LHH | 0.975 |
| Maximum Probability LHH | 0.975 |
| Cluster Prominence LHH | 0.966 |
| Gray Level Non Uniformity Normalized LHH (GLSZM) | 0.964 |
| Gray Level Variance LHH (GLSZM) | 0.943 |
| Short Run Emphasis LHH | 0.939 |
| Dependence Entropy LHH | 0.937 |
| Small Dependence Emphasis LHH | 0.936 |
| Run Length Non Uniformity Normalized LHH | 0.929 |
| Long Run Emphasis LHH | 0.928 |
| Interquartile Range HHH | 0.927 |
| Mean Absolute Deviation HHH | 0.927 |
| 90th Percentile HHH | 0.926 |
| Robust Mean Absolute Deviation HHH | 0.926 |
| Root Mean Squared HHH | 0.926 |
| Run Percentage LHH | 0.926 |
| Variance HHH | 0.926 |
| 10th Percentile HHH | 0.925 |
| Zone Percentage LHH | 0.922 |
| Gray Level Non Uniformity Normalized HHH (GLDM) | 0.913 |
| Uniformity HHH | 0.913 |
| Entropy HHH | 0.912 |
| Run Variance LHH | 0.912 |
| Large Dependence Emphasis LHH | 0.91 |
| Gray Level Variance HHH (GLSZM) | 0.908 |
| Gray Level Variance HHH (GLDM) | 0.908 |
| Joint Entropy HHH | 0.907 |
| Sum of Squares HHH | 0.904 |
| Difference Entropy HHH | 0.903 |
| Difference Variance HHH | 0.897 |
| Joint Energy HHH | 0.897 |
| Large Area Low Gray Level Emphasis LHH | 0.895 |
| Run Variance LHL | 0.894 |
| Long Run Emphasis LHL | 0.891 |
| Inverse Difference Moment LHL | 0.885 |
| Inverse Difference LHL | 0.883 |
| Inverse Difference Moment LLH | 0.881 |
| Inverse Difference LLH | 0.88 |
| Large Dependence Emphasis LHL | 0.879 |
| Run Percentage LHL | 0.879 |
| Small Dependence Emphasis LHL | 0.879 |
| Zone Percentage LHL | 0.879 |
| Dependence Non Uniformity Normalized LHL | 0.878 |
| Short Run Emphasis LHL | 0.878 |
| Size Zone Non Uniformity Normalized LHL | 0.877 |
| Small Area Emphasis LHL | 0.877 |
| Difference Entropy LHL | 0.876 |
| Cluster Prominence HHH | 0.874 |
| Gray Level Non Uniformity Normalized HHH (GLSZM) | 0.874 |
| Difference Average LHL | 0.873 |
| Run Variance LLH | 0.873 |
| Difference Entropy LLH | 0.872 |
| Large Area Emphasis LHL | 0.872 |
| Long Run Emphasis LLH | 0.872 |
| Small Dependence High Gray Level Emphasis LHH | 0.872 |
| Sum Entropy HHH | 0.872 |
| Dependence Variance LHL | 0.871 |
| Inverse Variance LLH | 0.871 |
| Inverse Variance LHL | 0.87 |
| Gray Level Variance HHH (GLRLM) | 0.869 |
| Run Length Non Uniformity Normalized LHL | 0.869 |
| Contrast LHL (GLCM) | 0.867 |
| Difference Average LLH | 0.867 |
| Zone Variance LHL | 0.867 |
| Complexity LHH | 0.864 |
| Run Variance | 0.864 |
| Size Zone Non Uniformity Normalized LLH | 0.863 |
| Small Area Emphasis LLH | 0.863 |
| Difference Variance LHL | 0.862 |
| Contrast LLH (GLCM) | 0.861 |
| Long Run Emphasis | 0.861 |
| Small Dependence Emphasis LLH | 0.86 |
| Mean Absolute Deviation LLH | 0.859 |
| Run Percentage LLH | 0.859 |
| Small Dependence Emphasis | 0.859 |
| Joint Energy LLH | 0.858 |
| Short Run Emphasis LLH | 0.858 |
| Zone Percentage | 0.858 |
| Dependence Non Uniformity Normalized LLH | 0.857 |
| Zone Percentage LLH | 0.857 |
| Entropy LLH | 0.856 |
| Joint Energy LHL | 0.856 |
| Large Dependence Emphasis LLH | 0.856 |
| Robust Mean Absolute Deviation LLH | 0.856 |
| Interquartile Range LLH | 0.855 |
| Uniformity LLH | 0.855 |
| Gray Level Non Uniformity Normalized LLH (GLDM) | 0.854 |
| Run Percentage | 0.854 |
| Small Area Emphasis | 0.854 |
| Difference Variance LLH | 0.853 |
| Joint Entropy LLH | 0.853 |
| Large Area Emphasis | 0.853 |
| Size Zone Non Uniformity Normalized | 0.853 |
| Sum of Squares LLH | 0.853 |
| Short Run Emphasis | 0.852 |
| Gray Level Non Uniformity Normalized LLH (GLSZM) | 0.851 |
| Dependence Non Uniformity Normalized | 0.85 |
| Joint Entropy LHL | 0.849 |
| Large Dependence Emphasis | 0.849 |
| Run Length Non Uniformity Normalized LLH | 0.849 |
| Large Area Low Gray Level Emphasis LHL | 0.848 |
| Large Dependence Low Gray Level Emphasis LHH | 0.847 |
| Maximum Probability LHL | 0.847 |
| Uniformity LHL | 0.847 |
| Gray Level Non Uniformity Normalized LHL (GLDM) | 0.846 |
| Gray Level Variance LLH (GLDM) | 0.846 |
| Run Length Non Uniformity Normalized | 0.846 |
| Variance LLH | 0.845 |

TABLE 3-continued

Groups of radiomic features collinear with significant features

| Radiomic features | \| rho \| with significant feature |
|---|---|
| Zone Variance | 0.845 |
| Interquartile Range LHL | 0.844 |
| Long Run Emphasis HHL | 0.844 |
| Robust Mean Absolute Deviation LHL | 0.844 |
| Gray Level Variance LLH (GLSZM) | 0.843 |
| Large Area Emphasis LLH | 0.843 |
| Small Area Emphasis HHL | 0.843 |
| Dependence Variance LLH | 0.842 |
| Maximum Probability LLH | 0.842 |
| Run Entropy LLH | 0.842 |
| Size Zone Non Uniformity Normalized HHL | 0.842 |
| Entropy LHL | 0.841 |
| Root Mean Squared LLH | 0.841 |
| Size Zone Non Uniformity Normalized LHH | 0.84 |
| Run Variance HHL | 0.839 |
| Difference Average | 0.838 |
| Gray Level Non Uniformity Normalized LHL (GLSZM) | 0.838 |
| Inverse Difference Moment | 0.838 |
| Inverse Variance | 0.838 |
| Short Run Emphasis HHL | 0.838 |
| Inverse Difference | 0.837 |
| Difference Entropy | 0.835 |
| Mean Absolute Deviation LHL | 0.835 |
| 90th Percentile LLH | 0.833 |
| Cluster Tendency LLH | 0.833 |
| Contrast (GLCM) | 0.833 |
| Small Area Emphasis HLH | 0.833 |
| Sum Entropy LLH | 0.833 |
| Complexity LHL | 0.832 |
| Small Dependence Emphasis HHL | 0.832 |
| Zone Variance LLH | 0.832 |
| Inverse Difference Normalized | 0.831 |
| Large Dependence Emphasis HHL | 0.831 |
| Run Percentage HHL | 0.831 |
| Size Zone Non Uniformity Normalized HLH | 0.83 |
| Large Area Emphasis LHH | 0.829 |
| Run Length Non Uniformity Normalized HHL | 0.829 |
| 10th Percentile LHL | 0.828 |
| Sum of Squares LHL | 0.828 |
| Dependence Variance | 0.827 |
| Inverse Difference Moment Normalized | 0.827 |
| Small Area Emphasis LHH | 0.827 |
| Cluster Tendency HHH | 0.826 |
| Gray Level Variance LHL (GLDM) | 0.826 |
| Run Entropy LHL | 0.826 |
| Variance LHL | 0.825 |
| Gray Level Variance LHL (GLSZM) | 0.824 |
| Zone Percentage HHL | 0.823 |
| Gray Level Variance LLH (GLRLM) | 0.822 |
| Dependence Non Uniformity Normalized HHL | 0.821 |
| Large Dependence Low Gray Level Emphasis LHL | 0.821 |
| Inverse Difference HHL | 0.819 |
| Inverse Difference Moment HHL | 0.818 |
| Large Area High Gray Level Emphasis | 0.818 |
| Small Dependence High Gray Level Emphasis LHL | 0.818 |
| Large Area Low Gray Level Emphasis HHL | 0.816 |
| Size Zone Non Uniformity HHH | 0.815 |
| Dependence Variance HHL | 0.814 |
| Zone Variance LHH | 0.814 |
| Difference Entropy HHL | 0.812 |
| Gray Level Variance LHL (GLDM) | 0.812 |
| Difference Average HHL | 0.811 |
| Long Run Emphasis HLH | 0.811 |
| Difference Variance | 0.81 |
| 10th Percentile LLH | 0.808 |
| Long Run Emphasis LLL | 0.808 |
| Sum Entropy LHL | 0.808 |
| Complexity | 0.807 |
| Maximum Probability HHL | 0.807 |
| Run Variance LLL | 0.807 |
| Dependence Non Uniformity Normalized LLL | 0.806 |
| Zone Percentage LLL | 0.806 |
| Inverse Difference HLH | 0.805 |
| Run Percentage LLL | 0.805 |
| Small Dependence Emphasis HLH | 0.805 |
| Small Dependence Emphasis LLL | 0.805 |
| Large Dependence Emphasis LLL | 0.804 |
| Short Run Emphasis HLH | 0.804 |
| Short Run Emphasis LLL | 0.804 |
| Small Area Emphasis HHH | 0.804 |
| Contrast HHL (GLCM) | 0.803 |
| Large Area Emphasis LLL | 0.803 |
| Joint Energy HHL | 0.802 |
| Maximum LHH | 0.802 |
| Run Length Non Uniformity Normalized LLL | 0.802 |
| Run Variance HLH | 0.802 |
| Size Zone Non Uniformity Normalized HHH | 0.802 |
| 10th Percentile HHL | 0.801 |
| Inverse Difference Moment HLH | 0.801 |
| Size Zone Non Uniformity Normalized LLL | 0.801 |
| Small Area Emphasis LLL | 0.801 |
| Small Area High Gray Level Emphasis HHH | 0.801 |
| Interquartile Range HHL | 0.799 |
| Difference Variance HHL | 0.798 |
| Robust Mean Absolute Deviation HHL | 0.798 |
| Root Mean Squared LHL | 0.798 |
| Short Run High Gray Level Emphasis LHH | 0.798 |
| Inverse Difference Moment LLL | 0.797 |
| Large Area Emphasis HHL | 0.797 |
| Dependence Variance LLL | 0.796 |
| Joint Entropy HHL | 0.796 |
| Uniformity HHL | 0.796 |
| Gray Level Non Uniformity Normalized HHL (GLDM) | 0.795 |
| Zone Variance LLL | 0.795 |
| Inverse Difference LLL | 0.794 |
| Mean Absolute Deviation HHL | 0.794 |
| Entropy HHL | 0.793 |
| Informational Measure of Correlation 1 | 0.793 |
| Total Energy LHH | 0.793 |
| Inverse Variance LLL | 0.792 |
| Range LHH | 0.792 |
| Root Mean Squared HHL | 0.792 |
| Run Percentage HLH | 0.792 |
| Variance HHL | 0.792 |
| 90th Percentile HHL | 0.79 |
| Gray Level Variance HHL (GLDM) | 0.79 |
| Difference Average HLH | 0.789 |
| Gray Level Variance HHL (GLSZM) | 0.789 |
| Difference Entropy HLH | 0.787 |
| Large Dependence Emphasis HLH | 0.787 |
| Zone Percentage HLH | 0.787 |
| Run Length Non Uniformity Normalized HLH | 0.786 |
| Zone Variance HHL | 0.786 |
| Run Entropy HHH | 0.785 |
| Small Area High Gray Level Emphasis LHL | 0.785 |
| Sum of Squares HHL | 0.785 |
| Cluster Tendency LHL | 0.784 |
| Long Run Low Gray Level Emphasis LHH | 0.783 |
| Maximum Probability HLH | 0.783 |
| Small Area High Gray Level Emphasis LHH | 0.783 |
| Small Dependence High Gray Level Emphasis HHL | 0.781 |
| Joint Energy HLH | 0.776 |
| Contrast HLH (GLCM) | 0.775 |
| Difference Average LLL | 0.775 |
| Small Dependence High Gray Level Emphasis HHH | 0.774 |
| Large Dependence Low Gray Level Emphasis HHL | 0.773 |
| Sum Entropy HHL | 0.771 |
| 10th Percentile HLH | 0.77 |
| Cluster Tendency HHL | 0.77 |
| Dependence Non Uniformity Normalized HLH | 0.769 |
| Gray Level Non Uniformity Normalized HHL (GLSZM) | 0.769 |
| High Gray Level Emphasis LHH | 0.768 |
| High Gray Level Run Emphasis LHH | 0.768 |
| Joint Entropy HLH | 0.768 |
| Robust Mean Absolute Deviation HLH | 0.768 |
| Interquartile Range HLH | 0.767 |
| Size Zone Non Uniformity LHH | 0.767 |
| Difference Entropy LLL | 0.766 |

TABLE 3-continued

Groups of radiomic features collinear with significant features

| Radiomic features | \|rho\| with significant feature |
|---|---|
| Difference Variance HLH | 0.766 |
| Run Entropy HHL | 0.766 |
| Contrast HHH (GLCM) | 0.765 |
| Gray Level Variance HHL (GLRLM) | 0.765 |
| Gray Level Variance HLH (GLSZM) | 0.765 |
| Mean Absolute Deviation HLH | 0.765 |
| Root Mean Squared HLH | 0.765 |
| Uniformity HLH | 0.765 |
| Variance HLH | 0.765 |
| Entropy HLH | 0.764 |
| Gray Level Non Uniformity Normalized HLH (GLDM) | 0.764 |
| Gray Level Variance HLH (GLDM) | 0.763 |
| Complexity HHL | 0.762 |
| Large Area Low Gray Level Emphasis HLH | 0.762 |
| Large Dependence High Gray Level Emphasis | 0.762 |
| Cluster Prominence HHL | 0.759 |
| Complexity LLH | 0.759 |
| 90th Percentile HLH | 0.758 |
| Energy LHH | 0.758 |
| Short Run High Gray Level Emphasis LHL | 0.756 |
| Sum of Squares HLH | 0.755 |
| Dependence Variance HLH | 0.753 |
| Short Run High Gray Level Emphasis HHH | 0.753 |
| High Gray Level Emphasis LHL | 0.752 |
| High Gray Level Run Emphasis LHL | 0.752 |
| Correlation | 0.751 |
| Run Variance HLL | 0.751 |
| High Gray Level Zone Emphasis LHH | 0.75 |
| Long Run Emphasis HLL | 0.75 |
| Small Dependence High Gray Level Emphasis HLH | 0.75 |

The groups identified in Table 3 may be reduced to include only those radiomic features that are correlated with the original significant feature of that group (i.e. one of the 15 significant features identified by the feature selection algorithm) to a degree of at least |rho|=0.800 (this includes the significant feature itself which is, by definition, correlated with itself to a degree of rho=1). For example, the groups may be reduced to those features that are correlated with the significant feature of that group to a degree of at least |rho|=0.850. For example, the groups may be reduced to those features that are correlated with the significant feature of that group to a degree of at least |rho|=0.900. For example, the groups may be reduced to those features that are correlated with the significant feature of that group to a degree of at least |rho|=0.950.

In addition to the radiomic signature being calculated on the basis of the at least two radiomic features from different clusters or groups, it may also be calculated on the basis of additional radiomic features. For example, the radiomic signature may include more than one radiomic feature from any given cluster or group, or may include radiomic features not included in any of the clusters or groups. Thus, it may be said that the radiomic signature is calculated on the basis of a plurality of radiomic features, and the plurality of radiomic features may comprise the at least two radiomic features referred to above.

Stroke

To maximise the association with stroke, again the radiomic signature is calculated on the basis of measured values of radiomic features obtained from medical imaging data. In particular the radiomic signature is preferably calculated on the basis of at least two radiomic features.

To improve the prognostic and diagnostic value of the signature, the signature is preferably calculated on the basis of at least two different radiomic features selected from different clusters of similar or correlated radiomic features, as already described. This reduces redundancy and improves the diversity of information included in the calculation of the signature because the features from different clusters relate to different textural aspects of the epicardial tissues.

Four clusters (A-D) have been identified using a hierarchical clustering algorithm. The members of the four clusters are identified in Table 1b. The radiomic signature may comprise at least two of the radiomic features from Table 1b. Advantageously, the radiomic signature may be calculated on the basis of radiomic features selected from at least two of the clusters A-D identified in Table 1b, the at least two radiomic features being selected from different clusters. Preferably, the radiomic signature may be calculated on the basis of at least one radiomic feature selected from each of the clusters A-D identified in Table 1b.

TABLE 1b

Radiomic feature clusters

| Radiomic feature | Cluster |
|---|---|
| 10$^{th}$ Percentile | A |
| ID HHL | A |
| Variance | A |
| Gray Level Non Uniformity Normalized (GLRLM) | A |
| Dependence Variance HLL | A |
| Elongation | A |
| Dependence Variance LLL | A |
| Large Dependence Emphasis LLL | A |
| Run Variance HLH | A |
| Dependence Variance HLH | A |
| Size Zone Non Uniformity LHL | B |
| Skewness | B |
| Root Mean Squared | B |
| Gray Level Non Uniformity LLH | B |
| Large Area Emphasis LLH | B |
| Large Area Emphasis LHL | B |
| Size Zone Non Uniformity LLH | B |
| Skewness LLH | B |
| Small Area High Gray level Emphasis LHH | B |
| Difference Entropy HHL | B |
| IDMN HHH | C |
| Zone Percentage HHL | C |
| Kurtosis | C |
| Kurtosis HHL | C |
| Zone Entropy HHH | C |
| Size Zone Non Uniformity HHL | C |
| Size Zone Non Uniformity Normalized HHH | D |
| Difference Entropy LLL | D |
| Autocorrelation HHL | D |
| Difference Variance LLL | D |
| Correlation HHL | D |
| Size Zone Non Uniformity Normalized HHL | D |

16 radiomic features were found to maximise the radiomic signature's association with ischaemic stroke and these are shown in Table 2b. The radiomic signature may advantageously be calculated on the basis of at least two of the radiomic features from Table 2b. Preferably, the radiomic signature is calculated on the basis of at least two radiomic features, each of the at least two radiomic features being selected from different clusters A-D. Further preferably, the radiomic signature may be calculated on the basis of at least one radiomic feature selected from each of the clusters A-D identified in Table 2b. To maximise the radiomic signature's association with stroke the radiomic signature may be calculated on the basis of all of the 16 radiomic features listed in Table 2b.

TABLE 2b

Further optimised radiomic feature clusters

| Radiomic feature | Cluster |
|---|---|
| 10$^{th}$ Percentile | A |
| ID HHL | A |
| Variance | A |
| Gray Level Non Uniformity Normalized (GLRLM) | A |
| Dependence Variance HLL | A |
| Size Zone Non-Uniformity LHL | B |
| Skewness | B |
| Root Mean Squared | B |
| Gray Level Non Uniformity LLH | B |
| Large Area Emphasis LLH | B |
| IDMN HHH | C |
| Zone Percentage HHL | C |
| Kurtosis | C |
| Size Zone Non Uniformity Normalized HHH | D |
| Difference Entropy LLL | D |
| Autocorrelation HHL | D |

As previously mentioned, the significant radiomic features of Tables 1b and 2b may be substituted with other radiomic features that are correlated, or collinear, with the replaced significant radiomic feature (i.e. collinear equivalents) to obtain a signature of similar diagnostic and prognostic usefulness. The radiomic signature may therefore be calculated on the basis of (i.e. comprise) at least two of the radiomic features selected from Table 3b. Each of the groups identified in Table 3b includes one of the 16 significant radiomic features that have been found to maximise the association of the signature with stroke along with those radiomic features that have been calculated to be collinear with that significant feature to a degree of at least |rho|=0.75, where rho is Spearman's rho. Thus, the radiomic signature may be constructed as set out above, but with one or more of the significant radiomic features of Table 2b being replaced with a radiomic feature that is collinear with that feature, as set out in Table 3b. For example, the radiomic signature may be calculated on the basis of at least two radiomic features, each of the at least two radiomic features being selected from different groups of Table 3b. In particular, the radiomic signature may be calculated on the basis of at least two radiomic features that are selected from groups corresponding to significant features belonging to different clusters A-D. Further preferably, the radiomic signature may be calculated on the basis of at least one radiomic feature selected from each of the clusters A-D identified in Table 1b or collinear equivalents thereof. In other words, the radiomic signature may be calculated on the basis of at least one radiomic feature selected from each of the clusters A-D identified in Table 3b below.

TABLE 3b

Groups of radiomic features collinear with significant features

| Radiomic features | \|rho\| with significant feature |
|---|---|
| Group 1 (cluster A) | |
| 10$^{th}$ Percentile | 1.000 |
| Range | 0.962 |
| Range HLL | 0.912 |
| Variance HLL | 0.855 |
| Range LHL | 0.784 |
| Skewness HLH | 0.763 |
| 10$^{th}$ Percentile LHH | 0.759 |
| Group 2 (cluster A) | |
| ID HHL | 1.000 |
| Inverse Variance HHL | 0.990 |
| Sum Entropy HHL | 0.988 |
| MCC HHL | 0.987 |
| Sum Squares HHL | 0.974 |
| Cluster Prominence HHL | 0.973 |
| IMC2 HHL | 0.960 |
| IMC1 HHL | 0.959 |
| Difference Average HHL | 0.958 |
| Run variance HHL | 0.936 |
| ID LLL | 0.924 |
| Low Gray Level Emphasis LLL | 0.911 |
| Joint Average LLL | 0.904 |
| Sum Average LLL | 0.897 |
| Joint Entropy LLL | 0.888 |
| Cluster Shade LLL | 0.887 |
| Maximum Probability LLL | 0.872 |
| IDMN LLL | 0.866 |
| Joint Energy LLL | 0.865 |
| Contrast LLL | 0.847 |
| Joint Energy HHH | 0.837 |
| Contrast HHH | 0.829 |
| Difference Entropy HHH | 0.815 |
| Inverse Variance HHH | 0.813 |
| Difference Variance HHH | 0.804 |
| IDN HHH | 0.801 |
| IDM HHH | 0.798 |
| Correlation HHH | 0.794 |
| Autocorrelation HHH | 0.789 |
| Sum Entropy HHH | 0.788 |
| Group 3 (cluster A) | |
| Variance | 1.000 |
| Run Variance (GLRLM) | 0.977 |
| Gray Level Variance (GLSZM) | 0.976 |
| Zone Variance (GLSZM) | 0.965 |
| Gray Level Non Uniformity (GLRLM) | 0.929 |
| Long Run Emphasis (GLRLM) | 0.900 |
| Short Run High Gray Level Emphasis (GLRLM) | 0.899 |
| Run Length Non Uniformity (GLRLM) | 0.885 |
| Gray Level Non Uniformity Normalized (GLSZM) | 0.885 |
| Size Zone Non Uniformity Normalized (GLSZM) | 0.864 |
| Size Zone Non Uniformity (GLSZM) | 0.825 |
| Gray Level Non Uniformity (GLSZM) | 0.812 |
| Large Area Emphasis (GLSZM) | 0.811 |
| Small Area High Gray Level Emphasis (GLSZM) | 0.805 |
| Zone Percentage (GLSZM) | 0.782 |
| Large Area Low Gray Level Emphasis (GLSZM) | 0.777 |
| Large Area High Gray Level Emphasis (GLSZM) | 0.776 |
| High Gray Level Zone Emphasis (GLSZM) | 0.764 |
| Small Area Emphasis (GLSZM) | 0.762 |
| Low Gray Level Zone Emphasis (GLSZM) | 0.753 |
| Zone Entropy (GLSZM) | 0.753 |
| Group 4 (cluster A) | |
| Gray Level Non Uniformity Normalized (GLRLM) | 1.000 |
| Gray Level Non Uniformity Normalized HLL (GLRLM) | 0.947 |
| Short Run Low Gray Level Emphasis HLL (GLRLM) | 0.882 |
| Gray Level Variance HLL (GLRLM) | 0.877 |
| Low Gray Level Run Emphasis HLL (GLRLM) | 0.864 |
| Gray Level Non Uniformity Normalized LHL (GLRLM) | 0.830 |
| Run Variance LHL (GLRLM) | 0.821 |
| Gray Level Non Uniformity LHL (GLRLM) | 0.793 |
| Long Run Emphasis LHL (GLRLM) | 0.765 |
| Short Run High Gray Level Emphasis LHL (GLRLM) | 0.751 |
| Group 5 (cluster A) | |
| Dependence Variance HLL | 1.000 |
| Large Dependence High Gray Level Emphasis HLL | 0.840 |
| Small Dependence Low Gray Level Emphasis HLL | 0.839 |

TABLE 3b-continued

Groups of radiomic features collinear with significant features

| Radiomic features | \|rho\| with significant feature |
|---|---|
| Low Gray Level Emphasis HLL | 0.828 |
| Joint Average HLL | 0.796 |
| Sum Average HLL | 0.779 |
| Joint Entropy HLL | 0.772 |
| Group 6 (cluster B) | |
| Size Zone Non-Uniformity LHL | 1.000 |
| Short Run Low Gray Level Emphasis LHL | 0.986 |
| Gray Level Variance LHL | 0.983 |
| Low Gray Level Run Emphasis LHL | 0.971 |
| Gray Level Non Uniformity Normalized LHL | 0.968 |
| Run Variance LHL | 0.954 |
| Gray Level Non Uniformity LHL | 0.944 |
| Long Run Emphasis LHL | 0.933 |
| Short Run High Gray Level Emphasis LHL | 0.925 |
| Run Length Non Uniformity LHL | 0.924 |
| Short Run Emphasis LHL | 0.916 |
| Long Run High Gray Level Emphasis LHL | 0.915 |
| Run Percentage LHL | 0.909 |
| Long Run Low Gray Level Emphasis LHL | 0.895 |
| Run Entropy LHL | 0.894 |
| High Gray Level Run Emphasis LHL | 0.889 |
| Run Length Non Uniformity Normalized LHL | 0.883 |
| Gray Level Variance LHL | 0.872 |
| Zone Variance LHL | 0.864 |
| Gray Level Non Uniformity Normalized LHL | 0.853 |
| Size Zone Non Uniformity Normalized LHL | 0.845 |
| Small Area High Gray Level Emphasis LHL | 0.838 |
| Zone Percentage LHL | 0.818 |
| Large Area Low Gray Level Emphasis LHL | 0.811 |
| Large Area High Gray Level Emphasis LHL | 0.791 |
| High Gray Level Zone Emphasis LHL | 0.785 |
| Small Area Emphasis LHL | 0.784 |
| Low Gray Level Zone Emphasis LHL | 0.778 |
| Zone Entropy LHL | 0.777 |
| Small Area Low Gray Level Emphasis LHL | 0.774 |
| Group 7 (cluster B) | |
| Skewness | 1.000 |
| Uniformity | 0.954 |
| Skewness HLL | 0.874 |
| Busyness HLL | 0.870 |
| Complexity HLH | 0.794 |
| Group 8 (cluster B) | |
| Root Mean Squared | 1.000 |
| Maximum | 0.966 |
| Root Mean Squared HLL | 0.876 |
| Sum Average LHH | 0.865 |
| Joint Entropy LHH | 0.789 |
| Cluster Shade LHH | 0.771 |
| Group 9 (cluster B) | |
| Gray Level Non Uniformity LLH | 1.000 |
| Small Dependence Emphasis LLH | 0.947 |
| Small Dependence High Gray Level Emphasis LLH | 0.941 |
| Dependence Non Uniformity Normalized LLH | 0.939 |
| Large Dependence Emphasis LLH | 0.927 |
| Large Dependence Low Gray Level Emphasis LLH | 0.880 |
| Dependence Variance LLH | 0.853 |
| Large Dependence High Gray Level Emphasis LLH | 0.842 |
| Joint Energy LLH | 0.825 |
| Contrast LLH | 0.814 |
| Difference Entropy LLH | 0.812 |
| Inverse Variance LLH | 0.774 |
| Difference Variance LLH | 0.764 |
| Group 10 (cluster B) | |
| Large Area Emphasis LLH | 1.000 |
| High Gray Level Emphasis LLH | 0.990 |
| Large Dependence Emphasis | 0.983 |
| Contrast LHH | 0.981 |
| LargeArea High Gray Level Emphasis | 0.981 |
| Low Gray Level Run Emphasis | 0.976 |
| Dependence Variance LHL | 0.976 |
| Variance LLL | 0.972 |
| Range HHH | 0.964 |
| Run Variance HHL | 0.947 |
| Maximum Probability HHL | 0.945 |
| 90th Percentile LLH | 0.936 |
| Entropy HLH | 0.926 |
| Dependence Variance LHH | 0.923 |
| Low Gray Level Emphasis LLH | 0.919 |
| Gray Level Variance LLH | 0.910 |
| Low Gray Level Emphasis | 0.900 |
| Long Run Low Gray Level Emphasis LLH | 0.895 |
| Maximum LLH | 0.895 |
| Uniformity | 0.888 |
| 10th Percentile LHH | 0.880 |
| Short Run Emphasis LHH | 0.876 |
| Complexity LHH | 0.876 |
| Coarseness HHL | 0.874 |
| Coarseness HLH | 0.872 |
| Gray Level Non Uniformity LHL | 0.865 |
| Gray Level Non Uniformity Normalized LLL (GLSZM) | 0.858 |
| Sum Entropy HHL | 0.856 |
| Low Gray Level Run Emphasis HLL | 0.855 |
| Large Area Low Gray Level Emphasis | 0.853 |
| Run Length Non Uniformity HLL | 0.848 |
| Entropy | 0.845 |
| Dependence Non Uniformity HLL | 0.845 |
| Large Area Emphasis LLL | 0.843 |
| Zone Percentage LLL | 0.839 |
| Robust Mean Absolute Deviation HLH | 0.832 |
| Auto correlation HLL | 0.830 |
| Dependence Entropy LLL | 0.827 |
| SumSquares LLH | 0.826 |
| Zone Entropy HLH | 0.825 |
| Cluster Tendency | 0.808 |
| 10th Percentile HLH | 0.805 |
| Inverse Variance LLL | 0.804 |
| Interquartile Range HLL | 0.803 |
| Root Mean Squared HHL | 0.800 |
| Joint Average LLH | 0.800 |
| Run Percentage HHH | 0.799 |
| Cluster Prominence LLL | 0.796 |
| Small Dependence Emphasis HHH | 0.795 |
| Gray Level Non Uniformity Normalized HLL (GLRLM) | 0.786 |
| Large Area High Gray Level Emphasis HHL | 0.786 |
| Coarseness LHL | 0.785 |
| Gray Level Variance (LLL) | 0.779 |
| Short Run Low Gray Level Emphasis (HLH) | 0.772 |
| Difference Entropy (HLL) | 0.763 |
| Group 11 (cluster C) | |
| IDMN HHH | 1.000 |
| Contrast LLL | 0.989 |
| Total Energy HLH | 0.988 |
| IDM LLL | 0.987 |
| Zone Percentage | 0.982 |
| Small Area Emphasis LLH | 0.973 |
| Strength | 0.969 |
| Cluster Prominence LHH | 0.963 |
| Sum Entropy | 0.963 |
| Gray Level Non Uniformity Normalized LHH | 0.961 |
| Gray Level Non Uniformity Normalized HHL | 0.953 |
| Short Run High Gray Level Emphasis LHL | 0.946 |
| Maximum 2 D Diameter Slice | 0.933 |
| Auto correlation LHH | 0.930 |
| IMC1 LHL | 0.930 |
| Uniformity | 0.928 |
| Long Run Low Gray Level Emphasis LHH | 0.928 |
| Difference Variance LHH | 0.922 |
| Interquartile Range HLH | 0.914 |
| High Gray Level Zone Emphasis HHL | 0.907 |
| Size Zone Non Uniformity HLL | 0.900 |

TABLE 3b-continued

Groups of radiomic features collinear with significant features

| Radiomic features | \|rho\| with significant feature |
|---|---|
| Difference Average | 0.900 |
| ID LHL | 0.898 |
| Range LLH | 0.897 |
| High Gray Level Emphasis HHH | 0.897 |
| Mean HLH | 0.892 |
| Small Area Low Gray Level Emphasis LLL | 0.888 |
| Dependence Non Uniformity Normalized HHL | 0.885 |
| Run Variance HLL | 0.885 |
| Joint Average | 0.883 |
| Entropy HLH | 0.882 |
| Maximum Probability LHH | 0.882 |
| IMC2 LLH | 0.878 |
| Sum Average LHH | 0.877 |
| Run Length Non Uniformity Normalized LHH | 0.872 |
| Gray Level Non Uniformity | 0.871 |
| Minimum LLH | 0.871 |
| Gray Level Variance LHL | 0.867 |
| Contrast HHH | 0.864 |
| Gray Level Non Uniformity Normalized HHH | 0.864 |
| Robust Mean Absolute Deviation HLH | 0.856 |
| Long Run Emphasis LHL | 0.852 |
| Run Length Non Uniformity Normalized | 0.850 |
| Dependence Non Uniformity LHL | 0.844 |
| IDMN | 0.843 |
| Small Dependence High Gray Level Emphasis LHH | 0.832 |
| IDM | 0.831 |
| Low Gray Level Zone Emphasis HHH | 0.828 |
| Complexity HHL | 0.819 |
| Small Area Low Gray Level Emphasis HHL | 0.815 |
| Long Run Emphasis HHH | 0.813 |
| Low Gray Level Emphasis | 0.811 |
| Dependence Non Uniformity Normalized HLL | 0.809 |
| Maximum Probability LLL | 0.808 |
| Gray Level Variance HLL | 0.807 |
| Large Dependence High Gray Level Emphasis | 0.802 |
| High Gray Level Run Emphasis LHL | 0.801 |
| Cluster Shade LHL | 0.793 |
| Sum Squares HHL | 0.792 |
| Large Area High Gray Level Emphasis LLL | 0.791 |
| Energy HHL | 0.790 |
| IDMN LLH | 0.782 |
| IDN HHL | 0.779 |
| Large Dependence Emphasis | 0.778 |
| Maximum Probability LLH | 0.774 |
| Large Dependence Emphasis LLH | 0.773 |
| Inverse Variance HLH | 0.769 |
| Gray Level Variance LHL | 0.769 |
| Complexity LLL | 0.768 |
| Low Gray Level Emphasis LLH | 0.759 |
| Strength LLH | 0.757 |
| Maximum HHL | 0.757 |
| Small Area High Gray Level Emphasis LLH | 0.750 |
| Group 12 (cluster C) | |
| Zone Percentage HHL | 1.000 |
| Small Dependence Emphasis HHL | 0.990 |
| Small Area High Gray Level Emphasis LLH | 0.990 |
| Contrast HLL | 0.989 |
| Autocorrelation HHH | 0.985 |
| Gray Level Non Uniformity HLH | 0.985 |
| Long Run High Gray Level Emphasis LHL | 0.985 |
| Complexity HHL | 0.984 |
| Contrast HLL | 0.984 |
| Total Energy LLL | 0.983 |
| Sum Squares LHL | 0.983 |
| Zone Variance LLH | 0.982 |
| Cluster Shade HHL | 0.981 |
| Total Energy LHH | 0.980 |
| Long Run High Gray Level Emphasis LLL | 0.979 |
| Size Zone Non Uniformity Normalized LLL | 0.978 |
| Joint Entropy LLL | 0.978 |
| Zone Entropy LHL | 0.974 |
| High Gray Level Zone Emphasis HLH | 0.973 |
| Joint Entropy LHH | 0.973 |
| Long Run Low Gray Level Emphasis LLL | 0.970 |
| Cluster Tendency LLL | 0.969 |
| Difference Average LHL | 0.967 |
| ID HLH | 0.966 |
| Short Run Low Gray Level Emphasis LLL | 0.964 |
| Large Area Low Gray Level Emphasis LLL | 0.962 |
| Dependence Non Uniformity LHH | 0.959 |
| Gray Level Non Uniformity Normalized LHH | 0.958 |
| Dependence Variance LLH | 0.957 |
| Coarseness LLH | 0.956 |
| Gray Level Non Uniformity LHH | 0.956 |
| Gray Level Variance | 0.955 |
| Small Area High Gray Level Emphasis HHH | 0.955 |
| Joint Entropy | 0.953 |
| Mean Absolute Deviation HHH | 0.953 |
| Small Dependence Emphasis | 0.952 |
| Mean HHL | 0.946 |
| Variance HLH | 0.946 |
| Long Run Emphasis HLL | 0.946 |
| Root Mean Squared HHH | 0.946 |
| Mean Absolute Deviation | 0.945 |
| Median HLL | 0.943 |
| Gray Level Variance LLL | 0.942 |
| Autocorrelation LLH | 0.941 |
| Total Energy HLH | 0.941 |
| IDM | 0.941 |
| Zone Entropy HHL | 0.940 |
| Voxel Volume | 0.940 |
| IMC1 | 0.940 |
| 90th Percentile LLH | 0.939 |
| Mean LHH | 0.939 |
| Run Length Non Uniformity Normalized LHL | 0.939 |
| IDM LHH | 0.938 |
| Small Dependence High Gray Level Emphasis HLH | 0.937 |
| MCC LLL | 0.937 |
| Large Area Emphasis HHL | 0.935 |
| Run Percentage LLL | 0.933 |
| Interquartile Range LLH | 0.933 |
| Small Area Low Gray Level Emphasis HHH | 0.932 |
| Correlation LLH | 0.931 |
| Long Run Low Gray Level Emphasis LHL | 0.931 |
| Joint Energy HHH | 0.930 |
| Complexity HLL | 0.930 |
| Large Area Low Gray Level Emphasis LLH | 0.926 |
| Large Dependence High Gray Level Emphasis LHL | 0.925 |
| Busyness HHL | 0.925 |
| 10th Percentile LLL | 0.924 |
| Short Run High Gray Level Emphasis LLH | 0.923 |
| Low Gray Level Run Emphasis HHL | 0.921 |
| Complexity LLL | 0.919 |
| Low Gray Level Run Emphasis LHH | 0.919 |
| Gray Level Variance LHH | 0.918 |
| Difference Variance HLL | 0.918 |
| Maximum Probability | 0.913 |
| Dependence Non Uniformity Normalized HHH | 0.912 |
| Correlation HHH | 0.912 |
| Dependence Non Uniformity Normalized HLL | 0.912 |
| High Gray Level Zone Emphasis HLL | 0.910 |
| Gray Level Non Uniformity LLH | 0.908 |
| Minimum LHL | 0.908 |
| Contrast HHL | 0.908 |
| Uniformity LHL | 0.908 |
| Low Gray Level Zone Emphasis LLH | 0.906 |
| Short Run Low Gray Level Emphasis HLH | 0.905 |
| Run Length Non Uniformity LLH | 0.903 |
| Large Area Low Gray Level Emphasis | 0.903 |
| Sum Average LLL | 0.900 |
| Entropy HLL | 0.900 |
| Energy | 0.897 |
| IDM HLH | 0.895 |
| ID LHH | 0.893 |
| Autocorrelation LHH | 0.889 |
| Skewness HLL | 0.888 |
| Minimum | 0.888 |

TABLE 3b-continued

Groups of radiomic features collinear with significant features

| Radiomic features | \|rho\| with significant feature |
|---|---|
| Variance HHH | 0.886 |
| IDM LLH | 0.886 |
| Dependence Variance | 0.885 |
| High Gray Level Run Emphasis LLL | 0.883 |
| Large Area Emphasis HHH | 0.883 |
| Uniformity LHH | 0.883 |
| Dependence Non Uniformity HHL | 0.881 |
| Large Area Emphasis | 0.881 |
| Large Dependence High Gray Level Emphasis HLH | 0.881 |
| IMC2 | 0.880 |
| IDMN LHH | 0.879 |
| Zone Variance LLL | 0.877 |
| Run Entropy HLH | 0.876 |
| Maximum Probability HHH | 0.872 |
| Busyness HLH | 0.872 |
| Contrast HHL | 0.872 |
| IMC1 HHH | 0.871 |
| Inverse Variance HLH | 0.870 |
| High Gray Level Zone Emphasis | 0.868 |
| Gray Level Variance HLH | 0.868 |
| Dependence Entropy | 0.867 |
| High Gray Level Zone Emphasis LHL | 0.865 |
| High Gray Level Zone Emphasis HHH | 0.862 |
| Large Dependence Emphasis LHL | 0.860 |
| Mean Absolute Deviation LLH | 0.860 |
| Short Run High Gray Level Emphasis HLL | 0.858 |
| Cluster Prominence LHH | 0.857 |
| Gray Level Non Uniformity LLL | 0.852 |
| Long Run Low Gray Level Emphasis LLH | 0.851 |
| ID HHH | 0.850 |
| Large Dependence High Gray Level Emphasis HLL | 0.849 |
| Joint Entropy LLH | 0.849 |
| Robust Mean Absolute Deviation | 0.846 |
| Large Dependence Low Gray Level Emphasis HLL | 0.846 |
| Run Length Non Uniformity LHL | 0.846 |
| High Gray Level Emphasis LHH | 0.845 |
| Entropy HHL | 0.843 |
| Long Run Emphasis HHH | 0.842 |
| Large Dependence Low Gray Level Emphasis HLH | 0.839 |
| Run Length Non Uniformity Normalized HLL | 0.836 |
| Small Dependence High Gray Level Emphasis HLL | 0.836 |
| Run Length Non Uniformity Normalized | 0.835 |
| Cluster Tendency | 0.832 |
| Short Run Emphasis LHH | 0.832 |
| Strength LLH | 0.831 |
| Low Gray Level Run Emphasis LLH | 0.830 |
| Cluster Tendency LHL | 0.830 |
| Maximum Probability HLH | 0.830 |
| Energy LHH | 0.828 |
| Robust Mean Absolute Deviation HHL | 0.827 |
| Correlation HLH | 0.827 |
| High Gray Level Zone Emphasis LLL | 0.826 |
| Run Percentage LLH | 0.825 |
| Small Dependence Emphasis LLH | 0.823 |
| Difference Entropy LLH | 0.823 |
| Entropy LLL | 0.823 |
| Contrast HHH | 0.822 |
| Skewness HHL | 0.822 |
| Strength LHL | 0.817 |
| Inverse Variance LHH | 0.817 |
| Coarseness LHL | 0.816 |
| Dependence Non Uniformity HHH | 0.812 |
| Correlation LHH | 0.811 |
| Sum Average HHH | 0.810 |
| Small Dependence Emphasis HLL | 0.810 |
| Low Gray Level Zone Emphasis LHH | 0.810 |
| High Gray Level Zone Emphasis LLH | 0.808 |
| Gray Level Non Uniformity LLL | 0.808 |
| Gray Level Variance LHL | 0.806 |
| Joint Average LHH | 0.803 |
| High Gray Level Run Emphasis LHL | 0.803 |
| Gray Level Non Uniformity Normalized LLL | 0.803 |
| Small Dependence Emphasis LHL | 0.802 |
| Entropy LHH | 0.798 |
| Short Run Emphasis HLH | 0.796 |
| Large Area High Gray Level Emphasis LLL | 0.796 |
| Dependence Non Uniformity HLH | 0.793 |
| Interquartile Range LLL | 0.793 |
| Gray Level Non Uniformity Normalized LLH | 0.790 |
| Joint Entropy LHL | 0.789 |
| Strength LHH | 0.789 |
| IDN LLH | 0.788 |
| Uniformity LLL | 0.788 |
| Small Area Low Gray Level Emphasis LHL | 0.785 |
| Run Variance LHH | 0.783 |
| Coarseness LLL | 0.783 |
| Coarseness HHH | 0.781 |
| Small Area Low Gray Level Emphasis LHH | 0.781 |
| Cluster Shade HLL | 0.779 |
| Small Dependence Emphasis LHH | 0.776 |
| Maximum HLL | 0.775 |
| IDN HHL | 0.774 |
| Sum Average LHL | 0.772 |
| Median LHH | 0.770 |
| Small Area Emphasis HHH | 0.770 |
| Energy HHL | 0.768 |
| Gray Level Variance LLH | 0.768 |
| Large Dependence High Gray Level Emphasis HHL | 0.767 |
| Joint Entropy HLL | 0.765 |
| Range LHH | 0.762 |
| Minor Axis Length | 0.761 |
| Gray Level Non Uniformity Normalized LHH | 0.760 |
| Kurtosis HHH | 0.760 |
| Gray Level Non Uniformity LHH | 0.758 |
| Run Length Non Uniformity Normalized HLH | 0.756 |
| Gray Level Non Uniformity Normalized HHL | 0.754 |
| Gray Level Non Uniformity Normalized LLH | 0.753 |
| Contrast HHH | 0.753 |
| Difference Average HHH | 0.752 |
| Contrast HLH | 0.751 |
| Interquartile Range HHL | 0.750 |
| Mean Absolute Deviation LHL | 0.750 |
| Group 13 (cluster C) | |
| Kurtosis | 1.000 |
| Small Dependence Low Gray Level Emphasis LHL | 0.989 |
| Run Percentage LHL | 0.989 |
| Contrast HHH | 0.989 |
| Busyness LLH | 0.988 |
| Variance HLL | 0.988 |
| IDMN LLH | 0.987 |
| Small Area High Gray Level Emphasis HHH | 0.986 |
| Short Run High Gray Level Emphasis LLH | 0.986 |
| Kurtosis LLH | 0.985 |
| Difference Variance HLL | 0.984 |
| Dependence Non Uniformity Normalized HHL | 0.983 |
| Difference Average LHH | 0.983 |
| Sum Entropy LHL | 0.982 |
| Coarseness | 0.982 |
| Joint Average HHL | 0.981 |
| Cluster Prominence HHH | 0.979 |
| Small Dependence Low Gray Level Emphasis LLH | 0.979 |
| Long Run High Gray Level Emphasis LHH | 0.978 |
| Small Dependence Emphasis HLL | 0.973 |
| Gray Level Non Uniformity Normalized LLH | 0.973 |
| Interquartile Range HHL | 0.973 |
| Long Run High Gray Level Emphasis HLL | 0.969 |
| Contrast | 0.968 |
| IMC2 | 0.967 |
| Gray Level Non Uniformity Normalized HHL | 0.964 |
| High Gray Level Zone Emphasis LHH | 0.963 |
| Low Gray Level Run Emphasis LLL | 0.958 |
| Long Run High Gray Level Emphasis HHH | 0.958 |
| Uniformity HLH | 0.956 |
| Small Dependence High Gray Level Emphasis HLH | 0.956 |
| Joint Energy HHH | 0.956 |
| Large Dependence High Gray Level Emphasis LHL | 0.955 |
| Low Gray Level Run Emphasis HHL | 0.952 |

TABLE 3b-continued

Groups of radiomic features collinear with significant features

| Radiomic features | \|rho\| with significant feature |
|---|---|
| Kurtosis LHH | 0.948 |
| Kurtosis HLL | 0.945 |
| IDM HLH | 0.945 |
| Robust Mean Absolute Deviation LLL | 0.944 |
| IDM LLH | 0.944 |
| Maximum3 D Diameter | 0.943 |
| Maximum | 0.943 |
| Cluster Tendency LLH | 0.939 |
| Robust Mean Absolute Deviation LLH | 0.937 |
| Dependence Non Uniformity LHH | 0.937 |
| Energy HLL | 0.936 |
| Gray Level Non Uniformity Normalized LHL | 0.934 |
| Gray Level Non Uniformity Normalized HLL | 0.934 |
| Skewness HLH | 0.934 |
| Busyness LHH | 0.933 |
| Cluster Tendency HHL | 0.932 |
| Short Run High Gray Level Emphasis HLL | 0.931 |
| Low Gray Level Emphasis HHL | 0.931 |
| Root Mean Squared HHL | 0.931 |
| Run Length Non Uniformity Normalized HHH | 0.930 |
| Inverse Variance HLH | 0.930 |
| Large Dependence Low Gray Level Emphasis LLL | 0.929 |
| Run Length Non Uniformity Normalized HLH | 0.928 |
| Mean LLL | 0.928 |
| Small Dependence Emphasis LHL | 0.924 |
| Correlation HLL | 0.921 |
| Gray Level Variance HLH | 0.920 |
| Autocorrelation HLH | 0.920 |
| Short Run Emphasis HHL | 0.920 |
| Short Run High Gray Level Emphasis HLH | 0.917 |
| Complexity LHH | 0.915 |
| Zone Variance HHH | 0.914 |
| 10th Percentile LLH | 0.911 |
| Small Dependence High Gray Level Emphasis HLL | 0.909 |
| Skewness HLL | 0.908 |
| Joint Average LHL | 0.908 |
| Short Run Low Gray Level Emphasis | 0.908 |
| Low Gray Level Zone Emphasis HHH | 0.903 |
| Run Entropy | 0.902 |
| Uniformity LLH | 0.899 |
| IDM LHH | 0.899 |
| Small Dependence Low Gray Level Emphasis HLH | 0.898 |
| Short Run Low Gray Level Emphasis HHH | 0.897 |
| 10th Percentile LHL | 0.895 |
| Gray Level Variance HLL | 0.891 |
| Coarseness LHH | 0.890 |
| Difference Variance | 0.890 |
| Interquartile Range HLH | 0.887 |
| Gray Level Non Uniformity HLL | 0.886 |
| Range LHH | 0.882 |
| Gray Level Non Uniformity Normalized HLL | 0.881 |
| Dependence Non Uniformity LHL | 0.879 |
| Gray Level Variance LHL | 0.877 |
| Strength LLH | 0.876 |
| Mean Absolute Deviation LHH | 0.874 |
| Sum Entropy LLL | 0.870 |
| Maximum LLH | 0.867 |
| Zone Variance HLH | 0.865 |
| Interquartile Range HHH | 0.864 |
| Dependence Non Uniformity LLL | 0.861 |
| Run Percentage HLH | 0.861 |
| Minimum HLL | 0.859 |
| IMC1 LLL | 0.858 |
| Zone Entropy | 0.857 |
| Busyness HHL | 0.856 |
| Large Area High Gray Level Emphasis HHL | 0.854 |
| Short Run Emphasis LLH | 0.854 |
| High Gray Level Zone Emphasis HHL | 0.852 |
| Large Dependence Low Gray Level Emphasis LHL | 0.850 |
| Low Gray Level Zone Emphasis LLH | 0.850 |
| Sum Entropy LLH | 0.847 |
| Dependence Non Uniformity HLL | 0.844 |
| Gray Level Non Uniformity HHL | 0.841 |
| Robust Mean Absolute Deviation LHL | 0.833 |
| Contrast HLH | 0.832 |
| Inverse Variance HHL | 0.831 |
| Mean Absolute Deviation LLL | 0.828 |
| Difference Variance HHH | 0.824 |
| Dependence Non Uniformity Normalized HHH | 0.824 |
| Gray Level Variance LLL | 0.824 |
| Inverse Variance HLL | 0.821 |
| Dependence Entropy | 0.821 |
| Joint Energy HLH | 0.821 |
| Joint Entropy LHL | 0.818 |
| Long Run Low Gray Level Emphasis LLH | 0.818 |
| Range | 0.817 |
| Short Run Low Gray Level Emphasis LHL | 0.811 |
| Long Run Low Gray Level Emphasis HHL | 0.811 |
| Short Run High Gray Level Emphasis | 0.806 |
| Median HLL | 0.798 |
| Dependence Non Uniformity Normalized HLH | 0.797 |
| Coarseness LLL | 0.797 |
| Zone Variance LLH | 0.797 |
| Sum Squares HHH | 0.796 |
| Large Area Emphasis HHH | 0.792 |
| ID HLL | 0.791 |
| ID LHL | 0.791 |
| Size Zone Non Uniformity Normalized | 0.790 |
| Run Entropy LLL | 0.789 |
| Sum Entropy HLH | 0.788 |
| Imc1 HLL | 0.786 |
| Maximum LLL | 0.783 |
| Small Area High Gray Level Emphasis LHL | 0.783 |
| Variance HHH | 0.779 |
| Coarseness HHH | 0.777 |
| Difference Entropy LLH | 0.776 |
| Dependence Variance | 0.774 |
| High Gray Level Run Emphasis LLH | 0.772 |
| Difference Average HHH | 0.770 |
| Energy HHH | 0.769 |
| Small Area High Gray Level Emphasis | 0.769 |
| 10th Percentile HLL | 0.768 |
| Energy LLH | 0.766 |
| Least Axis Length | 0.765 |
| Short Run Emphasis HLL | 0.765 |
| Size Zone Non Uniformity Normalized LHH | 0.761 |
| Range LLH | 0.760 |
| Short Run High Gray Level Emphasis LHL | 0.759 |
| Difference Average HLH | 0.759 |
| Large Area Emphasis LLL | 0.757 |
| Maximum Probability HLL | 0.756 |
| Gray Level Variance LLL | 0.753 |
| Short Run Low Gray Level Emphasis HLL | 0.752 |
| Group 14 (cluster D) | |
| Size Zone Non Uniformity Normalized HHH | 1.000 |
| Low Gray Level Emphasis HHH | 0.990 |
| Sum Entropy HHH | 0.987 |
| Large Area Low Gray Level Emphasis HHH | 0.986 |
| Gray Level Non Uniformity LLH | 0.985 |
| Low Gray Level Emphasis HHL | 0.985 |
| Maximum LLH | 0.984 |
| Dependence Non Uniformity Normalized LHL | 0.981 |
| Gray Level Non Uniformity HHH | 0.980 |
| IMC2 HLH | 0.978 |
| IMC2 HLL | 0.975 |
| Sum Entropy LLL | 0.975 |
| Small Dependence Emphasis HHH | 0.974 |
| Short Run Emphasis LLH | 0.973 |
| Small Dependence Emphasis HLL | 0.973 |
| Small Area Low Gray Level Emphasis LHH | 0.972 |
| Sum Entropy LHL | 0.972 |
| 90th Percentile LHH | 0.971 |
| Short Run High Gray Level Emphasis HLH | 0.970 |
| Large Area High Gray Level Emphasis | 0.969 |
| IDN LHH | 0.969 |
| Maximum Probability HHL | 0.967 |
| Mean Absolute Deviation HHH | 0.966 |

TABLE 3b-continued

Groups of radiomic features collinear with significant features

| Radiomic features | \|rho\| with significant feature |
|---|---|
| Strength LHH | 0.965 |
| Joint Energy HLH | 0.964 |
| Gray Level Non Uniformity Normalized HHL | 0.960 |
| Large Area Emphasis HLL | 0.960 |
| IDM LHH | 0.957 |
| Large Dependence Low Gray Level Emphasis LLH | 0.954 |
| Joint Average LLL | 0.950 |
| Mean LHL | 0.949 |
| Gray Level Non Uniformity HLL | 0.947 |
| Median LHH | 0.947 |
| Large Area Emphasis LHH | 0.943 |
| Short Run Low Gray Level Emphasis LLL | 0.940 |
| Contrast LLH | 0.939 |
| Joint Entropy HHH | 0.939 |
| Dependence Non Uniformity Normalized HLL | 0.938 |
| IMC1 HHL | 0.937 |
| Low Gray Level Emphasis LHL | 0.937 |
| Kurtosis LHH | 0.935 |
| Interquartile Range LHL | 0.934 |
| Variance HHH | 0.931 |
| Gray Level Non Uniformity Normalized HLH | 0.930 |
| Short Run High Gray Level Emphasis HLL | 0.929 |
| IDM | 0.929 |
| Complexity HHL | 0.927 |
| Skewness HLH | 0.926 |
| Gray Level Non Uniformity Normalized HHH | 0.925 |
| Large Area Low Gray Level Emphasis LLL | 0.924 |
| Low Gray Level Run Emphasis HHH | 0.919 |
| IDM LLL | 0.918 |
| Gray Level Non Uniformity Normalized LHL | 0.918 |
| Short Run High Gray Level Emphasis | 0.916 |
| Minimum LLL | 0.910 |
| Contrast LHL | 0.910 |
| 90th Percentile LLL | 0.910 |
| Run Entropy LHH | 0.909 |
| Large Area Emphasis HHH | 0.905 |
| Small Dependence High Gray Level Emphasis HLL | 0.902 |
| Gray Level Variance HLL | 0.901 |
| Difference Average LLL | 0.900 |
| Small Area Low Gray Level Emphasis LLL | 0.899 |
| Dependence Non Uniformity HLL | 0.898 |
| Joint Energy HLL | 0.894 |
| Kurtosis LLL | 0.891 |
| Large Dependence High Gray Level Emphasis HHL | 0.885 |
| Contrast | 0.884 |
| Zone Entropy LHL | 0.877 |
| IMC2 LLH | 0.876 |
| Long Run High Gray Level Emphasis HHH | 0.874 |
| Run Length Non Uniformity Normalized LHL | 0.874 |
| Median LLL | 0.873 |
| Maximum Probability LLH | 0.871 |
| Run Variance LLH | 0.870 |
| Short Run Low Gray Level Emphasis HHH | 0.866 |
| Difference Entropy HLH | 0.865 |
| IDMN LHH | 0.863 |
| 90th Percentile HLL | 0.863 |
| Dependence Non Uniformity Normalized HLH | 0.860 |
| High Gray Level Zone Emphasis HHH | 0.858 |
| Long Run High Gray Level Emphasis HLH | 0.857 |
| Size Zone Non Uniformity Normalized LLH | 0.855 |
| Large Area High Gray Level Emphasis LLL | 0.854 |
| Gray Level Non Uniformity Normalized HLH | 0.851 |
| Gray Level Non Uniformity LLL | 0.851 |
| Dependence Entropy HHL | 0.851 |
| IDN HHH | 0.848 |
| Median LHL | 0.847 |
| 10th Percentile LHH | 0.844 |
| Total Energy LLL | 0.844 |
| Sum Average HLL | 0.844 |
| Gray Level Variance HHH | 0.842 |
| Maximum HHH | 0.842 |
| Gray Level Non Uniformity LHH | 0.841 |
| Strength LLH | 0.840 |
| IDN HHL | 0.837 |
| Busyness LHL | 0.834 |
| Dependence Non Uniformity Normalized HHL | 0.833 |
| Low Gray Level Emphasis LLH | 0.830 |
| Small Dependence High Gray Level Emphasis LHL | 0.829 |
| Root Mean Squared LHL | 0.829 |
| Sum Average HLH | 0.827 |
| Mean HHL | 0.825 |
| Short Run Emphasis LLL | 0.825 |
| Gray Level Variance HHL | 0.824 |
| 10th Percentile HHH | 0.822 |
| Median HLH | 0.821 |
| Interquartile Range LLL | 0.821 |
| Large Dependence Low Gray Level Emphasis | 0.820 |
| Small Area Low Gray Level Emphasis HLL | 0.818 |
| Entropy HLH | 0.818 |
| Zone Percentage | 0.816 |
| Large Dependence Emphasis HHH | 0.814 |
| Energy LHH | 0.814 |
| Autocorrelation HHH | 0.814 |
| IMC1 HLL | 0.812 |
| 10th Percentile LLL | 0.810 |
| Sum Average LLH | 0.809 |
| Long Run Emphasis | 0.807 |
| Gray Level Non Uniformity HHH | 0.806 |
| Gray Level Variance LHH | 0.806 |
| Maximum2 D Diameter Slice | 0.805 |
| Maximum HLH | 0.804 |
| Dependence Entropy LLL | 0.801 |
| Long Run Emphasis LLL | 0.799 |
| Contrast LHH | 0.799 |
| Zone Percentage LHL | 0.798 |
| Coarseness LHL | 0.794 |
| Gray Level Non Uniformity Normalized LLH | 0.792 |
| Zone Variance LLL | 0.791 |
| Run Length Non Uniformity Normalized LHH | 0.787 |
| Large Area Low Gray Level Emphasis LHH | 0.786 |
| Large Area Low Gray Level Emphasis HLH | 0.785 |
| Dependence Non Uniformity HLH | 0.784 |
| Cluster Tendency HHH | 0.783 |
| Gray Level Non Uniformity | 0.783 |
| Cluster Shade LLH | 0.781 |
| Range LHL | 0.779 |
| ID HLL | 0.778 |
| Large Dependence High Gray Level Emphasis LLH | 0.776 |
| Long Run High Gray Level Emphasis LHH | 0.776 |
| Skewness LLL | 0.773 |
| Zone Entropy HLH | 0.771 |
| Busyness HLH | 0.770 |
| IMC1 HHH | 0.770 |
| Strength HLH | 0.768 |
| Sum Squares HHH | 0.767 |
| Small Area Emphasis HHH | 0.766 |
| Median | 0.765 |
| Run Length Non Uniformity HHL | 0.765 |
| High Gray Level Zone Emphasis LHH | 0.764 |
| Small Area High Gray Level Emphasis LLH | 0.759 |
| 10th Percentile HHL | 0.755 |
| IDMN LHL | 0.753 |
| Run Variance LHH | 0.752 |
| Autocorrelation HLH | 0.752 |
| High Gray Level Zone Emphasis HHL | 0.751 |
| Group 15 (cluster D) | |
| Difference Entropy LLL | 1.000 |
| Zone Variance LLL | 0.990 |
| 10th Percentile LLL | 0.988 |
| Contrast HLL | 0.986 |
| Interquartile Range HLL | 0.985 |
| Dependence Variance LLH | 0.984 |
| Difference Entropy HLH | 0.983 |
| Mean Absolute Deviation LHH | 0.983 |
| Sum Entropy LLH | 0.983 |
| Small Dependence Low Gray Level Emphasis LLH | 0.979 |
| Range LLL | 0.979 |

TABLE 3b-continued

Groups of radiomic features collinear with significant features

| Radiomic features | \|rho\| with significant feature |
|---|---|
| Low Gray Level Emphasis HLL | 0.979 |
| Large Area High Gray Level Emphasis HHH | 0.979 |
| Short Run Emphasis LHH | 0.979 |
| High Gray Level Emphasis HLH | 0.978 |
| High Gray Level Emphasis HLL | 0.977 |
| Short Run Low Gray Level Emphasis LLH | 0.976 |
| Run Percentage LHL | 0.975 |
| Cluster Prominence LHH | 0.975 |
| High Gray Level Zone Emphasis LLH | 0.975 |
| Cluster Prominence HLL | 0.974 |
| ID LHL | 0.974 |
| Sum Entropy HLL | 0.974 |
| Cluster Prominence HHH | 0.973 |
| Gray Level Non Uniformity Normalized LLH | 0.973 |
| Dependence Non Uniformity | 0.970 |
| IMC2 LHH | 0.969 |
| Dependence Entropy HHL | 0.969 |
| Joint Energy | 0.969 |
| Difference Variance HLL | 0.968 |
| Kurtosis LLL | 0.966 |
| Large Dependence Emphasis LHL | 0.965 |
| Zone Entropy HLH | 0.964 |
| Low Gray Level Run Emphasis HHL | 0.964 |
| Surface Area | 0.962 |
| Robust Mean Absolute Deviation HLL | 0.961 |
| IDM LLL | 0.961 |
| Entropy LLL | 0.959 |
| 90th Percentile LLL | 0.958 |
| Size Zone Non Uniformity Normalized HLL | 0.958 |
| Low Gray Level Run Emphasis LHH | 0.957 |
| Run Length Non Uniformity LLL | 0.957 |
| ID HLH | 0.955 |
| Gray Level Variance LLH | 0.954 |
| Energy | 0.953 |
| Coarseness HHL | 0.953 |
| Skewness HHL | 0.952 |
| Run Variance HHH | 0.952 |
| Joint Average HHH | 0.951 |
| Complexity | 0.949 |
| Range LHL | 0.949 |
| Gray Level Non Uniformity Normalized HHH | 0.949 |
| High Gray Level Zone Emphasis HLH | 0.949 |
| Gray Level Non Uniformity LHL | 0.948 |
| Contrast HHH | 0.948 |
| Cluster Tendency HLL | 0.948 |
| Sum Squares HHL | 0.947 |
| Gray Level Non Uniformity LLH | 0.941 |
| Contrast LLH | 0.939 |
| Gray Level Variance | 0.938 |
| Gray Level Non Uniformity Normalized HLH | 0.937 |
| Large Area High Gray Level Emphasis HLL | 0.937 |
| Run Length Non Uniformity Normalized LLH | 0.935 |
| Low Gray Level Run Emphasis HLH | 0.935 |
| Small Area Emphasis LHL | 0.934 |
| 10th Percentile HHH | 0.932 |
| Kurtosis HLL | 0.931 |
| Difference Variance HHL | 0.930 |
| Large Dependence Emphasis | 0.929 |
| Long Run Emphasis LHL | 0.928 |
| Gray Level Non Uniformity Normalized LLL | 0.928 |
| Maximum HHH | 0.928 |
| Small Dependence High Gray Level Emphasis HLL | 0.927 |
| Difference Average LHL | 0.927 |
| Robust Mean Absolute Deviation HLH | 0.926 |
| Sum Average HLH | 0.924 |
| Gray Level Variance LLL | 0.924 |
| Zone Variance | 0.923 |
| Entropy LLH | 0.922 |
| Large Dependence Low Gray Level Emphasis LLL | 0.922 |
| IDMN LHL | 0.921 |
| Short Run Low Gray Level Emphasis LLL | 0.920 |
| IDMN HHL | 0.920 |
| Inverse Variance LHH | 0.920 |
| Cluster Prominence HLH | 0.919 |
| Zone Percentage HLH | 0.919 |
| Zone Variance HHL | 0.918 |
| Range HHL | 0.917 |
| Entropy HHH | 0.917 |
| IMC1 HHL | 0.917 |
| Cluster Shade | 0.916 |
| Short Run Emphasis | 0.916 |
| Range LHH | 0.916 |
| Interquartile Range HHL | 0.915 |
| Large Dependence Low Gray Level Emphasis HLL | 0.915 |
| IDM HLH | 0.915 |
| Gray Level Variance LHL | 0.913 |
| Small Dependence High Gray Level Emphasis | 0.912 |
| IMC2 HLH | 0.911 |
| Zone Percentage LHL | 0.910 |
| Root Mean Squared HLL | 0.910 |
| Minimum | 0.906 |
| Cluster Prominence LHL | 0.906 |
| Joint Energy LLH | 0.899 |
| Small Area High Gray Level Emphasis HLL | 0.898 |
| Energy LLL | 0.898 |
| IDMN LHH | 0.897 |
| Long Run High Gray Level Emphasis HHH | 0.897 |
| High Gray Level Run Emphasis LLL | 0.897 |
| Small Area Low Gray Level Emphasis LHL | 0.897 |
| Large Dependence Low Gray Level Emphasis | 0.897 |
| Strength LHL | 0.896 |
| MCC LLH | 0.895 |
| Dependence Non Uniformity Normalized LHL | 0.893 |
| 90th Percentile | 0.891 |
| Complexity LHL | 0.891 |
| Gray Level Non Uniformity HLH | 0.891 |
| IMC1 LHH | 0.889 |
| Minimum HLH | 0.888 |
| Mean Absolute Deviation HHL | 0.885 |
| Small Area High Gray Level Emphasis HLH | 0.885 |
| Small Area Emphasis LLL | 0.884 |
| Contrast | 0.882 |
| Mean HHL | 0.882 |
| IMC2 LHL | 0.882 |
| Cluster Prominence LLH | 0.881 |
| High Gray Level Run Emphasis HLH | 0.881 |
| Minimum LHL | 0.881 |
| Correlation LHH | 0.881 |
| Correlation LLL | 0.880 |
| Kurtosis LLH | 0.880 |
| 10th Percentile LLH | 0.879 |
| Low Gray Level Zone Emphasis LLH | 0.879 |
| Sum Squares HLL | 0.879 |
| Zone Variance LHL | 0.878 |
| High Gray Level Run Emphasis LHH | 0.878 |
| IDM LHH | 0.877 |
| Mean Absolute Deviation HHH | 0.877 |
| Gray Level Variance HLH | 0.877 |
| Total Energy HHL | 0.874 |
| Long Run Low Gray Level Emphasis LLL | 0.874 |
| MCC LHH | 0.873 |
| Sum Average HLL | 0.873 |
| Short Run Emphasis HHL | 0.873 |
| Run Length Non Uniformity | 0.871 |
| Low Gray Level Zone Emphasis HHL | 0.871 |
| Gray Level Non Uniformity HHH | 0.871 |
| Busyness LLL | 0.871 |
| Minor Axis Length | 0.870 |
| Gray Level Non Uniformity LHH | 0.870 |
| Joint Average HLH | 0.870 |
| Zone Variance HLL | 0.869 |
| IMC1 HHH | 0.868 |
| Interquartile Range LHH | 0.868 |
| Autocorrelation | 0.867 |
| Small Area Emphasis LLH | 0.867 |
| Gray Level Non Uniformity HHL | 0.867 |
| Gray Level Variance HHL | 0.867 |
| Cluster Prominence | 0.867 |

TABLE 3b-continued

Groups of radiomic features collinear with significant features

| Radiomic features | \|rho\| with significant feature |
|---|---|
| Run Length Non Uniformity Normalized HHH | 0.864 |
| Run Entropy HHL | 0.863 |
| Difference Average LLL | 0.863 |
| Autocorrelation LHL | 0.861 |
| Correlation HHH | 0.861 |
| Run Length Non Uniformity HHH | 0.859 |
| Large Area Emphasis HLL | 0.859 |
| Uniformity LLH | 0.859 |
| Voxel Volume | 0.858 |
| Short Run High Gray Level Emphasis HHL | 0.855 |
| Variance HHL | 0.854 |
| Short Run High Gray Level Emphasis LLL | 0.853 |
| Difference Entropy HLL | 0.852 |
| Strength | 0.851 |
| Root Mean Squared LLL | 0.851 |
| Small Area Emphasis | 0.850 |
| Difference Average HHL | 0.849 |
| Low Gray Level Zone Emphasis LHL | 0.848 |
| Mean | 0.847 |
| Busyness HLL | 0.847 |
| High Gray Level Run Emphasis HHL | 0.846 |
| Autocorrelation HHH | 0.844 |
| Variance HHH | 0.843 |
| Busyness LHL | 0.843 |
| Gray Level Non Uniformity LLL | 0.842 |
| High Gray Level Zone Emphasis | 0.842 |
| IDMN LLL | 0.841 |
| Mean Absolute Deviation | 0.840 |
| Low Gray Level Emphasis LHL | 0.840 |
| Size Zone Non Uniformity Normalized | 0.838 |
| Joint Entropy LHH | 0.838 |
| Complexity LLH | 0.837 |
| Low Gray Level Run Emphasis HLL | 0.837 |
| Low Gray Level Zone Emphasis HHH | 0.836 |
| High Gray Level Zone Emphasis HHH | 0.835 |
| Robust Mean Absolute Deviation LLH | 0.834 |
| Short Run Low Gray Level Emphasis HLH | 0.830 |
| 90th Percentile LHL | 0.830 |
| Mean Absolute Deviation HLL | 0.828 |
| Gray Level Non Uniformity Normalized HLH | 0.827 |
| Gray Level Variance HHL | 0.826 |
| Dependence Non Uniformity Normalized LHH | 0.826 |
| Small Dependence Low Gray Level Emphasis | 0.826 |
| Minimum LLL | 0.825 |
| Small Dependence Low Gray Level Emphasis LHH | 0.825 |
| Large Dependence High Gray Level Emphasis HLH | 0.825 |
| Small Dependence Low Gray Level Emphasis HHL | 0.824 |
| Total Energy | 0.823 |
| Maximum Probability LLL | 0.823 |
| Small Dependence Low Gray Level Emphasis HLL | 0.823 |
| Minimum HHH | 0.822 |
| Difference Variance HHH | 0.821 |
| Size Zone Non Uniformity HLH | 0.820 |
| Autocorrelation HLH | 0.820 |
| Energy HLH | 0.819 |
| Large Dependence High Gray Level Emphasis LLL | 0.818 |
| Dependence Non Uniformity LHL | 0.818 |
| Strength LLH | 0.817 |
| High Gray Level Emphasis LHH | 0.817 |
| Dependence Entropy HLH | 0.816 |
| Contrast HHH | 0.815 |
| Large Area High Gray Level Emphasis LLH | 0.815 |
| Gray Level Variance LLL | 0.815 |
| Interquartile Range HLH | 0.815 |
| Robust Mean Absolute Deviation LHL | 0.813 |
| ID LHH | 0.813 |
| Maximum2 D Diameter Row | 0.811 |
| 10th Percentile HLL | 0.811 |
| Difference Variance LHL | 0.809 |
| IDM HHH | 0.808 |
| IDN LLL | 0.806 |
| Short Run Emphasis HHH | 0.806 |
| Low Gray Level Emphasis LHH | 0.802 |
| Joint Average | 0.802 |
| Dependence Variance LHH | 0.801 |
| Coarseness LLL | 0.800 |
| Low Gray Level Zone Emphasis LHH | 0.800 |
| Large Dependence Low Gray Level Emphasis LHH | 0.799 |
| Small Dependence Low Gray Level Emphasis LLL | 0.798 |
| Uniformity HHL | 0.797 |
| ID | 0.796 |
| Small Dependence Emphasis HLH | 0.795 |
| Gray Level Non Uniformity HLH | 0.795 |
| Root Mean Squared LHL | 0.795 |
| Inverse Variance | 0.793 |
| Difference Average HHH | 0.793 |
| Gray Level Non Uniformity | 0.793 |
| Autocorrelation LHH | 0.792 |
| Gray Level Non Uniformity HHL | 0.789 |
| Small Area Low Gray Level Emphasis LLL | 0.789 |
| Total Energy HHH | 0.788 |
| Mean LHL | 0.788 |
| Maximum LLL | 0.787 |
| Small Area High Gray Level Emphasis HHL | 0.787 |
| Size Zone Non Uniformity Normalized LLH | 0.786 |
| IDM HHL | 0.783 |
| Gray Level Variance HLH | 0.783 |
| Large Dependence Low Gray Level Emphasis LLH | 0.780 |
| Correlation HLL | 0.779 |
| Uniformity | 0.779 |
| Kurtosis HHH | 0.778 |
| Variance LHH | 0.777 |
| Sum Squares LHH | 0.776 |
| Run Entropy | 0.774 |
| Large Area Emphasis HLH | 0.774 |
| Gray Level Non Uniformity Normalized HHL | 0.774 |
| Total Energy LHL | 0.773 |
| Median LLL | 0.773 |
| Root Mean Squared LHH | 0.771 |
| Minimum LHL | 0.771 |
| Sum Entropy HHH | 0.770 |
| Sum Average LHL | 0.769 |
| Large Dependence Low Gray Level Emphasis HLH | 0.768 |
| Zone Entropy | 0.767 |
| Gray Level Variance LHH | 0.766 |
| MCC HLL | 0.766 |
| Difference Average LLH | 0.765 |
| Small Area High Gray Level Emphasis | 0.764 |
| High Gray Level Zone Emphasis HHL | 0.763 |
| Dependence Entropy LLH | 0.762 |
| Complexity HLH | 0.761 |
| Large Area High Gray Level Emphasis HLH | 0.761 |
| IDM LLH | 0.760 |
| Large Area High Gray Level Emphasis LHH | 0.760 |
| IMC2 HLL | 0.759 |
| Correlation | 0.758 |
| Cluster Prominence HHL | 0.758 |
| Small Dependence Emphasis HLL | 0.756 |
| Root Mean Squared HLH | 0.756 |
| Dependence Non Uniformity Normalized LLL | 0.755 |
| Contrast LHH | 0.754 |
| Joint Entropy HHL | 0.754 |
| Gray Level Non Uniformity Normalized LLH | 0.753 |
| Run Variance LLL | 0.753 |
| Large Area Low Gray Level Emphasis LHH | 0.752 |
| Low Gray Level Emphasis LLL | 0.752 |
| Small Area Emphasis LHH | 0.750 |
| Group 16 (cluster D) | |
| Autocorrelation HHL | 1.000 |
| Zone Entropy HHL | 0.990 |
| Low Gray Level Zone Emphasis HHL | 0.988 |
| 10th Percentile HHH | 0.985 |
| Small Area Low Gray Level Emphasis LHL | 0.982 |
| Run Percentage LHL | 0.982 |
| Gray Level Variance LLL | 0.981 |
| Run Variance LLL | 0.980 |
| Gray Level Non Uniformity Normalized HHL | 0.977 |

TABLE 3b-continued

Groups of radiomic features collinear with significant features

| Radiomic features | \|rho\| with significant feature |
|---|---|
| Large Dependence Emphasis | 0.974 |
| Gray Level Variance HHL | 0.973 |
| Minimum LHL | 0.971 |
| Sum Squares HLL | 0.971 |
| Difference Entropy HLL | 0.971 |
| Sum Average LHL | 0.968 |
| High Gray Level Run Emphasis LLL | 0.968 |
| Large Dependence Low Gray Level Emphasis LLL | 0.968 |
| Small Dependence Low Gray Level Emphasis | 0.965 |
| Contrast LHH | 0.963 |
| Dependence Non Uniformity Normalized LHL | 0.962 |
| Joint Average | 0.961 |
| Energy | 0.960 |
| Difference Average LLL | 0.958 |
| Mean Absolute Deviation LHH | 0.956 |
| Small Area Emphasis LHL | 0.955 |
| Coarseness LLL | 0.951 |
| Busyness HLL | 0.950 |
| Small Area Emphasis LLL | 0.948 |
| Kurtosis HHH | 0.948 |
| Cluster Prominence LHH | 0.945 |
| Small Dependence High Gray Level Emphasis | 0.944 |
| Long Run Emphasis LHL | 0.943 |
| High Gray Level Zone Emphasis HHL | 0.943 |
| Robust Mean Absolute Deviation HLL | 0.943 |
| Run Length Non Uniformity LLL | 0.941 |
| IDMN LHH | 0.941 |
| Low Gray Level Zone Emphasis LLH | 0.937 |
| Range HHL | 0.936 |
| Low Gray Level Run Emphasis HLH | 0.929 |
| Run Variance HHH | 0.927 |
| Complexity HLH | 0.927 |
| High Gray Level Zone Emphasis LLH | 0.926 |
| Uniformity LLH | 0.925 |
| Mean Absolute Deviation HLL | 0.922 |
| Difference Average LHL | 0.922 |
| Cluster Prominence HLH | 0.921 |
| High Gray Level Zone Emphasis HLH | 0.919 |
| Size Zone Non Uniformity HLH | 0.918 |
| High Gray Level Zone Emphasis HHH | 0.916 |
| Skewness HHL | 0.915 |
| Zone Percentage HLH | 0.911 |
| Joint Energy LLH | 0.910 |
| Autocorrelation HHH | 0.910 |
| Large Area Low Gray Level Emphasis HLH | 0.908 |
| Gray Level Variance LLL | 0.908 |
| Large Area Emphasis HLL | 0.907 |
| Short Run Emphasis | 0.907 |
| Low Gray Level Run Emphasis LHH | 0.906 |
| Short Run Emphasis LHH | 0.906 |
| Low Gray Level Run Emphasis HLL | 0.905 |
| Total Energy | 0.905 |
| Short Run High Gray Level Emphasis HHL | 0.903 |
| Joint Average HLH | 0.901 |
| Dependence Variance LLH | 0.900 |
| Dependence Variance LHH | 0.899 |
| Short Run Low Gray Level Emphasis HLH | 0.896 |
| Total Energy HHL | 0.895 |
| Complexity | 0.895 |
| Dependence Entropy LLH | 0.895 |
| Low Gray Level Emphasis LLL | 0.895 |
| Gray Level Variance | 0.895 |
| Voxel Volume | 0.894 |
| Robust Mean Absolute Deviation LLH | 0.894 |
| Zone Variance HLH | 0.894 |
| Gray Level Non Uniformity Normalized LLH | 0.894 |
| Sum Squares LHH | 0.893 |
| Cluster Prominence HHL | 0.891 |
| Interquartile Range HLH | 0.888 |
| Low Gray Level Zone Emphasis LHH | 0.887 |
| Sum Squares HHL | 0.886 |
| Variance LHH | 0.886 |
| MCC LHH | 0.885 |
| Run Length Non Uniformity HHH | 0.884 |
| Short Run Emphasis HHH | 0.882 |
| Autocorrelation | 0.882 |
| Run Length Non Uniformity Normalized LLH | 0.882 |
| Large Dependence High Gray Level Emphasis LLL | 0.880 |
| Small Area High Gray Level Emphasis HHL | 0.878 |
| Correlation | 0.878 |
| Robust Mean Absolute Deviation HLH | 0.876 |
| Gray Level Non Uniformity Normalized HHH | 0.875 |
| Strength LLH | 0.872 |
| Correlation HLL | 0.871 |
| Coarseness HHL | 0.867 |
| Dependence Entropy HLH | 0.866 |
| Joint Entropy LHH | 0.866 |
| 10th Percentile HLL | 0.866 |
| Large Area High Gray Level Emphasis HLH | 0.865 |
| Large Dependence Low Gray Level Emphasis HLH | 0.864 |
| Gray Level Non Uniformity HLH | 0.862 |
| Size Zone Non Uniformity Normalized | 0.861 |
| High Gray Level Run Emphasis HLH | 0.861 |
| Cluster Prominence HHH | 0.859 |
| Large Dependence Low Gray Level Emphasis LLH | 0.858 |
| Small Dependence Low Gray Level Emphasis HLL | 0.858 |
| 10th Percentile LLH | 0.858 |
| Gray Level Variance LHL | 0.858 |
| IDM HLH | 0.856 |
| IMC1 HHH | 0.852 |
| Large Area High Gray Level Emphasis LHH | 0.852 |
| Mean Absolute Deviation | 0.849 |
| Short Run Low Gray Level Emphasis LLL | 0.845 |
| Small Dependence Low Gray Level Emphasis LHH | 0.842 |
| Total Energy HHH | 0.841 |
| Small Dependence Low Gray Level Emphasis LLH | 0.841 |
| Kurtosis LLL | 0.837 |
| IDMN LLL | 0.836 |
| Large Dependence Emphasis LHL | 0.836 |
| MCC | 0.836 |
| Gray Level Variance LHH | 0.835 |
| Small Area High Gray Level Emphasis | 0.835 |
| IDM LHH | 0.835 |
| Gray Level Variance LLH | 0.832 |
| Zone Variance HLL | 0.832 |
| Small Dependence Emphasis HLL | 0.831 |
| Gray Level Variance HLH | 0.825 |
| Cluster Prominence | 0.825 |
| Dependence Non Uniformity | 0.820 |
| Joint Average HHH | 0.819 |
| Range LHH | 0.819 |
| Gray Level Non Uniformity LLL | 0.816 |
| Small Dependence Low Gray Level Emphasis LLL | 0.814 |
| High Gray Level Zone Emphasis | 0.812 |
| Maximum Probability LLL | 0.811 |
| Dependence Non Uniformity Normalized LHH | 0.810 |
| Minimum HHH | 0.808 |
| Gray Level Non Uniformity Normalized HLH | 0.806 |
| Long Run Low Gray Level Emphasis LLL | 0.806 |
| Short Run Low Gray Level Emphasis LLH | 0.803 |
| Large Area High Gray Level Emphasis LLH | 0.802 |
| Root Mean Squared LHH | 0.801 |
| Contrast HHH | 0.801 |
| Large Area High Gray Level Emphasis HLL | 0.800 |
| IDM LLL | 0.799 |
| Gray Level Non Uniformity LHH | 0.799 |
| Mean | 0.799 |
| Gray Level Non Uniformity HLH | 0.799 |
| IMC2 LHL | 0.798 |
| 90th Percentile | 0.797 |
| Interquartile Range HHL | 0.796 |
| MCC LLH | 0.796 |
| IMC1 LHH | 0.796 |
| Variance HHL | 0.795 |
| Median LLL | 0.793 |
| Mean Absolute Deviation HHH | 0.793 |
| Gray Level Non Uniformity LHL | 0.792 |
| Run Length Non Uniformity Normalized HHH | 0.790 |

TABLE 3b-continued

Groups of radiomic features collinear with significant features

| Radiomic features | \|rho\| with significant feature |
|---|---|
| Low Gray Level Run Emphasis HHL | 0.790 |
| Complexity LHL | 0.787 |
| Cluster Shade | 0.785 |
| Long Run High Gray Level Emphasis HHH | 0.785 |
| Gray Level Non Uniformity Normalized HLH | 0.783 |
| Minimum | 0.783 |
| Low Gray Level Emphasis HLL | 0.780 |
| Size Zone Non Uniformity Normalized LLH | 0.778 |
| Kurtosis HLL | 0.777 |
| Mean LHL | 0.774 |
| Zone Variance LHL | 0.773 |
| Total Energy LHL | 0.771 |
| Joint Entropy HHL | 0.769 |
| Dependence Non Uniformity Normalized LLL | 0.767 |
| Difference Entropy HLH | 0.766 |
| Gray Level Non Uniformity HHH | 0.765 |
| Low Gray Level Zone Emphasis LHL | 0.764 |
| Contrast LLH | 0.762 |
| Minimum LHH | 0.762 |
| Energy HLH | 0.760 |
| Entropy LLL | 0.760 |
| ID | 0.759 |
| Small Dependence Emphasis HLH | 0.759 |
| Minimum LLL | 0.757 |
| Short Run Emphasis HHL | 0.756 |
| Variance HHH | 0.755 |
| Gray Level Non Uniformity LLH | 0.755 |
| Large Dependence Low Gray Level Emphasis | 0.754 |
| Maximum HHH | 0.751 |

The groups identified in Table 3b may be reduced to include only those radiomic features that are correlated with the original significant feature of that group (i.e. one of the 16 significant features identified by the feature selection algorithm) to a degree of at least |rho|=0.800 (this includes the significant feature itself which is, by definition, correlated with itself to a degree of rho=1). For example, the groups may be reduced to those features that are correlated with the significant feature of that group to a degree of at least |rho|=0.850. For example, the groups may be reduced to those features that are correlated with the significant feature of that group to a degree of at least |rho|=0.900. For example, the groups may be reduced to those features that are correlated with the significant feature of that group to a degree of at least |rho|=0.950.

In addition to the radiomic signature being calculated on the basis of the at least two radiomic features from different clusters or groups, it may also be calculated on the basis of additional radiomic features. For example, the radiomic signature may include more than one radiomic feature from any given cluster or group, or may include radiomic features not included in any of the clusters or groups. Thus, it may be said that the radiomic signature is calculated on the basis of a plurality of radiomic features, and the plurality of radiomic features may comprise the at least two radiomic features.

For radiomic features that are associated with or predictive of stroke, the signature preferably comprises (i.e. is calculated on the basis of) two or more radiomic features of an ECR comprising or consisting of a peri-atrial region, specifically a peri-left atrial region, because these regions have been found to be most strongly associated with stroke. Specifically, the ECR preferably comprises or consists of the intra-atrial septum epicardial region and the anterior left (or right) atrial epicardial region. Radiomic features of these epicardial sub-regions have been found to be most strongly predictive of stroke and therefore provide a more reliable and useful signature for predicting stroke.

The epicardial radiomic signature may be calculated on the basis of measured values of a plurality of epicardial radiomic features of the epicardial region. The epicardial radiomic features may each be for the epicardial region as a whole, or may be calculated for sub-regions of the epicardial region, for example the intra-atrial septum region and/or the anterior left atrial region. All of the epicardial radiomic features may be calculated for the same region or sub-region, but this is not essential and different radiomic features may be calculated for different sub-regions.

Also, for stroke prediction, the radiomic features are preferably calculated for voxels within the broader attenuation (HU) range corresponding to adipose and other epicardial tissues (e.g. an attenuation range including voxels having a HU attenuation above −30 HU, e.g. about −190 to about +150). In other words, the epicardial region is preferably calculated for an epicardial region comprising or consisting of voxels within this broader HU range. This is because tissues other than adipose have been found to be predictive of stroke, so it improves the predictive power of the signature when the broader HU range is used corresponding to other epicardial tissues in addition to adipose.

Each of the radiomic signatures of the invention provides a straightforward means for characterising the peri-atrial tissue using medical imaging data. Because each of the radiomic signatures of the invention is based on a relatively small number of the total overall number of possible radiomic features that can be measured, the signature is simple to calculate and understand, and its physiological significance can be better appreciated by the clinician.

Each of the radiomic signatures of the invention provides a straightforward means for characterising an ECR using medical imaging data. Because each of the radiomic signatures of the invention is based on a relatively small number of the total overall number of possible radiomic features that can be measured, the signature is simple to calculate and understand, and its physiological significance can be better appreciated by the clinician.

System

The methods of the invention may be performed on a system, such as a computer system. The invention therefore also provides a system that is configured or arranged to perform one or more of the methods of the invention. For example, the system may comprise a computer processor configured to perform one or more of the methods, or steps of the methods, of the invention. The system may also comprise a computer-readable memory loaded with executable instructions for performing the steps of any of the methods of the invention.

In particular, the methods of deriving the radiomic signature may be performed on such a system and such systems are therefore provided in accordance with the invention. For example, the system may be configured to receive, and optionally store, a dataset comprising the values of a plurality of radiomic features of an ECR obtained from medical imaging data for each of a plurality of individuals. The system may be configured to use such a dataset to construct (e.g. derive and validate) a radiomic signature according to the methods of the invention.

Alternatively, the system may be configured to perform the method of characterising an ECR or assessing cardiac health. In particular, the invention provides a system for characterising an ECR or assessing cardiac health using medical imaging data of a subject. The system may be configured to calculate the value of a radiomic signature of an ECR using the medical imaging data. The radiomic signature may be calculated on the basis of measured values of at least two radiomic features of the ECR, and the measured values of the at least two radiomic features may be calculated from the medical imaging data.

The system may also be configured to calculate the radiomic features from medical imaging data, as described in more detail above. The system may therefore be configured to receive, and optionally store, medical imaging data, and to process the imaging data to calculate the radiomic features.

Definition of Radiomic Features

The definitions of the radiomic features referred to herein are generally well understood within the field of radiomics by reference to their name only. However, for ease or reference definitions of the features used herein are provided in Tables R1 to R7 below. The radiomic features in Tables R1 to R7 are defined in accordance with the radiomic features used by the Pyradiomics package (http://pyradiomics.readthedocs.io/en/latest/features.html, see van Griethuysen, J. J. M., Fedorov, A., Parmar, C., Hosny, A., Aucoin, N., Narayan, V., Beets-Tan, R. G. H., Fillon-Robin, J. C., Pieper, S., Aerts, H. J. W. L. (2017). Computational Radiomics System to Decode the Radiographic Phenotype. Cancer Research, 77(21), e104-e107. https://doi.org/10.1158/0008-5472.CAN-17-0339). Most features defined in Tables R1 to R7 are in compliance with feature definitions as described by the Imaging Biomarker Standardization Initiative (IBSI), which are available in Zwanenburg et al. (2016) (Zwanenburg, A., Leger, S., Vallibres, M., and Löck, S. (2016). Image biomarker standardisation initiative—feature definitions. In eprint arXiv:1612.07003 [cs.CV]). Where a definition provided below does not comply exactly from the IBSI definition, it should be understood that either definition could be used in accordance with the invention. Ultimately, the precise mathematical definition of the radiomic features is not crucial because slight modifications do not affect the general properties of the image that are measured by each of the features. Thus, slight modifications to the features (for example, the addition or subtraction of constants or scaling) and alternative definitions of the features are intended to be encompassed by the present invention.

a. First Order Statistics

These statistics describe the central tendency, variability, uniformity, asymmetry, skewness and magnitude of the attenuation values in a given region of interest (ROI), disregarding the spatial relationship of the individual voxels. As such, they describe quantitative and qualitative features of the whole ROI (ECR). A total of 19 features were calculated for each one of the eight wavelet transformations and the original CT image, as follows:

Let:

X be the attenuation or radiodensity values (e.g. in HU) of a set of $N_p$ voxels included in the region of interest (ROI)

P(i) be the first order histogram with $N_g$ discrete intensity levels, where $N_g$ is the number of non-zero bins, equally spaced from 0 with a width.

p(i) be the normalized first order histogram and equal to $$\frac{P(i)}{N_p}$$

c is a value that shifts the intensities to prevent negative values in X. This ensures that voxels with the lowest gray values contribute the least to Energy, instead of voxels with gray level intensity closest to 0. Since the HU range of adipose tissue (AT) within the ECR (−190 to −30 HU) does not include zero, c was set at c=0. Therefore, higher energy corresponds to less radiodense AT, and therefore a higher lipophilic content. However, other values of c could be used.

ε is an arbitrarily small positive number ($\approx 2.2 \times 10^{-16}$)

TABLE R1

First-order radiomic features for ECR characterization

| Radiomic feature | Interpretation |
|---|---|
| $\text{Energy} = \sum_{i=1}^{N_p} (X(i) + c)^2$ | Energy is a measure of the magnitude of voxel values in an image. A larger value implies a greater sum of the squares of these values. |
| $\text{Total Energy} = V_{voxel} \sum_{i=1}^{N_p} (X(i) + c)^2$ | Total Energy is the value of Energy feature scaled by the volume of the voxel in cubic mm. |
| $\text{Entropy} = -\sum_{i=1}^{N_g} p(i) \log_2(p(i) + \epsilon)$ | Entropy specifies the uncertainty/randomness in the image values. It measures the average amount of information required to encode the image values |
| Minimum = min(X) | The minimum gray level intensity within the ROI. |
| The 10th percentile of X | The 10th percentile of X |
| The 90th percentile of X | The 90th percentile of X |
| Maximum = max(X) | The maximum gray level intensity within the ROI. |
| $\text{Mean} = \frac{1}{N_p} \sum_{i=1}^{N_p} X(i)$ | The average (mean) gray level intensity within the ROI. |

TABLE R1-continued

First-order radiomic features for ECR characterization

| Radiomic feature | Interpretation |
| --- | --- |
| Median | The median gray level intensity within the ROI. |
| Interquartile range = $P_{75} - P_{25}$ | Here $P_{25}$ and $P_{75}$ are the $25^{th}$ and $75^{th}$ percentile of the image array, respectively. |
| Range = max(X) − min(X) | The range of gray values in the ROI. |
| $MAD = \frac{1}{N_p}\sum_{i=1}^{N_p}\lvert X(i) - \overline{X}\rvert$ | Mean Absolute Deviation (MAD) is the mean distance of all intensity values from the Mean Value of the image array. |
| $rMAD = \frac{1}{N_{10-90}}\sum_{i=1}^{N_{10-90}}\lvert X_{10-90}(i) - \overline{X}_{10-90}\rvert$ | Robust Mean Absolute Deviation (rMAD) is the mean distance of all intensity values from the Mean Value calculated on the subset of image array with gray levels in between, or equal to the $10^{th}$ and $90^{th}$ percentile. |
| $RMS\sqrt{\frac{1}{N_p}\sum_{i=1}^{N_p}(X(i)+c)^2}$ | Root Mean Squared (RMS) is the square-root of the mean of all the squared intensity values. It is another measure of the magnitude of the image values. This feature is volume-confounded, a larger value of c increases the effect of volume-confounding. |
| $\text{Skewness} = \frac{\mu_3}{\sigma^3} = \frac{\frac{1}{N_p}\sum_{i=1}^{N_p}(X(i)-\overline{X})^3}{\left(\sqrt{\frac{1}{N_p}\sum_{i=1}^{N_p}(X(i)-\overline{X})^2}\right)^3}$ | Skewness measures the asymmetry of the distribution of values about the Mean value. Depending on where the tail is elongated and the mass of the distribution is concentrated, this value can be positive or negative. (Where u3 is the 3rd central moment). |
| $\text{Kurtosis} = \frac{\mu_4}{\sigma^4} = \frac{\frac{1}{N_p}\sum_{i=1}^{N_p}(X(i)-\overline{X})^4}{\left(\frac{1}{N_p}\sum_{i=1}^{N_p}(X(i)-\overline{X})^2\right)^2}$ | Kurtosis is a measure of the 'peakedness' of the distribution of values in the image ROI. A higher kurtosis implies that the mass of the distribution is concentrated towards the tail(s) rather than towards the mean. A lower kurtosis implies the reverse: that the mass of the distribution is concentrated towards a spike near the Mean value. (Where u4 is the 4th central moment). |
| $\text{Variance} = \frac{1}{N_p}\sum_{i=1}^{N_p}(X(i)-\overline{X})^2$ | Variance is the mean of the squared distances of each intensity value from the Mean value. This is a measure of the spread of the distribution about the mean. |
| $\text{Uniformity} = \sum_{i=1}^{N_g}p(i)^2$ | Uniformity is a measure of the sum of the squares of each intensity value. This is a measure of the heterogeneity of the image array, where a greater uniformity implies a greater heterogeneity or a greater range of discrete intensity values. | b. Shape-Related Statistics

Shape-related statistics describe the size and shape of a given ROI, without taking into account the attenuation values of its voxels. Since they are independent of the gray level intensities, shape-related statistics were consistent across all wavelet transformation and the original CT image, and therefore were only calculated once. These were defined as follows:

Let:

V be the volume of the ROI in $mm^3$

A be the surface area of the ROI in $mm^2$

TABLE R2

Shape-related radiomic features for ECR characterization

| Radiomic feature | Interpretation |
| --- | --- |
| $\text{Volume} = \sum_{i=1}^{N} V_i$ | The volume of the ROI V is approximated by multiplying the number of voxels in the ROI by the volume of a single voxel $V_i$. |
| $\text{Surface Area} = \sum_{i=1}^{N} \frac{1}{2} |a_i b_i \times a_i c_i|$ | Surface Area is an approximation of the surface of the ROI in mm², calculated using a marching cubes algorithm, where N is the number of triangles forming the surface mesh of the volume (ROI), $a_i b_i$ and $a_i c_i$ are the edges of the $i^{th}$ triangle formed by points $a_i$, $b_i$ and $c_i$. |
| $\text{Surface to volume ratio} = \frac{A}{V}$ | Here, a lower value indicates a more compact (sphere-like) shape. This feature is not dimensionless, and is therefore (partly) dependent on the volume of the ROI. |
| $\text{Sphericity} = \frac{\sqrt[3]{36\pi V^2}}{A}$ | Sphericity is a measure of the roundness of the shape of the tumor region relative to a sphere. It is a dimensionless measure, independent of scale and orientation. The value range is $0 < \text{sphericity} \leq 1$, where a value of 1 indicates a perfect sphere (a sphere has the smallest possible surface area for a given volume, compared to other solids). |
| Volume Number | Total number of discrete volumes in the ROI. |
| Voxel Number | Total number of discrete voxels in the ROI. |
| Maximum 3D diameter | Maximum 3D diameter is defined as the largest pairwise Euclidean distance between surface voxels in the ROI (Feret Diameter). |
| Maximum 2D diameter (Slice) | Maximum 2D diameter (Slice) is defined as the largest pairwise Euclidean distance between ROI surface voxels in the row-column (generally the axial) plane. |
| Maximum 2D diameter (Column) | Maximum 2D diameter (Column) is defined as the largest pairwise Euclidean distance between ROI surface voxels in the row-slice (usually the coronal) plane. |
| Maximum 2D diameter (Row) | Maximum 2D diameter (Row) is defined as the largest pairwise Euclidean distance between tumor surface voxels in the column-slice (usually the sagittal) plane. |
| $\text{Major axis} = \sqrt[4]{\lambda_{major}}$ | $\lambda_{major}$ is the length of the largest principal component axis |
| $\text{Minor axis} = \sqrt[4]{\lambda_{minor}}$ | $\lambda_{minor}$ is the length of the second largest principal component axis |
| $\text{Least axis} = \sqrt[4]{\lambda_{least}}$ | $\lambda_{least}$ is the length of the smallest principal component axis |
| $\text{Elongation} = \sqrt{\frac{\lambda_{minor}}{\lambda_{major}}}$ | Here, $\lambda_{major}$ and $\lambda_{minor}$ are the lengths of the largest and second largest principal component axes. The values range between 1 (circle-like (non-elongated)) and 0 (single point or 1 dimensional line). |
| $\text{Flatness} = \sqrt{\frac{\lambda_{least}}{\lambda_{major}}}$ | Here, $\lambda_{major}$ and $\lambda_{minor}$ are the lengths of the largest and smallest principal component axes. The values range between 1 (non-flat, sphere-like) and 0 (a flat object). | c. Gray Level Co-Occurrence Matrix (GLCM)

In simple words, a GLCM describes the number of times a voxel of a given attenuation value i is located next to a voxel of j. A GLCM of size $N_g \times N_g$ describes the second-order joint probability function of an image region constrained by the mask and is defined as $P(i,j|\delta,\theta)$. The $(i,j)^{th}$ element of this matrix represents the number of times the combination of levels i and j occur in two pixels in the image, that are separated by a distance of $\delta$ pixels along angle $\theta$. The distance $\delta$ from the center voxel is defined as the distance according to the infinity norm. For $\delta=1$, this results in 2 neighbors for each of 13 angles in 3D (26-connectivity) and for $\delta=2$ a 98-connectivity (49 unique angles). In order to get rotationally invariant results, statistics are calculated in all directions and then averaged, to ensure a symmetrical GLCM.

Let:

$\epsilon$ be an arbitrarily small positive number ($\approx 2.2 \times 10^{-16}$)

$P(i,j)$ be the co-occurrence matrix for an arbitrary $\delta$ and $\theta$ $p(i,j)$ be the normalized co-occurence matrix and equal $$\frac{P(i,j)}{\sum P(i,j)}$$

$Ng$ be the number of discrete intensity levels in the image $$p_x(i) = \sum_{j=1}^{N_g} P(i,j)$$

be the marginal row probabilities $$p_y(j) = \sum_{i=1}^{N_g} P(i,j)$$

be the marginal column probabilities $\mu_x$ be the mean gray level intensity of $p_x$ and defined as $$\mu_x = \sum_{i=1}^{N_g} p_x(i) i$$

$\mu_y$ be the mean gray level intensity of $p_y$ and defined as $$\mu_y = \sum_{j=1}^{N_g} p_y(j) j$$

$\sigma_x$ be the standard deviation of $p_x$
$\sigma_y$ be the standard deviation of $p_y$ $$P_{x+y}(k) \sum_{i=1}^{N_g} \sum_{j=1}^{N_g} p(i,j), \text{ where } i+j=k, \text{ and } k=2,3,\ldots,2N_g$$

$$P_{x-y}(k) \sum_{i=1}^{N_g} \sum_{j=1}^{N_g} p(i,j), \text{ where } |i-j|=k, \text{ and } k=0,1,\ldots,N_g-1$$

$HX = -\sum_{i=1}^{N_g} p_x(i) \log_2(p_x(i) + \epsilon)$ be the entropy of $p_x$ $HY = -\sum_{j=1}^{N_g} p_y(j) \log_2(p_y(j) + \epsilon)$ be the entropy of $p_y$ $$HXY1 = -\sum_{i=1}^{N_g} \sum_{j=1}^{N_g} p(i,j) \log_2(p_x(i) p_y(j) + \epsilon)$$

$$HXY2 = -\sum_{i=1}^{N_g} \sum_{j=1}^{N_g} p_x(i) p_y(j) \log_2(p_x(i) p_y(j) + \epsilon)$$

For distance weighting, GLCM matrices are weighted by weighting factor W and then summed and normalised. Weighting factor W is calculated for the distance between neighbouring voxels by $$W = e^{-\|d\|^2},$$

where d is the distance for the associated angle.

TABLE R3

Gray Level Co-occurrence Matrix (GLCM) statistics for ECR characterization

| Radiomic feature | Interpretation |
|---|---|
| Autocorrelation $= \sum_{i=1}^{N_g} \sum_{j=1}^{N_g} p(i,j) ij$ | Autocorrelation is a measure of the magnitude of the fineness and coarseness of texture. |
| Joint average $= \mu_x = \sum_{i=1}^{N_g} \sum_{j=1}^{N_g} p(i,j) i$ | Returns the mean gray level intensity of the i distribution. |
| Cluster prominence $= \sum_{i=1}^{N_g} \sum_{j=1}^{N_g} (i+j-\mu_x-\mu_y)^4 p(i,j)$ | Cluster Prominence is a measure of the skewness and asymmetry of the GLCM. A higher value implies more asymmetry around the mean while a lower value indicates a peak near the mean value and less variation around the mean. |
| Cluster tendency $= \sum_{i=1}^{N_g} \sum_{j=1}^{N_g} (i+j-\mu_x-\mu_y)^2 p(i,j)$ | Cluster Tendency is a measure of groupings of voxels with similar gray-level values. |

TABLE R3-continued

Gray Level Co-occurrence Matrix (GLCM) statistics for ECR characterization

| Radiomic feature | Interpretation |
| --- | --- |
| $\text{Cluster shade} = \sum_{i=1}^{N_g}\sum_{j=1}^{N_g}(i+j-\mu_x-\mu_y)^3 p(i,j)$ | Cluster Shade is a measure of the skewness and uniformity of the GLCM. A higher cluster shade implies greater asymmetry about the mean. |
| $\text{Contrast} = \sum_{i=1}^{N_g}\sum_{j=1}^{N_g}(i-j)^2 p(i,j)$ | Contrast is a measure of the local intensity variation, favoring values away from the diagonal (i = j). A larger value correlates with a greater disparity in intensity values among neighboring voxels. |
| $\text{Correlation} = \dfrac{\sum_{i=1}^{N_g}\sum_{j=1}^{N_g} p(i,j)ij - \mu_x\mu_y}{\sigma_x(i)\sigma_y(j)}$ | Correlation is a value between 0 (uncorrelated) and 1 (perfectly correlated) showing the linear dependency of gray level values to their respective voxels in the GLCM |
| $\text{Difference average} = \sum_{k=0}^{N_g-1} k p_{x-y}(k)$ | Difference Average measures the relationship between occurrences of pairs with similar intensity values and occurrences of pairs with differing intensity values. |
| $\text{Difference entropy} = \sum_{k=0}^{N_g-1} p_{x-y}(k)\log_2(p_{x-y}(k)+\epsilon)$ | Difference Entropy is a measure of the randomness/variability in neighborhood intensity value differences. |
| $\text{Difference variance} = \sum_{k=0}^{N_g-1}(k-DA)^2 p_{x-y}(k)$ | Difference Variance is a measure of heterogeneity that places higher weights on differing intensity level pairs that deviate more from the mean. |
| $\text{Joint energy} = \sum_{i=1}^{N_g}\sum_{j=1}^{N_g}(p(i,j))^2$ | Joint energy is a measure of homogeneous patterns in the image. A greater joint energy implies that there are more instances of intensity value pairs in the image that neighbor each other at higher frequencies. (also known as Angular Second Moment). |
| $\text{Joint entropy} = -\sum_{i=1}^{N_g}\sum_{j=1}^{N_g} p(i,j)\log_2(p(i,j)+\epsilon)$ | Joint entropy is a measure of the randomness/variability in neighborhood intensity values. |

TABLE R3-continued

Gray Level Co-occurrence Matrix (GLCM) statistics for ECR characterization

| Radiomic feature | Interpretation |
| --- | --- |
| $IMC1 = \dfrac{HXY - HXY1}{\max\{HX, HY\}}$ | Informational measure of correlation 1 |
| $IMC2 = \sqrt{1 - e^{-2(HXYZ-HXY)}}$ | Informational measure of correlation 2 |
| $IDM = \sum_{i=1}^{N_g}\sum_{j=1}^{N_g} \dfrac{p(i,j)}{1+|i-j|^2}$ | IDM (inverse difference moment a.k.a Homogeneity 2) is a measure of the local homogeneity of an image. IDM weights are the inverse of the Contrast weights (decreasing exponentially from the diagonal i = j in the GLCM). |
| $IDMN = \sum_{i=1}^{N_g}\sum_{j=1}^{N_g} \dfrac{p(i,j)}{1+\left(\dfrac{|i-j|^2}{N_g^2}\right)}$ | IDMN (inverse difference moment normalized) is a measure of the local homogeneity of an image. IDMN weights are the inverse of the Contrast weights (decreasing exponentially from the diagonal i = j in the GLCM). Unlike Homogeneity 2, IDMN normalizes the square of the difference between neighboring intensity values by dividing over the square of the total number of discrete intensity values. |
| $ID = \sum_{i=1}^{N_g}\sum_{j=1}^{N_g} \dfrac{p(i,j)}{1+|i-j|}$ | ID (inverse difference a.k.a. Homogeneity 1) is another measure of the local homogeneity of an image. With more uniform gray levels, the denominator will remain low, resulting in a higher overall value. |
| $IDN = \sum_{i=1}^{N_g}\sum_{j=1}^{N_g} \dfrac{p(i,j)}{1+\left(\dfrac{|i-j|}{N_g}\right)}$ | IDN (inverse difference normalized) is another measure of the local homogeneity of an image. Unlike Homogeneity 1, IDN normalizes the difference between the neighboring intensity values by dividing over the total number of discrete intensity values. |
| Inverse variance $= \sum_{i=1}^{N_g}\sum_{j=1}^{N_g} \dfrac{p(i,j)}{|i-j|^2}, i \neq j$ | |

TABLE R3-continued

Gray Level Co-occurrence Matrix (GLCM) statistics for ECR characterization

| Radiomic feature | Interpretation |
| --- | --- |
| Maximum probability = max (p(i, j)) | Maximum Probability is occurrences of the most predominant pair of neighboring intensity values (also known as Joint maximum). |
| Sum average = $\sum_{k=2}^{2N_g} p_{x+y}(k)k$ | Sum Average measures the relationship between occurrences of pairs with lower intensity values and occurrences of pairs with higher intensity values. |
| Sum entropy = $\sum_{k=2}^{2N_g} p_{x+y}(k)\log_2(p_{x+y}(k) + \epsilon)$ | Sum Entropy is a sum of neighborhood intensity value differences. |
| Sum squares = $\sum_{i=1}^{N_g}\sum_{j=1}^{N_g}(i - \mu_x)^2 p(i, j)$ | Sum of Squares or Variance is a measure in the distribution of neighboring intensity level pairs about the mean intensity level in the GLCM. (Defined by IBSI as Joint Variance). | d. Gray Level Size Zone Matrix (GLSZM)

A Gray Level Size Zone (GLSZM) describes gray level zones in a ROI, which are defined as the number of connected voxels that share the same gray level intensity. A voxel is considered connected if the distance is 1 according to the infinity norm (26-connected region in a 3D, 8-connected region in 2D). In a gray level size zone matrix P(i,j) the (i,j)$^{th}$ element equals the number of zones with gray level i and size j appear in image. Contrary to GLCM and GLRLM, the GLSZM is rotation independent, with only one matrix calculated for all directions in the ROI.

Let:
$N_g$ be the number of discreet intensity values in the image
$N_s$ be the number of discreet zone sizes in the image
$N_p$ be the number of voxels in the image
$N_z$ be the number of zones in the ROI, which is equal to $$\sum_{i=1}^{N_g} \sum_{j=1}^{N_s} P(i, j)$$

and $1 \leq N_z \leq N_p$

P(i,j) be the size zone matrix p(i,j) be the normalized size zone matrix, defined as $$p(i, j) = \frac{P(i, j)}{N_z}$$

$\epsilon$ is an arbitrarily small positive number ($\approx 2.2 \times 10^{-16}$)

TABLE R4

Gray Level Size Zone Matrix (GLSZM) statistics for ECR characterization

| Radiomic feature | Interpretation |
| --- | --- |
| $SAE = \dfrac{\sum_{i=1}^{N_g}\sum_{j=1}^{N_z}\frac{P(i, j)}{j^2}}{N_z}$ | SAE (small area emphasis) is a measure of the distribution of small size zones, with a greater value indicative of smaller size zones and more fine textures. |
| $LAE = \dfrac{\sum_{i=1}^{N_g}\sum_{j=1}^{N_z} P(i, j)j^2}{N_g}$ | LAE (large area emphasis) is a measure of the distribution of large area size zones, with a greater value indicative of larger size zones and more coarse textures. |

TABLE R4-continued

Gray Level Size Zone Matrix (GLSZM) statistics for ECR characterization

| Radiomic feature | Interpretation |
|---|---|
| $GLN = \dfrac{\sum_{i=1}^{N_g}\left(\sum_{j=1}^{N_s} P(i,j)\right)^2}{N_z}$ | GLN (gray level non-uniformity) measures the variability of gray-level intensity values in the image, with a lower value indicating more homogeneity in intensity values. |
| $GLNN = \dfrac{\sum_{i=1}^{N_g}\left(\sum_{j=1}^{N_s} P(i,j)\right)^2}{N_z^2}$ | GLNN (gray level non-uniformity normalized) measures the variability of gray-level intensity values in the image, with a lower value indicating a greater similarity in intensity values. This is the normalized version of the GLN formula. |
| $SZN = \dfrac{\sum_{j=1}^{N_s}\left(\sum_{i=1}^{N_g} P(i,j)\right)^2}{N_z}$ | SZN (size zone non-uniformity) measures the variability of size zone volumes in the image, with a lower value indicating more homogeneity in size zone volumes. |
| $SZNN = \dfrac{\sum_{j=1}^{N_s}\left(\sum_{i=1}^{N_g} P(i,j)\right)^2}{N_z^2}$ | SZNN (size zone non-uniformity normalized) measures the variability of size zone volumes throughout the image, with a lower value indicating more homogeneity among zone size volumes in the image. This is the normalized version of the SZN formula. |
| Zone Percentage $= \dfrac{N_z}{N_p}$ | ZP (Zone Percentage) measures the coarseness of the texture by taking the ratio of number of zones and number of voxels in the ROI. Values are in range $1/N_p \leq ZP \leq 1$, with higher values indicating a larger portion of the ROI consists of small zones (indicates a more fine texture). |
| $GLV = \sum_{i=1}^{N_g}\sum_{j=1}^{N_s} p(i,j)(i-\mu)^2$, where $\mu = \sum_{i=1}^{N_g}\sum_{j=1}^{N_s} p(i,j)i$ | Gray level variance (GLV) measures the variance in gray level intensities for the zones. |
| $ZV = \sum_{i=1}^{N_g}\sum_{j=1}^{N_s} p(i,j)(j-\mu)^2$, where $\mu = \sum_{i=1}^{N_g}\sum_{j=1}^{N_s} p(i,j)j$ | Zone Variance (ZV) measures the variance in zone size volumes for the zones. |
| $ZE = -\sum_{i=1}^{N_g}\sum_{j=1}^{N_s} p(i,j)\log_2(p(i,j)+\epsilon)$ | Zone Entropy (ZE) measures the uncertainty/randomness in the distribution of zone sizes and gray levels. A higher value indicates more heterogeneneity in the texture patterns. |
| $LGLZE = \dfrac{\sum_{i=1}^{N_g}\sum_{j=1}^{N_s} \dfrac{P(i,j)}{i^2}}{N_z}$ | LGLZE (low gray level zone emphasis) measures the distribution of lower gray-level size zones, with a higher value indicating a greater proportion of lower gray-level values and size zones in the image. |
| $HGLZE = \dfrac{\sum_{i=1}^{N_g}\sum_{j=1}^{N_s} P(i,j)i^2}{N_z}$ | HGLZE (high gray level zone emphasis) measures the distribution of the higher gray-level values, with a higher value indicating a greater proportion of higher gray-level values and size zones in the image. |
| $SALGLE = \dfrac{\sum_{i=1}^{N_g}\sum_{j=1}^{N_s} \dfrac{P(i,j)}{i^2 j^2}}{N_z}$ | SALGLE (small area low gray level emphasis) measures the proportion in the image of the joint distribution of smaller size zones with lower gray-level values. |

TABLE R4-continued

Gray Level Size Zone Matrix (GLSZM) statistics for ECR characterization

| Radiomic feature | Interpretation |
| --- | --- |
| $SAHGLE = \dfrac{\sum_{i=1}^{N_g}\sum_{j=1}^{N_s}\dfrac{P(i,j)i^2}{j^2}}{N_z}$ | SAHGLE (small area high gray level emphasis) measures the proportion in the image of the joint distribution of smaller size zones with higher gray-level values. |
| $LALGLE = \dfrac{\sum_{i=1}^{N_g}\sum_{j=1}^{N_s}\dfrac{P(i,j)j^2}{i^2}}{N_z}$ | LALGLE (low area low gray level emphasis) measures the proportion in the image of the joint distribution of larger size zones with lower gray-level values. |
| $LAHGLE = \dfrac{\sum_{i=1}^{N_g}\sum_{j=1}^{N_s}P(i,j)i^2 j^2}{N_z}$ | LAHGLE (low area high gray level emphasis) measures the proportion in the image of the joint distribution of larger size zones with higher gray-level values. | e. Gray Level Run Length Matrix (GLRLM)

A Gray Level Run Length Matrix (GLRLM) describes gray level runs, which are defined as the length in number of pixels, of consecutive pixels that have the same gray level value. In a gray level run length matrix $P(i,j|\theta)$, the $(i,j)^{th}$ element describes the number of runs with gray level $i$ and length $j$ occur in the image (ROI) along angle $\theta$.

Let:

$N_g$ be the number of discreet intensity values in the image
$N_r$ be the number of discreet run lengths in the image
$N_p$ be the number of voxels in the image
$N_z(\theta)$ be the number of runs in the image along angle $\theta$, which is equal to $$\sum_{i=1}^{N_g}\sum_{j=1}^{N_r} P(i,j|\theta) \text{ and } 1 \leq N_z(\theta) \leq N_p$$

$P(i,j|\theta)$ be the run length matrix for an arbitrary direction $\theta$ $p(i,j|\theta)$ be the normalized run length matrix, defined as $$p(i,j|\theta) \dfrac{P(i,j|\theta)}{N_z(\theta)}$$

$\epsilon$ is an arbitrarily small positive number ($\approx 2.2\times 10^{-16}$)

By default, the value of a feature is calculated on the GLRLM for each angle separately, after which the mean of these values is returned. If distance weighting is enabled, GLRLMs are weighted by the distance between neighbouring voxels and then summed and normalised. Features are then calculated on the resultant matrix. The distance between neighbouring voxels is calculated for each angle using the norm specified in 'weightingNorm'

TABLE R5

Gray Level Run Length Matrix (GLRLM) statistics for ECR characterization

| Radiomic feature | Interpretation |
| --- | --- |
| $SRE = \dfrac{\sum_{i=1}^{N_g}\sum_{j=1}^{N_r}\dfrac{P(i,j|\theta)}{j^2}}{N_z(\theta)}$ | SRE (Short Run Emphasis) is a measure of the distribution of short run lengths, with a greater value indicative of shorter run lengths and more fine textural textures |
| $LRE = \dfrac{\sum_{i=1}^{N_g}\sum_{j=1}^{N_r} P(i,j|\theta)j^2}{N_z(\theta)}$ | LRE (Long Run Emphasis) is a measure of the distribution of long run lengths, with greater value indicative of longer run lengths and more coarse structural textures. |
| $GLN = \dfrac{\sum_{i=1}^{N_g}\left(\sum_{j=1}^{N_r} P(i,j|\theta)\right)^2}{N_z(\theta)}$ | GLN (Gray Level Non-uniformity) measures the similarity of gray-level intensity values in the image, where a lower GLN value correlates with a greater similarity in intensity values. |

TABLE R5-continued

Gray Level Run Length Matrix (GLRLM) statistics for ECR characterization

| Radiomic feature | Interpretation |
| --- | --- |
| $GLNN = \dfrac{\sum_{i=1}^{N_g}\left(\sum_{j=1}^{N_r} P(i,j\|\theta)\right)^2}{N_z(\theta)^2}$ | GLNN (Gray Level Non-uniformity Normalized) measures the similarity of gray-level intensity values in the image, where a lower GLNN value correlates with a greater similarity in intensity values. This is the normalized version of the GLN formula. |
| $RLN = \dfrac{\sum_{j=1}^{N_r}\left(\sum_{i=1}^{N_g} P(i,j\|\theta)\right)^2}{N_z(\theta)}$ | RLN (Run Length Non-uniformity) measures the similarity of run lengths throughout the image, with a lower value indicating more homogeneity among run lengths in the image. |
| $RLNN = \dfrac{\sum_{j=1}^{N_r}\left(\sum_{i=1}^{N_g} P(i,j\|\theta)\right)^2}{N_z(\theta)^2}$ | RLNN (Run Length Non-uniformity) measures the similarity of run lengths throughout the image, with a lower value indicating more homogeneity among run lengths in the image. This is the normalized version of the RLN formula. |
| $RP = \dfrac{N_z(\theta)}{N_p}$ | RP (Run Percentage) measures the coarseness of the texture by taking the ratio of number of runs and number of voxels in the ROI. Values are in range $1/N_vHD_p \leq RP \leq 1$, with higher values indicating a larger portion of the ROI consists of short runs (indicates a more fine texture) |
| $GLV = \sum_{i=1}^{N_g}\sum_{j=1}^{N_r} p(i,j\|\theta)(i-\mu)^2$, where $\mu = \sum_{i=1}^{N_g}\sum_{j=1}^{N_r} p(i,j\|\theta)i$ | GLV (Gray Level Variance) measures the variance in gray level intensity for the runs. |
| $RV = \sum_{i=1}^{N_g}\sum_{j=1}^{N_r} p(i,j\|\theta)(j-\mu)^2$, where $\mu = \sum_{i=1}^{N_g}\sum_{j=1}^{N_r} p(i,j\|\theta)j$ | RV (Run Variance) is a measure of the variance in runs for the run lengths. |
| $RE = -\sum_{i=1}^{N_g}\sum_{j=1}^{N_r} p(i,j\|\theta)\log_2(p(i,j\|\theta)+\epsilon)$ | RE (Run Entropy) measures the uncertainty/randomness in the distribution of run lengths and gray levels. A higher value indicates more heterogeneity in the texture patterns. |
| $LGLRE = \dfrac{\sum_{i=1}^{N_g}\sum_{j=1}^{N_r}\dfrac{P(i,j\|\theta)}{i^2}}{N_z(\theta)}$ | LGLRE (low gray level run emphasis) measures the distribution of low gray-level values, with a higher value indicating a greater concentration of low gray-level values in the image. |

TABLE R5-continued

Gray Level Run Length Matrix (GLRLM) statistics for ECR characterization

| Radiomic feature | Interpretation |
| --- | --- |
| $HGLRE = \dfrac{\sum_{i=1}^{N_g}\sum_{j=1}^{N_r} P(i,j|\theta)i^2}{N_z(\theta)}$ | HGLRE (high gray level run emphasis) measures the distribution of the higher gray-level values, with a higher value indicating a greater concentration of high gray-level values in the image. |
| $SRLGLE = \dfrac{\sum_{i=1}^{N_g}\sum_{j=1}^{N_r} \dfrac{P(i,j|\theta)}{i^2 j^2}}{N_z(\theta)}$ | SRLGLE (short run low gray level emphasis) measures the joint distribution of shorter run lengths with lower gray-level values |
| $SRHGLE = \dfrac{\sum_{i=1}^{N_g}\sum_{j=1}^{N_r} \dfrac{P(i,j|\theta)i^2}{j^2}}{N_z(\theta)}$ | SRHGLE (short run high gray level emphasis) measures the joint distribution of shorter run lengths with higher gray-level values |
| $LRLGLRE = \dfrac{\sum_{i=1}^{N_g}\sum_{j=1}^{N_r} \dfrac{P(i,j|\theta)j^2}{i^2}}{N_z(\theta)}$ | LRLGLRE (long run low gray level emphasis) measures the joint distribution of long run lengths with lower gray-level values. |
| $LRHGLRE = \dfrac{\sum_{i=1}^{N_g}\sum_{j=1}^{N_r} P(i,j|\theta)i^2 j^2}{N_z(\theta)}$ | LRHGLRE (long run high gray level run emphasis) measures the joint distribution of long run lengths with higher gray-level values. | f. Neigbouring Gray Tone Difference Matrix (NGTDM) Features

A Neighbouring Gray Tone Difference Matrix quantifies the difference between a gray value and the average gray value of its neighbours within distance δ. The sum of absolute differences for gray level i is stored in the matrix. Let $X_{gl}$ be a set of segmented voxels and $x_{gl}(j_x,j_y,j_z)\in X_{gl}$ be the gray level of a voxel at position $(j_x,j_y,j_z)$, then the average gray level of the neighbourhood is:

$$\overline{A}_i = \overline{A}(j_x, j_y, j_z) = \frac{1}{W}\sum_{k_x=-\delta}^{\delta}\sum_{k_y=-\delta}^{\delta}\sum_{k_z=-\delta}^{\delta} x_{gl}(j_x+k_x, j_y+k_y, j_z+k_z),$$

where $(k_x, k_y, k_z) \neq (0,0,0)$ and $x_{gl}(j_x+k_x, j_y+k_y, j_z+k_z) \in X_{gl}$ Here, W is the number of voxels in the neighbourhood that are also in $X_{gl}$.

Let:

$n_i$ be the number of voxels in $X_{gl}$ with gray level i Nv,p be the total number of voxels in $X_{gl}$ and equal to $\Sigma n_i$ (i.e. the number of voxels with a valid region; at least 1 neighbor). $N_{v,p} \leq N_p$, where $N_p$ is the total number of voxels in the ROI.

$p_i$ be the gray level probability and equal to $n_i/N_v$ $$s_i = \begin{cases} \sum^{n_i} |i - \overline{A}_i| & \text{for } n_i \neq 0 \\ 0 & \text{for } n_i = 0 \end{cases}$$

be the sum of absolute differences for gray level i $N_g$ be the number of discreet gray levels $N_{g,p}$ be the number of gray levels where $p_i \neq 0$

TABLE R6

Neigbouring Gray Tone Difference Matrix (NGTDM) for ECR characterization

| Radiomic feature | Interpretation |
| --- | --- |
| $\text{Coarseness} = \dfrac{1}{\sum_{i=1}^{N_g} p_i s_i}$ | Coarseness is a measure of average difference between the |

TABLE R6-continued

Neigbouring Gray Tone Difference Matrix (NGTDM) for ECR characterization

| Radiomic feature | Interpretation |
|---|---|
| | center voxel and its neighbourhood and is an indication of the spatial rate of change. A higher value indicates a lower spatial change rate and a locally more uniform texture. |
| $\text{Contrast} = \left(\frac{1}{N_{g,p}(N_{g,p}-1)}\sum_{i=1}^{N_g}\sum_{j=1}^{N_g} p_i p_j (i-j)^2\right)\left(\frac{1}{N_{v,p}}\sum_{i=1}^{N_g} s_i\right),$ where $p_i \neq 0, p_j \neq 0$ | Contrast is a measure of the spatial intensity change, but is |
| | also dependent on the overall gray level dynamic range. Contrast is high when both the dynamic range and the spatial change rate are high, i.e. an image with a large range of gray levels, with large changes between voxels and their neighbourhood. |
| $\text{Busyness} = \frac{\sum_{i=1}^{N_g} p_i s_i}{\sum_{i=1}^{N_g}\sum_{j=1}^{N_g} |ip_i - jp_i|},$ where $p_i \neq 0, p_j \neq 0$ | A measure of the change from a pixel to its neighbour. A high value for busyness indicates a 'busy' image, with rapid changes of intensity between pixels and its neighbourhood. |
| $\text{Complexity} = \frac{1}{N_{v,p}}\sum_{i=1}^{N_g}\sum_{j=1}^{N_g} |i-j|\frac{p_i s_i + p_j s_j}{p_i + p_j},$ where $p_i \neq 0, p_j \neq 0$ | An image is considered complex when there are many primitive components in the image, i.e. the image is non-uniform and there are many rapid changes in gray level intensity. |

TABLE R6-continued

Neigbouring Gray Tone Difference Matrix (NGTDM) for ECR characterization

| Radiomic feature | Interpretation |
|---|---|
| $\text{Strength} = \dfrac{\sum_{i=1}^{N_g} \sum_{j=1}^{N_g} (p_i + p_j)(i-j)^2}{\sum_{i=1}^{N_g} s_i}$, where $p_i \neq 0, p_j \neq 0$ | Strength is a measure of the primitives in an image. Its value is high when the primitives are easily defined and visible, i.e. an image with slow change in intensity but more large coarse differences in gray level intensities. | g. Gray Level Dependence Matrix (GLDM)

A Gray Level Dependence Matrix (GLDM) quantifies gray level dependencies in an image. A gray level dependency is defined as the number of connected voxels within distance $\delta$ that are dependent on the center voxel. A neighbouring voxel with gray level j is considered dependent on center voxel with gray level i if $|i-j| \leq \alpha$. In a gray level dependence matrix $P(i,j)$ the $(i,j)^{th}$ element describes the number of times a voxel with gray level i with j dependent voxels in its neighbourhood appears in image.

$N_g$ be the number of discreet intensity values in the image
$N_d$ be the number of discreet dependency sizes in the image
$N_z$ be the number of dependency zones in the image, which is equal to $$\sum_{i=1}^{N_g} \sum_{j=1}^{N_d} P(i,j)$$

$P(i,j)$ be the dependence matrix
$p(i,j)$ be the normalized dependence matrix, defined as $$p(i,j) \frac{P(i,j)}{N_z}$$

TABLE R7

Gray Level Dependence Matrix (GLDM) statistics for ECR characterization

| Radiomic feature | Interpretation |
|---|---|
| $SDE = \dfrac{\sum_{i=1}^{N_g} \sum_{j=1}^{N_d} \frac{P(i,j)}{i^2}}{N_z}$ | SDE (Small Dependence Emphasis): A measure of the distribution of small dependencies, with a greater value indicative of smaller dependence and less homogeneous textures. |
| $LDE = \dfrac{\sum_{i=1}^{N_g} \sum_{j=1}^{N_d} P(i,j) j^2}{N_z}$ | LDE (Large Dependence Emphasis): A measure of the distribution of large dependencies, with a greater value indicative of larger dependence and more homogeneous textures |

TABLE R7-continued

Gray Level Dependence Matrix (GLDM) statistics for ECR characterization

| Radiomic feature | Interpretation |
|---|---|
| $GLN = \dfrac{\sum_{i=1}^{N_g} \left(\sum_{j=1}^{N_d} P(i,j)\right)^2}{\sum_{i=1}^{N_g} \sum_{j=1}^{N_d} P(i,j)}$ | GLN (Gray Level Non-Uniformity): Measures the similarity of gray-level intensity values in the image, where a lower GLN value correlates with a greater similarity in intensity values. |
| $DN = \dfrac{\sum_{j=1}^{N_d} \left(\sum_{i=1}^{N_g} P(i,j)\right)^2}{N_z}$ | DN (Dependence Non-Uniformity): Measures the similarity of dependence throughout the image, with a lower value indicating more homogeneity among dependencies in the image. |
| $DNN = \dfrac{\sum_{j=1}^{N_d} \left(\sum_{i=1}^{N_g} P(i,j)\right)^2}{N_z^2}$ | DNN (Dependence Non-Uniformity Normalized): Measures the similarity of dependence throughout the image, with a lower value indicating more homogeneity among dependencies in the image. This is the normalized version of the DLN formula. |
| $GLV = \sum_{i=1}^{N_g} \sum_{j=1}^{N_d} p(i,j)(i-\mu)^2$, where $\mu = \sum_{i=1}^{N_g} \sum_{j=1}^{N_d} ip(i,j)$ | GLV (Gray Level Variance): Measures the variance in grey level in the image. |
| $DV = \sum_{i=1}^{N_g} \sum_{j=1}^{N_d} p(i,j)(j-\mu)^2$, where $\mu = \sum_{i=1}^{N_g} \sum_{j=1}^{N_d} jp(i,j)$ | DV (Dependence Variance): Measures the variance in dependence size in the image. |
| $DE = -\sum_{i=1}^{N_g} \sum_{j=1}^{N_d} p(i,j) \log_2(p(i,j) + \epsilon)$ | DE (Dependence Entropy): Measures the entropy in dependence size in the image. |

TABLE R7-continued

Gray Level Dependence Matrix (GLDM) statistics for ECR characterization

| Radiomic feature | Interpretation |
| --- | --- |
| $LGLE = \dfrac{\sum_{i=1}^{N_g} \sum_{j=1}^{N_d} \dfrac{P(i,j)}{i^2}}{N_z}$ | LGLE (Low Gray Level Emphasis): Measures the distribution of low gray-level values, with a higher value indicating a greater concentration of low gray-level values in the image |
| $HGLE = \dfrac{\sum_{i=1}^{N_g} \sum_{j=1}^{N_d} P(i,j) i^2}{N_z}$ | HGLE (High Gray Level Emphasis): Measures the distribution of the higher gray-level values, with a higher value indicating a greater concentration of high gray-level values in the image. |
| $SDLGLE = \dfrac{\sum_{i=1}^{N_g} \sum_{j=1}^{N_d} \dfrac{P(i,j)}{i^2 j^2}}{N_z}$ | SDLGLE (Small Dependence Low Gray Level Emphasis): Measures the joint distribution of small dependence with lower gray-level values. |
| $SDHGLE = \dfrac{\sum_{i=1}^{N_g} \sum_{j=1}^{N_d} \dfrac{P(i,j) i^2}{j^2}}{N_z}$ | SDHGLE (Small Dependence High Gray Level Emphasis): Measures the joint distribution of small dependence with higher gray-level values. |
| $LDLGLE = \dfrac{\sum_{i=1}^{N_g} \sum_{j=1}^{N_d} \dfrac{P(i,j) j^2}{i^2}}{N_z}$ | LDLGLE (Large Dependence Low Gray Level Emphasis): Measures the joint distribution of large dependence with lower gray-level values. |
| $LDHGLE = \dfrac{\sum_{i=1}^{N_g} \sum_{j=1}^{N_d} P(i,j) i^2 j^2}{N_z}$ | LDHGLE (Large Dependence High Gray Level Emphasis): Measures the joint distribution of large dependence with higher gray-level values. |

EXAMPLES

Example 1

Methods

Study Design

Arm A was a nested cases-controls study from a cohort (cohort A) of 2,246 patients undergoing diagnostic coronary CT angiography (Cleveland Clinic, US). Patients with AF (n=155) were 1:1 matched to control subjects (n=155) without known AF history. The two groups were matched for age, sex, cardiovascular risk factors and scan acquisition details. This arm was used to identify radiomic features of an epicardial region, in particular periatrial fat or adipose tissue, that are independently associated with AF in order to develop a relevant radiomic score of periatrial fat associated with cardiac, and in particular atrial health.

Arm B comprised of an independent cohort (cohort B) of 225 patients undergoing coronary artery bypass grafting surgery (CABG). Patients underwent coronary CT angiography scans and atrial tissue samples were collected perioperatively for myocardial phenotyping as described below. Patients were followed-up in-hospital for the development of AF. This cohort was used a) for the external validation of the developed epicardial radiomic score from Arm A against atrial biology and b) to explore its predictive value for postoperative heart arrhythmia development, in particular AF development.

Computerised Tomography Studies

Participants in Study Arms A and B underwent coronary CT angiography imaging using a standardized clinical protocol. Heart rate was optimised using intravenous injection of beta-blockers and sublingual glyceryl-trinitrate (800 ug) was also administered to achieve maximum coronary vasodilatation. An iodine-based contrast was administered intravenously to achieve vessel opacification and diagnosis of obstructive coronary artery disease. A prospectively ECG-triggered axial acquisition CT scan was obtained with the carina and the diaphragm used as cranial and caudal landmarks respectively. For the analysis of adipose tissue radiomic features raw DICOM (Digital Imaging and Communications in Medicine) images were transferred to a dedicated workstation and further post-processed by using 3D Slicer (see below).

Radiomic Feature Extraction of Periatrial Adipose Tissue

Calculation of radiomic features in periatrial adipose tissue was performed in CT scans using the 3D Slicer software (v.4.9.0-2017-12-18 r26813, available at http://www.slicer.org; see Fedorov, A. et al. 3D Slicer as an image computing platform for the Quantitative Imaging Network. *Magn Reson Imaging* 30, 1323-1341, doi:10.1016/j.mri.2012.05.001 (2012)). Segmentation of adipose tissue was performed by manual contouring of periatrial epicardial adipose tissue located in-between the level of the pulmonary veins and by using a −190 to −30 Hounsfield Units (HU) mask for fat identification. The segmented adipose tissue was subsequently used to calculate and extract a series of radiomic features, using the SlicerRadiomics extension of 3D Slicer, which incorporates the Pyradiomics library of radiomic features into 3D Slicer (see van Griethuysen, J. J. M. et al. Computational Radiomics System to Decode the Radiographic Phenotype. *Cancer Res* 77, e104-e107, doi: 10.1158/0008-5472.CAN-17-0339 (2017)). Shape-related and first-order radiomic features were calculated using the raw HU values of the segmented adipose tissue. For calculation of texture features (GLCM, GLDM, GLRLM, GLSZM, and NGTDM), adipose tissue voxels were discretized into 16 bins of equal width (width of 10 HU), to reduce noise while allowing a sufficient resolution to detect biologically significant spatial changes in adipose tissue attenuation. First order and texture-based statistics were also calculated for three-dimensional wavelet transformations of the original image resulting in eight additional sets of radiomic features, as described above.

Harvesting of Human Myocardium Samples

During CABG, myocardial tissue samples were collected from the site of right atrial appendage (as previously described in Antonopoulos, A. S. et al. Mutual Regulation of Epicardial Adipose Tissue and Myocardial Redox State by PPAR-gamma/Adiponectin Signalling. *Circ Res* 118, 842-855, doi:10.1161/CIRCRESAHA.115.307856 (2016)) and transferred to the lab into oxygenated (95% $O_2$/5% $CO_2$) ice-cold buffer for further studies.

Myocardial Superoxide Measurements

Myocardial $O_2^-$ production was measured in samples of right atrium appendages using lucigenin (5 μmol/L)-enhanced chemiluminescence, as described in Antoniades, C. et al. Myocardial redox state predicts in-hospital clinical outcome after cardiac surgery effects of short-term preoperative statin treatment. *J Am Coll Cardiol* 59, 60-70, doi:10.1016/j.jacc.2011.08.062 (2012). Myocardial tissue was homogenised in ice-cold Krebs HEPES Buffer pH 7.35 in the presence of protease inhibitor (Roche Applied Science, Indianapolis, IN) using a pre-cooled Polytron homogeniser.

Gene Expression Studies in Human Atrial Myocardium

Samples of atrial myocardial tissue were snap frozen in QIAzol (Qiagen) and stored at −80° C. RNA was extracted using the RNeasy Micro or Mini kit (Qiagen) and ribonucleic acid was converted into complementary DNA (Quantitect Rev. Transcription kit—Qiagen). The cDNA was then subjected to qPCR using TaqMan probes (Applied Biosystems) for TNFA (Assay ID Hs01113624_g1), IL6 (Assay ID Hs00985639_m1), IFNG (Assay ID Hs00989291_m1), COLIA1 (Assay ID Hs00164004_m1), NPPA (Assay ID Hs00383230_g1), BNP (Assay ID Hs00173590_m1 and PGK1 was used as house-keeping gene (Assay ID Hs00943178_g1). The reactions were performed in triplicate in 384-well plates, using 5 ng of cDNA per reaction, on an ABI 7900HT Fast Real-Time PCR System (Applied Biosystems). The efficiency of the reaction in each plate was determined based on the slope of the standard curve; expression of each gene of interest relative to its housekeeping gene was calculated using the Pfaffl method.

Statistical Analysis

Principal components analysis: In Cohort A, all 843 calculated adipose tissue radiomic features were included in principal component analysis to identify principal components that describe most of the phenotypic variation in the study population. A scree plot of principal components against their eigenvalues was constructed. All principal components with an eigenvalue above 1 were then included in a logistic regression model with a backward elimination for AF classification as the dependent variable, to identify principal components (PCs) of periatrial fat radiomic features that are independently associated with AF.

Unsupervised clustering of the study population by adipose tissue radiomic features: The association of each of the radiomic features with AF in Arm A was initially explored by receiver operating characteristic (ROC) curve analysis for AF classification. The strength of the statistical association (p-value, where the p-value is the probability value or asymptotic significance) for all radiomic features was graphically represented on a Manhattan plot, and was further rigorously adjusted by Benjamini-Hochberg correction using a false discovery rate of 0.10. The final 33 radiomic features that were independently associated with AF were then used to perform hierarchical clustering of the population of Arm A (using the Ward D2 method and the squared Euclidean distance, hclust R package, for example, as described in Langfelder, P. & Horvath, S. Fast R Functions for Robust Correlations and Hierarchical Clustering. *J Stat Softw* 46 (2012)). The variation in each of the selected radiomic features across the observations of Arm A cohort was represented in a relevant heat map with a row dendrogram indicating the clustering of patients. Differences in the distribution of AF prevalence, risk factors or biochemical data between the two clusters of patients was then explored by use of chi-square or independent t-test as appropriate.

Feature selection and machine learning for the radiomic fingerprint of AF on periatrial fat: The relationships between the selected radiomic features were visually inspected by a correlation plot. For further feature selection and development of a radiomic score of periatrial fat, the cohort was split using a random seed into a training (80%) and test (20%) cohort. The features were then fed into machine learning algorithms (caret R package, see Kuhn, M. *Caret: Classification and regression training*. Vol. 1 (2013)) to identify the one with the best performance (AUC or c-statistics) for AF classification (i.e. distinguishing those with versus those without AF). The model was trained using 5-fold internal cross-validation repeated 3 times (5×3 folds). The accuracy of the final model was assessed in the training cohort, and then externally validated in the test cohort. The final model was used to develop a radiomic score of periatrial fat based on the predicted probability for AF.

Validation of a radiomic score of periatrial fat against atrial tissue phenotype: The developed radiomic score of periatrial fat was externally tested in an independent cohort of patients undergoing CABG (n=225, Arm B) to validate it against atrial tissue phenotype. The radiomic features of periatrial fat of Arm B patients were extracted using a similar approach and then a radiomic score of periatrial fat was assigned to each of them based on the developed algorithm of Arm A. The associations of periatrial fat radiomic score against atrial gene expression profile, atrial redox state were assessed in bivariate analysis using unpaired t-test between groups, while the risk of postoperative AF was explored in Kaplan-Meier curves in survival analysis as appropriate.

Continuous variables between two groups were compared by Student's t-test, whereas categorical variables were compared using Pearson's Chi-square test. The analysis was performed using R v3.4 (packages: caret, hclust) and SPSS version 25.0. All tests were two-sided and a was set at 0.05, unless specified otherwise.

Results

Radiomic Feature Extraction and Principal Component Analysis

The study design is summarized in FIG. 1. In cohort A, a total of 2,246 patients underwent diagnostic coronary CT angiography (Cleveland Clinic, US). The CT imaging datasets were used to extract the radiomic features of periatrial fat. A nested cases-controls analysis (n=310) of 155 subjects with AF versus 155 control individuals (in sinus rhythm) was performed, by complete 1:1 matching of subjects for age, sex, cardiovascular risk factors and scan acquisition details (Table 4).

TABLE 4

| Study population demographics | | | | |
|---|---|---|---|---|
| | Arm A | | | Arm B |
| | Controls (n = 155) | AF (n = 155) | p-value | (n = 225) |
| Clinical demographics | | | | |
| Age, years | 54.40 (14.4) | 54.29 (14.5) | 0.947 | 66.2 ± 0.6 |
| Male sex (%) | 100 (64.5) | 96 (64.4) | 0.999 | 193 (86) |
| Body mass index, kg/m$^2$ | 29.38 (5.85) | 29.57 (6.04) | 0.773 | 28.2 ± 0.28 |
| Smoking history (%) | 35 (22.6) | 27 (18.1) | 0.411 | 135 (60) |
| Hypertension (%) | 75 (48.4) | 72 (48.3) | 0.999 | 166 (73.8) |
| Dyslipidaemia (%) | 88 (56.8) | 85 (57.0) | 0.999 | 202 (89.8) |
| Diabetes (%) | 15 (9.7) | 13 (8.7) | 0.929 | 54 (24.0) |

TABLE 4-continued

| | Study population demographics | | | |
|---|---|---|---|---|
| | Arm A | | | Arm B |
| | Controls (n = 155) | AF (n = 155) | p-value | (n = 225) |
| Myocardial infarction (%) | 8 (5.2) | 11 (8.4) | 0.441 | 103 (45.8) |
| ICD/PPM (%) | 5 (3.2) | 19 (12.8) | 0.004 | — |
| Stroke (%) | 8 (5.2) | 19 (12.8) | 0.195 | 20 (8.9) |
| Medication | | | | |
| Beta blockers (%) | 24 (15.5) | 42 (28.2) | 0.011 | 143 (63.5) |
| Statins (%) | 58 (37.4) | 68 (45.6) | 0.181 | 202 (89.8) |
| Aspirin (%) | 78 (50.3) | 77 (51.7) | 0.903 | 168 (74.7) |
| $P2Y_{12}$ inhibitors (%) | 10 (6.4) | 9 (6.1) | 0.999 | 56 (24.8) |
| Calcium channel blockers (%) | 26 (16.8) | 39 (26.2) | 0.063 | 59 (26.0) |
| ACEi/ARBS (%) | 49 (31.6) | 58 (38.9) | 0.204 | 149 (66.2) |
| OACs (%) | 8 (5.2) | 94 (63.1) | <0.001 | |
| Biochemical data | | | | |
| Hemoglobin, % | 13.92 (1.30) | 13.55 (1.75) | 0.038 | 7.25 (4.95) |
| Creatinine, md/dL | 0.97 (0.45) | 0.92 (0.19) | 0.225 | 0.92 (0.24) |
| Total cholesterol, mg/dL | 179.5 (40.4) | 168.3 (40.0) | 0.055 | 130.7 (40.6) |
| LDL, mg/dL | 92.3 (66.4) | 100.5 (68.2) | 0.401 | 70.8 (34.8) |
| HDL, mg/dL | 51.8 (19.2) | 51.19 (16.1) | 0.795 | 33.3 (11.6) |
| Triglycerides, mg/dL | 125.1 (126.1) | 116.2 (74.9) | 0.545 | 132.9 (106.3) |
| Technical acquisition details | | | | |
| Slice thickness (%) | | | 0.093 | |
| 0.75 mm | 13 (8.4) | 23 (15.4) | | |
| 0.90 mm | 142 (91.6) | 125 (83.9) | | |
| Tube voltage 120ke V (%) | 118 (76.1) | 115 (77.2) | 0.935 | |
| Scanner type (%) | | | 0.124 | |
| SOMATOM Definition | | | | |
| Flash | 11 (7.1) | 21 (14.1) | | |
| Philips Brilliance iCT | 142 (91.6) | 127 (85.2) | | |
| SOMATOM Force | 2 (1.3) | 1 (0.7) | | |

ACEi: angiotensin converting enzyme inhibitors; ARBs: angiotensin receptor blockers; HDL: high density lipoprotein; ICD: intracardiac defibrillator; LDL: low density lipoproteinl; PPM: permanent pacemaker.

A total of 843 radiomic features were calculated by segmentation of periatrial adipose tissue (around the left atrium located at the level between the pulmonary veins), as summarised in Table 5. These included 15 shape-related features, 18 first order statistics, 15 Gray Level Co-occurrence Matrix (GLCM), 18 Gray Level Dependence Matrix (GLDM), 16 Gray Level Run-Length Matrix (GLRLM), 16 Gray Level Size Zone Matrix (GLSZM), and 5 Neighbouring Gray Tone Difference Matrix (NGTDM) features, as defined in Tables R1 to R7, as well as eight wavelet transformations for each one of them.

TABLE 5

| | Breakdown of radiomic features. | | |
|---|---|---|---|
| | Original | Wavelets transformations (n = 8) | All |
| First order | 18 | 144 | 162 |
| Shape-related | 15 | — | 15 |
| GLCM | 23 | 184 | 207 |
| GLDM | 14 | 112 | 126 |
| GLRLM | 16 | 128 | 144 |
| GLSZM | 16 | 128 | 144 |
| NGTDM | 5 | 40 | 45 |
| Total | 107 | 736 | 843 |

GLCM: gray level co-occurrence matrix; GLDM: gray level dependence matrix; GLRLM: gray level run length matrix; GLSZM: gray level size zone matrix; NGTDM: neighbouring gray tone dependence matrix; AT: adipose tissue.

Figure 2A:
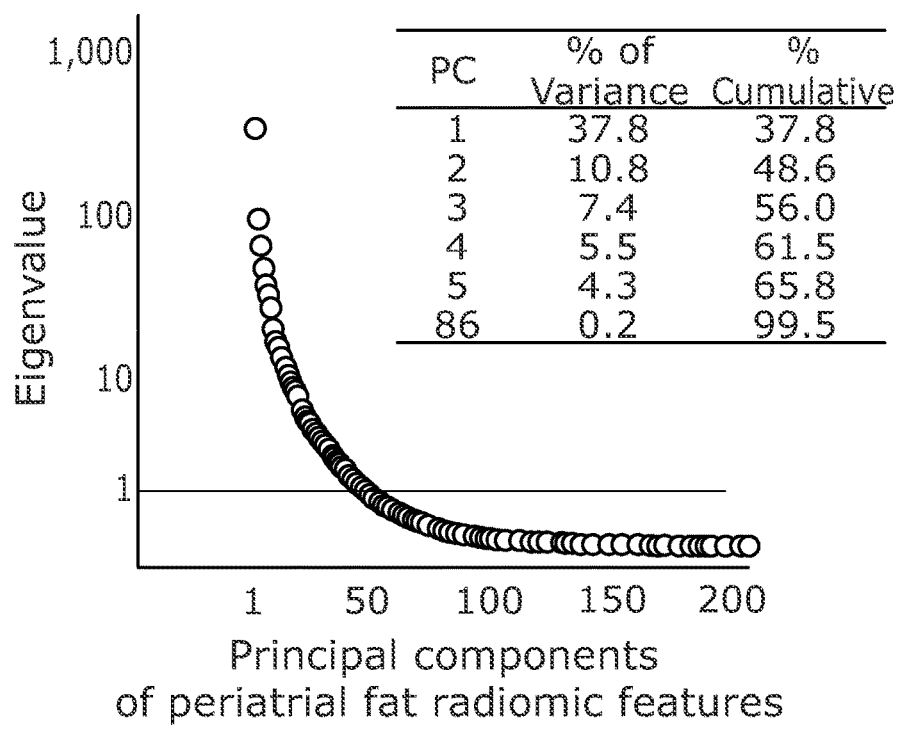
FIG. 2(a) shows a scree plot of the percentage of variation explained by the 86 first principal components, accounting for 99.5% of variation in Study Arm A (843 radiomic features from 310 patients).
Figure 2B:
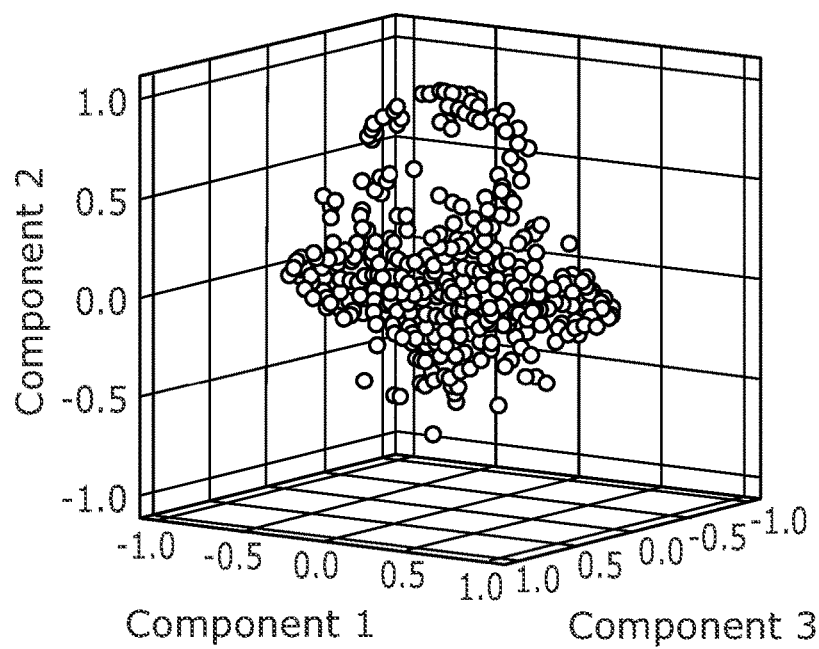
FIG. 2(b) shows a component plot of the three major principal components.
Figure 2C:
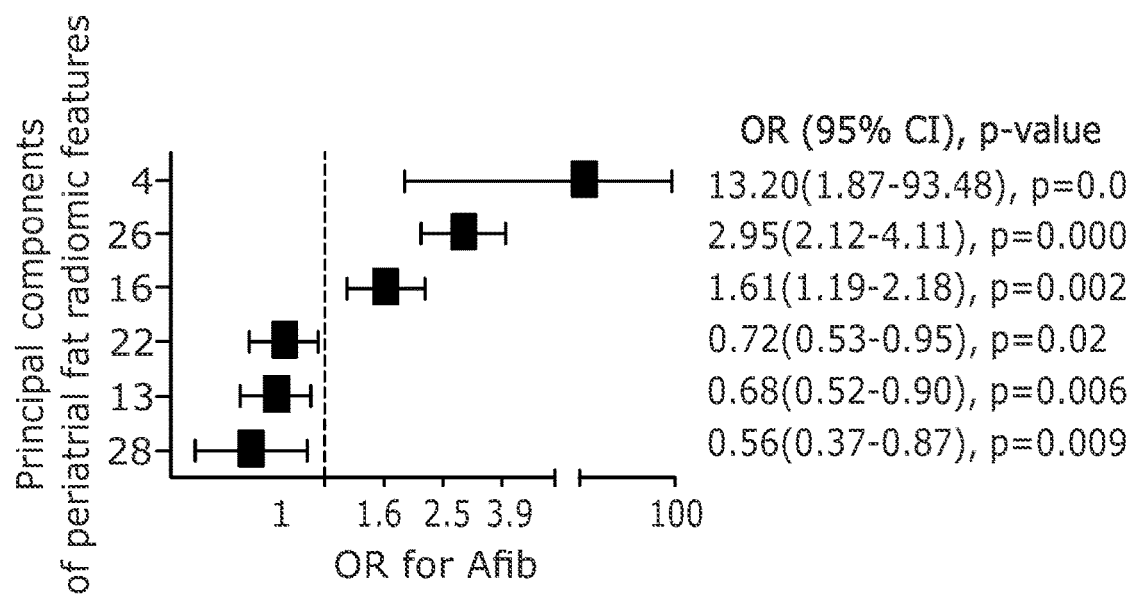
FIG. 2(c) shows principal components of periatrial adipose tissue radiomics identified as independent predictors of atrial fibrillation in logistic regression with backward elimination.

Initially an exploratory data analysis was performed by reducing the original radiomic dataset of possibly correlated features to its principal components. A total of 86 components accounted for the 99.5% of variation in the study population (scree plot, FIG. 2a), while the first 3 components explained 56% of the observed variation (FIG. 2b). Out of the 51 individual components with an eigenvalue ≥1, five of them (principal components 4, 13, 16, 22, 26, and 28) were significantly independently associated with AF in logistic regression (FIG. 2c), suggesting that texture-related characteristics of periatrial fat on standard CT images, contain rich extractable information distinctly associated with AF and possibly atrial tissue phenotype too.

Figure 2D:
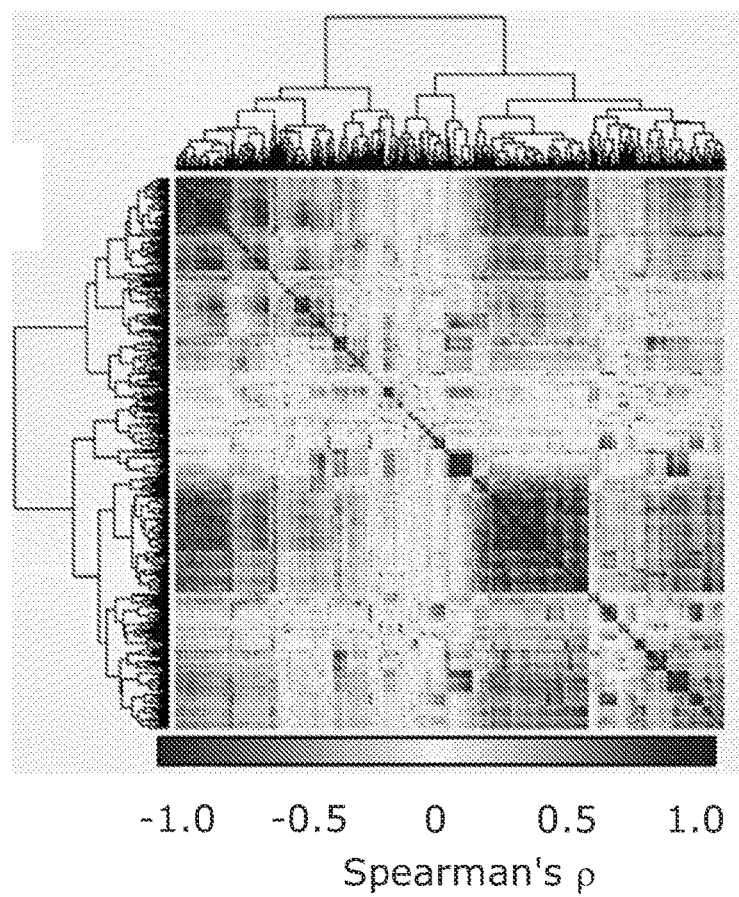
FIG. 2(d) shows a correlation plot for the inter-correlations between the 843 quantified radiomic features of periatrial adipose tissue in the same patients.
Figure 2E:
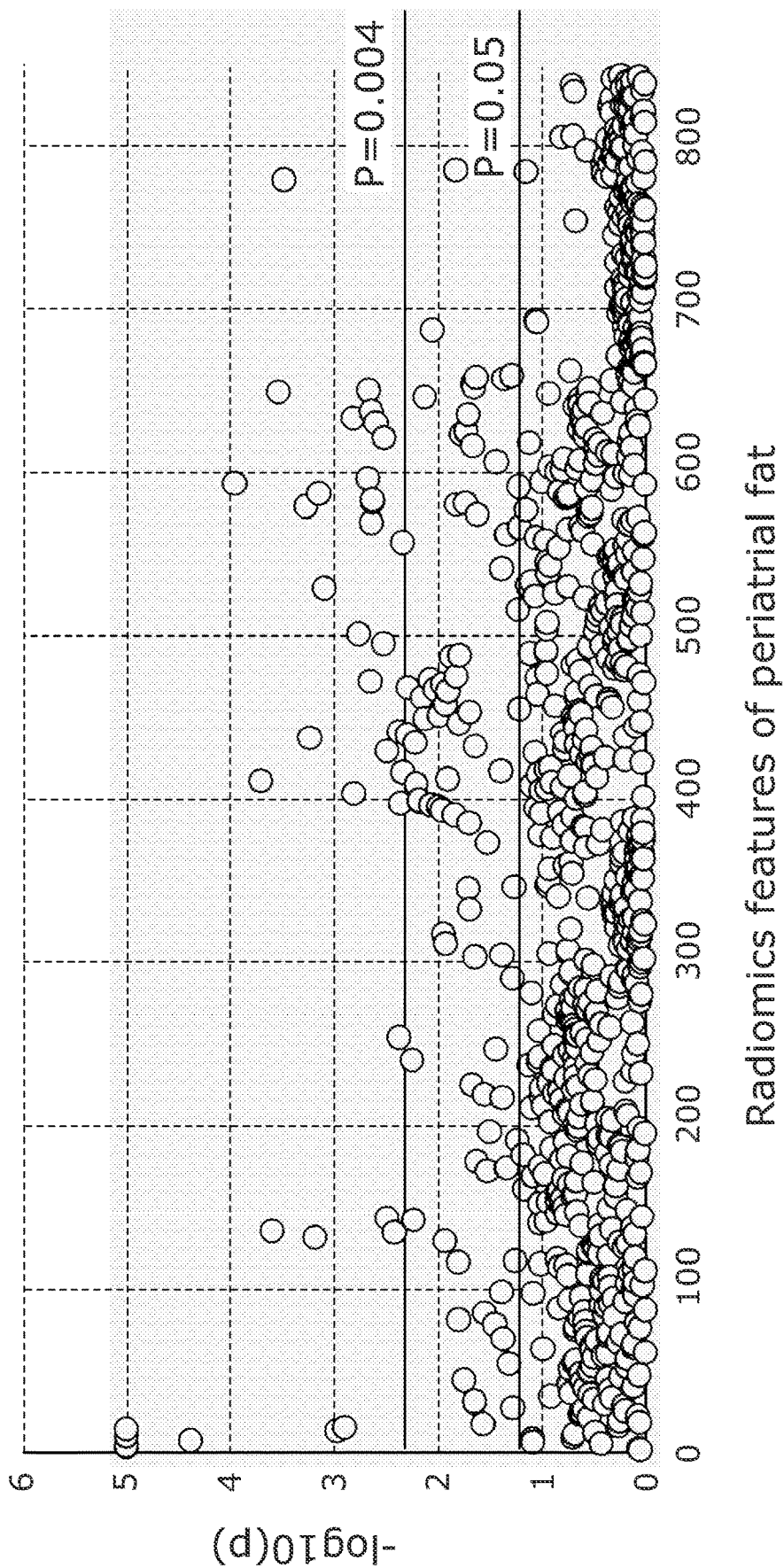
FIG. 2(e) shows a Manhattan plot for the classification value of periatrial adipose tissue radiomic features for atrial fibrillation in the nested case-control cohort of Arm A.

Unsupervised Clustering Based on the Radiomic Phenotyping of Periatrial Adipose Tissue Since principal components are inherent to the sample population studied and not of transferrable value as quantifiable biomarkers, an analysis of periatrial radiomic features per se was performed. The inter-correlations between the 843 radiomic features of periatrial fat are shown on the correlation plot of FIG. 2d; certain features were highly inter-correlated, while others less so. From the initial pool of 843 quantified radiomic features, a set of 33 features was significantly associated with AF after rigorous statistical adjustment (Manhattan plot FIG. 2e). Unsupervised hierarchical clustering of the population of Arm A by use of the radiomic features of periatrial adipose tissue identified two distinct clusters of patients, which significantly differed in the prevalence of AF (heatmap FIG. 3a). These findings support that the presence of AF is associated with a certain radiomic fingerprint of an epicardial region, such as a region of periatrial fat, which may be useful for the extraction of imaging biomarkers of atrial disease.

Machine Learning to Identify the Radiomic Signature of Atrial Fibrillation on Periatrial Fat Having demonstrated the proof-of-concept that the radiomic features of periatrial adipose tissue are different in the presence of AF, a radiomic signature or "fingerprint" of AF on periatrial adipose tissue was constructed. The inter-correlations and hierarchical clustering of the selected 33 radiomic features of periatrial fat is demonstrated on FIG. 3b. The correlation plot shows that periatrial adipose tissue radiomic features are clustered in distinct groups of correlated features (one shape-related and five texture-related groups).

Figure 4A:
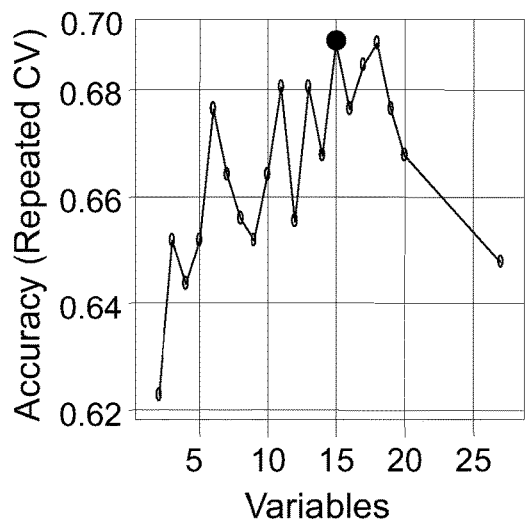
FIG. 4(a) illustrates the recursive feature elimination for selection of the optimum number and top features to be included in the machine learning algorithms.

In order to identify selected radiomic features that could be used to construct the radiomic fingerprint of AF on periatrial fat, the cohort of Arm A was split using a random seed into a training (80%) and test dataset (20%), for model training and testing respectively. Recursive feature elimination with a random forest algorithm was first used to a) find the number of features required to maximize model's accuracy for AF and b) select the top features to be included in the model. Out of the 33 selected radiomic features, a set of 15 features maximized algorithm's diagnostic accuracy for AF (FIG. 4a).

Figure 4B:
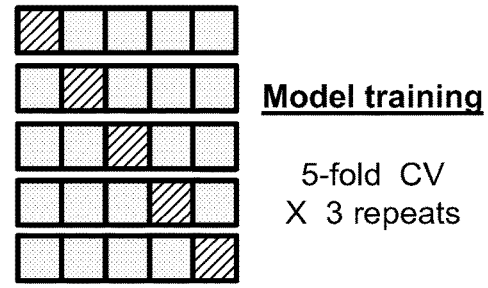
FIG. 4(b) illustrates model training by 5-fold cross-validation repeated 3 times.
Figure 4C:
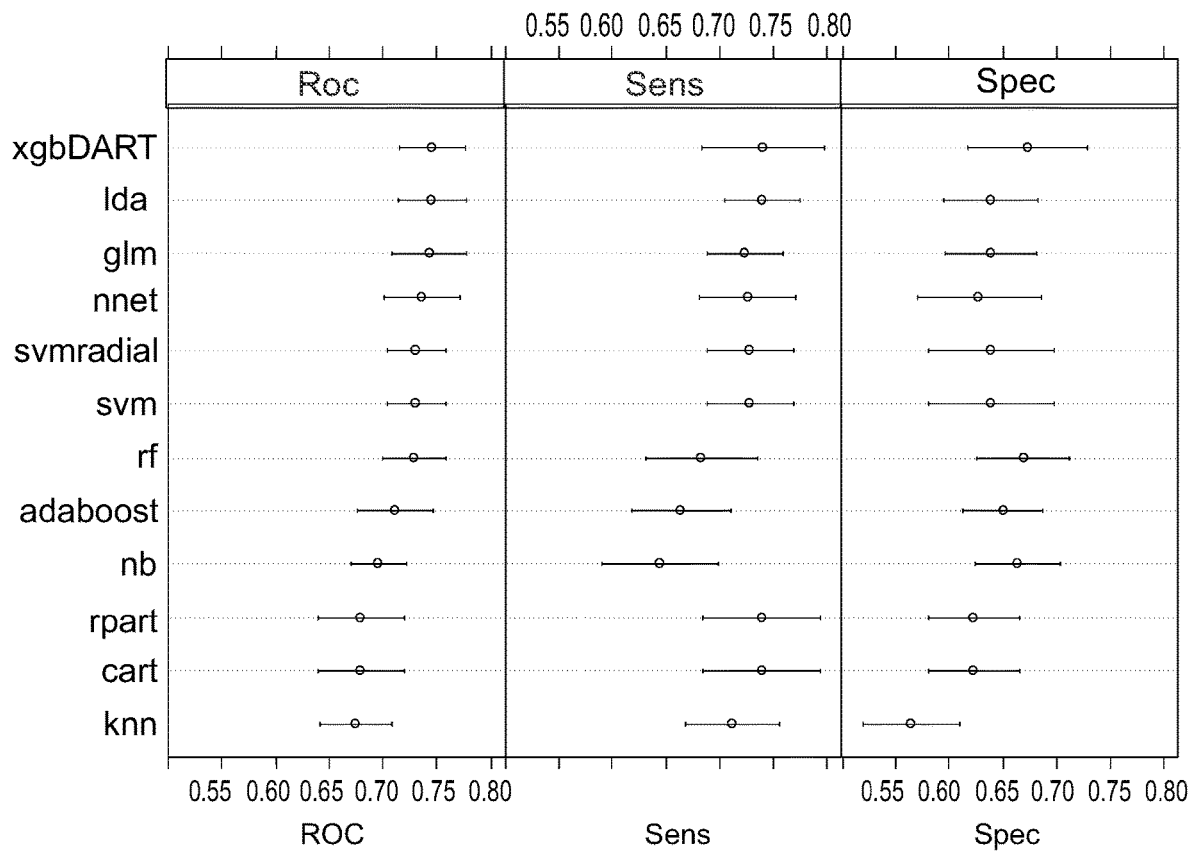
FIG. 4(c) illustrates the performance of various machine learning algorithms for developing a radiomic signature for atrial fibrillation classification in the training dataset.
Figures 4D, 4E:
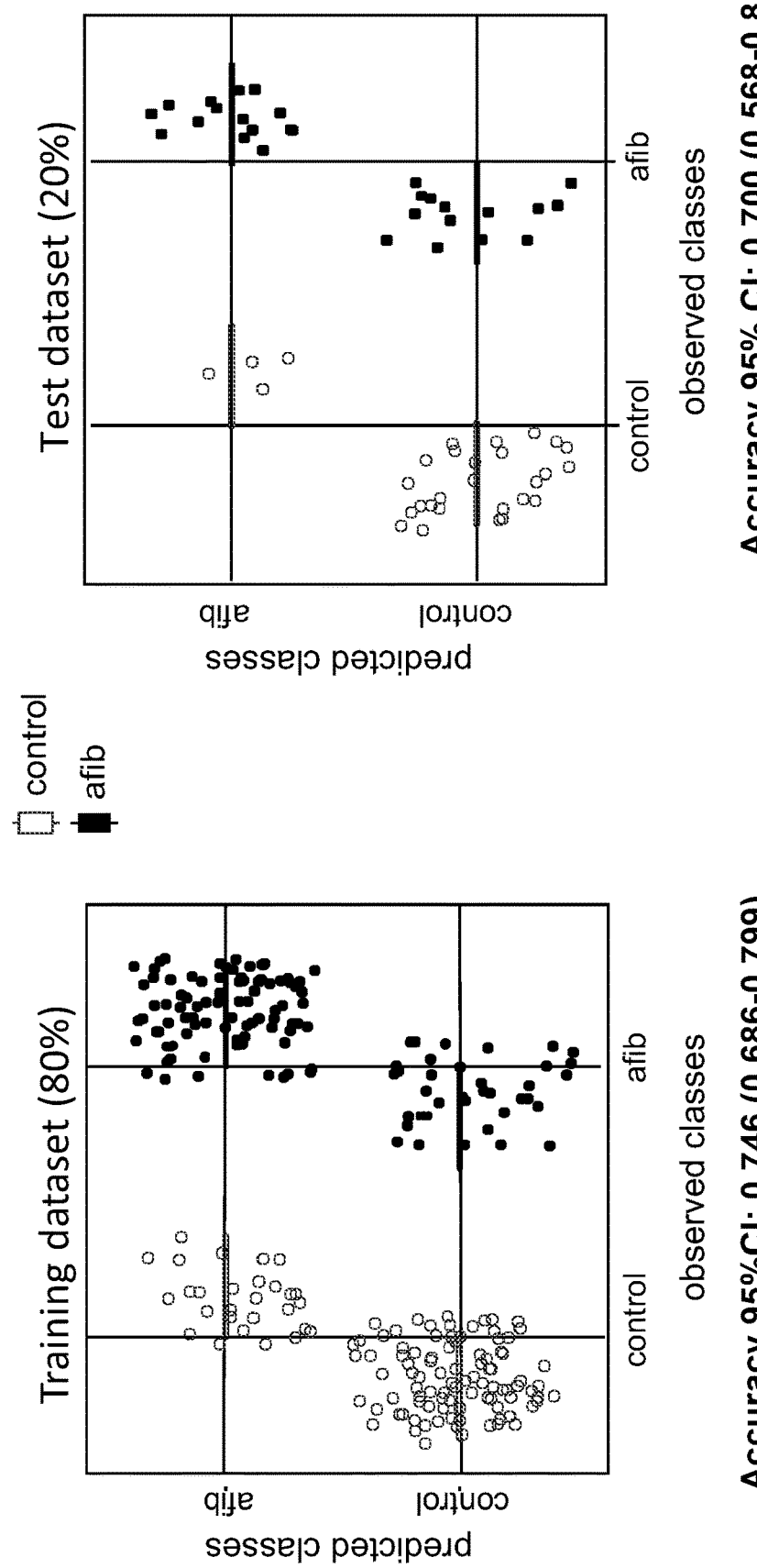
FIGS. 4(d) and (e) illustrate the application of the developed signature (by using 15 epicardial radiomic features of periatrial fat) for atrial fibrillation classification and relevant confusion matrix in (d) the training dataset and (e) validation (test) dataset. ROC: receiver operating characteristic; Sens: sensitivity; Spec: specificity.

These 15 radiomic features of periatrial fat (Table 2) were then fed into various machine learning algorithms as independent variables and explored each algorithm's performance for classification of AF. After internal 5-fold cross-validation repeated three times, (5×3 folds) the algorithm with the best performance for AF classification was identified (FIG. 4b,c). An extreme gradient boosting algorithm (xgbDART, originally described in V. K. Rashmi & R. Gilad-Bachrach, DART: Dropouts meet Multiple Additive Regression Trees *JMLR* (2015), and which is described and available at https://xgboost.readthedocs.io/) used 15 radiomic features, and had 74.5% accuracy for AF classification (discrimination between those with AF versus those without) in the training dataset (FIG. 4d). The performance of the same algorithm was then evaluated in the test dataset, where correctly classified 70% of cases (FIG. 4e). The value of the calculated radiomic signature was P×10, where P was the predicted probability (P) of the presence of AF output by the decision tree of the radiomic signature.

The parameters used for the xgbDART algorithm were as follows: max_depth=2, eta=0.4, rate_drop=0.5, skip_drop=0.05, subsample=0.5, colsample_bytree=0.8, nrounds=150. These parameters were optimised by maximising the ROC value for AF discrimination in Arm 1. The other parameters were kept at their default values, in particular tuning parameter 'gamma' was kept at 0 and tuning parameter 'min_child_weight' was kept at 1.

Investigating Whether the Radiomic Signature Detects Myocardial Disease (Myocardial Tissue Redox State, Fibrosis and Inflammation)

Figure 5A:
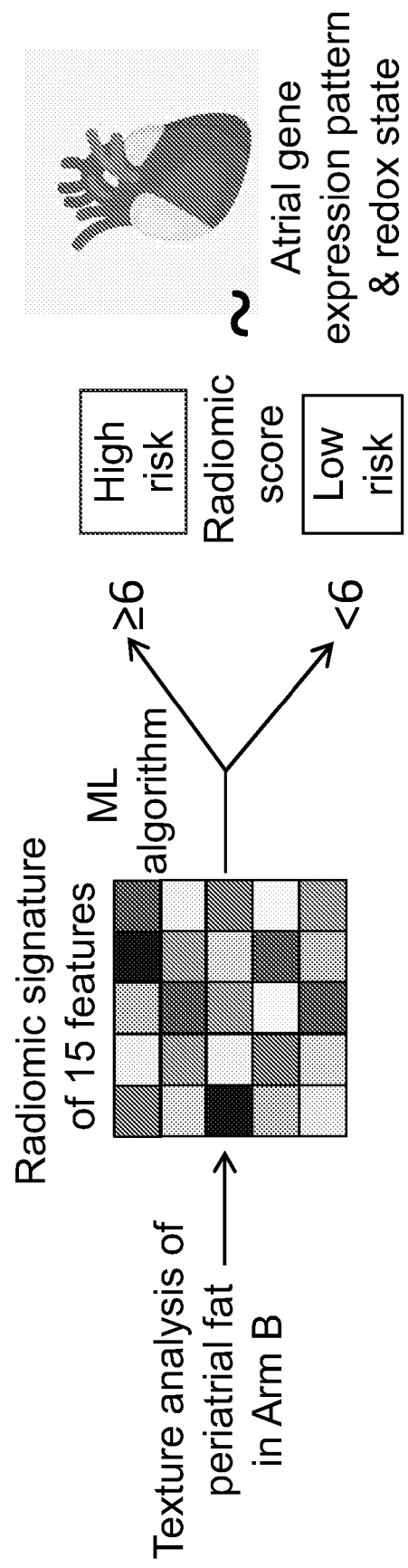
FIG. 5(a) illustrates how the developed epicardial radiomic signature from Arm A was applied to the Arm B cohort to characterize periatrial adipose tissue and explore associations with atrial gene expression profiles and atrial redox state. A score (calculated value of the signature) of less than 6 was associated with a low risk of developing post-operative atrial fibrillation and a score of 6 or more was associated with a high risk of developing post-operative atrial fibrillation.

Having identifying the fingerprint of AF on periatrial fat, it was investigated whether this radiomic signature could be used to assess changes in atrial biology. In the cohort of Arm B, in 225 patients undergoing coronary artery bypass grafting (prevalence of AF=7.3%), periatrial fat was imaged by CT and samples of atrial tissue were collected peri-operatively for gene expression studies and to assess myocardial redox state. To each patient, periatrial adipose tissue texture was assessed by the same radiomic score by using the machine learning algorithm developed in the population of Arm A (FIG. 5a). Periatrial fat radiomic score was positively associated with atrial myocardium gene expression levels of COL1A1, natriuretic peptides (ANP, BNP) and proinflammatory genes such as IL6 and TNFA (FIG. 5b,c). A higher radiomic score of periatrial fat was also associated with increased superoxide generation in human atrial tissue (FIG. 5d).

Figure 5E:
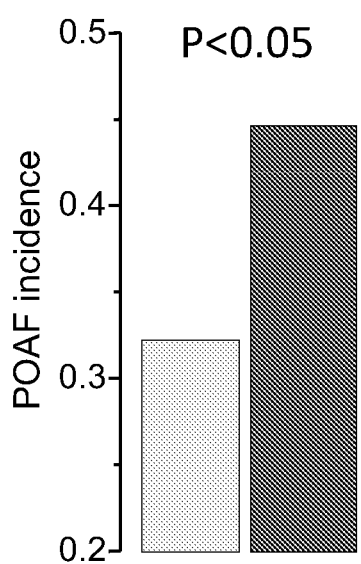
FIG. 5(e) shows that in the same patients there was a significant association between periatrial adipose tissue epicardial radiomic score (right, darker shading=6 or higher; left, lighter shading=below 6) and the incidence of postoperative atrial fibrillation (POAF).
Figure 5F:
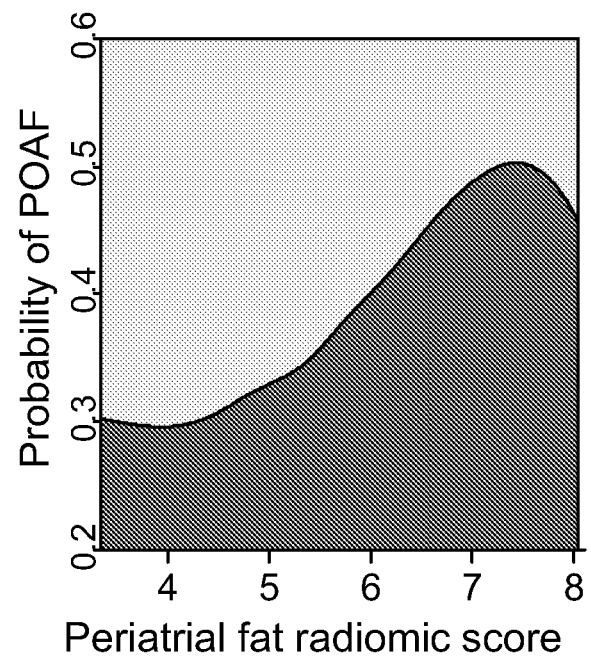
FIG. 5(f) shows a density plot for the correlation between the periatrial epicardial radiomic score and post-operative atrial fibrillation (POAF) probability.
Figure 5G:
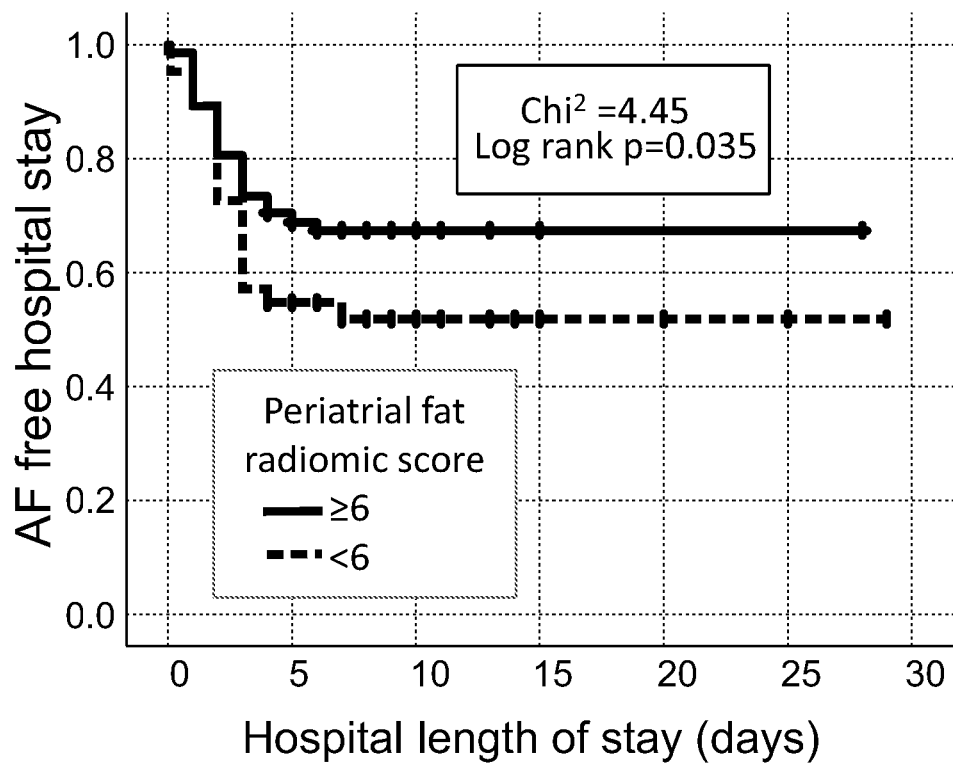
FIG. 5(g) shows relevant Kaplan-Meier curves for the incidence of POAF by periatrial epicardial radiomic score subgroups.

Finally it was investigated whether this developed radiomic score of periatrial fat, which is of diagnostic value for AF and atrial tissue phenotype, could also predict the risk for post-operative AF. A cut-off of 6 in the radiomic score of periatrial fat was associated with increased risk of post-operative AF (FIG. 5e,f). In survival analysis, the periatrial adipose tissue radiomic score was significantly associated with the development of post-operative AF (FIG. 5g).

Validating Alternative Radiomic Signatures of the Invention

The discussion above demonstrates that the radiomic signature calculated on the basis of the 15 radiomic features identified using the unbiased machine learning approach and listed in Table 2 provides a significant improvement in the discriminatory value of the model for heart arrhythmia, and therefore for underlying cardiac health, for which heart arrhythmia is used as a surrogate marker. Thus, the radiomic signature of the invention is able to discriminate for underlying conditions, such as myocardial fibrosis, oxidative stress (i.e. redox state), and inflammation. To validate the usefulness of alternative radiomic signatures of the invention that include different selections of radiomic features, a series of several different radiomic signatures were tested for AF detection, again as a surrogate marker for underlying myocardial health. The results are shown in Table 6.

The radiomic signature of Example 1 is calculated on the basis of the 15 radiomic features identified using the unbiased machine learning approach and listed in Table 2. In Example 2, each of the 15 original radiomic features has been substituted by the radiomic feature that is most collinear with it, and in Example 3 each of the 15 original radiomic features has been substituted by the radiomic feature that is least collinear with it (see Table 3). Finally, in Example 4 each of the original radiomic features is substituted for a different radiomic feature from the same cluster (clusters A-D in Table 1). Each of these signatures was tested for its accuracy in detecting atrial fibrillation (AF) in Arm 1, and the results are presented in Table 6.

TABLE 6

Performance of various radiomic features comprising different combinations of radiomic features

| Combination of features | Accuracy for AF detection |
|---|---|
| Example 1. Originally selected features using an unbiased machine learning approach (Atriomic Index) | |
| Inverse Difference Moment HHH, Minimum LHH, Low Gray Level Zone Emphasis LLL, Maximum Probability LLL, Busyness LHH, Zone Entropy LLL, Run Entropy LLL, Maximum 3D Diameter, Long Run High Gray Level Emphasis LLL, Joint Average LLL, Difference Entropy LLL, Sum Entropy HHH, Difference Entropy LHH, | 0.746 |

TABLE 6-continued

Performance of various radiomic features comprising different combinations of radiomic features

| Combination of features | Accuracy for AF detection |
|---|---|
| Sum of Squares LHH, Gray Level Variance LHH (GLDM). | |
| Example 2. Substituting each of the features with their most collinear feature from Table 3 | |
| Inverse Difference Normalized HHH, Long Run Low Gray Level Emphasis LHH, Short Run Low Gray Level Emphasis LLL, Joint Energy LLL, Strength LHH, Dependence Entropy LLL, Entropy LLL, Maximum 2D Diameter Slice, High Gray Level Emphasis LLL, Autocorrelation LLL, Difference Average LLL, Cluster Tendency HHH, Contrast LHH (GLCM), Cluster Tendency LHH, Variance LHH. | 0.737 |
| Example 3. Substituting each of the features with their least collinear feature from Table 3 | |
| Short Run Low Gray Level Emphasis HHH, Maximum LHH, Large Dependence Low Gray Level Emphasis LLL, Run Entropy, Large Area Low Gray Level Emphasis LHH, Uniformity LLL, Maximum Probability LLL, Major Axis, Short Run Low Gray Level Emphasis LLL, Low Gray Level Zone Emphasis LLL, 90th Percentile HLL, Dependence Non Uniformity Normalized LHH, Maximum Probability HHH, Small Dependence High Gray Level Emphasis HHH, Long Run Emphasis HLL. | 0.773 |
| Example 4. Substituting each feature with an alternative feature from the same cluster (Table 1) | |
| Zone Variance LLL, Elongation, Cluster Shade LLL, Gray Level Non Uniformity LLL (GLDM), Cluster Prominence LLL, Gray Level Variance LLL (GLDM), Major Axis, Autocorrelation LLH, Long Run High Gray Level Emphasis LLL, Autocorrelation LLL, Difference Entropy LLH, Sum of Squares HLH, Sum of Squares HHH, Gray Level Variance LLH (GLDM). | 0.815 |

It can clearly be seen from Table 6 that all of the tested radiomic signatures of the invention provide a high accuracy of atrial fibrillation detection. Thus, the data presented in Table 6 demonstrate that regardless of which features are selected from each of the identified clusters or groups the radiomic signature of the invention provides improved prediction of cardiovascular risk over previously used models. Furthermore, the data presented in FIG. 4a demonstrate that fewer than 15 radiomic features may be used to calculate the radiomic signature and the radiomic signature will still be capable of discriminating for cardiac health. In fact, it can be seen from FIG. 4a that radiomic signatures comprising as few as two radiomic features are of useful discriminatory value for cardiac health. It can be seen from FIG. 4a that there is a sharp increase in the accuracy of the signature when at least three radiomic features are included in the signature. Therefore, it is preferable for the radiomic signature to comprise at least three radiomic features, and wherever at least two radiomic features are referred to herein, it should be understood that this could mean at least three radiomic features.

Example 2

Figure 6B:
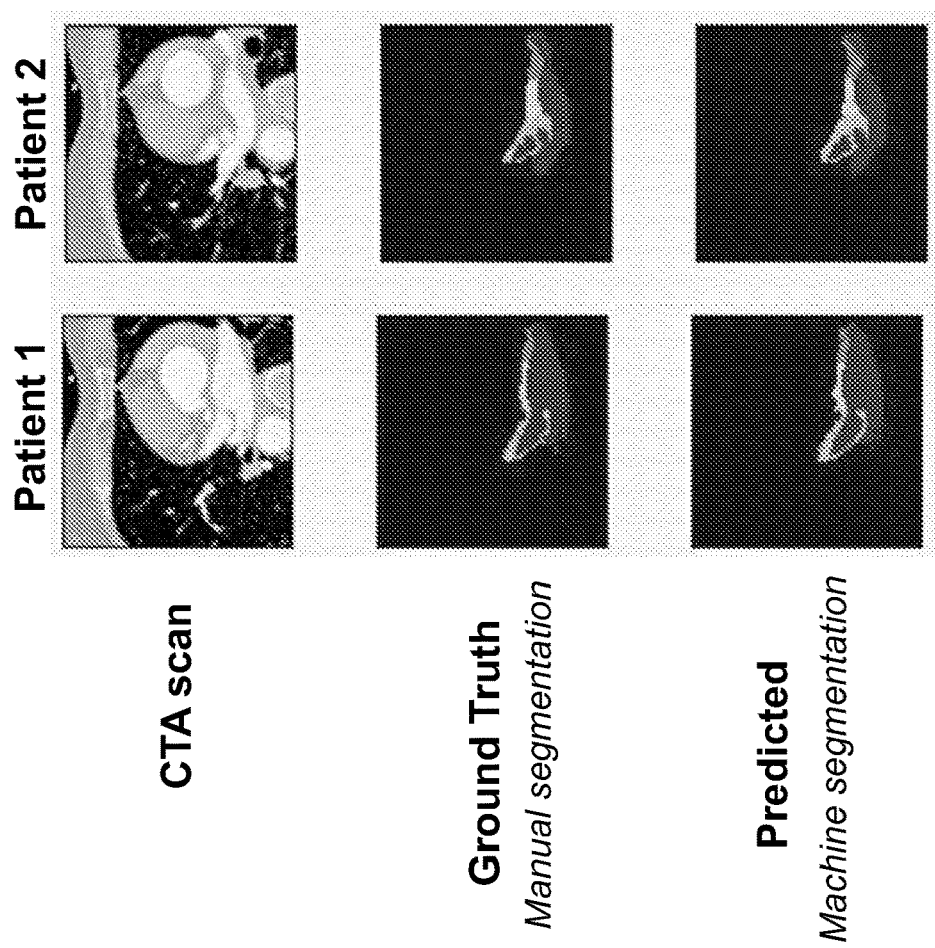
FIG. 6(b) illustrates screen captures of two patients demonstrating the cardiac anatomy as visible on a CTA scan (top row), then (second row) ground truth as fed into the deep-learning model, which is a manual segmentation of the LA, left atrial appendage region, anterior LA wall region and the intra-atrial septum region, each differently shaded. The predicted images (bottom row) represent the learnt segmentation as an output of the deep-learning model. To compute this model, a 3D convolutional neural network with 11-layers of depth and double-pathway to incorporate multiple scaling was employed to voxel-wise segment the regions of interest in the scan. CTA: Computed tomography angiography.
Figure 6A:
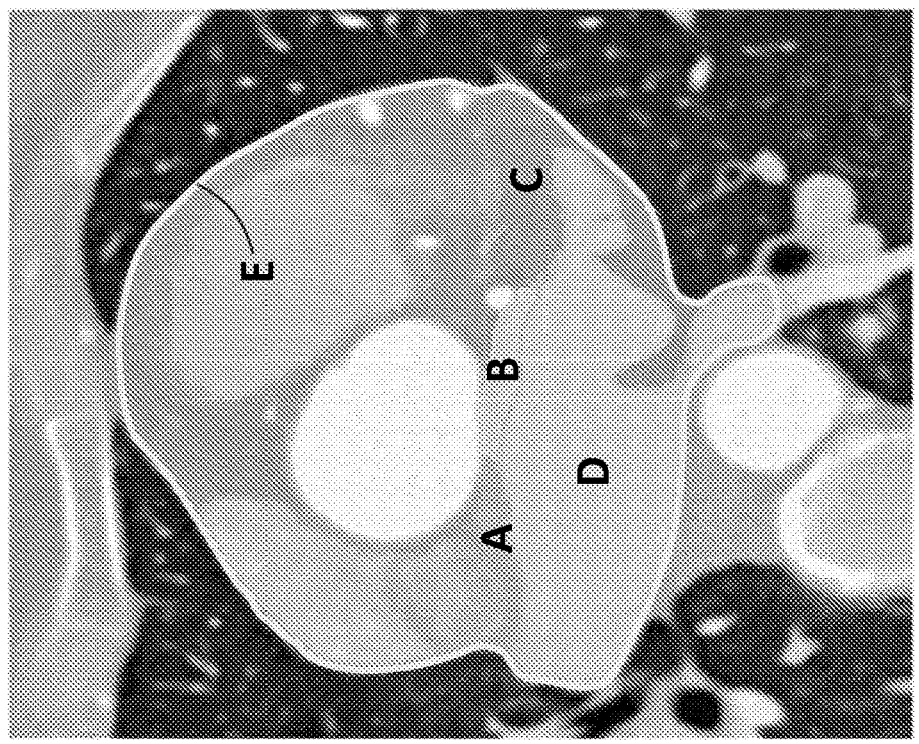
FIG. 6(a) shows a coronary computed tomography angiography image captured at the level just inferior to the aortic valve. This slice demonstrates manual segmentation of the left atrium (LA) and three segmentations of peri-left atrium (LA) tissue (masking of all voxels with attenuation −190 HU to +150 HU) and anatomical annotations (letters A-D). These three peri-LA tissue depots (A, B, C) are the segmented volumes from which radiomic features are subsequently extracted. The LA segment (D) is utilised for deep-learning automation of the segmentation process. A: intra atrial septum ROI; B: anterior LA wall ROI; C: Left atrial appendage ROI; D: LA ROI; E (encircling outline): pericardium. ROI: Region of Interest.

A deep learning approach for automation of CT scan segmentation 400 diagnostic coronary CT angiographs were manually segmented to identify three discrete segments: the intra atrial appendage epicardial region of interest (FIG. 6a, annotation A), the anterior left atrial wall epicardial region of interest (FIG. 6a, annotation B) and the left atrial appendage epicardial region of interest (FIG. 6a, annotation C). The whole of the left atrium (LA) itself was also segmented (FIG. 6a, annotation D). The scans were segmented using the broader HU range (−190 HU to +150 HU).

Figure 6D:
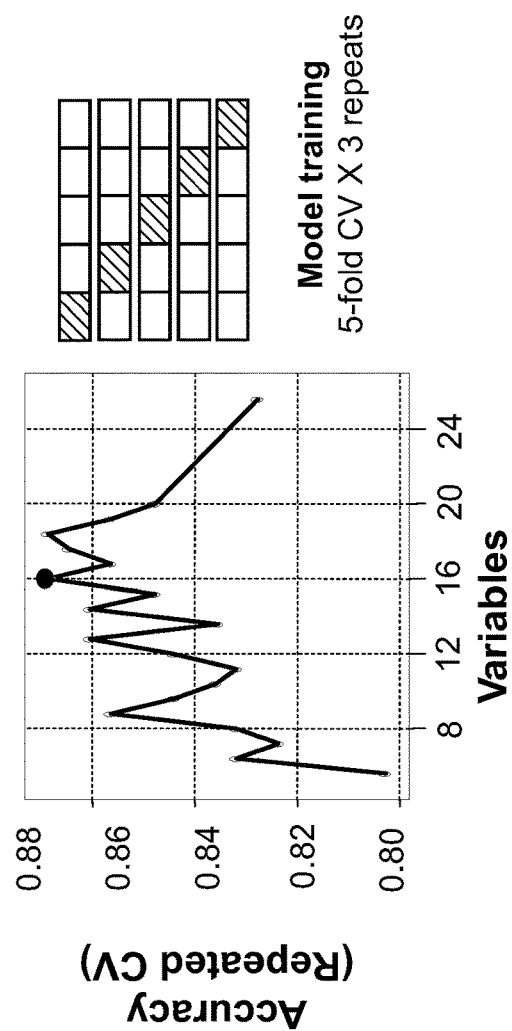
FIG. 6(d) illustrates the utilisation of machine learning for identification of the radiomic fingerprint (signature) of stroke on peri-LA tissues—recursive feature elimination for selection of the best number and top features to be included in the machine learning algorithms revealed that out of the 843 radiomic features, a set of 16 features maximized Atriomic algorithm accuracy for predicting stroke. At right, machine learning schematic demonstrating model training by 5 fold cross-validation (CV) repeated 3 times.
Figure 6C:
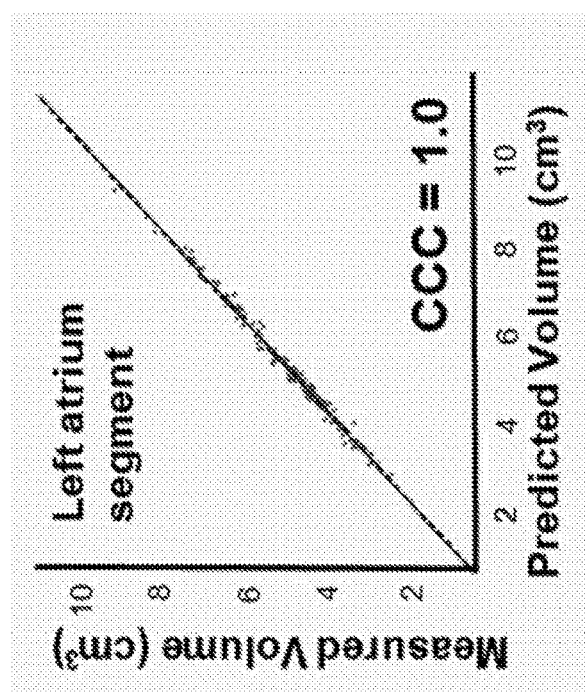
FIG. 6(c) shows a plot representing the excellent concordance between manual left atrium segmentation (ground truth) and the automatically segmented left atrium (deep-learning). Number of segmentations performed is 286. CCC: concordance correlation coefficient.

These scans and the manually segmented regions of interest were fed into a deep-learning system capable of learning the characteristics of the anatomical volumes which have been manually segmented. The deep learning approach employed allowed the computation of a multi-layer neural network, and used a convolutional neural network (CNN). The results of the deep-learning automated segmentation from the first 300 scans (training set) were excellent (FIG. 6b), with consistent performance of 100% agreement between human vs machine segmented scans in an external dataset in the 100 scans from the external validation set (FIG. 6c). This automated segmentation may be combined with radiomic features extraction to provide a complete application for automated radiomic analysis of the peri-left atrial tissues.

Example 3

Where not otherwise mentioned, the following example was conducted largely similarly to Example 1.

To demonstrate that stroke is associated with a different peri-LA tissue radiomic signature, an independent cohort of 98 patients undergoing diagnostic coronary CT angiography (Erlangen, Germany) was analysed. Patients with history of stroke (n=49) were 1:1 matched to control subjects (n=49) without known stroke history. The two groups were matched for age, sex, cardiovascular risk factors and scan acquisition details.

This study was used to identify radiomic features of an epicardial region that are independently associated with stroke in order to develop a relevant radiomic score of peri-left atrial tissue associated with cardiac, and in particularly atrial health. The cohort sample was drawn from a mixed population in regards to atrial fibrillation (AF), with incidence of stroke being 2.4% over 5 years of follow up.

The scans were manually segmented by a single reader at the Oxford Academic Cardiovascular Computed Tomography Core Lab. The four broad attenuation-defined segments (−190 HU to +150 HU) as already described were identified for each scan. These segments included 1) the intra-atrial septum, 2) the anterior surface of the LA, and 3) the left atrial appendage (FIG. 6a). Radiomic features were extracted from each segment, as well as combined segments. Variables were first extracted for peri-LA adipose tissue only (−190 HU to −30 HU) and then for the full range of voxels within each segment (−190 HU to +150 HU).

To construct the most highly predictive radiomic signature for atrial myopathy leading to stroke within the tissues surrounding the LA we applied machine learning analysis for each of the three individual segments (1-3), the three merged segments of adjacent individual segments (1+2, 2+3 and 1+2+3), and for both the narrower peri-LA adipose tissue and broader peri-LA Hounsfield ranges. This totaled 12 different analysis groups.

For each analysis group, the 98 patients were split using a random seed into a training (80%) and external validation (20%) dataset. Recursive feature elimination with a random forest algorithm was first used to a) find the number of features required to maximize the model's accuracy for stroke and b) select the top features for the model.

Figure 6E:
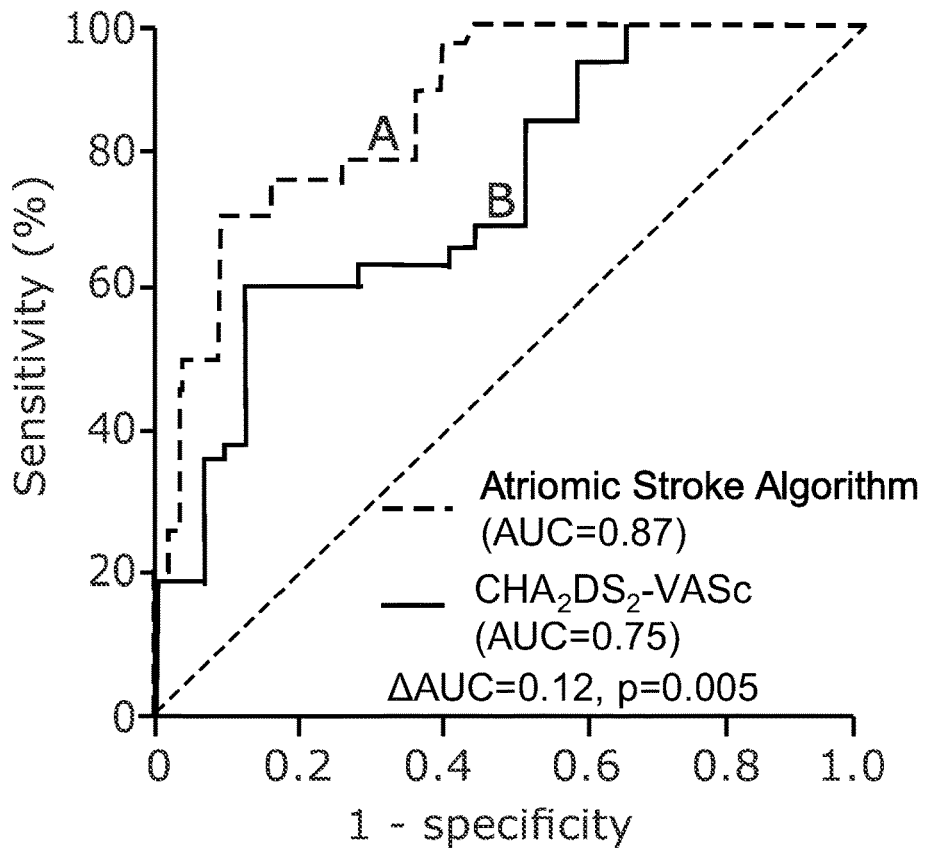
FIG. 6(e) demonstrates the incremental prognostic value of the Atriomic Algorithm beyond $CHA_2DS_2$-VASc risk prediction for stroke. Presented are the ROC curves and AUC of two nested models for discrimination of stroke in the CRISP-CT cohort. Line A represents the Atriomic Algorithm, the radiomic signature to predict stroke within the CRISP-CT cohort. Line B represents the $CHA_2DS_2$-VASc score for the prediction for the stroke risk. The Atriomic algorithm curve is the best performing model from 12 experimental models and incorporated the radiomic signature from two merged peri-left atrium segmentations. The final segment utilised in this model includes the adipose tissue and connective tissues of the intra-atrial septum and the anterior wall of the left atrium. The attenuation mask applied was −190 to +150. AUC=area under the curve.

A set of 16 radiomic features was found to maximize the algorithm's diagnostic accuracy for stroke. These 16 features are detailed in Table 2b. The 16 radiomic features were calculated for both the narrowed peri-LA adipose tissue and the broader peri-LA tissue HU ranges were then fed into various machine learning algorithms as independent variables and explored each algorithm's performance for classification of the participants for stroke. After internal 5-fold cross-validation repeated 3 times (FIG. 6d) the Atriomic Stroke Algorithm (an epicardial radiomic signature predictive of stroke) was derived for optimum stroke prediction. The most successful model of prediction used the 16 radiomic features calculated for the combined segment of the intra-atrial septum and the anterior LA wall. The Atriomic Stroke Algorithm employed an extreme gradient boosting algorithm using 16 radiomic features with excellent accuracy for stroke classification (0.87+0.04) in the external validation dataset (FIG. 6e—line A).

In more detail, a principal component analysis was utilised and the eigenvalue above 1 was used for the cut off for inclusion of the components in a logistic regression model with a backward elimination for stroke classification as the dependent variable, to detect the principal components of peri-atrial tissue radiomic features that are independently associated with the occurrence of stroke.

The same machine learning approach as outlined in Example 1 was used for the development of the Atriomic Stroke Algorithm, employing the Extreme Gradient Boosting package in the R environment to achieve the model with best performance as measured by the AUC for stoke classification (i.e. distinguishing those who went on to have a stroke versus those who did not). The model was trained using 5-fold internal cross-validation repeated 3 times (5×3 folds). The accuracy of the final model was assessed in the training cohort, and then externally validated in the test cohort. The final model was used to develop the Atriomic Stroke Algorithm based on the predicted probability for stoke in this sample.

The Atriomic Stroke Algorithm Identifies Genes Related to Inflammation and Fibrosis within the Atrial Tissue An independent cohort comprising of 86 patients undergoing coronary artery bypass grafting surgery (CABG) was assembled. Patients underwent coronary CT angiography scans and atrial tissue samples were collected peri-operatively for targeted myocardial tissue phenotyping (as described previously). This cohort was use for the external validation of the developed Atriomic Stroke Algorithm against atrial biology.

The associations of periatrial tissue radiomic score against atrial gene expression profile were assessed in bivariate analysis using unpaired t-test between groups.

Figure 6F:
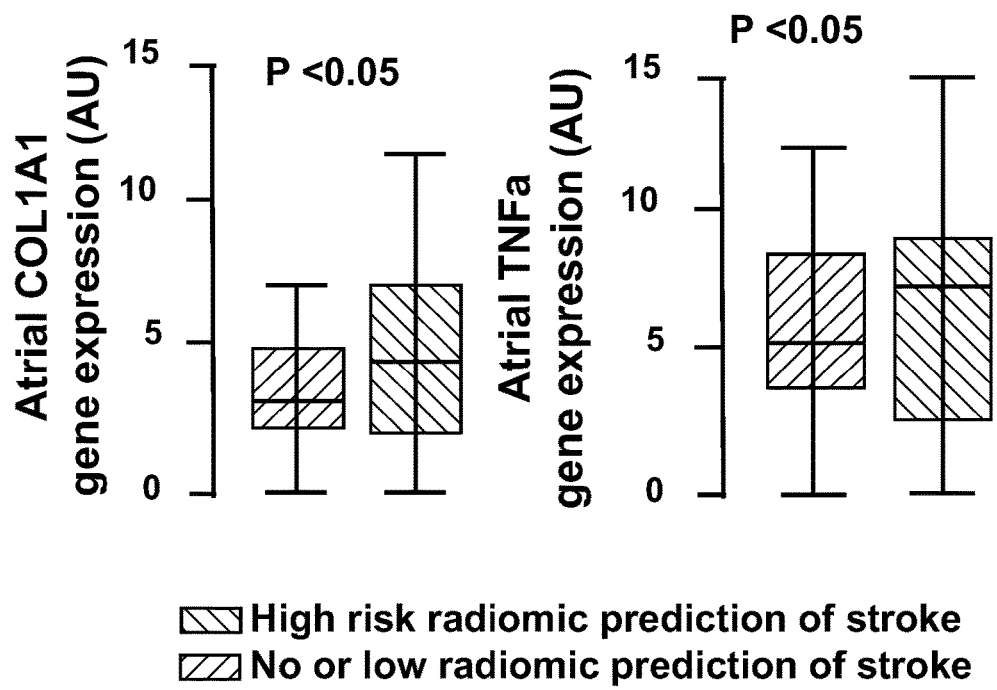
FIG. 6(f) illustrates the relationship between the Atriomic Stroke Algorithm and atrial biology in 86 patients undergoing cardiac surgery recruited in the OX-HVF cohort. High risk Atriomic Stroke profile was associated with a pathological gene expression profile within atrial myocardium tissue samples, shown here for fibrosis related collagen (COL1A1) and pro-inflammatory gene tumor necrosis factor alpha (TNFa). Box-plots demonstrate that individuals identified as high risk for stroke based on the Atriomic Stroke Algorithm in CRISP-CT, had higher expression of inflammatory and pro-fibrotic genes in atrial appendage tissue collected during surgery.

The Atriomic Stroke Algorithm was associated with adverse atrial health processes and could detect high atrial expression of collagen (COL1A1), reflecting high fibrosis activity, and pro-inflammatory genes including TNFA, reflecting active inflammation (see FIG. 6f).

The Atriomic Stroke Algorithm Outperforms Current Stroke Risk Prediction Tools

To demonstrate that the Atriomic Stroke Algorithm could be utilised clinically, an independent cohort of 98 patients undergoing diagnostic coronary CT angiography (as used for the development of the Algorithm) was used. The ability of the Atriomic Stroke Algorithm to predict stroke vs $CHA_2DS_2$-VASc score was tested. This is the widely used clinical scoring system for stroke stratification in clinical practice. The Atriomic Stroke Algorithm was proven to be by far superior to $CHA_2DS_2$-VASc in predicting stroke in the CRISP-CT, with change in AUC of 0.12 (p=0.005) (see FIG. 6e).

Validating Alternative Radiomic Signatures of the Invention

The discussion above demonstrates that the radiomic signature calculated on the basis of the 16 radiomic features identified using the unbiased machine learning approach and listed in Table 2b provides a significant improvement in the discriminatory value of the model for ischaemic stroke, and therefore for underlying cardiac health, for which ischaemic is used as a surrogate marker. Thus, the radiomic signature of the invention is able to discriminate for underlying conditions, such as myocardial fibrosis, oxidative stress (i.e. redox state), and inflammation. To validate the usefulness of alternative radiomic signatures of the invention that include different selections of radiomic features, a series of several different radiomic signatures were tested for stroke detection. The results are shown in Table 7.

The radiomic signature of Example 1 is calculated on the basis of the 16 radiomic features identified using the unbiased machine learning approach and listed in Table 2b. In Example 2, each of the 16 original radiomic features has been substituted by the radiomic feature that is most collinear with it, and in Example 3 each of the 16 original radiomic features has been substituted by the radiomic feature that is least collinear with it (see Table 3b). Finally, in Example 4 each of the original radiomic features is substituted for a different radiomic feature from the same cluster (clusters A-D in Table 1b). Each of these signatures was tested for its accuracy in detecting stroke in the CRISP-CT cohort, and the results are presented in Table 7.

TABLE 7

Performance of various radiomic signatures comprising different combinations of radiomic features

| Combination of features | Accuracy for stroke detection |
|---|---|
| Example 1. Originally selected features using an unbiased machine learning approach (Atriomic Stroke Algorithm) | |
| 10th Percentile | 0.870 |
| ID HHL | |
| Variance | |
| Gray Level Non Uniformity Normalized (GLRLM) | |
| Dependence Variance HLL | |
| Size Zone Non-Uniformity LHL | |
| Skewness | |
| Root Mean Squared | |
| Gray Level Non Uniformity LLH | |
| Large Area Emphasis LLH | |
| IDMN HHH | |
| Zone Percentage HHL | |
| Kurtosis | |

TABLE 7-continued

Performance of various radiomic signatures comprising different combinations of radiomic features

| Combination of features | Accuracy for stroke detection |
|---|---|
| Size Zone Non Uniformity Normalized HHH | |
| Difference Entropy LLL | |
| Autocorrelation HHL | |
| Example 2. Substituting each of the features with their most collinear feature from Table 3b | |
| Range | 0.821 |
| Inverse Variance HHL | |
| Run Variance (GLRLM) | |
| Gray Level Non Uniformity Normalized HLL (GLRLM) | |
| Large Dependence High Gray Level Emphasis HLL | |
| Short Run Low Gray Level Emphasis LHL | |
| Uniformity | |
| Maximum | |
| Small Dependence Emphasis LLH | |
| High Gray Level Emphasis LLH | |
| Contrast LLL | |
| Small Dependence Emphasis HHL | |
| Small Dependence Low Gray Level Emphasis LHL | |
| Low Gray Level Emphasis HHH | |
| Zone Variance LLL | |
| Zone Entropy HHL | |
| Example 3. Substituting each of the features with their least collinear feature from Table 3b | |
| 10th Percentile LHH | 0.731 |
| Sum Entropy HHH | |
| Zone Entropy (GLSZM) | |
| Short Run High Gray Level Emphasis LHL (GLRLM) | |
| Joint Entropy HLL | |
| Small Area Low Gray Level Emphasis LHL | |
| Complexity HLH | |
| Cluster Shade LHH | |
| Difference Variance LLH | |
| Difference Entropy (HLL) | |
| Small Area High Gray Level Emphasis LLH | |
| Mean Absolute Deviation LHL | |
| Short Run Low Gray Level Emphasis HLL | |
| High Gray Level Zone Emphasis HHL | |
| Small Area Emphasis LHH | |
| Maximum HHH | |
| Example 4. Substituting each feature with an alternative feature from the same cluster (Table 1b) | |
| Elongation | 0.832 |
| Dependence Variance LLL | |
| Large Dependence Emphasis LLL | |
| Run Variance HLH | |
| Dependence Variance HLH | |
| Large Area Emphasis LHL | |
| Size Zone Non Uniformity LLH | |
| Skewness LLH | |
| Small Area High Gray level Emphasis LHH | |
| Difference Entropy HHL | |
| Kurtosis HHL | |
| Zone Entropy HHH | |
| Size Zone Non Uniformity HHL | |
| Variance LLL | |
| Correlation HHL | |
| Size Zone Non Uniformity Normalized HHL | |

It can clearly be seen from Table 7 that all of the tested radiomic signatures of the invention provide a high accuracy of ischaemic stroke detection. Thus, the data presented in Table 7 demonstrate that regardless of which features are selected from each of the identified clusters or groups the radiomic signature of the invention provides improved prediction of cardiovascular risk over previously used models.

Summary of Findings

The studies outlined above demonstrate that radiomic phenotyping of a human epicardial region, for example periatrial tissue, may be used to assess phenotypic changes related to cardiac health. Following an unbiased process for feature selection, and machine learning for algorithm training, internal cross-validation, and external testing, it is possible to identify a radiomic fingerprint of myocardial health (for example using a cardiac condition such as heart arrhythmia as a surrogate marker of myocardial health) in epicardial tissue and to develop a radiomic signature or score to characterise the epicardial region and therefore also to indirectly characterise the adjacent myocardium.

The ECR radiomic signature of the invention also adds incremental value beyond traditional risk factors in predicting the development of cardiac conditions such as heart arrhythmia, for example post-operative atrial fibrillation, and captures features of myocardial biology, in particular of the atria, such as fibrosis and myocardial oxidative stress.

Surprisingly, the radiomic signature need not be constructed from the radiomic features that are most strongly independently associated with the cardiac condition or myocardial disease. Instead, it is actually advantageous to include a selection of radiomic features from different "clusters" of correlated or similar radiomic features instead of merely including those radiomic features that are individually most associated with the cardiac condition or myocardial disease. Furthermore, the significant radiomic features may be substituted with collinear equivalents while still providing an effective signature that is indicative of myocardial disease.

A particularly attractive aspect of the invention is that it can be performed on historic medical imaging data that have been collected previously. The signature of the invention may be derived and calculated based on historic imaging data and the invention therefore provides a convenient tool for assessing a large number of patients without the need to perform further scans. The method of the invention need not therefore include the step of collecting the medical imaging data and can be performed based on a post-hoc analysis of existing medical imaging data.

The invention claimed is:

1. A method for characterising an epicardial region comprising epicardial tissue, the method comprising calculating the value of an epicardial radiomic signature of the epicardial region using medical imaging data;
   wherein the epicardial radiomic signature is calculated on the basis of measured values of a plurality of epicardial radiomic features of the epicardial region, the measured values of the epicardial radiomic features being calculated from the medical imaging data; and
   wherein the epicardial radiomic signature provides a measure of the texture of the epicardial tissue.

2. The method of claim 1, wherein the epicardial radiomic signature is indicative of cardiac health.

3. The method of claim 1 or 2, wherein the epicardial radiomic signature is predictive of the likelihood of the subject developing a cardiac condition, optionally wherein the cardiac condition is heart arrhythmia.

4. The method of claim 1 or 2, wherein the epicardial radiomic signature is predictive of the likelihood of the subject experiencing stroke.

5. The method of claim 4, wherein the epicardial region comprises a peri-atrial region, optionally wherein the peri atrial region comprises the intra-atrial septum epicardial region and the anterior left or right atrium epicardial region.

6. The method of claim 1, wherein the plurality of epicardial radiomic features comprises at least two epicardial radiomic features selected from the epicardial radiomic features of groups 1 to 15, wherein the at least two epicardial radiomic features are each selected from different groups, and wherein:

group 1 consists of Inverse Difference Moment HHH, Inverse Difference Normalized HHH, Contrast HHH (GLCM), Range HHH, Complexity HHH, Maximum HHH, Large Dependence High Gray Level Emphasis HHH, and Short Run Low Gray Level Emphasis HHH;

group 2 consists of Minimum LHH, Long Run Low Gray Level Emphasis LHH, Short Run High Gray Level Emphasis LHH, High Gray Level Emphasis LHH, High Gray Level Run Emphasis LHH, Small Area High Gray Level Emphasis LHH, High Gray Level Zone Emphasis LHH, Autocorrelation LHH, Joint Average LHH, Sum Average LHH, Short Run Low Gray Level Emphasis LHH, Long Run High Gray Level Emphasis LHH, Range LHH, Low Gray Level Emphasis LHH, Low Gray Level Run Emphasis LHH, Large Dependence Low Gray Level Emphasis LHH, Low Gray Level Zone Emphasis LHH, Small Area Low Gray Level Emphasis LHH, Small Dependence High Gray Level Emphasis LHH, Complexity LHH, Large Dependence High Gray Level Emphasis LHH, Cluster Prominence LHH, Gray Level Variance LHH (GLSZM), and Maximum LHH;

group 3 consists of Low Gray Level Zone Emphasis LLL, Short Run Low Gray Level Emphasis LLL, Low Gray Level Run Emphasis LLL, Low Gray Level Emphasis LLL, Long Run Low Gray Level Emphasis LLL, Small Area Low Gray Level Emphasis LLL, Small Dependence Low Gray Level Emphasis LLL, Large Area Low Gray Level Emphasis LLL, and Large Dependence Low Gray Level Emphasis LLL;

group 4 consists of Maximum Probability LLL, Joint Energy LLL, Joint Entropy LLL, Maximum Probability, Joint Energy, Joint Entropy, Gray Level Non Uniformity Normalized, Energy LHL, Uniformity, Size Zone Non Uniformity, Sum Entropy, Gray Level Non Uniformity Normalized, Entropy, Gray Level Non Uniformity Normalized LLL, Uniformity LLL, Mean, Gray Level Non Uniformity Normalized LLL, Root Mean Squared, Interquartile Range, Sum Entropy LLL, Robust Mean Absolute Deviation, Size Zone Non Uniformity HLL, Size Zone Non Uniformity LHL, 10th Percentile, Energy HHL, Median, Dependence Non Uniformity LHL, Entropy LLL, Mean Absolute Deviation, Energy LLH, Run Entropy LLL, Interquartile Range LLL, Size Zone Non Uniformity LLH, Energy HLL, Sum of Squares, Dependence Non Uniformity HLL, Robust Mean Absolute Deviation LLL, 10th Percentile LLL, Energy LHH, Dependence Non Uniformity, and Run Entropy;

group 5 consists of Busyness LHH, Strength LHH, Strength HHH, Busyness HHH, Busyness LHL, and Large Area Low Gray Level Emphasis LHH;

group 6 consists of Zone Entropy LLL, Dependence Entropy LLL, Root Mean Squared LLL, Mean LLL, Run Entropy, Dependence Entropy, Median LLL, Median, Mean, 10th Percentile LLL, Uniformity, Gray Level Non Uniformity Normalized (GLDM), Root Mean Squared, 90th Percentile, Entropy, 10th Percentile, Interquartile Range LLL, Run Entropy LLL, Robust Mean Absolute Deviation LLL, Gray Level Non Uniformity Normalized LLL (GLDM), and Uniformity LLL;

group 7 consists of Run Entropy LLL, Entropy LLL, Mean Absolute Deviation LLL, Mean Absolute Deviation, Robust Mean Absolute Deviation, Robust Mean Absolute Deviation LLL, Variance, Gray Level Variance (GLDM), Gray Level Variance LLL (GLDM), Variance LLL, Gray Level Variance LLL (GLSZM), Gray Level Variance (GLZM), Interquartile Range, Interquartile Range LLL, Entropy, Gray Level Variance LLL (GLDM), Root Mean Squared, Run Entropy, Gray Level Variance (GLDM), Sum Entropy, Sum of Squares, Sum Entropy LLL, Sum of Squares LLL, Cluster Tendency, Cluster Tendency LLL, Joint Entropy, Root Mean Squared LLL, Contrast (GLCM), Joint Entropy LLL, Cluster Prominence, Cluster Prominence LLL, Low Gray Level Emphasis, Short Run Low Gray Level Emphasis, Low Gray Level Run Emphasis, Long Run Low Gray Level Emphasis, Zone Entropy LLL, Low Gray Level Zone Emphasis, Uniformity LLL, Gray Level Non Uniformity Normalized LLL (GLDM), Gray Level Non Uniformity Normalized LLL (GLSZM), 10th Percentile, 10th Percentile LLL, Gray Level Non Uniformity Normalized (GLDM), Gray Level Non Uniformity Normalized (GLSZM), Mean, Uniformity, Joint Energy, Median, Joint Energy LLL, Maximum Probability, Mean LLL, and Maximum Probability LLL;

group 8 consists of Maximum 3D Diameter, Maximum 2D Diameter Slice, Maximum 2D Diameter Column, and Major Axis;

group 9 consists of Long Run High Gray Level Emphasis LLL, High Gray Level Emphasis LLL, High Gray Level Run Emphasis LLL, High Gray Level Zone Emphasis LLL, Short Run High Gray Level Emphasis LLL, Autocorrelation LLL, Joint Average LLL, Small Area High Gray Level Emphasis LLL, Small Dependence High Gray Level Emphasis LLL, Minimum LLL, Large Dependence Low Gray Level Emphasis LLL, Large Dependence High Gray Level Emphasis LLL, Large Area High Gray Level Emphasis LLL, Large Area Low Gray Level Emphasis LLL, Long Run Low Gray Level Emphasis LLL, Low Gray Level Emphasis LLL, Low Gray Level Run Emphasis LLL, and Short Run Low Gray Level Emphasis LLL;

group 10 consists of Joint Average LLL, Autocorrelation LLL, Long Run High Gray Level Emphasis LLL, High Gray Level Emphasis LLL, High Gray Level Run Emphasis LLL, High Gray Level Zone Emphasis LLL, Short Run High Gray Level Emphasis LLL, Small Area High Gray Level Emphasis LLL, Small Dependence High Gray Level Emphasis LLL, Minimum LLL, Large Dependence Low Gray Level Emphasis LLL, Large Dependence High Gray Level Emphasis LLL, Large Area High Gray Level Emphasis LLL, Large Area Low Gray Level Emphasis LLL, Long Run Low Gray Level Emphasis LLL, Low Gray Level Emphasis LLL, Low Gray Level Run Emphasis LLL, Short Run Low Gray Level Emphasis LLL, and Low Gray Level Zone Emphasis LLL;

group 11 consists of Difference Entropy LLL, Difference Average LLL, Contrast LLL (NGTDM), Difference Entropy, Inverse Difference LLL, Contrast (GLCM), Difference Variance, Inverse Difference Moment LLL, Difference Average, Inverse Variance LLL, Inverse Variance, Difference Variance LLL, Inverse Difference, Inverse Difference Moment, Inverse Difference Moment Normalized, Inverse Difference Normalized, Contrast (GNGTDM), Joint Entropy, Sum Entropy LHL, Joint Energy LHL, Run Entropy LHL, Size Zone Non Uniformity Normalized LLL, Small Area Emphasis LLL, Short Run Emphasis, Size Zone Non Uniformity Normalized, Small Area Emphasis, Gray Level Non Uniformity Normalized LHL (GLSZM), Joint Entropy LHL, Short Run Emphasis LLL, Small Dependence Emphasis LLL, Dependence Non Uniformity Normalized LLL, Gray Level Non Uniformity Normalized LHL (GLDM), Small Dependence Emphasis, Entropy LHL, Long Run Emphasis LLL, Mean Absolute Deviation LHL, Robust Mean Absolute Deviation LHL, Uniformity LHL, Interquartile Range LHL, Joint Energy, Run Length Non Uniformity Normalized LLL, Run Percentage LLL, Zone Percentage LLL, Long Run Emphasis, Sum of Squares LHL, Complexity LLL, Run Length Non Uniformity Normalized, Run Percentage, Zone Percentage, Cluster Tendency LHL, Run Variance LLL, Large Dependence Emphasis LLL, Dependence Non Uniformity Normalized, Run Variance, Gray Level Variance LHL (GLDM), Large Area Emphasis LLL, Variance LHL, Gray Level Variance LHL (GLSZM), Large Dependence Emphasis, Large Area Emphasis, Maximum Probability LHL, Root Mean Squared LHL, Difference Entropy LHL, Gray Level Variance LHL (GLRLM), Zone Variance LLL, Dependence Variance LLL, Inverse Difference LHL, Inverse Difference Moment LHL, Zone Variance, Large Area High Gray Level Emphasis, 90th Percentile LHL, Sum Entropy LLH, Difference Average LHL, Sum of Squares, Dependence Entropy LHH, Contrast LHL (GLCM), Joint Energy HLL, Difference Entropy HLL, Difference Variance LHL, Dependence Variance, Maximum Probability HLL, Complexity, Joint Entropy HLL, Joint Energy LLL, Sum Entropy LHH, Inverse Variance LHL, 90th Percentile LLH, Inverse Difference HLL, Inverse Difference Moment HLL, Difference Variance HLL, Cluster Tendency LHH, Difference Average HLL, Cluster Tendency LLH, Contrast HLL (GLCM), Run Entropy LHH, Inverse Variance HLL, Joint Energy LLH, Joint Energy HHL, Joint Entropy LLL, Run Entropy LLH, Joint Entropy LLH, Large Dependence High Gray Level Emphasis, Maximum Probability HHL, Joint Entropy HHL, Sum Entropy HHL, Gray Level Non Uniformity Normalized HLL (GLDM), Robust Mean Absolute Deviation LLH, Uniformity HLL, Cluster Prominence LHL, Complexity LHL, Entropy LLH, Gray Level Non Uniformity Normalized LLH (GLDM), Mean Absolute Deviation LLH, Run Entropy HHL, Uniformity LLH, Gray Level Non Uniformity Normalized LLH (GLSZM), Interquartile Range HLL, Interquartile Range LLH, Maximum Probability LLH, Robust Mean Absolute Deviation HLL, Gray Level Non Uniformity Normalized HHL (GLDM), Long Run Emphasis LHL, Robust Mean Absolute Deviation HHL, Run Variance LHL, Uniformity HHL, Interquartile Range HHL, Joint Entropy LHH, Sum of Squares LLH, 10th Percentile HHL, 90th Percentile HHL, Entropy HHL, Cluster Tendency HHL, Gray Level Non Uniformity Normalized HLL (GLSZM), Mean Absolute Deviation HHL, 10th Percentile LHL, Difference Entropy HHL, Sum of Squares HHL, Contrast LLL (GLCM), Gray Level Variance HHL (GLDM), Variance HHL, Entropy HLL, Gray Level Non Uniformity Normalized HHL (GLSZM), Gray Level Variance HHL (GLSZM), Inverse Difference HHL, Joint Energy LHH, Root Mean Squared HHL, Short Run Emphasis LHL, Sum of Squares LHH, 10th Percentile LHH, Inverse Difference Moment HHL, Mean Absolute Deviation LHH, Run Percentage LHL, Zone Percentage LHL, Dependence Non Uniformity Normalized LHL, Entropy LHH, Gray Level Non Uniformity Normalized LHH (GLSZM), Large Dependence Emphasis LHL, Interquartile Range LHH, Maximum Probability LHH, Small Dependence Emphasis LHL, Uniformity LHH, Large Area Emphasis LHL, Robust Mean Absolute Deviation LHH, Root Mean Squared LLH, Difference Average HHL, Small Dependence Low Gray Level Emphasis, Entropy LLL, Gray Level Variance (GLDM), Run Length Non Uniformity Normalized LHL, Variance, Zone Variance LHL, Cluster Prominence HHL, Dependence Variance LHL, Gray Level Variance LHH (GLDM), Root Mean Squared LHH, Gray Level Variance (GLSZM), Variance LHH, Contrast HHL (GLCM), Dependence Entropy HHL, Size Zone Non Uniformity Normalized LHL, Small Area Emphasis LHL, Sum Entropy HHH, Difference Variance HHL, Gray Level Variance HHL (GLRLM), Dependence Entropy LHL, Gray Level Variance LLH (GLSZM), Run Entropy HLL, Variance LLH, 90th Percentile LHH, Mean Absolute Deviation HLL, Gray Level Variance LLH (GLDM), Cluster Tendency HHH, Difference Entropy LLH, Inverse Difference Moment LLH, Gray Level Non Uniformity Normalized LHH (GLDM), Inverse Difference LLH, Mean Absolute Deviation, and 90th Percentile HLL;

group 12 consists of Sum Entropy HHH, Cluster Tendency HHH, Cluster Prominence HHH, Joint Entropy HHH, Joint Energy HHH, Difference Entropy HHH, Difference Variance HHH, Sum of Squares HHH, Gray Level Non Uniformity Normalized HHH (GLSZM), Uniformity HHH, Entropy HHH, Gray Level Variance HHH (GLDM), Gray Level Variance HHH (GLSZM), Root Mean Squared HHH, Variance HHH, Mean Absolute Deviation HHH, 10th Percentile HHH, Robust Mean Absolute Deviation HHH, 90th Percentile HHH, Interquartile Range HHH, Gray Level Non Uniformity Normalized HHH (GLDM), Gray Level Variance HHH (GLRLM), Sum Entropy LHH, Joint Entropy HHL, Difference Entropy HHL, Cluster Tendency LHH, Joint Energy HHL, Long Run Emphasis HHL, Maximum Probability HHL, Short Run Emphasis HHL, Large Area Low Gray Level Emphasis HHL, Sum Entropy HHL, Size Zone Non Uniformity Normalized HHL, Sum of Squares HHL, Difference Variance HHL, Joint Entropy LHH, Run Length Non Uniformity Normalized HHL, Cluster Tendency HHL, Contrast HHL (GLCM), Difference Average HHL, Inverse Difference HHL, Large Dependence Emphasis HHL, Run Percentage HHL, Run Variance HHL, Small Area Emphasis HHL, Inverse Difference Moment HHL, Small Dependence Emphasis HHL, Sum of Squares LHH, Gray Level Variance LHH (GLDM), Root Mean Squared HHL, Variance HHL, Difference Variance LHH, Entropy HHL, Gray Level Variance HHL (GLDM), Gray Level Variance HHL (GLSZM), Gray Level Variance LHH (GLSZM), Mean Absolute Deviation HHL, Root Mean Squared LHH, Variance LHH, Joint Energy HLH, 90th Percentile HHL, Joint Energy LHH, Dependence Non Uniformity Normalized HHL, Entropy LHH, Gray Level Non Uniformity Normalized HHL (GLSZM), Joint Entropy HLH, Uniformity HHL, Cluster Prominence HHL, Cluster Prominence LHH, Mean Absolute Deviation LHH, 10th Percentile HHL, Maximum Probability HLH, Robust Mean Absolute Deviation HHL, Difference Entropy LHH, Gray Level Non Uniformity Normalized LHH (GLSZM), Maximum Probability LHH, Zone Percentage HHL, Uniformity LHH, Interquartile Range HHL, 90th Percentile LHH, Dependence Variance HHL, Robust Mean Absolute Deviation LHH, Interquartile Range LHH, Run Entropy LHH, Small Dependence High Gray Level Emphasis HHL, Sum Entropy HLH, Contrast LHH (GLCM), 10th Percentile LHH, Gray Level Variance HHL (GLRLM), Cluster Tendency HLH, Run Entropy HHH, Small Area Emphasis HLH, Difference Entropy HLL, Gray Level Non Uniformity Normalized HHL (GLDM), Large Dependence Low Gray Level Emphasis HHL, Size Zone Non Uniformity Normalized HLH, Inverse Difference HLH, Long Run Emphasis HLH, Sum of Squares HLH, Run Entropy HHL, Small Area Emphasis HLL, Inverse Difference Moment HLH, Size Zone Non Uniformity Normalized HLL, Short Run Emphasis HLH, Small Dependence Emphasis HLL, Difference Variance HLL, Large Dependence Emphasis HLL, Difference Average LHH, Difference Variance HLH, Gray Level Variance HLH (GLDM), Root Mean Squared HLH, Run Percentage HLL, Short Run Emphasis HLL, Variance HLH, Gray Level Variance HLH (GLSZM), Long Run Emphasis HLL, Run Length Non Uniformity Normalized HLL, Zone Percentage HLL, 10th Percentile HLH, Cluster Prominence HLH, Dependence Non Uniformity Normalized HLL, Entropy HLH, Gray Level Non Uniformity Normalized LHH (GLDM), Small Dependence Emphasis HLH, Difference Average HLH, Mean Absolute Deviation HLH, Run Variance HLH, Run Variance HLL, Robust Mean Absolute Deviation HLH, Gray Level Non Uniformity Normalized HLH (GLSZM), Uniformity HLH, Interquartile Range HLH, Joint Entropy HLL, Inverse Difference Moment LHH, Joint Energy HLL, Large Area Emphasis HLL, Small Dependence Emphasis, Complexity HHL, Dependence Variance HLL, Large Area Emphasis HHL, 90th Percentile HLH, Inverse Difference LHH, Run Percentage HLH, Run Variance, Zone Percentage, Contrast HLH (GLCM), Long Run Emphasis, Large Area Emphasis, Run Length Non Uniformity Normalized HLH, Size Zone Non Uniformity Normalized, Small Area Emphasis, Large Dependence Emphasis HLH, Dependence Non Uniformity Normalized, Large Dependence Emphasis, Run Percentage, Short Run Emphasis, Zone Percentage HLH, Zone Variance HLL, Contrast HLL (GLCM), Large Area Low Gray Level Emphasis HLH, Zone Variance, Difference Average HLL, Gray Level Variance LHH (GLRLM), Inverse Difference HLL, Dependence Entropy HHH, Difference Entropy, Inverse Difference Moment HLL, Joint Energy LHL, Joint Energy LLH, Run Length Non Uniformity Normalized, Zone Variance HHL, Difference Entropy LHL, Small Area High Gray Level Emphasis HHL, Maximum Probability HLL, Gray Level Variance HLH (GLRLM), Inverse Variance, Dependence Entropy LHH, Gray Level Non Uniformity Normalized HLH_GLSDM, Inverse Difference LHL, Inverse Difference Moment LHL, Small Dependence High Gray Level Emphasis HLH, Dependence Non Uniformity Normalized HLH, Joint Entropy LHL, Long Run Emphasis LHL, Run Variance LHL, Inverse Difference Moment LLH, Joint Entropy LLH, Large Dependence Emphasis LHL, Dependence Variance, Dependence Variance LHL, Inverse Difference LLH, Maximum Probability LHL, Difference Average, Run Entropy HLH, Dependence Non Uniformity Normalized LHL, Difference Entropy LLH, Large Area Emphasis LHL, Maximum Probability LLH, Contrast (GLCM), Run Percentage LHL, Short Run Emphasis LHL, Short Run High Gray Level Emphasis HHL, Sum Entropy LLH, Long Run Low Gray Level Emphasis HHL, Short Run Emphasis LHH, Small Dependence Emphasis LHH, Zone Percentage LHL, Zone Variance LHL, Inverse Difference, Inverse Difference Moment, Small Dependence Emphasis LHL, Zone Percentage LHH, Inverse Variance HLL, Large Dependence Low Gray Level Emphasis HLH, Difference Average LHL, Small Area High Gray Level Emphasis HHH, Run Variance LLH, Difference Variance LHL, Large Area Low Gray Level Emphasis HLL, Run Length Non Uniformity Normalized LHL, Contrast LHL (GLCM), Dependence Variance HLH, Inverse Difference Normalized, Maximum LLL, Run Length Non Uniformity Normalized LHH, Inverse Difference Moment Normalized, Long Run Emphasis LLH, Size Zone Non Uniformity HHH, Size Zone Non Uniformity Normalized LHL, Small Area Emphasis LHL, Interquartile Range LHL, Gray Level Non Uniformity Normalized LHL (GLSZM), Run Percentage LHH, Small Area High Gray Level Emphasis HLH, Uniformity LHL, Difference Average LLH, Difference Variance, Large Area High Gray Level Emphasis, Long Run Emphasis LHH, Small Dependence High Gray Level Emphasis HHH, High Gray Level Run Emphasis HHL, Range HHL, Robust Mean Absolute Deviation LHL, High Gray Level Emphasis HHL, Inverse Variance LHL, Inverse Variance LLH, Uniformity HLL, Gray Level Non Uniformity Normalized HLL_GLSDM, Large Dependence Emphasis LLH, Entropy LHL, Sum of Squares LLH, Interquartile Range HLL, Interquartile Range LLH, Robust Mean Absolute Deviation HLL, Sum Entropy LHL, 90th Percentile LLH, Complexity, Dependence Non Uniformity Normalized LLH, Gray Level Non Uniformity Normalized LHL (GLDM), Robust Mean Absolute Deviation LLH, Run Percentage LLH, Small Dependence Emphasis LLH, Entropy HLL, High Gray Level Zone Emphasis HHL, Short Run Emphasis LLH, Uniformity LLH, Zone Percentage LLH, Dependence Variance LLH, Gray Level Non Uniformity Normalized LLH (GLSZM), Mean Absolute Deviation LHL, Sum of Squares LHL, Contrast LLH (GLCM), Large Area Low Gray Level Emphasis LHH, Entropy LLH, Cluster Tendency LLH, Mean Absolute Deviation LLH, Size Zone Non Uniformity Normalized LLH, Small Area Emphasis LLH, Complexity HLH, High Gray Level Run Emphasis HHH, Large Area Emphasis LLH, Large Dependence Emphasis LHH, Difference Variance LLH, Informational Measure of Correlation 1, Large Area Low Gray Level Emphasis LHL, Run Length Non Uniformity Normalized LLH, Run Variance LHH, Complexity HLL, Large Dependence Emphasis LLL, Dependence Non Uniformity Normalized LLL, Short Run High Gray Level Emphasis HLH, Run Entropy LHL, Small Dependence Emphasis LLL, Dependence Variance LLL, Gray Level Non Uniformity Normalized HLL (GLDM), Gray Level Non Uniformity Normalized LLH (GLDM), Gray Level Variance LHL (GLDM), High Gray Level Zone Emphasis HHH, Large Area Emphasis HLH, Large Area Emphasis LLL, Long Run Emphasis LLL, Mean Absolute Deviation HLL, Run Percentage LLL, Short Run Emphasis LLL, Zone Percentage LLL, Zone Variance LLH, Run Length Non Uniformity Normalized LLL, Variance LHL, Complexity LHL, Gray Level Variance LHL (GLSZM), Long Run Low Gray Level Emphasis HLH, Run Variance LLL, Zone Variance LLL, Range HHH, Small Area Emphasis LLL, Sum of Squares HLL, Variance HLL, Gray Level Variance HLL (GLSZM), Gray Level Variance HLL (GLDM), Inverse Difference Moment LLL, Size Zone Non Uniformity Normalized HHH, Size Zone Non Uniformity Normalized LLL, Small Dependence High Gray Level Emphasis LHH, Inverse Difference LLL, Minimum HHH, Minimum HHL, Run Entropy LLH, Small Area Emphasis HHH, 10th Percentile HLL, Inverse Variance LLL, High Gray Level Emphasis HHH, Root Mean Squared LLH, Small Dependence High Gray Level Emphasis HLL, Gray Level Variance LHL (GLRLM), Gray Level Variance LLH (GLDM), Autocorrelation HHL, Variance LLH, 10th Percentile LHL, Maximum HHL, Short Run High Gray Level Emphasis HHH, Gray Level Variance LLH (GLSZM), Sum Entropy HLL, Difference Entropy LLL, Cluster Tendency LHL, Zone Variance HLH, Difference Average LLL, Large Dependence Low Gray Level Emphasis LHL, Root Mean Squared HLL, Complexity LHH, High Gray Level Emphasis HLH, Large Dependence Low Gray Level Emphasis HLL, High Gray Level Run Emphasis HLH, Root Mean Squared LHL, Small Dependence High Gray Level Emphasis LHL, Dependence Entropy HHL, Run Entropy HLL, Large Dependence Low Gray Level Emphasis LHH, Size Zone Non Uniformity HHL, Cluster Tendency HLL, and Maximum Probability HHH;

group 13 consists of Difference Entropy LHH, Contrast LHH (GLCM), Difference Average LHH, Joint Entropy LHH, Difference Variance LHH, Sum of Squares LHH, Entropy LHH, Mean Absolute Deviation LHH, Gray Level Variance LHH (GLDM), Robust Mean Absolute Deviation LHH, Root Mean Squared LHH, Sum Entropy LHH, Variance LHH, Gray Level Variance LHH (GLSZM), Interquartile Range LHH, Cluster Tendency LHH, 90th Percentile LHH, Run Entropy LHH, Short Run Emphasis LHH, Run Length Non Uniformity Normalized LHH, Cluster Prominence LHH, Small Dependence Emphasis LHH, Run Percentage LHH, Interquartile Range HHH, Robust Mean Absolute Deviation HHH, 90th Percentile HHH, Mean Absolute Deviation HHH, Gray Level Variance LHH (GLRLM), Root Mean Squared HHH, Variance HHH, Zone Percentage LHH, Joint Entropy HHH, Dependence Entropy LHH, Difference Entropy HHH, Sum of Squares HHH, Entropy HHH, Difference Variance HHH, Gray Level Variance HHH (GLSZM), Gray Level Variance HHH (GLDM), Difference Entropy LLH, Difference Entropy LHL, Sum Entropy HHH, Gray Level Variance HHH (GLRLM), Cluster Prominence HHH, Difference Average LLH, Run Percentage LHL, Difference Average LHL, Short Run Emphasis LHL, Dependence Non Uniformity Normalized LHL, Small Dependence Emphasis LHL, Zone Percentage LHL, Joint Entropy LLH, Size Zone Non Uniformity Normalized LHH, Size Zone Non Uniformity Normalized LHL, Small Area Emphasis LHL, Contrast LHL (GLCM), Run Length Non Uniformity Normalized LHL, Contrast LLH (GLCM), Difference Variance LHL, Run Percentage LLH, Short Run Emphasis LLH, Small Area Emphasis LHH, Joint Entropy LHL, Dependence Non Uniformity Normalized LLH, Small Area Emphasis LLH, Small Dependence Emphasis LLH, Size Zone Non Uniformity Normalized LLH, Difference Variance LLH, Zone Percentage LLH, Small Dependence High Gray Level Emphasis LHH, Interquartile Range LLH, Robust Mean Absolute Deviation LLH, Run Length Non Uniformity Normalized LLH, Complexity LHH, Small Dependence Emphasis, Run Percentage, Sum of Squares LLH, Zone Percentage, Entropy LLH, Mean Absolute Deviation LLH, Short Run Emphasis, Dependence Non Uniformity Normalized, Sum Entropy LLH, Run Length Non Uniformity Normalized, Size Zone Non Uniformity Normalized, Small Area Emphasis, Interquartile Range LHL, Robust Mean Absolute Deviation LHL, Difference Entropy, Short Run Emphasis HHL, Small Area Emphasis HHL, Size Zone Non Uniformity Normalized HHL, Entropy LHL, Size Zone Non Uniformity HHH, Difference Average, Run Entropy LLH, Run Length Non Uniformity Normalized HHL, Run Percentage HHL, Cluster Tendency HHH, 90th Percentile LLH, Gray Level Variance LLH (GLDM), Small Area Emphasis HHH, Variance LLH, Mean Absolute Deviation LHL, Small Dependence Emphasis HHL, Contrast (GLCM), Small Area Emphasis HLH, Cluster Tendency LLH, Gray Level Variance LLH (GLSZM), Sum of Squares LHL, Dependence Non Uniformity Normalized HHL, Root Mean Squared LLH, Size Zone Non Uniformity Normalized HHH, Size Zone Non Uniformity Normalized HLH, Complexity LHL, Difference Entropy HHL, Informational Measure of Correlation 1, Total Energy LHH, Run Entropy LHL, Zone Percentage HHL, Difference Average HHL, Sum Entropy LHL, Gray Level Variance LHL (GLDM), Variance LHL, Gray Level Variance LHL (GLSZM), Contrast HHL (GLCM), Difference Variance, Difference Variance HHL, Short Run Emphasis HLH, Joint Entropy HHL, Small Area High Gray Level Emphasis HHH, Small Dependence High Gray Level Emphasis LHL, Difference Entropy HLH, Small Dependence Emphasis HLH, Gray Level Variance LLH (GLRLM), Dependence Non Uniformity Normalized LLL, Gray Level Variance LHL (GLRLM), Interquartile Range HHL, Run Percentage LLL, Zone Percentage LLL, Robust Mean Absolute Deviation HHL, Short Run Emphasis LLL, Size Zone Non Uniformity LHH, Small Dependence Emphasis LLL, Run Length Non Uniformity Normalized LLL, Complexity, Run Percentage HLH, Contrast HHH (GLCM), Maximum LHH, Mean Absolute Deviation HHL, Entropy HHL, Size Zone Non Uniformity Normalized LLL, Small Area Emphasis LLL, Difference Average HLH, Sum of Squares HHL, 90th Percentile HHL, Root Mean Squared HHL, Run Length Non Uniformity Normalized HLH, Variance HHL, Gray Level Variance HHL (GLSZM), Gray Level Variance HHL (GLDM), Root Mean Squared LHL, Joint Entropy HLH, Run Entropy HHH, Zone Percentage HLH, Total Energy HHH, Cluster Tendency LHL, Sum Entropy HHL, Energy LHH, Contrast HLH (GLCM), Difference Variance HLH, Dependence Non Uniformity Normalized LHH, Small Dependence High Gray Level Emphasis HHL, Cluster Tendency HHL, Short Run High Gray Level Emphasis LHH, Dependence Non Uniformity Normalized HLH, Robust Mean Absolute Deviation HLH, Small Area High Gray Level Emphasis LHL, Interquartile Range HLH, Range LHH, and Small Dependence High Gray Level Emphasis HHH;

group 14 consists of Sum of Squares LHH, Cluster Tendency LHH, Entropy LHH, Gray Level Variance LHH (GLDM), Joint Entropy LHH, Gray Level Variance LHH (GLSZM), Mean Absolute Deviation LHH, Root Mean Squared LHH, Variance LHH, Contrast LHH (GLCM), Difference Entropy LHH, Difference Variance LHH, Sum Entropy LHH, Difference Average LHH, Robust Mean Absolute Deviation LHH, Interquartile Range LHH, 90th Percentile LHH, Run Entropy LHH, Cluster Prominence LHH, Short Run Emphasis LHH, Small Dependence Emphasis LHH, Run Length Non Uniformity Normalized LHH, Run Percentage LHH, Gray Level Variance LHH (GLRLM), Interquartile Range HHH, Robust Mean Absolute Deviation HHH, 90th Percentile HHH, Dependence Entropy LHH, Mean Absolute Deviation HHH, Zone Percentage LHH, Root Mean Squared HHH, Variance HHH, Joint Entropy HHH, Entropy HHH, Difference Entropy HHH, Sum of Squares HHH, Gray Level Variance HHH (GLSZM), Gray Level Variance HHH (GLDM), Difference Variance HHH, Run Percentage LHL, Difference Entropy LHL, Dependence Non Uniformity Normalized LHL, Short Run Emphasis LHL, Small Dependence Emphasis LHL, Zone Percentage LHL, Difference Entropy LLH, Size Zone Non Uniformity Normalized LHL, Small Area Emphasis LHL, Difference Average LHL, Run Length Non Uniformity Normalized LHL, Difference Average LLH, Sum Entropy HHH, Contrast LHL (GLCM), Cluster Prominence HHH, Difference Variance LHL, Run Percentage LLH, Small Area Emphasis LLH, Small Dependence Emphasis, Short Run Emphasis LLH, Size Zone Non Uniformity Normalized LLH, Small Dependence Emphasis LLH, Zone Percentage, Contrast LLH (GLCM), Dependence Non Uniformity Normalized LLH, Joint Entropy LLH, Run Percentage, Zone Percentage LLH, Short Run Emphasis, Dependence Non Uniformity Normalized, Gray Level Variance HHH (GLRLM), Joint Entropy LHL, Mean Absolute Deviation LLH, Robust Mean Absolute Deviation LLH, Size Zone Non Uniformity Normalized, Small Area Emphasis, Interquartile Range LLH, Entropy LLH, Run Length Non Uniformity Normalized LLH, Run Length Non Uniformity Normalized, Sum of Squares LLH, Difference Variance LLH, Small Dependence High Gray Level Emphasis LHH, Interquartile Range LHL, Robust Mean Absolute Deviation LHL, Complexity LHH, Difference Entropy, Entropy LHL, Gray Level Variance LLH (GLDM), Sum Entropy LLH, Variance LLH, Difference Average, Short Run Emphasis HHL, Run Entropy LLH, Small Area Emphasis HHL, Gray Level Variance LLH (GLSZM), Size Zone Non Uniformity Normalized HHL, Root Mean Squared LLH, 90th Percentile LLH, Contrast (GLCM), Mean Absolute Deviation LHL, Run Percentage HHL, Cluster Tendency LLH, Run Length Non Uniformity Normalized HHL, Small Dependence Emphasis HHL, Size Zone Non Uniformity Normalized LHH, Sum of Squares LHL, Small Area Emphasis HLH, Dependence Non Uniformity Normalized HHL, Cluster Tendency HHH, Run Entropy LHL, Size Zone Non Uniformity Normalized HLH, Zone Percentage HHL, Complexity LHL, Gray Level Variance LHL (GLSZM), Variance LHL, Gray Level Variance LHL (GLDM), Small Area Emphasis LHH, Sum Entropy LHL, Difference Entropy HHL, Difference Variance, Dependence Non Uniformity Normalized LLL, Difference Average HHL, Gray Level Variance LLH (GLRLM), Zone Percentage LLL, Run Percentage LLL, Size Zone Non Uniformity HHH, Small Dependence Emphasis LLL, Short Run Emphasis LLL, Run Length Non Uniformity Normalized LLL, Informational Measure of Correlation 1, Size Zone Non Uniformity Normalized LLL, Small Area Emphasis LLL, Complexity, Contrast HHL (GLCM), Small Dependence High Gray Level Emphasis LHL, Short Run Emphasis HLH, Small Dependence Emphasis HLH, Gray Level Variance LHL (GLRLM), Joint Entropy HHL, Difference Variance HHL, Interquartile Range HHL, Robust Mean Absolute Deviation HHL, Small Area Emphasis HHH, Mean Absolute Deviation HHL, Root Mean Squared LHL, Run Percentage HLH, Size Zone Non Uniformity Normalized HHH, Entropy HHL, 90th Percentile HHL, Root Mean Squared HHL, Total Energy LHH, Variance HHL, Difference Entropy HLH, Gray Level Variance HHL (GLSZM), Sum of Squares HHL, Gray Level Variance HHL (GLDM), Run Length Non Uniformity Normalized HLH, Zone Percentage HLH, Cluster Tendency LHL, Difference Average HLH, Small Area High Gray Level Emphasis HHH, Maximum LHH, Difference Average LLL, Sum Entropy HHL, Small Dependence High Gray Level Emphasis HHH, Cluster Tendency HHL, Dependence Non Uniformity Normalized HLH, Difference Entropy LLL, Joint Entropy HLH, Short Run High Gray Level Emphasis LHH, Contrast HLH (GLCM), Run Entropy HHH, Size Zone Non Uniformity LHH, Small Area High Gray Level Emphasis LHL, Robust Mean Absolute Deviation HLH, Interquartile Range HLH, Difference Variance HLH, Range LHH, Mean Absolute Deviation HLH, Run Entropy HHL, Cluster Prominence HHL, Gray Level Variance HLH (GLDM), Entropy HLH, Root Mean Squared HLH, Small Dependence High Gray Level Emphasis HHH, Variance HLH, Gray Level Variance HHL (GLRLM), Gray Level Variance HLH (GLSZM), Energy LHH, Small Area High Gray Level Emphasis LHH, Complexity HHL, Contrast HHH (GLCM), 90th Percentile HLH, Sum of Squares HLH, Run Percentage HLL, Size Zone Non Uniformity HHL, Complexity LLH, Dependence Non Uniformity Normalized HLL, Small Dependence Emphasis HLL, 90th Percentile LHL, Dependence Non Uniformity Normalized LHH, and Zone Percentage HLL; and group 15 consists of Gray Level Variance LHH (GLDM), Root Mean Squared LHH, Variance LHH, Entropy LHH, Mean Absolute Deviation LHH, Sum of Squares LHH, Gray Level Non Uniformity Normalized LHH (GLDM), Cluster Tendency LHH, Uniformity LHH, Contrast LHH (GLCM), Difference Variance LHH, Run Entropy LHH, 90th Percentile LHH, Joint Entropy LHH, Robust Mean Absolute Deviation LHH, 10th Percentile LHH, Interquartile Range LHH, Sum Entropy LHH, Difference Average LHH, Joint Energy LHH, Inverse Difference Moment LHH, Inverse Difference LHH, Maximum Probability LHH, Cluster Prominence LHH, Gray Level Non Uniformity Normalized LHH (GLSZM), Gray Level Variance LHH (GLSZM), Short Run Emphasis LHH, Dependence Entropy LHH, Small Dependence Emphasis LHH, Run Length Non Uniformity Normalized LHH, Long Run Emphasis LHH, Interquartile Range HHH, Mean Absolute Deviation HHH, 90th Percentile HHH, Robust Mean Absolute Deviation HHH, Root Mean Squared HHH, Run Percentage LHH, Variance HHH, 10th Percentile HHH, Zone Percentage LHH, Gray Level Non Uniformity Normalized HHH (GLDM), Uniformity HHH, Entropy HHH, Run Variance LHH, Large Dependence Emphasis LHH, Gray Level Variance HHH (GLSZM), Gray Level Variance HHH (GLDM), Joint Entropy HHH, Sum of Squares HHH, Difference Entropy HHH, Difference Variance HHH, Joint Energy HHH, Large Area Low Gray Level Emphasis LHH, Run Variance LHL, Long Run Emphasis LHL, Inverse Difference Moment LHL, Inverse Difference LHL, Inverse Difference Moment LLH, Inverse Difference LLH, Large Dependence Emphasis LHL, Run Percentage LHL, Small Dependence Emphasis LHL, Zone Percentage LHL, Dependence Non Uniformity Normalized LHL, Short Run Emphasis LHL, Size Zone Non Uniformity Normalized LHL, Small Area Emphasis LHL, Difference Entropy LHL, Cluster Prominence HHH, Gray Level Non Uniformity Normalized HHH (GLSZM), Difference Average LHL, Run Variance LLH, Difference Entropy LLH, Large Area Emphasis LHL, Long Run Emphasis LLH, Small Dependence High Gray Level Emphasis LHH, Sum Entropy HHH, Dependence Variance LHL, Inverse Variance LLH, Inverse Variance LHL, Gray Level Variance HHH (GLRLM), Run Length Non Uniformity Normalized LHL, Contrast LHL (GLCM), Difference Average LLH, Zone Variance LHL, Complexity LHH, Run Variance, Size Zone Non Uniformity Normalized LLH, Small Area Emphasis LLH, Difference Variance LHL, Contrast LLH (GLCM), Long Run Emphasis, Small Dependence Emphasis LLH, Mean Absolute Deviation LLH, Run Percentage LLH, Small Dependence Emphasis, Joint Energy LLH, Short Run Emphasis LLH, Zone Percentage, Dependence Non Uniformity Normalized LLH, Zone Percentage LLH, Entropy LLH, Joint Energy LHL, Large Dependence Emphasis LLH, Robust Mean Absolute Deviation LLH, Interquartile Range LLH, Uniformity LLH, Gray Level Non Uniformity Normalized LLH (GLDM), Run Percentage, Small Area Emphasis, Difference Variance LLH, Joint Entropy LLH, Large Area Emphasis, Size Zone Non Uniformity Normalized, Sum of Squares LLH, Short Run Emphasis, Gray Level Non Uniformity Normalized LLH (GLSZM), Dependence Non Uniformity Normalized, Joint Entropy LHL, Large Dependence Emphasis, Run Length Non Uniformity Normalized LLH, Large Area Low Gray Level Emphasis LHL, Large Dependence Low Gray Level Emphasis LHH, Maximum Probability LHL, Uniformity LHL, Gray Level Non Uniformity Normalized LHL (GLDM), Gray Level Variance LLH (GLDM), Run Length Non Uniformity Normalized, Variance LLH, Zone Variance, Interquartile Range LHL, Long Run Emphasis HHL, Robust Mean Absolute Deviation LHL, Gray Level Variance LLH (GLSZM), Large Area Emphasis LLH, Small Area Emphasis HHL, Dependence Variance LLH, Maximum Probability LLH, Run Entropy LLH, Size Zone Non Uniformity Normalized HHL, Entropy LHL, Root Mean Squared LLH, Size Zone Non Uniformity Normalized LHH, Run Variance HHL, Difference Average, Gray Level Non Uniformity Normalized LHL (GLSZM), Inverse Difference Moment, Inverse Variance, Short Run Emphasis HHL, Inverse Difference, Difference Entropy, Mean Absolute Deviation LHL, 90th Percentile LLH, Cluster Tendency LLH, Contrast (GLCM), Small Area Emphasis HLH, Sum Entropy LLH, Complexity LHL, Small Dependence Emphasis HHL, Zone Variance LLH, Inverse Difference Normalized, Large Dependence Emphasis HHL, Run Percentage HHL, Size Zone Non Uniformity Normalized HLH, Large Area Emphasis LHH, Run Length Non Uniformity Normalized HHL, 10th Percentile LHL, Sum of Squares LHL, Dependence Variance, Inverse Difference Moment Normalized, Small Area Emphasis LHL, Cluster Tendency HHH, Gray Level Variance LHL (GLDM), Run Entropy LHL, Variance LHL, Gray Level Variance LHL (GLSZM), Zone Percentage HHL, Gray Level Variance LLH (GLRLM), Dependence Non Uniformity Normalized HHL, Large Dependence Low Gray Level Emphasis LHL, Inverse Difference HHL, Inverse Difference Moment HHL, Large Area High Gray Level Emphasis, Small Dependence High Gray Level Emphasis LHL, Large Area Low Gray Level Emphasis HHL, Size Zone Non Uniformity HHH, Dependence Variance HHL, Zone Variance LHH, Difference Entropy HHL, Gray Level Variance LHL (GLDM), Difference Average HHL, Long Run Emphasis HLH, Difference Variance, 10th Percentile LLH, Long Run Emphasis LLL, Sum Entropy LHL, Complexity, Maximum Probability HHL, Run Variance LLL, Dependence Non Uniformity Normalized LLL, Zone Percentage LLL, Inverse Difference HLH, Run Percentage LLL, Small Dependence Emphasis HLH, Small Dependence Emphasis LLL, Large Dependence Emphasis LLL, Short Run Emphasis HLH, Short Run Emphasis LLL, Small Area Emphasis HHH, Contrast HHL (GLCM), Large Area Emphasis LLL, Joint Energy HHL, Maximum LHH, Run Length Non Uniformity Normalized LLL, Run Variance HLH, Size Zone Non Uniformity Normalized HHH, 10th Percentile HHL, Inverse Difference Moment HLH, Size Zone Non Uniformity Normalized LLL, Small Area Emphasis LLL, Small Area High Gray Level Emphasis HHH, Interquartile Range HHL, Difference Variance HHL, Robust Mean Absolute Deviation HHL, Root Mean Squared LHL, Short Run High Gray Level Emphasis LHH, Inverse Difference Moment LLL, Large Area Emphasis HHL, Dependence Variance LLL, Joint Entropy HHL, Uniformity HHL, Gray Level Non Uniformity Normalized HHL (GLDM), Zone Variance LLL, Inverse Difference LLL, Mean Absolute Deviation HHL, Entropy HHL, Informational Measure of Correlation 1, Total Energy LHH, Inverse Variance LLL, Range LHH, Root Mean Squared HHL, Run Percentage HLH, Variance HHL, 90th Percentile HHL, Gray Level Variance HHL (GLDM), Difference Average HLH, Gray Level Variance HHL (GLSZM), Difference Entropy HLH, Large Dependence Emphasis HLH, Zone Percentage HLH, Run Length Non Uniformity Normalized HLH, Zone Variance HHL, Run Entropy HHH, Small Area High Gray Level Emphasis LHL, Sum of Squares HHL, Cluster Tendency LHL, Long Run Low Gray Level Emphasis LHH, Maximum Probability HLH, Small Area High Gray Level Emphasis LHH, Small Dependence High Gray Level Emphasis HHL, Joint Energy HLH, Contrast HLH (GLCM), Difference Average LLL, Small Dependence High Gray Level Emphasis HHH, Large Dependence Low Gray Level Emphasis HHL, Sum Entropy HHL, 10th Percentile HLH, Cluster Tendency HHL, Dependence Non Uniformity Normalized HLH, Gray Level Non Uniformity Normalized HHL (GLSZM), High Gray Level Emphasis LHH, High Gray Level Run Emphasis LHH, Joint Entropy HLH, Robust Mean Absolute Deviation HLH, Interquartile Range HLH, Size Zone Non Uniformity LHH, Difference Entropy LLL, Difference Variance HLH, Run Entropy HHL, Contrast HHH (GLCM), Gray Level Variance HHL (GLRLM), Gray Level Variance HLH (GLSZM), Mean Absolute Deviation HLH, Root Mean Squared HLH, Uniformity HLH, Variance HLH, Entropy HLH, Gray Level Non Uniformity Normalized HLH (GLDM), Gray Level Variance HLH (GLDM), Complexity HHL, Large Area Low Gray Level Emphasis HLH, Large Dependence High Gray Level Emphasis, Cluster Prominence HHL, Complexity LLH, 90th Percentile HLH, Energy LHH, Short Run High Gray Level Emphasis LHL, Sum of Squares HLH, Dependence Variance HLH, Short Run High Gray Level Emphasis HHH, High Gray Level Emphasis LHL, High Gray Level Run Emphasis LHL, Correlation, Run Variance HLL, High Gray Level Zone Emphasis LHH, Long Run Emphasis HLL, and Small Dependence High Gray Level Emphasis HLH.

7. The method of claim 6, wherein the at least two epicardial radiomic features comprise at least two of Inverse Difference Moment HHH, Minimum LHH, Low Gray Level Zone Emphasis LLL, Maximum Probability LLL, Busyness LHH, Zone Entropy LLL, Run Entropy LLL Maximum 3D Diameter, Long Run High Gray Level Emphasis LLL, Joint Average LLL, Difference Entropy LLL, Sum Entropy HHH, Difference Entropy LHH, Sum Squares LHH, and Gray Level Variance LHH (GLDM).

8. The method of claim 6, wherein the at least two epicardial radiomic features are selected from the epicardial radiomic features of clusters A to D, wherein the at least two epicardial radiomic features are each selected from different clusters, and wherein:
cluster A consists of the epicardial radiomic features of groups 1 to 5;
cluster B consists of the epicardial radiomic features of groups 6 and 7;
cluster C consists of the epicardial radiomic features of group 8; and
cluster D consists of the epicardial radiomic features of groups 9 to 15.

9. The method of claim 1, wherein the plurality of epicardial radiomic features comprises at least two epicardial radiomic features selected from the epicardial radiomic features of clusters A to D, wherein the at least two epicardial radiomic features are each selected from different clusters, and wherein:
cluster A consists of Inverse Difference Moment HHH, Minimum LHH, Zone Variance LLL, Low Gray Level Zone Emphasis LLL, Maximum Probability LLL, Elongation, Cluster Shade LLL, Busyness LHH, Gray Level Non Uniformity LLL, and Skewness HHH;
cluster B consists of Zone Entropy LLL, Cluster Prominence LLL, Gray Level Variance LLL (GLDM), and Run Entropy LLL;
cluster C consists of Least Axis, Maximum 2D Diameter Row, Major Axis, Maximum 2D Diameter Column, Maximum 2D Diameter Slice, and Maximum 3D Diameter; and
cluster D consists of Autocorrelation LLH, Long Run High Gray Level Emphasis LLL, Joint Average LLL, Autocorrelation LLL, Difference Entropy LLL, Difference Entropy LLH, Sum of Squares HLH, Sum of Squares HHH, Sum Entropy HHH, Gray Level Variance LLH (GLDM), Difference Entropy LHH, Sum Squares LHH, and Gray Level Variance LHH (GLDM).

10. The method of claim 9, wherein:
cluster A consists of Inverse Difference Moment HHH, Minimum LHH, Low Gray Level Zone Emphasis LLL, Maximum Probability LLL, and Busyness LHH;
cluster B consists of Zone Entropy LLL, and Run Entropy LLL;
cluster C consists of Maximum 3D Diameter; and
cluster D consists of Long Run High Gray Level Emphasis LLL, Joint Average LLL, Difference Entropy LLL, Sum Entropy HHH, Difference Entropy LHH, Sum Squares LHH, and Gray Level Variance LHH (GLDM).

11. The method of claim 1, further comprising identifying the epicardial region using an automated segmentation algorithm, optionally wherein the segmentation algorithm has been trained using machine learning to segment the medical imaging data.

12. The method of claim 1 wherein the epicardial region consists of voxels of the medical imaging data having an attenuation value falling within a given range of attenuation values, optionally wherein the range of attenuation values corresponds to adipose and/or connective tissue.

13. The method of claim 12, wherein the given range comprises attenuation values from about −190 to about −30 Hounsfield Units or from about −190 to about +150 Hounsfield Units.

14. The method of claim 1, further comprising predicting the risk of the subject developing a cardiac condition or experiencing stroke based on at least the calculated value of the epicardial radiomic signature, optionally wherein the cardiac condition is heart arrhythmia.

15. The method of claim 1, further comprising identifying, based on the calculated value of the epicardial radiomic signature, whether an individual is at risk of stroke.

16. The method of claim 15, further comprising administering or prescribing a preventative treatment to the individual to reduce the risk of stroke if the individual is identified as being at risk of stroke.

17. The method of claim 1, further comprising determining whether the subject has myocardial disease based on at least the calculated value of the epicardial radiomic signature, optionally wherein the myocardial disease is fibrosis, inflammation or oxidative stress.

18. A method for deriving an epicardial radiomic signature indicative of cardiac health, the method comprising using a radiomic dataset to construct an epicardial radiomic signature indicative of cardiac health, the epicardial radiomic signature being calculated on the basis of a second plurality of epicardial radiomic features;
wherein the dataset comprises the values of a first plurality of epicardial radiomic features obtained from medical imaging data of an epicardial region comprising epicardial tissue for each of a plurality of individuals, the plurality of individuals comprising a first group of individuals having a cardiac condition or myocardial disease or having a history of stroke and a second group of individuals not having the cardiac condition or myocardial disease or a history of stroke;
wherein the second plurality of epicardial radiomic features is selected from amongst the first plurality of epicardial radiomic features; and
wherein the epicardial radiomic signature is constructed to provide a measure of the texture of the epicardial tissue.

19. The method according to claim 18, wherein the method further comprises identifying significant epicardial radiomic features from amongst the first plurality of epicardial radiomic features that are each significantly associated with the cardiac condition or myocardial disease or history of stroke, the second plurality of epicardial radiomic features comprising at least two epicardial radiomic features that are, or are collinear with, different significant epicardial radiomic features.

20. The method according to claim 19, wherein the method further comprises using a feature selection machine learning algorithm to identify a subset of the significant epicardial radiomic features, wherein the at least two epicardial radiomic features are, or are collinear with, different significant epicardial radiomic features belonging to the subset, optionally wherein the at least two epicardial radiomic features comprises all of the significant epicardial radiomic features belonging to the subset, or collinear equivalents thereof.

21. The method according to claim 19, further comprising identifying groups of epicardial radiomic features, each of the groups comprising one of the significant epicardial radiomic features and collinear equivalents thereof that are collinear with the significant epicardial radiomic feature, the at least two epicardial radiomic features being selected from different groups.

22. The method of claim 19, wherein the method comprises identifying a plurality of clusters of the significant epicardial radiomic features by performing a cluster analysis, and wherein the at least two epicardial radiomic features are each selected from, or are selected to be collinear with significant epicardial radiomic features from, different clusters, optionally wherein the cluster analysis identifies the clusters based on the strength of the correlations between the significant epicardial radiomic features.

23. The method of claim 18, wherein the epicardial radiomic signature is constructed to be correlated with the cardiac condition or myocardial disease or history of stroke, optionally wherein the epicardial radiomic signature is constructed to be significantly associated with the cardiac condition or myocardial disease or history of stroke.

24. The method of claim 18, wherein the step of constructing the epicardial radiomic signature is performed using a machine learning algorithm.

25. The method of claim 18, wherein the cardiac condition is associated with myocardial health or disease, optionally wherein the cardiac condition is heart arrhythmia.

26. The method of claim 18, further comprising configuring a system for calculating the value of the epicardial radiomic signature for a patient.

27. The method of claim 18, further comprising characterising an epicardial region of a patient by calculating the value of the epicardial radiomic signature for an epicardial region of the patient.

28. The method of claim 18, wherein the epicardial region comprises epicardial adipose tissue and/or connective tissue.

29. The method of claim 18, wherein the epicardial radiomic signature comprises a decision tree, optionally wherein the epicardial radiomic signature comprises a regression tree.

30. A system configured to perform the method of claim 18.

* * * * *